US011439703B2

(12) United States Patent
Abraham et al.

(10) Patent No.: US 11,439,703 B2
(45) Date of Patent: *Sep. 13, 2022

(54) ENHANCED IMMUNE RESPONSE IN PORCINE SPECIES

(71) Applicant: BAYER ANIMAL HEALTH GMBH, Leverkusen (DE)

(72) Inventors: Albert Abraham, Shawnee, KS (US); Jason Nickell, Parkville, MO (US); Daniel Keil, Spring Hill, KS (US); Christian Weiss, Leverkusen (DE)

(73) Assignee: ELANCO US, INC., Greenfield, IN (US)

( * ) Notice: Subject to any disclaimer, the term of this patent is extended or adjusted under 35 U.S.C. 154(b) by 507 days.

This patent is subject to a terminal disclaimer.

(21) Appl. No.: 15/748,444

(22) PCT Filed: Jul. 28, 2016

(86) PCT No.: PCT/EP2016/067971
§ 371 (c)(1),
(2) Date: Jan. 29, 2018

(87) PCT Pub. No.: WO2017/021266
PCT Pub. Date: Feb. 9, 2017

(65) Prior Publication Data
US 2018/0326049 A1 Nov. 15, 2018

Related U.S. Application Data

(60) Provisional application No. 62/199,848, filed on Jul. 31, 2015.

(51) Int. Cl.
| | | |
|---|---|---|
| *A61K 31/70* | (2006.01) |
| *C07H 21/02* | (2006.01) |
| *A61K 39/39* | (2006.01) |
| *A61P 31/14* | (2006.01) |
| *A61K 9/127* | (2006.01) |
| *A61K 39/12* | (2006.01) |
| *A61K 45/06* | (2006.01) |
| *A01K 67/00* | (2006.01) |
| *A61K 39/00* | (2006.01) |

(52) U.S. Cl.
CPC ............. *A61K 39/39* (2013.01); *A61K 9/127* (2013.01); *A61K 39/12* (2013.01); *A61K 45/06* (2013.01); *A61P 31/14* (2018.01); *A61K 2039/552* (2013.01); *A61K 2039/55555* (2013.01); *A61K 2039/55561* (2013.01)

(58) Field of Classification Search
CPC ........ A61K 39/39; A61K 9/127; A61K 39/12; A61K 45/06; A61K 2039/552; A61K 2039/55555; A61K 2039/55561; A61P 31/14

See application file for complete search history.

(56) References Cited

U.S. PATENT DOCUMENTS

| | | | |
|---|---|---|---|
| 5,075,109 A | 12/1991 | Tice et al. | |
| 6,207,646 B1 | 3/2001 | Krieg et al. | |
| 6,239,116 B1 | 5/2001 | Krieg et al. | |
| 6,339,068 B1 * | 1/2002 | Krieg ................... | A61K 39/292 424/93.2 |
| 6,429,199 B1 | 8/2002 | Krieg et al. | |
| 6,693,086 B1 * | 2/2004 | Dow .................... | A61K 9/1272 424/450 |
| 7,163,820 B1 * | 1/2007 | Nagy .................... | C12N 1/205 435/243 |
| 7,527,802 B2 * | 5/2009 | Glenn .................. | A61K 47/32 424/257.1 |
| 10,155,950 B2 * | 12/2018 | Munnes ............... | C12N 15/117 |
| 2003/0022854 A1 | 1/2003 | Dow et al. | |
| 2003/0191082 A1 | 10/2003 | Wheeler | |
| 2004/0002472 A1 | 1/2004 | Audonnet et al. | |
| 2005/0191342 A1 | 9/2005 | Tam et al. | |
| 2006/0223769 A1 | 10/2006 | Dow et al. | |
| 2007/0134200 A1 | 6/2007 | Eldridge et al. | |
| 2009/0263423 A1 | 10/2009 | Fairman et al. | |
| 2010/0065151 A1 | 3/2010 | Nelson et al. | |
| 2011/0111017 A1 * | 5/2011 | Bosio ..................... | A61P 37/00 424/450 |
| 2013/0295167 A1 | 11/2013 | Abraham et al. | |
| 2014/0010865 A1 | 1/2014 | Abraham et al. | |
| 2019/0201434 A1 | 7/2019 | Abraham et al. | |

FOREIGN PATENT DOCUMENTS

| | | |
|---|---|---|
| WO | 99/66879 A2 | 12/1999 |
| WO | 2005/079511 A2 | 9/2005 |
| WO | 2005079506 A2 | 9/2005 |
| WO | 2006/017857 A2 | 2/2006 |

(Continued)

OTHER PUBLICATIONS

US 10,683,508 B2, 06/2020, Munnes (withdrawn)*
Dwivedi, et al., "Cross-protective immunity to porcine reproductive and respiratory syndrome virus by intranasal delivery of a live virus vaccine with a potent adjuvant," Vaccine, (2011), vol. 29, No. 23: 4058-4066.
Lay, et al., "Cationic lipid/DNA complexes (JVRS-100) combined with influenza vaccine (Fluzone) increases antibody response, cellular immunity, and antigenically drifted protection," Vaccine, (2009), vol. 27, No. 29: 3811-3820.
Dong, et al., "Cationic liposome-DNA complexes (CLDC) adjuvant enhances the immunogenicity and cross-protective efficacy of a pre-pandemic influenza A H5N1 vaccine in mice," Vaccine, (2011), vol. 30, No. 2: 254-264.
Mitsui et al., J. Gene Med., 2009, 11: 435-143.
Magnusson, Dissertation, 201 O: 1-80.
Sato et al., Science, 1996, 273: 352-354.

(Continued)

*Primary Examiner* — Quang Nguyen
(74) *Attorney, Agent, or Firm* — McBee Moore & Vanik IP, LLC; Susan E. Shaw McBee

(57) ABSTRACT

The present invention generally relates to methods of eliciting an immune response in a porcine species subject. In particular, an immunomodulator composition is used to induce an immune response to enhance the subject's ability to fight infectious pathogens.

9 Claims, 49 Drawing Sheets

Specification includes a Sequence Listing.

(56) References Cited

FOREIGN PATENT DOCUMENTS

WO 2009120811 A1 10/2009
WO 2012/084951 A1 6/2012

OTHER PUBLICATIONS

Pontarollo et al., J. Gen. Virol., 2002, 83: 2973-2981.
Rice, et al., "Mannheimia haemolytica and bovine respiratory disease", Animal Health Research Reviews, (2008), vol. 8, No. 2: 117-128.
Babiuk, L.A., "Broadening the Approaches to Developing More Effective Vaccines," 1999, Vaccine, 1587-1595.
Dow, et al., "Lipid-DNA Complexes Induce Potent Activation of Innate Immune Responses and Antitumor Activity Wehn Administered Intravenously," 1999, J Immun, 163:1552-1561.
Morrey et al., "Efficacy of Cationic Lipid-DNA Complexes (CLDC) on Hepatitis B Virus in Transgenic Mice," 2008, Antiviral Res., 79:71-79.
Pneumonia—Bovine Respiratory Disease—Dairy (BRD), www.zoetis.com.au/diseases/2105/pneumonia, downloaded Jan. 24, 2014, 4 pages.
Bryant et al., "Mice, men and the relatives: cross-species studies underpin innate immunity", Open Biology, 2012, 120015, 11 pages.
Taghavi, Azita, "Immunostimulatory effects and delivery of oligodeoxynucleotides containing CpG motifs (CpG-ODN) in neonatal broiler chickens", Thesis, University of Saskatchewan, Apr. 2008, 175 pages.
Mak et al., "Comparative Immunology", The Immune Response, Basic and Clinical Principles, Chapter 21, 2006, pp. 611-637.
Sellins et al., "Type I Interferons Potently Suppress Gene Expression Following Gene Delivery Using Liposome-DNA Complexes", Molecular Therapy, 2005, 12(3), pp. 451-459.
Butiaro, C., et al., "Engineered *E. coli* as Vehicles for Targeted Therapeutics," 2010, Current Gene Therapy, 10:27-33.
Vaccine Adjuvants: Preparation Methods and Research Protocols, D. T. O'Hagan, Ed., 2000, Human Press Inc., Totowa. NJ 07512, Chapter 18, "DNA as an Adjuvant", pp. 300-301, XP055136002, 6 pages.
Dow et al., (Expert Opin Drug Deliv, Jan. 2008, 5: 1-16.
Patel, et al., 4MLINOLOGY. (200S), ?.2, pp. 1041-104B.
Cornelie, J. et al, Methylated CPG-Containing Plasmid Activates the Immune System; Scandinavian Journal of Immunology, 2004, vol. 59, No. 2, pp. 143-151.
Gursel, I., et al., Sterically Stabilized Cationic Liposomes Improve the Uptake and Immunostimulatory Activity of CPG Oligonucleotides; Journal of Immunology, 2001, vol. 167, No. 6, pp. 3324-3328.
Luo et al., Plasmid DNA containing multiple CpG motifs triggers a strong immune response to hepatitis B surface antigen when combined with incomplete Freund's adjuvant but not aluminum hydroxide. Molecular Medicine Reports 6:1309-1314.
Chikh et al., Synthetic methylated CpG ODNs are potent in vivo adjuvants when delivered in liposomal nanoparticles. International Immunology, 2009; 21(7): 757-67.
Krieg, et al., "CPG Motifs in Bacterial DNA and Their Immune Effects*," Annu. Rev. Immunol., (2002), vol. 20: 709-760.
Quan, et al., "Plasmid containing CpG oligodeoxynucleotides can augment the immune responses of pigs immunized with porcine reproductive and respiratory syndrome killed virus vaccine," Veterinary Immunology and Immunopathology, (2010), vol 136: 257-264.
Yew, et al., "Reducing the immunostimulatory activity of CpG-containing plasmid DNA vectors for non-viral gene therapy," Expert Opin. Drug Deliv., (2004), vol. 1: 115-125.
Li, et al., Heterogeneity in the Response of Different Animals to Specific CpG Oligodeoxynucleotides, Journal of Agricultural Biotechnology, (2004), vol. 12, No. 1: 66-70.
Zhang, et al., "Immunostimulatory Effect of CpG ODN Recombinant Plasmid on Peripheral Blood Lymphocytes of Pigs," Chinese Journal of Veterinary Drug, (2020), vol. 54, No. 2: 59-64.

* cited by examiner

FIG. 11 Average Body Weight

FIG. 12 Average Weight Gain (pounds) from Day -39

FIG. 13: Average Post Challenge Body Weight

FIG. 14: Body Weight Gain – Post Challenge

FIG. 16: Lung Weight by group

FIG. 19: Lung Virus Titer (Group)

FIG. 23

FIG. 30. CD172a positive magnetic cell separation

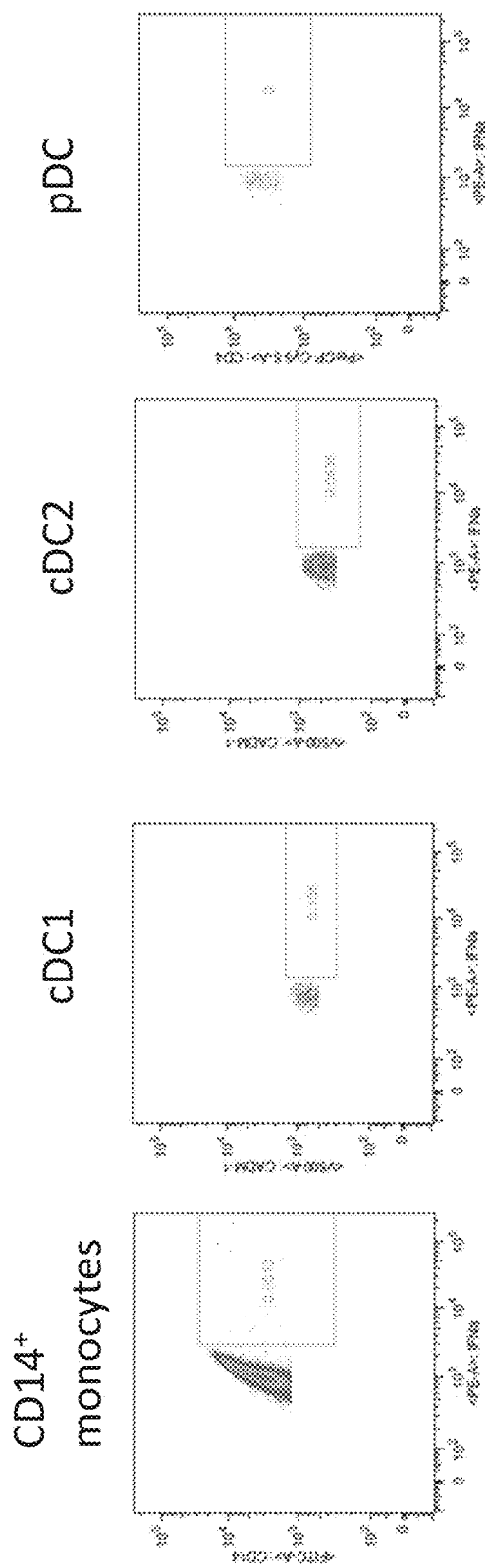

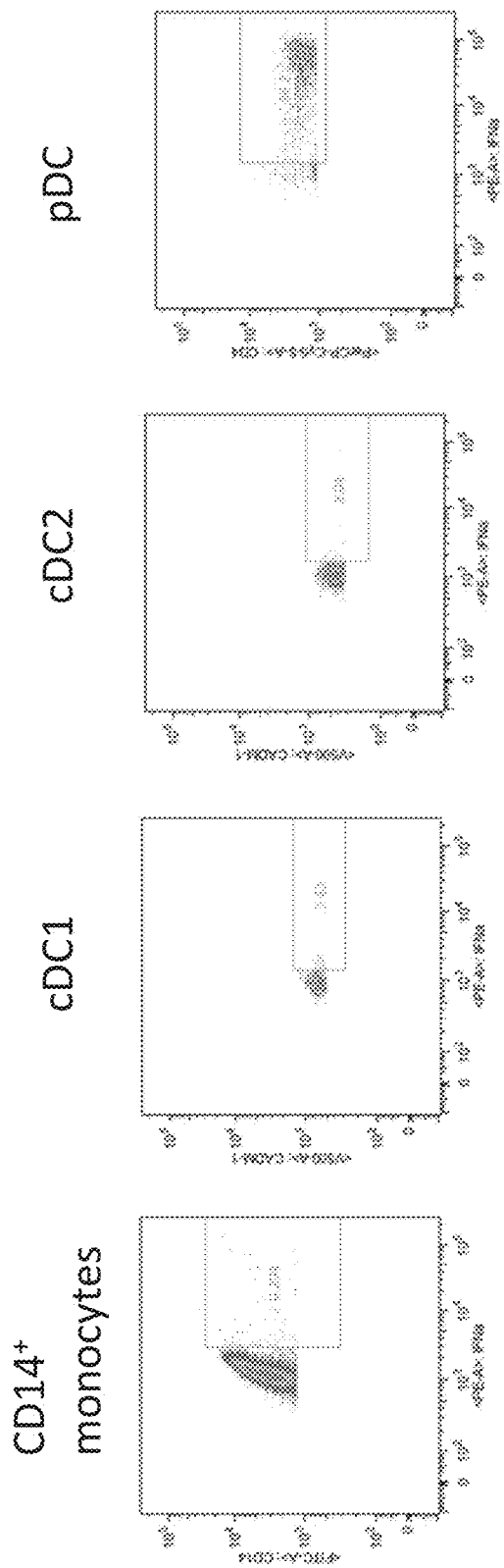

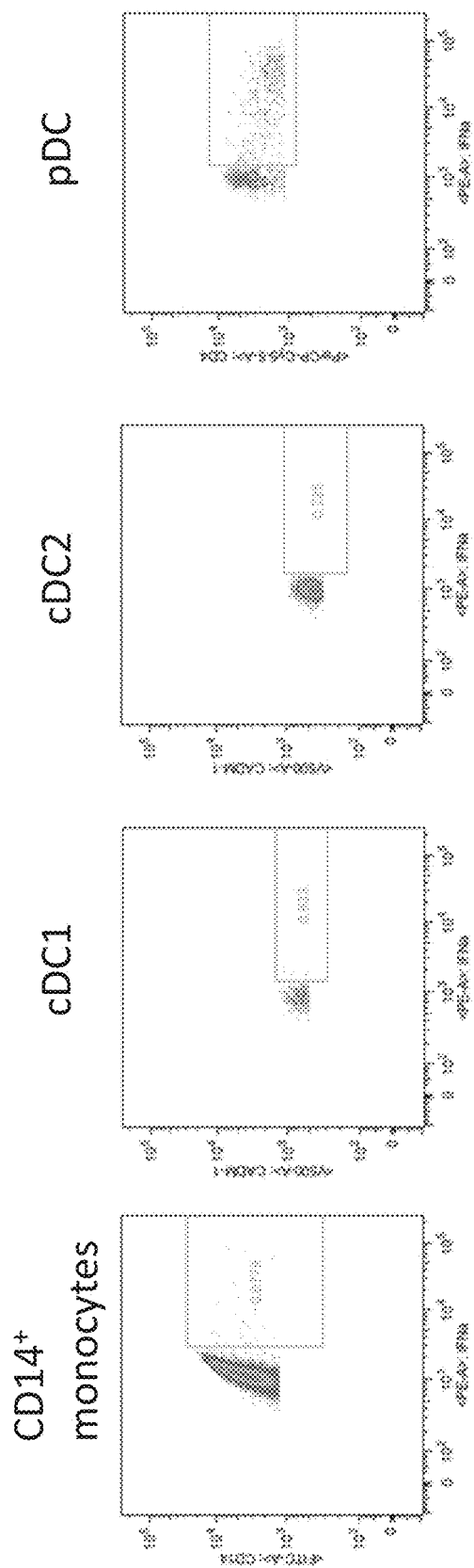

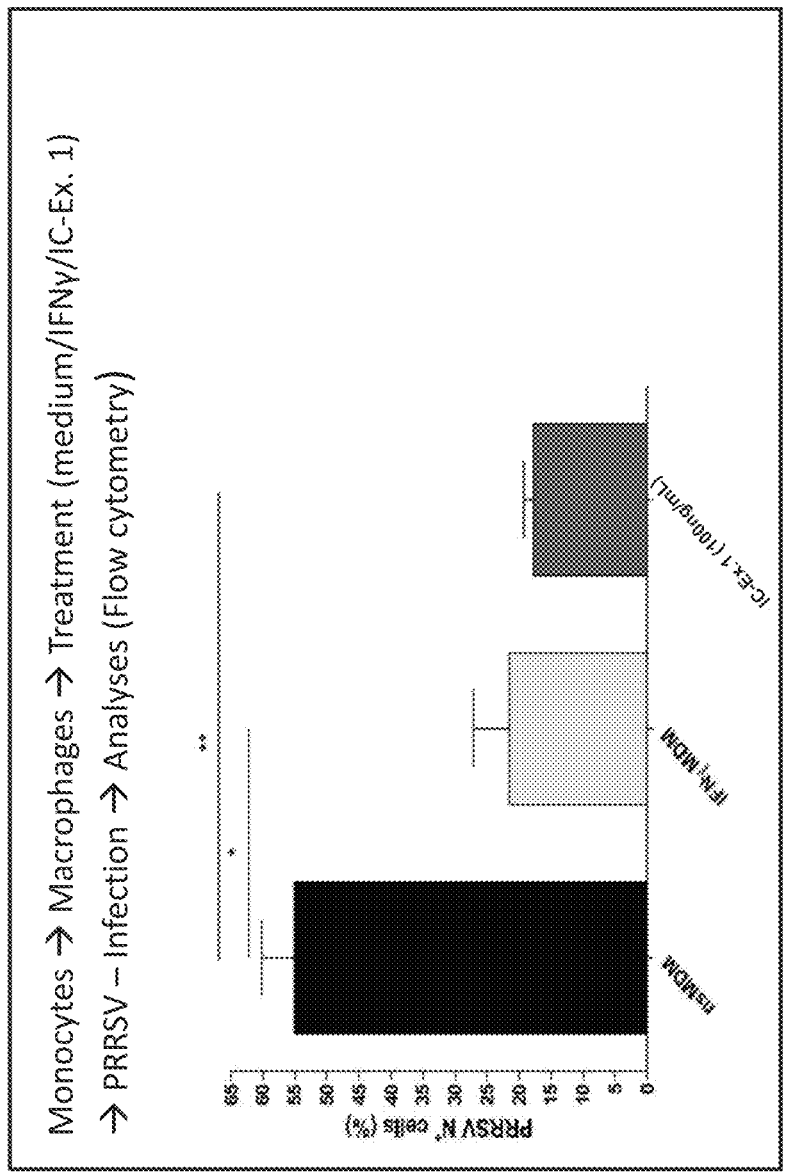
FIG. 49: PRRSV infected Macrophages

SEQUENCE LISTING

```
<160> NUMBER OF SEQ ID NOS: 4

<210> SEQ ID NO 1
<211> LENGTH: 4242
<212> TYPE: DNA
<213> ORGANISM: Artificial sequence
<220> FEATURE:
<223> OTHER INFORMATION: Nucleotide sequence of plasmid pGCMB75.6

<400> SEQUENCE: 1
tgaccgccca acgaccccg cccattgacg tcaataatga cgtatgttcc catagtaacg      60
ccaataggga ctttccattg acgtcaatgg gtggagtatt tacggtaaac tgcccacttg     120
gcagtacatc aagtgtatca tatgccaagt ccgcccccta ttgacgtcaa tgacggtaaa    180
tggcccgcct ggcattatgc ccagtacatg accttacggg actttcctac ttggcagtac     240
atctacgtat tagtcatcgc tattaccatg gtgatgcggt tttggcagta catcaatggg    300
cgtggatagc ggtttgactc acggggattt ccaagtctcc accccattga cgtcaatggg    360
agtttgtttt ggcaccaaaa tcaacgggac tttccaaaat gtcgtaacaa ctccgcccca    420
ttgacgcaaa tgggcggtag gcgtgtacgg tgggaggtct atataagcag agctcgttta    480
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgcaagcttg atatcgaatt cctgcagccc    840
gggggatcca ctagttctag agcggccgcc accgcggtgg agctcgaatt atcagatcga    900
ttaataacta tgctcaaaaa ttgtgtacct ttagcttttt aatttgtaaa gggggttaata    960 aggaatattt gatgtatagt gccttgacta gagatcataa tcagccatac cacatttgta   1020
gaggttttac ttgctttaaa aaacctccca cacctccccc tgaacctgaa acataaaatg   1080
aatgcaattg ttgttgttaa cttgtttatt gcagcttata atggttacaa ataaagcaat   1140
agcatcacaa atttcacaaa taaagcattt tttcactgc attctagttg tggtttgtcc     1200
aaactcatca atgtatctta tcatgtctgg atcatcagat ctgccggtct ccctatagtg    1260
agtcgtatta atttcgataa gccaggttaa cctgcattaa tgaatcggcc aacgcgcggg   1320
gagaggcggt ttgcgtattg ggcgctcttc cgcttcctcg ctcactgact cgctgcgctc   1380
ggtcgttcgg ctgcggcgag cggtatcagc tcactcaaag gcggtaatac ggttatccac   1440
agaatcaggg gataacgcag gaaagaacat gtgagcaaaa ggccagcaaa aggccaggaa   1500
ccgtaaaaag gccgcgttgc tggcgttttt ccataggctc cgcccccctg acgagcatca   1560
caaaaatcga cgctcaagtc agaggtggcg aaacccgaca ggactataaa gataccaggc    1620
gtttccccct ggaagctccc tcgtgcgctc tcctgttccg accctgccgc ttaccggata   1680
```

```
cctgtccgcc tttctccctt cgggaagcgt ggcgctttct catagctcac gctgtaggta   1740
tctcagttcg gtgtaggtcg ttcgctccaa gctgggctgt gtgcacgaac ccccgttca    1800 gcccgaccgc tgcgccttat ccggtaacta tcgtcttgag tccaacccgg taagacacga   1860
cttatcgcca ctggcagcag ccactggtaa caggattagc agagcgaggt atgtaggcgg   1920
tgctacagag ttcttgaagt ggtggcctaa ctacggctac actagaagaa cagtatttgg   1980
tatctgcgct ctgctgaagc cagttacctt cggaaaaaga gttggtagct cttgatccgg   2040
caaacaaacc accgctggta gcggtggttt ttttgtttgc aagcagcaga ttacgcgcag   2100
aaaaaaagga tctcaagaag atcctttgat cttttctacg gggtctgacg ctcagtggaa   2160
cgaaaactca cgttaaggga ttttggtcat gggcgcgcct aggcttttgc aaagatcgat   2220
caagagacag gatgaggatc gtttcgcagc ttttcattct gactgcaacg ggcaataagt   2280
ctctgtgtgg attaaaaaaa gagtgtctga tagcagcttc tgaactggtt acctgccgtg   2340
agtaaattaa aattttattg acttaggtca ctaaggcgcc ttgcgctgag gttgcgtcgt   2400
gatatcatca gggcagaccg gttacatccc cctaacaagc tgtataaaga gaaatactat   2460
ctcattggcg ttgcccgcac ctgacagtgc gacgttgggc tgcgtccgtc gaccaacggt   2520
accgaggtaa cagcccaatc tatccatgat ctcggccagg ccgggtcggc cgttatgcag   2580
cccggctcgg gtatgaagcc attaaggagc gacccagcg cgaccgggcg gccggtcacg    2640
ctgcctctgc tgaagcctgc ctgtcactcc ctgcgcggcg tacccgccgt tctcatcgag   2700
taggctccgg atcgcgaccc cggacgggcc ctgggcccag gagcggccta tgacaaatgc   2760
cgggtagcga tccggcattc agcattgact gcgcacggat ccagtccttg caggagcctt   2820
atgccgaccg tagcaaaaaa tgagcccgag ccgatcgcga gttgtgatcc ggtcccgccg   2880
attgccggtc gcgatgacgg tcctgtgtaa gcgttatcgt taccaattgt ttaagaagta   2940
tatacgctac gaggtacttg ataacttctg cgtagcatac atgaggtttt gtataaaaat   3000
ggcgggcgat atcaacgcag tgtcagaaat ccgaaacagt ctgcgggact ctggggttcg   3060
aaatgaccga ccaagcgacg cccaacctgc catcacgaga tttcgattcc accgccgcct   3120
tctatgaaag gttgggcttc ggaatcgttt tccgggacgc cggctggatg atcctccagc   3180
gcggggatct catgctggag ttcttcgccc accctaggcg cgctcatgag cggatacata   3240
tttgaatgta tttagaaaaa taaacaaata ggggttccgc gcacatttcc ccgaaaagtg   3300
ccacctaaat tgtaagcgtt aatattttgt taaaattcgc gttaaatttt tgttaaatca   3360
gctcattttt taaccaatag gccgaaatcg gcaaaatccc ttataaatca aagaatagac   3420
ccgagatagg gttgagtgtt gttccagttt ggaacaagag tccactatta agaacgtgg    3480 actccaacgt caaagggcga aaaccgtctc atcagggcga tggcccacta cgtgaaccat   3540
caccctaatc aagttttttg gggtcgaggt gccgtaaagc actaaatcgg aaccctaaag   3600 ggagccccg atttagagct tgacggggaa agccggcgaa cgtggcgaga aggaaggga    3660 agaaagcgaa aggagcgggc gctagggcgc tggcaagtgt agcggtcacg ctgcgcgtaa   3720
ccaccacacc cgccgcgctt aatgcgccgc tacagggcgc gtcccattcg ccattcaggc   3780
tgcgcaactg ttgggaaggg cgatcggtgc gggcctcttc gctattacgc cagctggcga   3840 aaggggggatg tgctgcaagg cgattaagtt gggtaacgcc agggttttcc cagtcacgac   3900
gttgtaaaac gacggccagt gagcgcgcgt aatacgactc actatagggc gaattgggta   3960
ccgggccccc cctcgagcag gatctataca ttgaatcaat attggcaatt agccatatta   4020
```

| | |
|---|---|
| gtcattggtt atatagcata aatcaatatt ggctattggc cattgcatac gttgtatcta | 4080 |
| tatcataata tgtacattta tattggctca tgtccaatat gaccgccatg ttgacattga | 4140 |
| ttattgacta gttattaata gtaatcaatt acggggtcat tagttcatag cccatatatg | 4200 |
| gagttccgcg ttacataact tacggtaaat ggcccgcctg gc | 4242 |

<210> SEQ ID NO 2
<211> LENGTH: 4242
<212> TYPE: DNA
<213> ORGANISM: Artificial sequence
<220> FEATURE:
<223> OTHER INFORMATION: Nucleotide sequence of plasmid pMB75.6

<400> SEQUENCE: 2

| | |
|---|---|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta gggcgaat tgggtaccgg | 660 |
| gccccccctc gagcaggatc tatacattga atcaatattg gcaattagcc atattagtca | 720 |
| ttggttatat agcataaatc aatattggct attggccatt gcatacgttg tatctatatc | 780 |
| ataatatgta catttatatt ggctcatgtc caatatgacc gccatgttga cattgattat | 840 |
| tgactagtta ttaatagtaa tcaattacgg ggtcattagt tcatagccca tatatggagt | 900 |
| tccgcgttac ataacttacg gtaaatggcc cgcctggctg accgcccaac gacccccgcc | 960 |
| cattgacgtc aataatgacg tatgttccca tagtaacgcc aatagggact ttccattgac | 1020 |
| gtcaatgggt ggagtattta cggtaaactg cccacttggc agtacatcaa gtgtatcata | 1080 |
| tgccaagtcc gccccctatt gacgtcaatg acggtaaatg gcccgcctgg cattatgccc | 1140 |
| agtacatgac cttacgggac tttcctactt ggcagtacat ctacgtatta gtcatcgcta | 1200 |
| ttaccatggt gatgcggttt tggcagtaca tcaatgggcg tggatagcgg tttgactcac | 1260 |
| ggggatttcc aagtctccac cccattgacg tcaatgggag tttgttttgg caccaaaatc | 1320 |
| aacgggactt tccaaaatgt cgtaacaact ccgccccatt gacgcaaatg ggcggtaggc | 1380 |
| gtgtacggtg ggaggtctat ataagcagag ctcgtttagt gaaccgtcag atcgcctgga | 1440 |
| gacgccatcc acgctgtttt gacctccata agagacaccg ggaccgatcc agcctcccct | 1500 |
| cgaagccgat ctgataacgg taccgataag ctggcggccg attaagctac agaagttggt | 1560 |
| cgtgaggcac tgggcaggta agtatcaagg ttacaagaca ggtttaagga gaccaataga | 1620 |
| aactgggctt gtcgagacag agaagactct tgcgtttctg ataggcacct attggtctta | 1680 |
| ctgacatcca ctttgccttt ctctccacag gtgtccactc ccaggttcaa ttacagctct | 1740 |
| taagcagccg caagcttgat atcgaattcc tgcagcccgg ggatccact agttctagag | 1800 |
| cggccgccac cgcggtggag ctcgaattat cagatcgatt aataactatg ctcaaaaatt | 1860 |

```
gtgtaccttt agctttttaa tttgtaaagg ggttaataag gaatatttga tgtatagtgc   1920
cttgactaga gatcataatc agccatacca catttgtaga ggttttactt gctttaaaaa   1980
acctcccaca cctcccctg aacctgaaac ataaaatgaa tgcaattgtt gttgttaact    2040
tgtttattgc agcttataat ggttacaaat aaagcaatag catcacaaat ttcacaaata   2100
aagcattttt ttcactgcat tctagttgtg gtttgtccaa actcatcaat gtatcttatc   2160
atgtctggat catcagatct gccggtctcc ctatagtgag tcgtattaat ttcgataagc   2220
caggttaacc tgcattaatg aatcggccaa cgcgcgggga gaggcggttt gcgtattggg   2280
cgctcttccg cttcctcgct cactgactcg ctgcgctcgg tcgttcggct gcggcgagcg   2340
gtatcagctc actcaaaggc ggtaatacgg ttatccacag aatcagggga taacgcagga   2400
aagaacatgt gagcaaaagg ccagcaaaag gccaggaacc gtaaaaaggc cgcgttgctg   2460
gcgtttttcc ataggctccg cccccctgac gagcatcaca aaaatcgacg ctcaagtcag   2520
aggtggcgaa acccgacagg actataaaga taccaggcgt ttccccctgg aagctccctc   2580
gtgcgctctc ctgttccgac cctgccgctt accggatacc tgtccgcctt tctcccttcg   2640
ggaagcgtgg cgctttctca tagctcacgc tgtaggtatc tcagttcggt gtaggtcgtt   2700
cgctccaagc tgggctgtgt gcacgaaccc cccgttcagc ccgaccgctg cgccttatcc   2760
ggtaactatc gtcttgagtc caacccggta agacacgact tatcgccact ggcagcagcc   2820
actggtaaca ggattagcag agcgaggtat gtaggcggtg ctacagagtt cttgaagtgg   2880
tggcctaact acggctacac tagaagaaca gtatttggta tctgcgctct gctgaagcca   2940
gttaccttcg gaaaaagagt tggtagctct tgatccggca acaaaccac cgctggtagc    3000 ggtggttttt ttgtttgcaa gcagcagatt acgcgcagaa aaaaaggatc tcaagaagat   3060
cctttgatct tttctacggg gtctgacgct cagtggaacg aaaactcacg ttaagggatt   3120
ttggtcatga gcgcgcctag gctttttgcaa agatcgatca agagacagga tgaggatcgt   3180
ttcgcatgat tgaacaagat ggattgcacg caggttctcc ggccgcttgg gtggagaggc   3240
tattcggcta tgactgggca acagacaa tcggctgctc tgatgccgcc gtgttccggc     3300
tgtcagcgca ggggcgcccg gttcttttg tcaagaccga cctgtccggt gccctgaatg    3360
aactgcaaga cgaggcagcg cggctatcgt ggctggccac gacgggcgtt ccttgcgcag   3420
ctgtgctcga cgttgtcact gaagcgggaa gggactggct gctattgggc gaagtgccgg   3480
ggcaggatct cctgtcatct caccttgctc ctgccgagaa agtatccatc atggctgatg   3540
caatgcggcg gctgcatacg cttgatccgg ctacctgccc attcgaccac caagcgaaac   3600
atcgcatcga gcgagcacgt actcggatgg aagccggtct tgtcgatcag gatgatctgg   3660
acgaagagca tcagggctc gcgccagccg aactgttcgc caggctcaag gcgagcatgc    3720
ccgacggcga ggatctcgtc gtgacccatg gcgatgcctg cttgccgaat atcatggtgg   3780
aaaatggccg cttttctgga ttcatcgact gtggccggct gggtgtggcg gaccgctatc   3840
aggacatagc gttggctacc cgtgatattg ctgaagagct tggcggcgaa tgggctgacc   3900
gcttcctcgt gctttacggt atcgccgctc ccgattcgca gcgcatcgcc ttctatcgcc   3960
ttcttgacga gttcttctga gcgggactct ggggttcgaa atgaccgacc aagcgacgcc   4020
caacctgcca tcacgagatt tcgattccac cgccgccttc tatgaaaggt tgggcttcgg   4080
aatcgttttc cgggacgccg gctggatgat cctccagcgc ggggatctca tgctggagtt   4140
cttcgcccac cctaggcgcg ctcatgagcg gatacatatt tgaatgtatt tagaaaaata   4200
```

```
aacaaatagg ggttccgcgc acatttcccc gaaaagtgcc ac                          4242
```

<210> SEQ ID NO 3
<211> LENGTH: 4242
<212> TYPE: DNA
<213> ORGANISM: Artificial sequence
<220> FEATURE:
<223> OTHER INFORMATION: Nucleotide sequence of plasmid pMB75.6_AscI

<400> SEQUENCE: 3

```
tgaccgccca acgaccccg cccattgacg tcaataatga cgtatgttcc catagtaacg          60
ccaataggga ctttccattg acgtcaatgg gtggagtatt tacggtaaac tgcccacttg         120
gcagtacatc aagtgtatca tatgccaagt ccgcccccta ttgacgtcaa tgacggtaaa        180
tggcccgcct ggcattatgc ccagtacatg accttacggg actttcctac ttggcagtac        240
atctacgtat tagtcatcgc tattaccatg gtgatgcggt tttggcagta catcaatggg        300
cgtggatagc ggtttgactc acggggattt ccaagtctcc accccattga cgtcaatggg        360
agtttgtttt ggcaccaaaa tcaacgggac tttccaaaat gtcgtaacaa ctccgcccca        420
ttgacgcaaa tgggcggtag gcgtgtacgg tgggaggtct atataagcag agctcgttta        480
gtgaaccgtc agatcgcctg gagacgccat ccacgctgtt tgacctccat agaagacac         540
cgggaccgat ccagcctccc ctcgaagccg atctgataac ggtaccgata agctggcggc        600
cgattaagct acagaagttg gtcgtgaggc actgggcagg taagtatcaa ggttacaaga        660
caggtttaag gagaccaata gaaactgggc ttgtcgagac agagaagact cttgcgtttc        720
tgataggcac ctattggtct tactgacatc cactttgcct ttctctccac aggtgtccac        780
tcccaggttc aattacagct cttaagcagc cgcaagcttg atatcgaatt cctgcagccc        840
gggggatcca ctagttctag agcggccgcc accgcggtgg agctcgaatt atcagatcga        900
ttaataacta tgctcaaaaa ttgtgtacct ttagcttttt aatttgtaaa ggggttaata        960
aggaatattt gatgtatagt gccttgacta gagatcataa tcagccatac cacatttgta       1020
gaggttttac ttgctttaaa aaacctccca cacctccccc tgaacctgaa acataaaatg       1080
aatgcaattg ttgttgttaa cttgtttatt gcagcttata atggttacaa ataaagcaat       1140
agcatcacaa atttcacaaa taaagcattt ttttcactgc attctagttg tggtttgtcc       1200
aaactcatca atgtatctta tcatgtctgg atcatcagat ctgccggtct ccctatagtg       1260
agtcgtatta atttcgataa gccaggttaa cctgcattaa tgaatcggcc aacgcgcggg       1320
gagaggcggt ttgcgtattg ggcgctcttc cgcttcctcg ctcactgact cgctgcgctc       1380
ggtcgttcgg ctgcggcgag cggtatcagc tcactcaaag gcggtaatac ggttatccac       1440
agaatcaggg gataacgcag gaaagaacat gtgagcaaaa ggccagcaaa aggccaggaa       1500
ccgtaaaaag gccgcgttgc tggcgttttt ccataggctc cgcccccctg acgagcatca       1560
caaaaatcga cgctcaagtc agaggtggcg aaacccgaca ggactataaa gataccaggc       1620
gtttccccct ggaagctccc tcgtgcgctc tcctgttccg accctgccgc ttaccggata       1680
cctgtccgcc tttctccctt cgggaagcgt ggcgctttct catagctcac gctgtaggta       1740
tctcagttcg gtgtaggtcg ttcgctccaa gctgggctgt gtgcacgaac cccccgttca       1800
gcccgaccgc tgcgccttat ccggtaacta tcgtcttgag tccaacccgg taagacacga       1860
cttatcgcca ctggcagcag ccactggtaa caggattagc agagcgaggt atgtaggcgg       1920
tgctacagag ttcttgaagt ggtggcctaa ctacggctac actagaagaa cagtatttgg       1980
tatctgcgct ctgctgaagc cagttacctt cggaaaaaga gttggtagct cttgatccgg       2040
```

```
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcatg attgaacaag atggattgca cgcaggttct    2280
ccggccgctt gggtggagag gctattcggc tatgactggg cacaacagac aatcggctgc    2340
tctgatgccg ccgtgttccg gctgtcagcg caggggcgcc cggttctttt tgtcaagacc    2400
gacctgtccg gtgccctgaa tgaactgcaa gacgaggcag cgcggctatc gtggctggcc    2460
acgacgggcg ttccttgcgc agctgtgctc gacgttgtca ctgaagcggg aagggactgg    2520
ctgctattgg gcgaagtgcc ggggcaggat ctcctgtcat ctcaccttgc tcctgccgag    2580
aaagtatcca tcatggctga tgcaatgcgg cggctgcata cgcttgatcc ggctacctgc    2640
ccattcgacc accaagcgaa acatcgcatc gagcgagcac gtactcggat ggaagccggt    2700
cttgtcgatc aggatgatct ggacgaagag catcaggggc tcgcgccagc cgaactgttc    2760
gccaggctca aggcgagcat gcccgacggc gaggatctcg tcgtgaccca tggcgatgcc    2820
tgcttgccga atatcatggt ggaaaatggc cgcttttctg gattcatcga ctgtggccgg    2880
ctgggtgtgg cggaccgcta tcaggacata gcgttggcta cccgtgatat tgctgaagag    2940
cttggcggcg aatgggctga ccgcttcctc gtgctttacg gtatcgccgc tcccgattcg    3000
cagcgcatcg ccttctatcg ccttcttgac gagttcttct gagcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
gctcattttt taaccaatag gccgaaatcg gcaaaatccc ttataaatca aagaataga    3420
ccgagatagg gttgagtgtt gttccagttt ggaacaagag tccactatta agaacgtgg    3480
actccaacgt caaagggcga aaaccgtct atcagggcga tggcccacta cgtgaaccat    3540
caccctaatc aagttttttg gggtcgaggt gccgtaaagc actaaatcgg aaccctaaag    3600
ggagccccg atttagagct tgacggggaa agccggcgaa cgtggcgaga aggaaggga    3660
agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840
aagggggatg tgctgcaagg cgattaagtt gggtaacgcc agggttttcc cagtcacgac    3900
gttgtaaaac gacggccagt gagcgcgcgt aatacgactc actatagggc gaattgggta    3960
ccgggccccc cctcgagcag gatctataca ttgaatcaat attggcaatt agccatatta    4020
gtcattggtt atatagcata aatcaatatt ggctattggc cattgcatac gttgtatcta    4080
tatcataata tgtacattta tattggctca tgtccaatat gaccgccatg ttgacattga    4140
ttattgacta gttattaata gtaatcaatt acggggtcat tagttcatag cccatatatg    4200
gagttccgcg ttacataact tacggtaaat ggcccgcctg gc                       4242
```

<210> SEQ ID NO 4
<211> LENGTH: 4242
<212> TYPE: DNA

<213> ORGANISM: Artificial sequence
<220> FEATURE:
<223> OTHER INFORMATION: Nucelotide sequence of plasmid pLacZMB75.6

<400> SEQUENCE: 4

```
tgaccgccca acgaccccg cccattgacg tcaataatga cgtatgttcc catagtaacg      60
ccaataggga ctttccattg acgtcaatgg gtggagtatt tacggtaaac tgcccacttg     120
gcagtacatc aagtgtatca tatgccaagt ccgcccccta ttgacgtcaa tgacggtaaa    180
tggcccgcct ggcattatgc ccagtacatg accttacggg actttcctac ttggcagtac    240
atctacgtat tagtcatcgc tattaccatg gtgatgcggt tttggcagta catcaatggg    300
cgtggatagc ggtttgactc acggggattt ccaagtctcc accccattga cgtcaatggg    360
agtttgtttt ggcaccaaaa tcaacgggac tttccaaaat gtcgtaacaa ctccgcccca    420
ttgacgcaaa tgggcggtag cgtgtacgg tgggaggtct atataagcag agctcgttta     480
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgccaaaaca aaattcctca aaaatcatca    840
tcgaatgaat ggtgaaataa tttccctgaa taactgtagt gttttcaggg cgcggcataa    900
taattaacta tgctcaaaaa ttgtgtacct ttagcttttt aatttgtaaa ggggttaata    960
aggaatattt gatgtatagt gccttgacta gagatcataa tcagccatac cacatttgta   1020
gaggttttac ttgctttaaa aaacctccca cacctccccc tgaacctgaa acataaaatg   1080
aatgcaattg ttgttgttaa cttgtttatt gcagcttata atggttacaa ataaagcaat   1140
agcatcacaa atttcacaaa taaagcattt ttttcactgc attctagttg tggtttgtcc   1200
aaactcatca atgtatctta tcatgtctgg atcatcagat ctgccggtct ccctatagtg   1260
agtcgtatta atttcgataa gccaggttaa cctgcattaa tgaatcggcc aacgcgcggg   1320
gagaggcggt ttgcgtattg ggcgctcttc cgcttcctcg ctcactgact cgctgcgctc   1380
ggtcgttcgg ctgcggcgag cggtatcagc tcactcaaag gcggtaatac ggttatccac   1440
agaatcaggg gataacgcag gaaagaacat gtgagcaaaa ggccagcaaa aggccaggaa   1500
ccgtaaaaag gccgcgttgc tggcgttttt ccataggctc cgcccccctg acgagcatca   1560
caaaaatcga cgctcaagtc agaggtggcg aaacccgaca ggactataaa gataccaggc   1620
gtttccccct ggaagctccc tcgtgcgctc tcctgttccg accctgccgc ttaccggata   1680
cctgtccgcc tttctccctt cgggaagcgt ggcgctttct catagctcac gctgtaggta   1740
tctcagttcg gtgtaggtcg ttcgctccaa gctgggctgt gtgcacgaac cccccgttca   1800
gcccgaccgc tgcgccttat ccggtaacta tcgtcttgag tccaacccgg taagacacga   1860
cttatcgcca ctggcagcag ccactggtaa caggattagc agagcgaggt atgtaggcgg   1920
tgctacagag ttcttgaagt ggtggcctaa ctacggctac actagaagaa cagtatttgg   1980
tatctgcgct ctgctgaagc cagttacctt cggaaaaaga gttggtagct cttgatccgg   2040
caaacaaacc accgctggta gcggtggttt ttttgtttgc aagcagcaga ttacgcgcag   2100
aaaaaaagga tctcaagaag atcctttgat cttttctacg gggtctgacg ctcagtggaa   2160
cgaaaactca cgttaaggga ttttggtcat gggcgcgcct aggcttttgc aaagatcgat   2220
```

-continued

```
caagagacag gatgaggatc gtttcgcagc ttttcattct gactgcaacg ggcaataagt      2280
ctctgtgtgg attaaaaaaa gagtgtctga tagcagcttc tgaactggtt acctgccgtg      2340
agtaaattaa aattttattg acttaggtca ctaaggcgcc ttgcgctgag gttgcgtcgt      2400
gatatcatca gggcagaccg gttacatccc cctaacaagc tgtataaaga gaaatactat      2460
ctcattggcg ttgcccgcac ctgacagtgc gacgttgggc tgcgtccgtc gaccaacggt      2520
accgaggtaa cagcccaatc tatccatgat ctcggccagg ccgggtcggc cgttatgcag      2580
cccggctcgg gtatgaagcc attaaggagc cgacccagcg cgaccgggcg gccggtcacg      2640
ctgcctctgc tgaagcctgc ctgtcactcc ctgcgcggcg tacccgccgt tctcatcgag      2700
taggctccgg atcgcgaccc cggacgggcc ctgggcccag gagcggccta tgacaaatgc      2760
cgggtagcga tccggcattc agcattgact gcgcacggat ccagtccttg caggagcctt      2820
atgccgaccg tagcaaaaaa tgagcccgag ccgatcgcga gttgtgatcc ggtcccgccg      2880
attgccggtc gcgatgacgg tcctgtgtaa gcgttatcgt taccaattgt ttaagaagta      2940
tatacgctac gaggtacttg ataacttctg cgtagcatac atgaggtttt gtataaaaat      3000
ggcgggcgat atcaacgcag tgtcagaaat ccgaaacagt ctgcgggact ctggggttcg      3060
aaatgaccga ccaagcgacg cccaacctgc catcacgaga tttcgattcc accgccgcct      3120
tctatgaaag gttgggcttc ggaatcgttt tccgggacgc cggctggatg atcctccagc      3180
gcggggatct catgctggag ttcttcgccc accctaggcg cgctcatgag cggatacata      3240
tttgaatgta tttagaaaaa taaacaaata ggggttccgc gcacatttcc ccgaaaagtg      3300
ccacctaaat tgtaagcgtt aatatttgt taaaattcgc gttaaatttt tgttaaatca      3360
gctcattttt taaccaatag gccgaaatcg gcaaaatccc ttataaatca aagaataga       3420 ccgagatagg gttgagtgtt gttccagttt ggaacaagag tccactatta aagaacgtgg      3480
actccaacgt caaagggcga aaaccgtct atcagggcga tggcccacta cgtgaaccat       3540
caccctaatc aagttttttg gggtcgaggt gccgtaaagc actaaatcgg aaccctaaag      3600
ggagcccccg atttagagct tgacggggaa agccggcgaa cgtggcgaga aggaaggga       3660 agaaagcgaa aggagcgggc gctagggcgc tggcaagtgt agcggtcacg ctgcgcgtaa      3720
ccaccacacc cgccgcgctt aatgcgccgc tacagggcgc gtcccattcg ccattcaggc      3780
tgcgcaactg ttgggaaggg cgatcggtgc gggcctcttc gctattacgc cagctggcga      3840 aaggggatg tgctgcaagg cgattaagtt gggtaacgcc agggttttcc cagtcacgac       3900
gttgtaaaac gacggccagt gagcgcgcgt aatacgactc actatagggc gaattgggta     3960
ccgggccccc cctcgaggtc gacggtatcg ataagcttga tatcgaattc ctgcagcccg      4020
ggggatccac tagttctaga gcggccgcca ccgcggtgga gctccagctt tgttcccctt     4080
tagtgagggt taattgcgcg cttggcgtaa tcatggtcat agctgtttcc tgtgtgaaat      4140
tgttatccgc tcacaattcc acacaacata cgagccggaa gcataaagtg taaagcctgg     4200
ggtgcctaat gagtgagcta actcacatta attgcgttgc gc                        4242
```

ENHANCED IMMUNE RESPONSE IN PORCINE SPECIES

CROSS-REFERENCE

This application claims the benefit under 35 U.S.C § 119(e) of Provisional U.S. Patent Application No. 62/199,848, filed on Jul. 31, 2015, and entitled ENHANCED IMMUNE RESPONSE IN PORCINE SPECIES the content of which is incorporated by reference herein in its entirety.

SEQUENCE LISTING

The instant application contains a Sequence Listing that has been submitted electronically in ASCII format and is hereby incorporated by reference in its entirety. The ASCII copy, created on Jul. 22, 2016, is named eolf-seql.pTXT, and is 23 Kb in size.

FIELD OF THE INVENTION

The present invention generally relates to methods of eliciting an immune response in a subject by activating innate immunity. In particular, an immunomodulator composition is used to stimulate innate immunity in a member of the porcine species.

SUMMARY OF THE INVENTION

The present invention relates to methods of using immunostimulatory plasmids to modulate innate immunity in a porcine species subject. The immunostimulatory plasmid may comprise a nucleic acid sequence having at least 80% sequence identity with the sequence of SEQ ID NO: 1, SEQ ID NO: 2, SEQ ID NO: 3, SEQ ID NO: 4, or a combination thereof. In some aspects, the immunostimulatory plasmid may comprise a nucleic acid molecule having at least 84% sequence identity with the sequence of SEQ ID NO: 4. In some aspects, the immunostimulatory plasmid may comprise the sequence of SEQ ID NO: 1. In some aspects, the immunostimulatory plasmid may comprise the sequence of SEQ ID NO: 4. In some aspects, the immunostimulatory plasmid may comprise the sequence of SEQ ID NO: 2. In some aspects, the immunostimulatory plasmid may comprise the sequence of SEQ ID NO: 3.

In other aspects, the immunostimulatory plasmid may consist of a nucleic acid sequence having at least 80% sequence identity with the sequence of SEQ ID NO: 1, SEQ ID NO: 2, SEQ ID NO: 3, SEQ ID NO: 4 or a combination thereof. In some aspects, the immunostimulatory plasmid may consist of a nucleic acid molecule having at least 84% sequence identity with the sequence of SEQ ID NO: 4. In some aspects, the immunostimulatory plasmid may consist of the sequence of SEQ ID NO: 1. In some aspects, the immunostimulatory plasmid may consist of the sequence of SEQ ID NO: 4. In some aspects, the immunostimulatory plasmid may consist of the sequence of SEQ ID NO: 2. In some aspects, the immunostimulatory plasmid may consist of the sequence of SEQ ID NO: 3.

In some aspects, the immunostimulatory plasmid preferably does not comprise a nucleic acid sequence encoding a full-length or functional selectable or screenable marker. In other aspects, the immunostimulatory plasmid comprises a nucleic acid sequence encoding a selectable or screenable marker that is not an antibiotic resistance gene.

The present invention also relates to pharmaceutical formulations comprising any of the immunostimulatory plasmids, or DNA sequences, described herein and a pharmaceutically acceptable carrier.

The present invention further relates to immunomodulator compositions comprising a cationic liposome delivery vehicle and any of the immunostimulatory plasmids, or DNA sequences, described herein.

In some aspects, the present invention relates to methods of using the immunostimulatory plasmids, or DNA sequences, described herein. Suitable methods of use include therapeutic administration to a subject of the porcine species. Such therapeutic administration includes prophylactic treatment, metaphylactic treatment, and post-infection treatment of a subject or subjects.

The present invention relates to methods of stimulating or eliciting an immune response in a subject. In some aspects, the methods include stimulating an immune response in a subject by administering to the subject an immunomodulator composition described herein. In some aspects, the methods include stimulating an immune response in a subject by administering to the subject an immunostimulatory plasmid, or DNA sequence, described herein. In some aspects, the immunomodulator may also comprise or be administered in combination with a biological agent, such as, for example, a vaccine.

The present invention also provides methods of reducing diarrhea in a pig comprising administering to the pig an effective amount of an immunomodulator composition, wherein the immunomodulator comprises a cationic lipid delivery vehicle and a nucleic acid molecule that does not code for an immunogen, wherein said administration reduces diarrhea in said pig following a challenge with *Escherichia coli*.

The present invention also provides methods of increasing weight gain in a pig comprising administering to the pig an immunomodulator composition, the immunomodulator comprising a cationic lipid delivery vehicle and a nucleic acid molecule that does not code for an immunogen, wherein said administration increases weight gain in said pig following a challenge with porcine reproductive and respiratory syndrome virus (PRRSV).

Other objects and features will be in part apparent and in part pointed out hereinafter.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 23 graphically illustrates the viral lung load of PRRSV in treatment groups relative to placebo treated pigs;

FIGS. 34A-D illustrate IFN-α production after stimulation with a cell medium control in CD14+, two types of conventional dendritic cells, and plasmacytoid dendritic cells, respectively.

FIGS. 35A-D illustrate IFN-α production after stimulation with CpG ODN in CD14+, two types of conventional dendritic cells, and plasmacytoid dendritic cells, respectively.

FIGS. 36A-D illustrate IFN-α production after stimulation with IC-Ex.1 (100 ng/mL) in CD14+, two types of conventional dendritic cells, and plasmacytoid dendritic cells, respectively.

FIG. 49 compares the percentages of macrophages infected with porcine reproductive and respiratory virus after treatment with controls or IC-Ex.1.

DETAILED DESCRIPTION OF THE INVENTION

Figure 1:
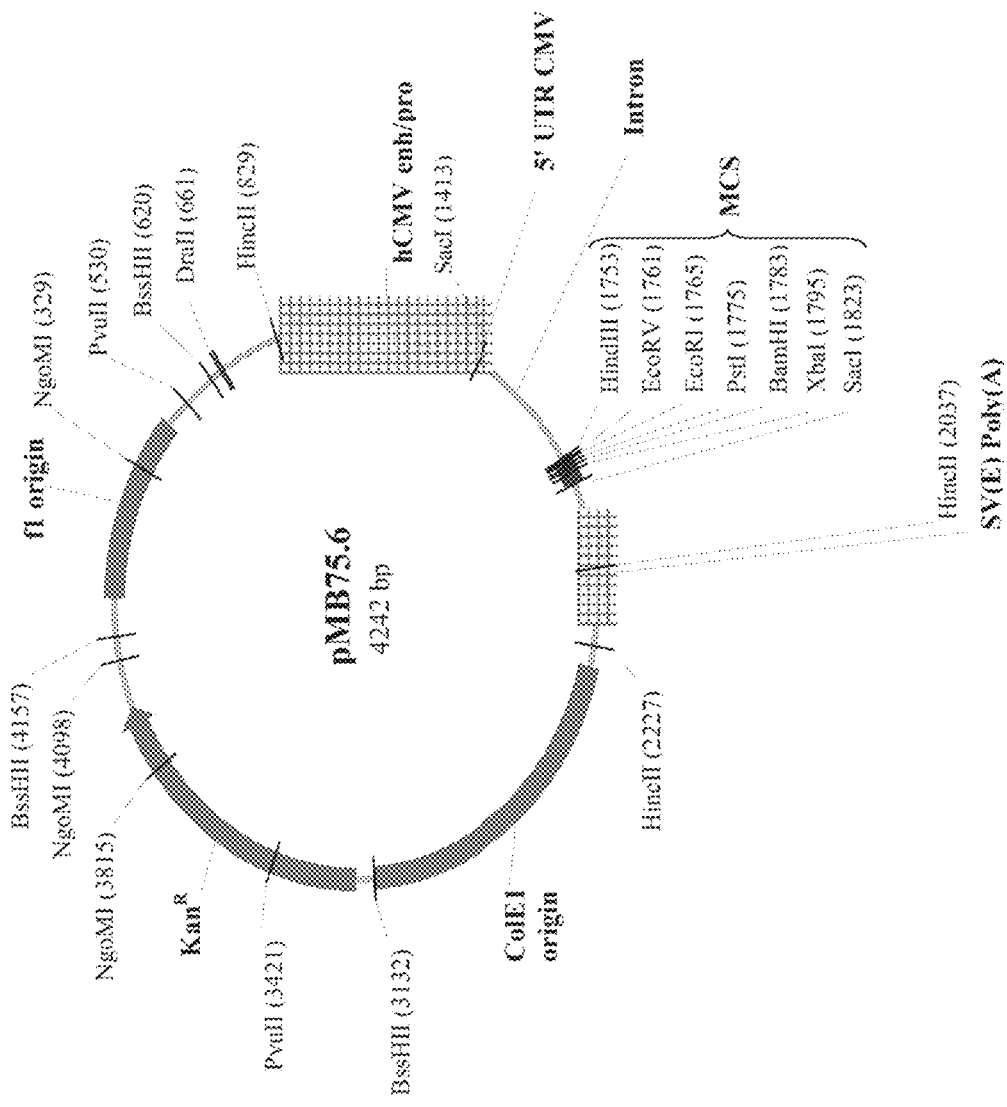
FIG. 1 shows a map of the pMB75.6 plasmid (SEQ ID NO: 2)
Figure 2:
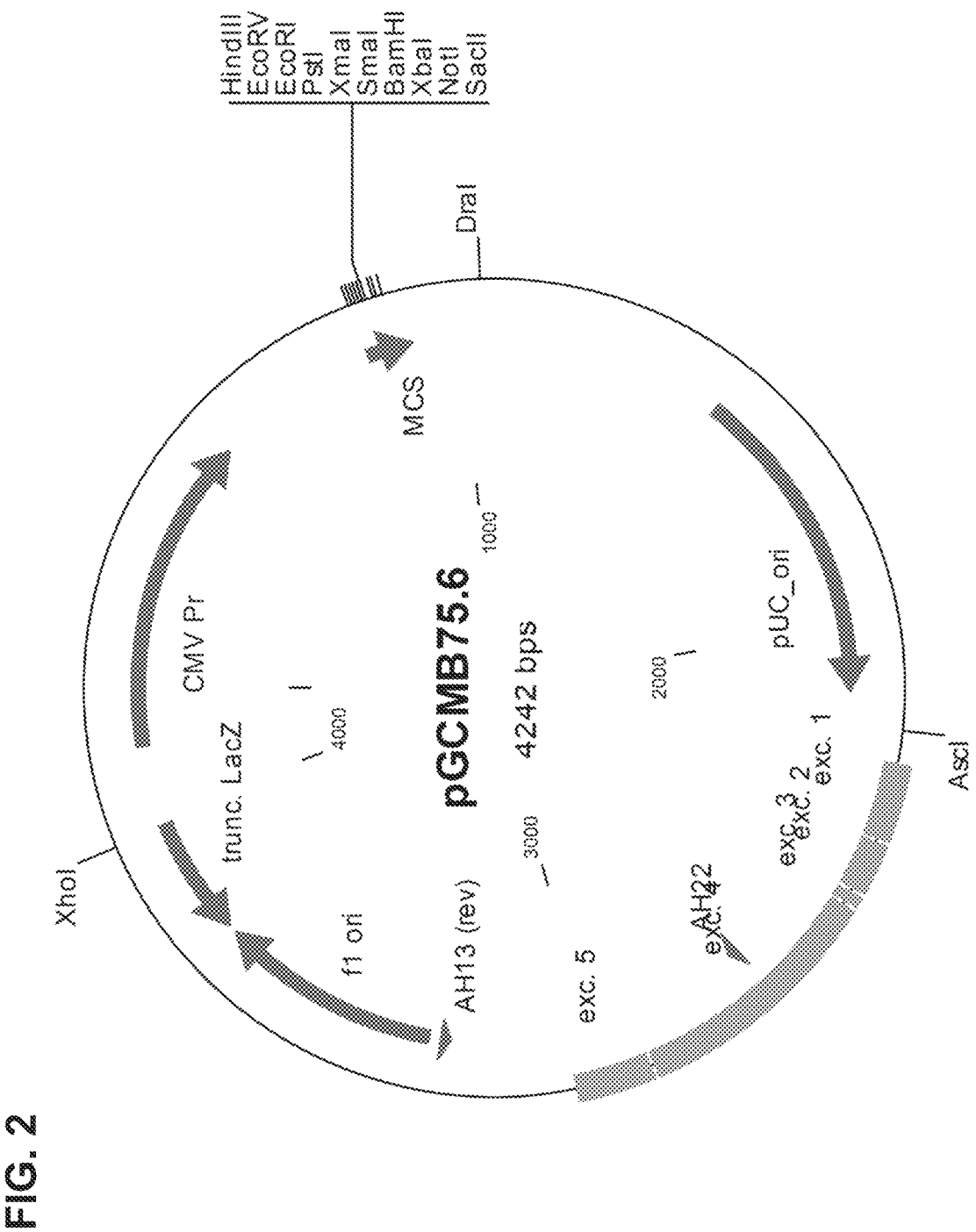
FIG. 2 shows a map of the pGCMB75.6 plasmid (SEQ ID NO: 1)

In accordance with the present invention, a composition capable of eliciting an immune response in a recipient subject, as well as methods of use, has been discovered. In particular, the present invention relates to nucleic acid compositions, or immunomodulator compositions, and uses thereof. It has been discovered that such immunomodulator compositions may be used to modulate the immune system of a member of the porcine species. The invention is particularly useful in the treatment and prevention of infectious diseases caused by microorganisms, such as, without limitation, viruses, bacteria, mold, fungus, yeast, parasites and other microbes known in the art. The compositions and methods of using the immunomodulator compositions are discussed in more detail below.

I. Compositions

Compositions useful in this invention, such as those described herein, are generally able to be used as a prophylactic therapy, metaphylactic therapy, or treatment therapy for infectious diseases. Such compositions are referred to herein as immunomodulator compositions. The immunomodulator compositions include at least an immunostimulatory plasmid, or immunostimulatory DNA sequence, capable of inducing an immune response in a recipient subject. In some aspects, the immune response is an innate immune response. In some aspects, the immune response is a combination of innate immune response and acquired immune response. In some aspects, the immunomodulator compositions may also include a liposome delivery vehicle.

A. Nucleic Acids

In some aspects the present invention relates to nucleic acid molecules useful for the treatment or prevention of infectious disease causing agents. The nucleic acid molecules described herein may be included in an immunostimulatory plasmid, as linear double stranded or single stranded DNA, amino acid sequence, ribonucleic acid (RNA), or combinations thereof. In some aspects, the present invention relates to nucleic acid molecules, vectors, and host cells (in vitro, in vivo, or ex vivo) which contain the immunostimulatory plasmid or immunostimulatory DNA sequence.

The nucleic acid molecules described herein are highly enriched in CpG motifs. In some aspects, the nucleic acid molecules contain more than 20% CpG motifs over the frequency of CpG motifs found in vertebrate nucleic acid sequence. Such CpG motifs include immune stimulatory and non-stimulatory CpG motifs.

In some aspects, the present invention relates to immunostimulatory plasmids, or DNA sequences, that do not comprise an antibiotic resistance gene. The plasmids may be devoid of any selectable or screenable marker genes. For example, the pGCMB75.6 plasmid described herein does not comprise any full-length or functional selectable or screenable marker genes. The sequence of pGCMB75.6 is provided in SEQ ID NO: 1.

In some aspects, the immunostimulatory plasmids described herein preferably do not comprise a nucleic acid sequence coding for a full-length or functional selectable or screenable marker. In some aspects, the immunostimulatory plasmids do not comprise an antibiotic resistance gene. For example, the plasmids do not comprise a kanamycin resistance gene. In some aspects, the plasmids described herein preferably do not encode an immunogen.

Figure 3:
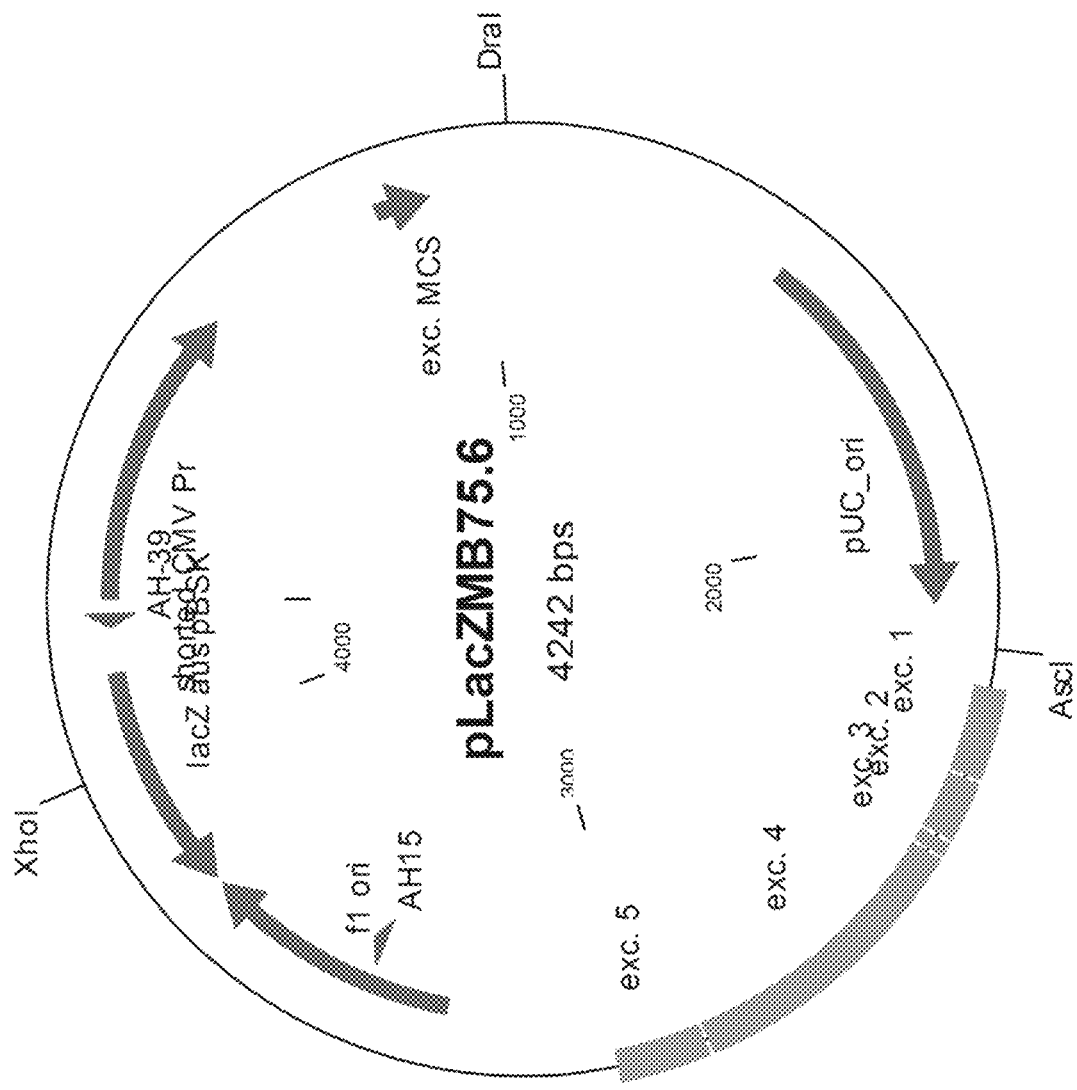
FIG. 3 shows a map of the pLacZ75.6 plasmid (SEQ ID NO: 4)
Figure 4:
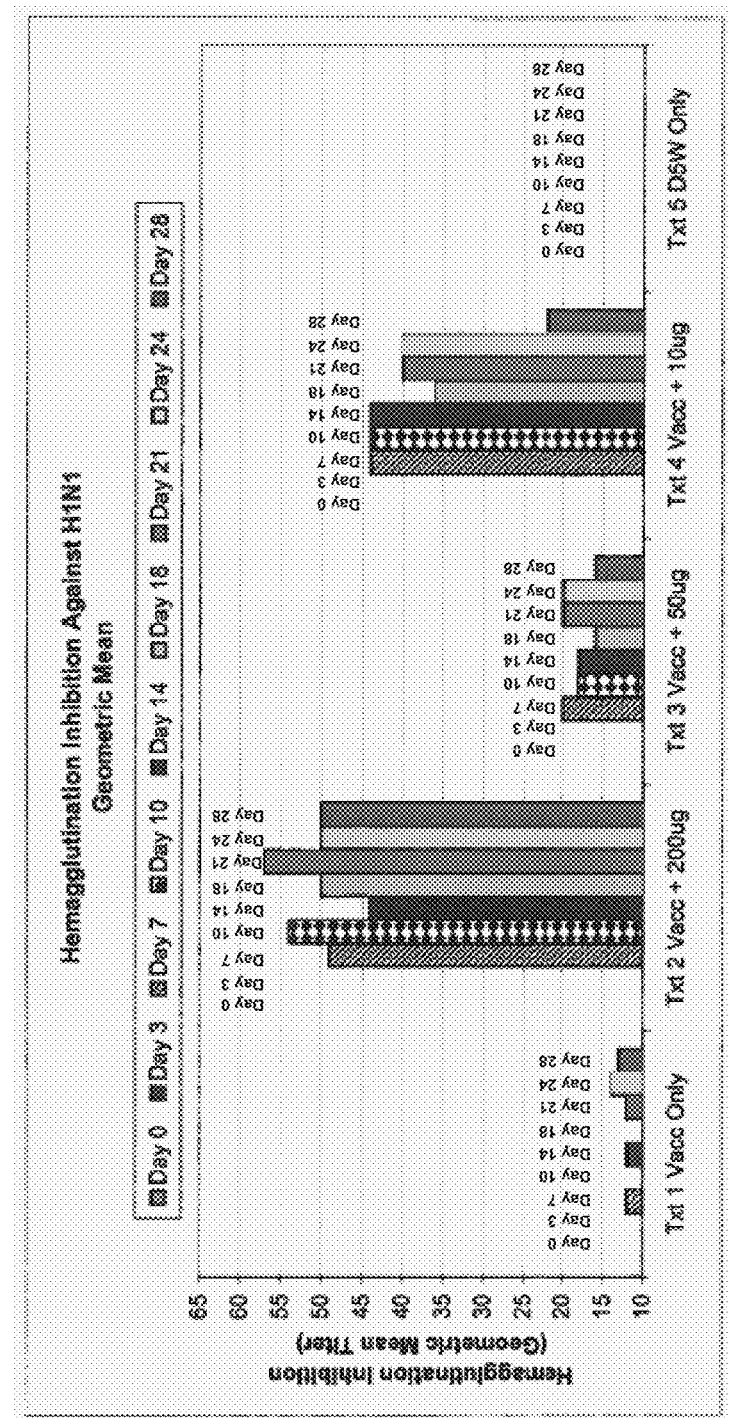
FIG. 4 graphically illustrates the geometric mean of hemagglutination inhibition against H1N1 for Days 0 (solid, light gray), 3 (solid, dark gray), 7 (diagonal lines), 10 (black diamonds), 14 (solid, dark red), 18 (solid, pink), 21 (solid, blue), 24 (solid, light blue), and 28 (solid, dark blue) of each treatment group (Txt 1: vaccine only; Txt 2: vaccine and 200 µg immunomodulator composition; Txt 3: vaccine and 50 µg immunomodulator composition; Txt 4: vaccine and 10 µg immunomodulator composition; and, Txt 5: Diluent (5% Dextrose and water))
Figure 5:
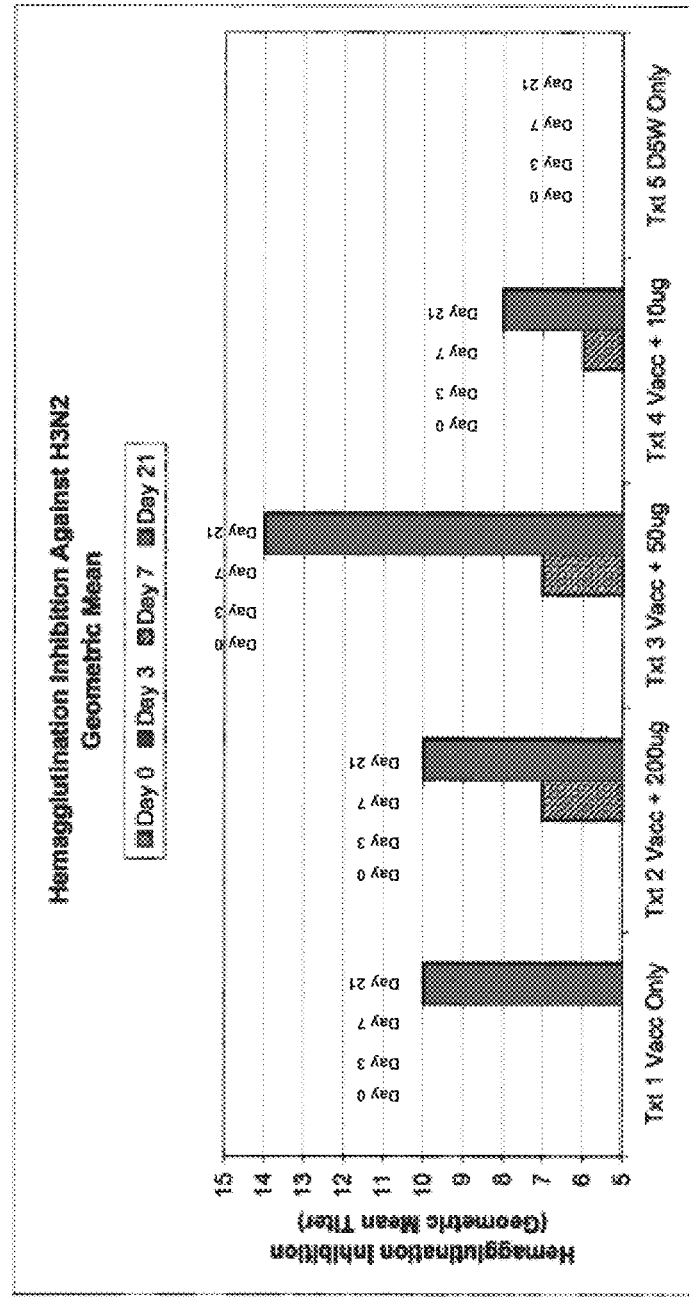
FIG. 5 graphically illustrates the geometric mean of hemagglutination inhibition against H3N2 for Days 0 (solid, light gray), 3 (solid, dark gray), 7 (diagonal lines), and 21 (solid, blue) of each treatment group (Txt 1: vaccine only; Txt 2: vaccine and 200 µg immunomodulator composition; Txt 3: vaccine and 50 µg immunomodulator composition; Txt 4: vaccine and 10 µg immunomodulator composition; and, Txt 5: Diluent (5% Dextrose and water))
Figure 6:
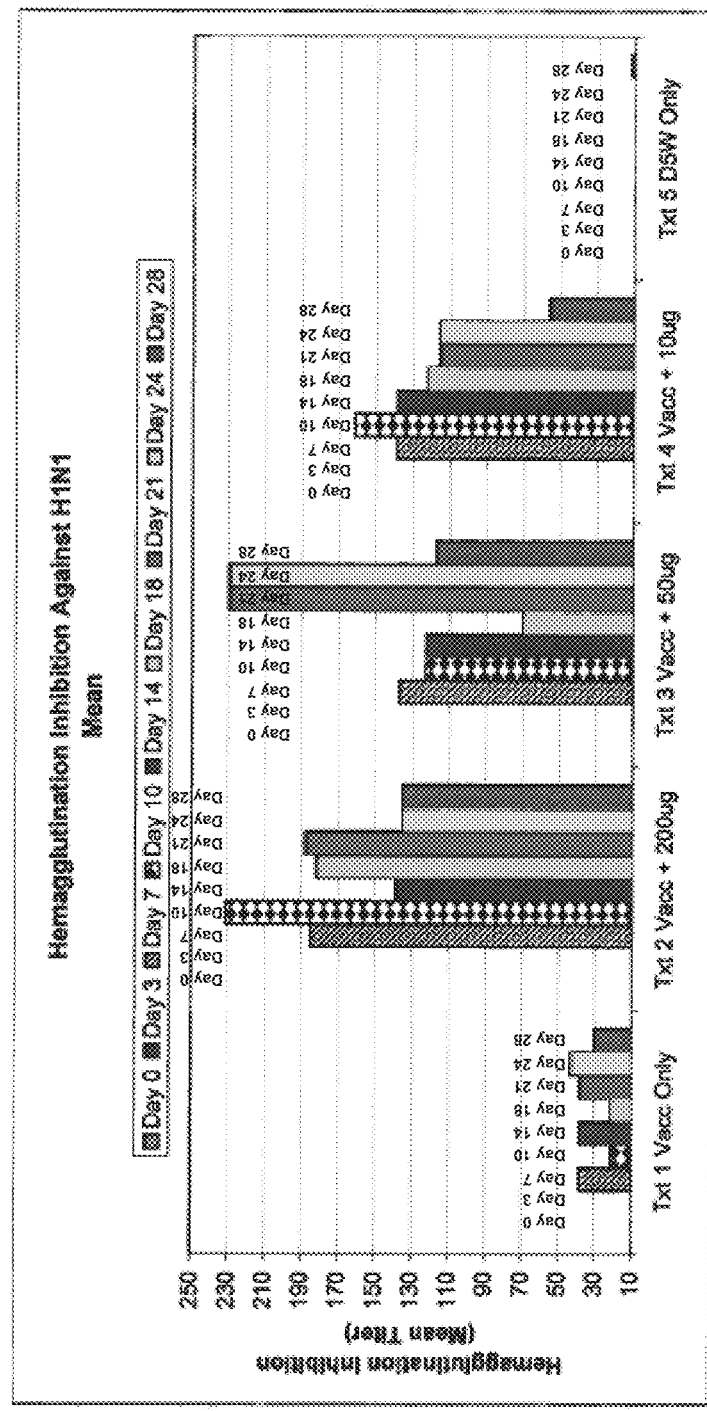
FIG. 6 graphically illustrates the actual mean of hemagglutination inhibition against H1N1 for Days 0 (solid, light gray), 3 (solid, dark gray), 7 (diagonal lines), 10 (black diamonds), 14 (solid, dark red), 18 (solid, pink), 21 (solid, blue), 24 (solid, light blue), and 28 (solid, dark blue) of each treatment group (Txt 1: vaccine only; Txt 2: vaccine and 200 µg immunomodulator composition; Txt 3: vaccine and 50 µg immunomodulator composition; Txt 4: vaccine and 10 µg immunomodulator composition; and, Txt 5: Diluent (5% Dextrose and water))
Figure 7:
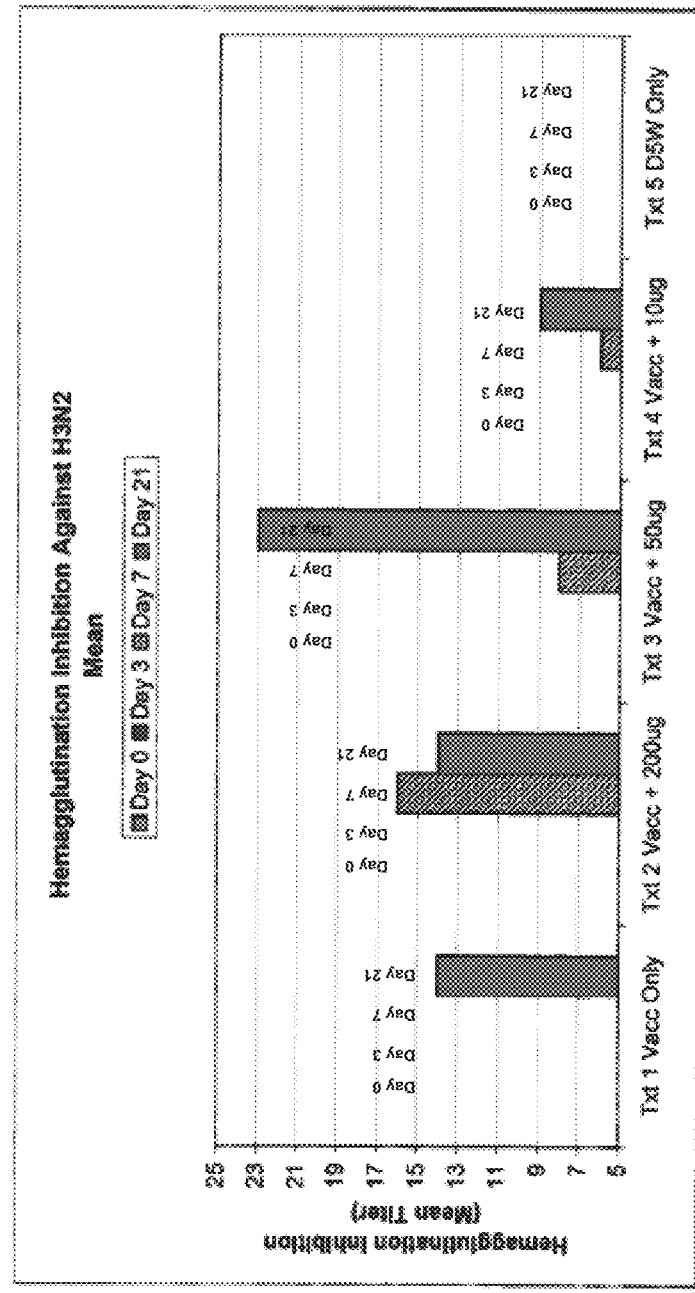
FIG. 7 graphically illustrates the actual mean of hemagglutination inhibition against H3N2 for Days 0 (solid, light gray), 3 (solid, dark gray), 7 (diagonal lines), and 21 (solid, blue) of each treatment group (Txt 1: vaccine only; Txt 2: vaccine and 200 µg immunomodulator composition; Txt 3: vaccine and 50 µg immunomodulator composition; Txt 4: vaccine and 10 µs immunomodulator composition; and, Txt 5: Diluent (5% Dextrose and water))
Figure 8:
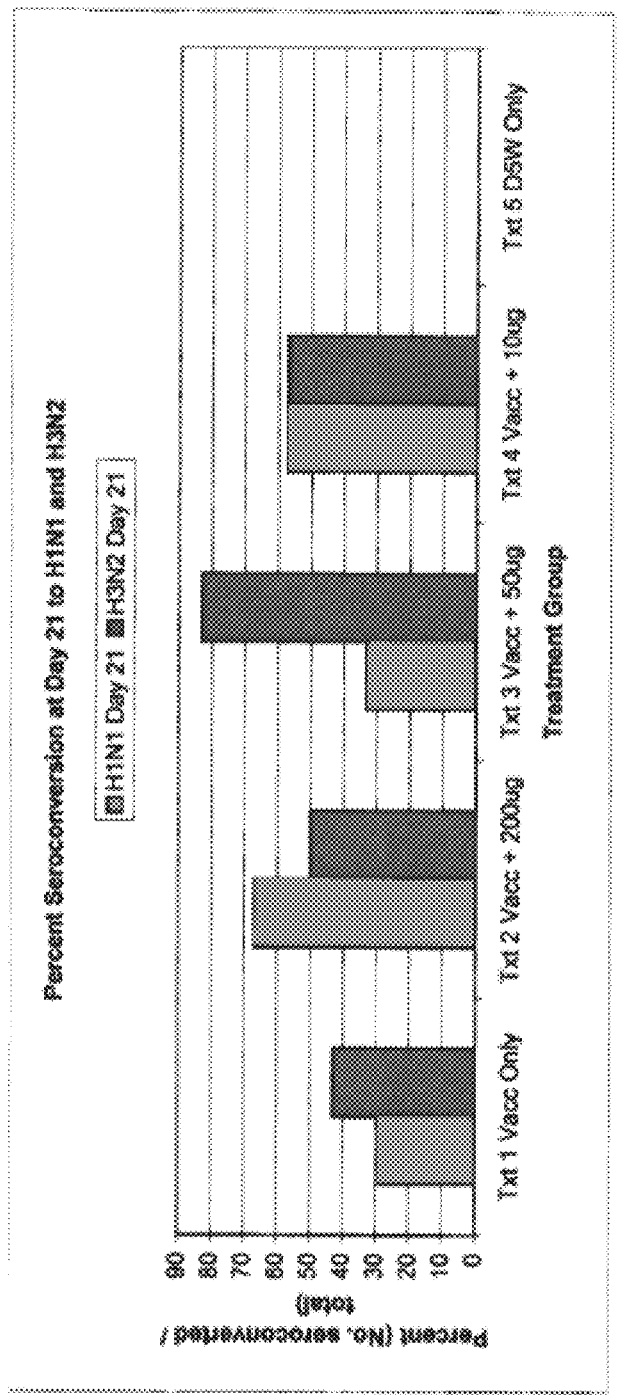
FIG. 8 graphically illustrates the percent of pigs seroconverted to H1N1 and H3N2 isolates at Day 21 for each treatment group (Txt 1: vaccine only; Txt 2: vaccine and 200 µg immunomodulator composition; Txt 3: vaccine and 50 µg immunomodulator composition; Txt 4: vaccine and 10 µg immunomodulator composition; and, Txt 5: Diluent (5% Dextrose and water))

In some aspects, the immunostimulatory plasmids may comprise a nucleic acid sequence coding for a selectable or screenable marker gene that is not an antibiotic resistance gene. For example, the pLacZMB75.6 plasmid described herein comprises a LacZ gene as a screenable marker. A map of pLacZMB75.6 is provided in FIG. 3 and the nucleotide sequence of pLacZMB75.6 is provided as SEQ ID NO: 4. As shown in FIG. 3, pLacZMB75.6 is similar to pGCMB75.6, but contains a LacZ screenable marker.

It will be appreciated that the nucleotide sequences of the pMB75.6, pGCMB75.6 or pLacZMB75.6 plasmids may be varied to a certain extent without significantly adversely affecting their immunostimulatory properties. In some aspects, the present invention relates to an immunostimulatory plasmid comprising a nucleic acid sequence having at least 89% sequence identity with the sequence of pGCMB75.6 (SEQ ID NO: 1). The immunostimulatory plasmid preferably comprises a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 1). In some aspects, the immunostimulatory plasmid more preferably comprises the sequence of pGCMB75.6 (SEQ ID NO: 1).

In some aspects, the present invention relates to an immunostimulatory plasmid comprising a nucleic acid sequence having at least 84% sequence identity with the sequence of pLacZMB75.6 (SEQ ID NO: 4). The immunostimulatory plasmid preferably comprises a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pLacZMB75.6 (SEQ ID NO: 4). In some aspects, the immunostimulatory plasmid more preferably comprises the sequence of pLacZMB75.6 (SEQ ID NO: 4).

In some aspects, the present invention relates to an immunostimulatory plasmid comprising a nucleic acid sequence having at least 80% sequence identity with the sequence of SEQ ID NO: 2. The immunostimulatory plasmid preferably comprises a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO: 2. In some aspects, the immunostimulatory plasmid more preferably comprises the sequence of SEQ ID NO: 2.

In some aspects, the present invention relates to an immunostimulatory plasmid comprising a nucleic acid sequence having at least 80% sequence identity with the sequence of SEQ ID NO: 3. The immunostimulatory plasmid preferably comprises a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO: 3. In some aspects, the immunostimulatory plasmid more preferably comprises the sequence of SEQ ID NO: 3.

In some aspects, the present invention relates to an immunostimulatory plasmid consisting of a nucleic acid sequence having at least 89% sequence identity with the sequence of pGCMB75.6 (SEQ ID NO: 1). The immunostimulatory plasmid preferably consists of a nucleic acid sequence having at least 75%, at least 76%, at least 77%, at least 78%, at least 79%, at least 80%, at least 81%, at least 82%, at least 83%, at least 84%, at least, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 1). In some aspects, the immunostimulatory plasmid more preferably consists of the sequence of pGCMB75.6 (SEQ ID NO: 1).

In some aspects, the present invention relates to an immunostimulatory plasmid consisting of a nucleic acid sequence having at least 84% sequence identity with the sequence of pLacZMB75.6 (SEQ ID NO: 4). The immunostimulatory plasmid preferably consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pLacZMB75.6 (SEQ ID NO: 4). In some aspects, the immunostimulatory plasmid more preferably consists of the sequence of pLacZMB75.6 (SEQ ID NO: 4).

In some aspects, the present invention relates to an immunostimulatory plasmid consisting of a nucleic acid sequence having at least 80% sequence identity with the sequence of SEQ ID NO: 2. The immunostimulatory plasmid preferably consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO: 2. In some aspects, the immunostimulatory plasmid more preferably consists of the sequence of SEQ ID NO: 2.

In some aspects, the present invention relates to an immunostimulatory plasmid consisting of a nucleic acid sequence having at least 80% sequence identity with the sequence of SEQ ID NO: 3. The immunostimulatory plasmid preferably consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO: 3. In some aspects, the immunostimulatory plasmid more preferably consists of the sequence of SEQ ID NO: 3.

Another important aspect of this invention provides for immunostimulatory DNA sequences or immunostimulatory plasmids capable of stimulating an immune response including nucleic acid sequences that hybridize under high stringency conditions to SEQ ID NO: 1, SEQ ID NO: 2, SEQ ID NO: 3, or SEQ ID NO: 4. Suitable nucleic acid sequences include those that are homologous, substantially similar, or identical to the nucleic acids of the present invention. In some aspects, homologous nucleic acid sequences will have a sequence similarity of at least about 75%, 76%, 77%, 78%, 79%, 80% 81%, 82%, 83%, 84%, 85%, 86%, 87%, 88%, 89%, 90%, 91%, 92%, 93%, 94%, 95%, 96%, 97%, 98%, 99%, or 100% to SEQ ID NO: 1 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO: 4 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO: 2 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO: 3 or the respective complementary sequence. Sequence similarity may be calculated using a number of algorithms known in the art, such as BLAST, described in Altschul, S. F., et al., J. Mol. Biol. 215:403-10, 1990. The nucleic acids may differ in sequence from the above-described nucleic acids due to the degeneracy of the genetic code. In general, a reference sequence will be 18 nucleotides, more usually 30 or more nucleotides, and may comprise the entire nucleic acid sequence of the composition for comparison purposes.

Nucleotide sequences that can hybridize to SEQ ID NO: 1, SEQ ID NO: 2, SEQ ID NO: 3, or SEQ ID NO: 4 are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y. 1989).

Mutant nucleotides of the DNA molecules described herein may be used, so long as mutants include nucleic acid sequences maintain the ability to stimulate an innate immune response as described herein. The DNA sequence of such a mutation will usually differ by one or more nucleotides. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. In summary, the invention relates to nucleic acid sequences, and variants or mutants thereof, capable of stimulating an innate immune response in a subject. Also, the invention encompasses the intermediary RNAs encoded by the described nucleic acid sequences, as well as any resultant amino acid sequences encoded by the nucleic acids described herein.

In some aspects, where the nucleotide sequence of the immunostimulatory plasmid varies from the sequences provided in SEQ ID NOs. 1, 2, 3, and 4 the CpG dinucleotides in the plasmid are preferably left intact. Alternatively, if the nucleotide sequence of the plasmid is altered such that a CpG dinucleotide is eliminated, the sequence of the plasmid may be altered at another location such that the total number of CpG dinucleotides in the plasmid remains the same. Further CpG dinucleotides in addition to those already present in the nucleotide sequences of pGCMB75.6 or pLacZMB75.6 may also be introduced into the plasmid. Thus, for example, the immunostimulatory plasmids described herein preferably comprise at least about 200, at least about 220, at least about 240, at least about 260, at least about 270, at least about 275, at least about 280, at least about 283, at least about 285, or at least about 288 CpG dinucleotides. For example, the immunostimulatory plasmid can comprise 283 CpG dinucleotides.

In some aspects, where the nucleotide sequence of the immunostimulatory plasmid varies from the sequences provided herein, the CpG motif types in the plasmid are varied to modulate the resultant activation of the cytosolic DNA surveillance molecules. For example, the number of immune stimulatory CpG motifs may be increased to increase the activation of specific cytosolic DNA surveillance molecules responsive to a specific threshold of immunostimulatory plasmid/DNA. By way of further example, the number of non-immune stimulatory CpG motifs may be increased to decrease the activation of specific cytosolic DNA surveillance molecules and/or increase activation of other DNA surveillance molecules.

In particular, the present invention relates to pharmaceutical formulations comprising any of the immunostimulatory plasmids or DNA sequences described herein and a pharmaceutically acceptable carrier.

B. Immunomodulator

Suitable immunomodulator compositions for use with the immunostimulatory plasmids described herein are described in U.S. Patent Application Publications Nos. 2012/0064151 A1 and 2013/0295167 A1 the contents of both of which are hereby incorporated by reference in their entirety.

The immunomodulator composition comprises a liposome delivery vehicle and at least one of the immunostimulatory plasmids, or DNA sequences, described herein.

A suitable liposome delivery vehicle comprises a lipid composition that is capable of delivering nucleic acid molecules to the tissues of the treated subject. A liposome delivery vehicle is preferably capable of remaining stable in a subject for a sufficient amount of time to deliver a nucleic acid molecule and/or a biological agent. For example, the liposome delivery vehicle is stable in the recipient subject for at least about five minutes, for at least about 1 hour, or for at least about 24 hours.

A liposome delivery vehicle of the present invention comprises a lipid composition that is capable of fusing with the plasma membrane of a cell to deliver a nucleic acid molecule into a cell. When the nucleic acid molecule encodes one or more proteins, the nucleic acid:liposome complex preferably has a transfection efficiency of at least about 1 picogram (pg) of protein expressed per milligram (mg) of total tissue protein per microgram (pig) of nucleic acid delivered. For example, the transfection efficiency of a nucleic acid: liposome complex can be at least about 10 pg of protein expressed per mg of total tissue protein per µg of nucleic acid delivered; or at least about 50 pg of protein expressed per mg of total tissue protein per µg of nucleic acid delivered. The transfection efficiency of the complex may be as low as 1 femtogram (fg) of protein expressed per mg of total tissue protein per µg of nucleic acid delivered, with the above amounts being more preferred.

A preferred liposome delivery vehicle of the present invention is between about 100 and 500 nanometers (nm) in diameter. For example, the liposome delivery vehicle can be between about 150 and 450 nm or between about 200 and 400 nm in diameter.

Suitable liposomes include any liposome, such as those commonly used in, for example, gene delivery methods known to those of skill in the art. Preferred liposome delivery vehicles comprise multilamellar vesicle (MLV) lipids and extruded lipids. Methods for preparation of MLVs are well known in the art. More preferred liposome delivery vehicles comprise liposomes having a polycationic lipid composition (i.e., cationic liposomes) and/or liposomes having a cholesterol backbone conjugated to polyethylene glycol. Exemplary cationic liposome compositions include, but are not limited to, N-[1-(2,3-dioleyloxy)propyl]-N,N,N-trimethylammonium chloride (DOTMA) and cholesterol, N-[1-(2,3-dioleoyloxy)propyl]-N,N,N-trimethylammonium chloride (DOTAP) and cholesterol, 1-[2-(oleoyloxy)ethyl]-2-oleyl-3-(2-hydroxyethyl)-imidazolinium chloride (DOTIM) and cholesterol, dimethyldioctadecylammonium bromide (DDAB) and cholesterol, and combinations thereof. A most preferred liposome composition for use as a delivery vehicle includes DOTIM and cholesterol.

A suitable nucleic acid molecule includes any of the immunostimulatory plasmids described herein. Coding nucleic acid sequences encode at least a portion of a protein or peptide, while non-coding sequence does not encode any portion of a protein or peptide. According to the present invention, "non-coding" nucleic acids can include regulatory regions of a transcription unit, such as a promoter region. The term, "empty vector" can be used interchangeably with the term "non-coding," and particularly refers to a nucleic acid sequence in the absence of a protein coding portion, such as a plasmid vector without a gene insert. Expression of a protein encoded by the plasmids described herein is not required for inducing an immune response; therefore the plasmids need not contain any coding sequences operatively linked to a transcription control sequence. However, further advantages may be obtained (i.e., antigen-specific and enhanced immunity) by including in the composition nucleic acid sequence (DNA or RNA) which encodes an immunogen and/or a cytokine. Such a nucleic acid sequence encoding an immunogen and/or a cytokine may be included in the immunostimulatory plasmids described herein, or may be included in a separate nucleic acid (e.g., a separate plasmid) in the composition.

Complexing a liposome with the immunostimulatory plasmids, or immunostimulatory DNA sequence, described herein may be achieved using methods standard in the art or as described in U.S. Pat. No. 6,693,086, the contents of which are hereby incorporated by reference in their entirety. A suitable concentration of a plasmid to add to a liposome includes a concentration effective for delivering a sufficient amount of the plasmid into a subject such that a systemic immune response is elicited. For example, from about 0.1 µg to about 10 µg of plasmid can be combined with about 8 nmol liposomes, from about 0.5 µg to about 5 µg of plasmid can be combined with about 8 nmol liposomes, or about 1.0 µg of plasmid can be combined with about 8 nmol liposomes. The ratio of plasmid to lipid (µg plasmid:nmol lipid) in a composition can be at least about 1:1 plasmid:lipid by weight (e.g., 1 µg plasmid:1 nmol lipid). For example, the ratio of plasmid to lipids can be at least about 1:5, at least about 1:10, or at least about 1:20. Ratios expressed herein are based on the amount of cationic lipid in the composition, and not on the total amount of lipid in the composition. The ratio of plasmid to lipids in a composition of the invention is suitably from about 1:1 to about 1:80 plasmid:lipid by weight; from about 1:2 to about 1:40 plasmid:lipid by weight; from about 1:3 to about 1:30 plasmid: lipid by weight; or from about 1:6 to about 1:15 plasmid:lipid by weight.

C. Biological Agent

Any of the immunomodulator compositions described herein can further comprise at least one biological agent, in addition to the liposome delivery vehicle and at least one of the plasmids described herein.

Suitable biological agents are agents that are effective in preventing or treating diseases. Such biological agents include immune enhancer proteins, immunogens, vaccines, antimicrobials or any combination thereof. Suitable immune enhancer proteins are those proteins known to enhance immunity. By way of a non-limiting example, a cytokine, which includes a family of proteins, is a known immunity enhancing protein family. Suitable immunogens are proteins which elicit a humoral and/or cellular immune response such that administration of the immunogen to a subject mounts an immunogen-specific immune response against the same or similar proteins that are encountered within the tissues of the subject. An immunogen may include a pathogenic antigen expressed by a bacterium, a virus, a parasite or a fungus. Preferred antigens include antigens derived from organisms which cause an infectious disease in a subject. According to the present invention, an immunogen may be any portion of a protein, naturally occurring or synthetically derived, which elicits a humoral and/or cellular immune response. As such, the size of an antigen or immunogen may be as small as about 5-12 amino acids and as large as a full length protein, including any sizes in between. The antigen may be a multimer protein or fusion protein. The antigen may be a purified antigen. Alternatively, the immune enhancer protein or immunogen can be encoded by the immunostimulatory plasmid or by another nucleic acid included in the immunomodulator composition. Where the immune enhancer protein or immunogen is encoded by a nucleic acid molecule in the immunomodulator composition, the nucleic acid sequence encoding the immune enhancer protein or immunogen is operatively linked to a transcription control sequence, such that the immunogen is expressed in a tissue of a subject, thereby eliciting an immunogen-specific immune response in the subject, in addition to the non-specific immune response. Techniques to screen for immunogenicity, such as pathogen antigen immunogenicity or cytokine activity are known to those of skill in the art and include a variety of in vitro and in vivo assays.

Where the biological agent is a vaccine, the vaccine may include a live, infectious, viral, bacterial, or parasite vaccine or a killed, inactivated, viral, bacterial, or parasite vaccine. One or more vaccines, live or killed viral vaccines, may be used in combination with the immunomodulator composition of the present invention. Suitable vaccines include those known in the art for porcine species.

The biological agent can be an antimicrobial. Suitable antimicrobials include: quinolones, preferably fluoroquinolones, β-lactams, and macrolide-lincosamide-streptogramin (MLS) antibiotics.

Suitable quinolones include benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, sarafloxacin, sparfloxacin, temafloxacin, and tosufloxacin. Preferred fluoroquinolones include ciprofloxacin, danofloxacin, enrofloxacin, moxifloxacin, and pradofloxacin. Suitable naphthyridones include nalidixic acid.

Suitable β-lactams include penicillins (e.g., amoxicillin, ampicillin, azlocillin, benzathine penicillin, benzylpenicillin, carbenicillin, cloxacillin, co-amoxiclav [i.e. amoxicillin/ clavulanic acid], dicloxacillin, flucloxacillin, methicillin, mezlocillin, nafcillin, oxacillin, phenoxymethylpenicillin, piperacillin, procaine penicillin, temocillin, and ticarcillin); cephalosporins (e.g., cefaclor, cefalonium, cefamandole, cefapririn, cefazolin, cefepime, cefixime, cefotaxime, cefoxitin, cefpirome, cefpodoxime, cefquinome, ceftazidime, ceftiofur, ceftriaxone, cefuroxime, cephalexin, cephalothin, and defotetan); carbapenems and penems (e.g., doripenem, ertapenem, faropenem, imipenem, and meropenem); monobactams (e.g., aztreonam, nocardicin A, tabtoxinine-β-lactam, and tigemonam); and β-lactamase inhibitors (e.g., clavulanic acid, sulbactam, and tazobactam). Preferred β-lactams include cephalosporins, in particular, cefazolin.

Suitable MLS antibiotics include clindamycin, lincomycin, pirlimycin, and any macrolide antibiotic. A preferred lincosamide antibiotic is pirlimycin.

Other antimicrobials include aminoglycosides, clopidol, dimetridazoles, erythromycin, framycetin, furazolidone, halofuginone, 2-pyridones, robenidine, sulfonamides, tetracyclines, trimethoprim, various pleuromutilins (e.g., tiamulin and valnemulin), and various streptomycin (e.g., monensin, narasin, and salinomycin).

II. Methods

An object of the present invention is to provide immunomodulator compositions, immunostimulatory plasmids (or DNA sequence), and methods that stimulate immunity and provide protective immunity to uninfected subjects, protective immunity to infected subjects, enhanced immunity to uninfected subjects, enhanced immunity to infected subjects, therapeutic immunity to infected subjects, or combinations thereof. As such, the compositions of the invention may be used to prophylactically protect a subject or be used to treat a subject. The methods described herein include administering an immunostimulatory plasmid, or DNA sequence, described herein to a subject, and stimulating the immune system in the subject.

A. Methods of Stimulating the Immune System of a Subject

The present invention is related to methods of stimulating, or enhancing, the immune system, in a recipient subject. The methods comprise administering to a subject an effective amount of an immunomodulator composition described herein. In some aspects, the immunomodulator composition stimulates an immune response in a recipient subject and the immune response helps fight off infection. In some aspects, the immunomodulator composition activates cytosolic DNA surveillance molecules. In some aspects, the immunomodulator composition enhances the operation of at least one biological agent such as a vaccine, when administered prior to such a vaccine, co-administered with a vaccine, administered post vaccination, or mixed with the vaccine. In some aspects, the methods provide new treatment strategies for protecting recipient subjects from infectious diseases and treating populations having infectious disease. In some aspects, the methods provide a more rapid, a longer and better protection against a disease when the immunomodulator is used in combination with a vaccine, compared to use of the vaccine without the immunomodulator composition.

An immune response can be activated in a recipient subject by administering an effective amount of an immunomodulator composition, which includes any of the liposome delivery vehicles described herein, any of the immunostimulatory plasmids (or DNA sequences) described herein, and optionally in combination with any of the biological agents described herein. As used herein, "in combination with" is understood to mean that the biological agent may be mixed with or co-administered with the immunomodulator or independently thereof. Such independent administration may be prior to or after administration of the immunomodulator. It is also contemplated that combined administration may include more than one administration of the immunomodulator or biological agent may be used. Furthermore, more than one biological agent may be co-administered with the immunomodulator, administered prior to the immunomodulator, administered after administration of the immunomodulator, or concurrently with the immunomodulator.

B. Methods of Improving Survivability of a Subject

The present invention is related to methods of improving survivability of a member of the porcine species. Methods of improving survivability include administering to a subject an effective amount of an immunomodulator composition described herein. In some aspects, the methods provide improved survivability of recipient subjects compared to subject not receiving the immunomodulator composition.

C. Methods of Improving Production

The present invention is related to methods of improving production of a member of the porcine species. Methods of improving production include administering to a subject an effective amount of an immunomodulator composition described herein. In some aspects, the methods provide improved production of recipient subjects compared to subjects not receiving the immunomodulator composition. Methods of assessing improved production are known in the art. A skilled artisan will recognize that improved production may be measured comparing the health, weight, size, meat quality, and other parameters between subjects receiving the immunomodulator composition and those subjects not receiving the immunomodulator composition.

An effective amount of any of the immunomodulator compositions described herein may be administered to a subject. The effective amount is sufficient to activate an immune response in the recipient subject. Methods of measuring such activation are known in the art. Also, a skilled artisan will recognize that the effective amount will depend upon age, weight, species of the subject and stage of infection, as well as other factors known in the art. Suitable effective amounts may range from about 0.1 µg to 1,000 µg per subject. In some aspects, the effective amount may range from about 0.1 µg to about 10 µg, from about 0.1 µg to about 5 µg, from about 0.5 µg to about 5 µg, from about 0.25 µg to about 5 µg, from about 0.05 µg to about 10 µg, from about 5 µg to about 15 µg, from about 10 µg to about 15 µg, from about 10 µg to about 20 µg, from about 20 µg to about 30 µg, from about 30 µg to about 40 µg, from about 40 µg to about 50 µg, from about 50 µg to about 70 µg, from about 70 µg to about 90 µg, from about 50 µg to about 100 µg, from about 100 µg to about 150 µg, from about 150 µg to about 200 µg, from about 200 µg to about 250 µg, from about 250 µg to about 300 µg, from about 300 µg to about 350 µg, from about 350 µg to about 400 µg, from about 400 µg to about 450 µg, from about 450 µg, to about 500 µg, from about 500 µg to about 550 µg, from about 550 µg to about 600 µg, from about 600 µg to about 650 µg, from about 650 µg to about 700 µg, from about 700 µg to about 750 µg, from about 750 µg to about 800 µg, from about 800 µg to about 850 µg, from about 850 µg to about 900 µg, from about 900 µg to about 950 µg, from about 950 µg to about 1000 µg. Preferably, in some aspects, the effective amount ranges from about 0.5 µg to about 10 µg. Yet, preferably in other aspects the effective amount ranges from about 50 µg to about 100 µg. And, preferably in other aspects, the effective amount ranges from about 40 µg to about 70 µg.

D. Conditions for Use

The methods of the invention activate an immune response in a subject such that the subject is protected from a disease that is amenable to elicitation of an immune response. As used herein, the phrase "protected from a disease" refers to reducing the symptoms of the disease; reducing the occurrence of the disease; reducing the clinical or pathologic severity of the disease; or reducing shedding of a pathogen causing a disease. Protecting a subject can refer to the ability of a therapeutic composition of the present invention, when administered to a subject, to prevent a disease from occurring, cure, and/or alleviate or reduce disease symptoms, clinical signs, pathology, or causes. As such, protecting a subject from a disease encompasses both preventing disease occurrence (prophylactic treatment) and treating a subject that has a disease (therapeutic treatment). The term "disease" refers to any deviation from the normal health of a subject and includes a state when disease symptoms are present, as well as conditions in which a deviation (e.g., infection, gene mutation, genetic defect, etc.) has occurred, but symptoms are not yet manifested.

Methods of the invention may be used for the prevention of disease, stimulation of effector cell immunity against disease, elimination of disease, alleviation of disease, and prevention of a secondary disease resulting from the occurrence of a primary disease.

In some aspects, methods described herein may be used to improve the innate immune response of the subject when co-administered with a vaccine versus administration of the vaccine by itself. In some aspects, methods described herein may be used to improve the acquired immune response of the subject when co-administered with a vaccine versus administration of the vaccine by itself. Generally a vaccine once administered does not immediately protect the subject as it takes time to stimulate acquired immunity. The term "improve" refers, in the present invention, to elicitation of an innate immune response in the subject until the vaccine starts to protect the subject and/or to prolong the period of protection, via acquired immunity, given by the vaccine.

In some aspects, methods of the invention include administering the composition to protect against infection of a wide variety of pathogens. The composition administered may or may not include a specific antigen to elicit a specific response. It is contemplated that the methods of the invention will protect the recipient subject from disease resulting from infectious microbial agents including, without limitation, viruses, bacteria, fungi, and parasites. In some aspects, methods of the invention include administering the composition to alleviate or reduce the symptoms or severity of an infection due to an infectious agent. A skilled artisan will recognize and appreciate that an immunomodulator composition, as described herein, is effective against numerous infectious agents, which are too numerous to list. The infectious agents provided herein are provided for exemplary purposes and are provided without limitation of the scope of use.

Exemplary conditions for which the immunomodulator compositions described herein may be useful for include those in a subject caused by an infectious agent. Such conditions may include, without limitation, Actinobacillosis, African swine fever, anthrax, atrophic rhinitis, Aujeszky's disease, botulism, brucellosis, bullnose, classical swine fever, clostridial enterotoxaemia, colibacillosis, contagious pyoderma in sucking pigs, encephalomyocarditis, enterovirus infection, exudative epidermitis, foot and mouth disease, foot rot, Glasser's disease, greasy pig disease, hog cholera, inclusion body rhinitis, intestinal adenomatosis, joint-ill, leptospirosis, listeriosis (septicaemic/visceral), liver lesions, mastitis-metritis-agalactia syndrome, malignant oedema, mycoplasmal pneumonia, mycoplasmal polyarthritis, mycoplasmal polyserositis, necrotic ear syndrome of pigs, necrotic rhinitis, necrotic stomatitis, oedema disease, osteomyelitis, otitis externa, parvovirus infection, pasteurellosis, *Pityriasis rosea*, pleuropneumonia, polyarthritis, porcine epidemic diarrhea, porcine reproductive and respiratory syndrome (PPRS), proliferative haemorrhagic enteropathy, *pseudotuberculosis*, pyelonephritis, rabies, ringworm, rotavirus infection, *salmonellosis*, streptococcal meningitis, streptococcal meningitis and arthritis, swine dysentery, swine erysipelas, swine fever, swine influenza, swine pox, swine vesicular disease, talfan, teschen, tetanus, transmissible gastroenteritis, vesicular diseases, vesicular exanthema of swine, vesicular stomatitis, vomiting and wasting disease, white-spotted kidney, and other conditions known in the art.

Exemplary infectious agents for which the immunomodulator compositions described herein may be useful for treating or preventing include those infectious agents that are impacted by a subject's innate immune response. Such infectious agents may include, without limitation, *Actinobacillus* sp., *Actinobacillus pleuropneumoniae*, *Actinobacillus suis*, *Actinomyces pyogenes*, Alphaherpersvirinae, Aphthovirus, *Bacillus anthracis*, Betaherpesvirinae, *Bordetella bronchiseptica*, *Brucella abortus*, *Brucella suis*, Calicivirus, *Campylobacter* sp., *Campylobacter* hyointestinalis, *Campylobacter mucosalis*, Cardiovirus, Clostridial *perfringens*, *Clostridium botulinum*, *Clostridium septicum*, *Clostridium tetani*, Coronavirus, Cytomegalovirus, Enterovirus, *Erysipelothrix rhusiopathiae*, *Escherichia coli*, *Eubacterium suis*, *Erysipelothrix rhusiopathiae*, Flaviviridae, *Fusobacterium necrophorum*, Haemagglutinating encephalomyelitis virus, *Haemophilus parasuis*, *Leptospira interrogans*, Lelystad virus, *Listeria monocytogenes*, Lyssavirus, *Microsporum nanum*, *Mycoplasma* sp., *Mycoplasma hyopneumoniae*, *Mycoplasma hyorhinis*, *Mycoplasma hyosynoviae*, *Pasteurella multocida*, Pestivirus, Picornaviridae, Porcine arterivirus, Porcine circovirus (PCV), Porcine enterovirus, Procine epidemic diarrhea virus (PEDv), Porcine herpesvirus 1, Porcine herpesvirus 2, Porcine parvovirus, Pestivirus, Rhabdoviridae, Rotavirus, *Salmonella* sp., *Salmonella choleraesuis*, *Serpulina hyodysenteriae*, Spirochaetes, Staphylococci, *Staphylococcus hyicus*, Streptococci, *Streptococcus suis*, Suipoxvirus, Swine influenzavirus, Togaviridae, Unclassified DNA virus, Vesiculovirus, *Yersinia pseudotuberculosis*, and others known in the art.

The immunomodulator compositions described herein may be particularly useful for treating or preventing enteric conditions caused by an infectious agent. Such conditions include enteric conditions that impact digestive/intestinal system of a subject. These enteric conditions include, without limitation, African swine fever, classical swine fever, clostridial enterotoxaemia, colibacillosis, foot and mouth disease, hog cholera, intestinal adenomatosis, necrotic stomatitis, oedema disease, porcine epidemic diarrhea, proliferative haemorrhagic enteropathy, rotavirus infection, *salmonellosis*, swine dysentery, swine vesicular disease, transmissible gastroenteritis, vesicular exanthema of swine, vesicular stomatitis, and other conditions known in the art.

Exemplary infectious agents for which the immunomodulator compositions described herein may be useful for include those infectious agents that are impacted by a subject's innate immune response. Such infectious agents may include, without limitation, *Actinobacillus* sp., *Actinobacillus pleuropneumoniae*, *Actinobacillus suis*, *Actinomyces pyogenes*, African swine fever virus, Alphacoronavirus, Alphaherpesvirinae, Aphthovirus, Asfivirus, Arterivirus, *Bacillus anthracis*, Betacoronavirus, Betaherpesvirinae, *Bordetella bronchiseptica*, *Brachyspira hyodysenteriae*, *Brucella abortus*, *Brucella suis*, Calicivirus, *Campylobacter* sp., *Campylobacter hyointestinalis*, *Campylobacter mucosalis*, Cardiovirus, Circovirus, Classical swine fever virus, Clostridial *perfringens*, *Clostridium botulinum*, *Clostridium septicum*, *Clostridium tetani*, Coronavirus, Cytomegalovirus, Encephalomyocarditis virus, Enterovirus, *Erysipelothrix rhusiopathiae*, *Escherichia coli*, *Eubacterium suis*, *Erysipelothrix rhusiopathiae*, *Escherichia coli*, Flaviviridae, *Fusobacterium necrophorum*, Haemagglutinating encephalomyelitis virus, *Haemophilus parasuis*, *Lawsonia intracellularis*, *Leptospira interrogans serovars*, Lelystad virus, *Listeria monocytogenes*, Lyssavirus, *Microsporum nanum*, *Mycoplasma* sp., *Mycoplasma hyopneumoniae*, *Mycoplasma hyorhinis*, *Mycoplasma hyosynoviae*, *Pasteurella multocida*, Pestivirus, Picornaviridae, Porcine arterivirus, Porcine enterovirus, Porcine epidemic diarrhea virus, Porcine herpesvirus 1, Porcine herpesvirus 2, Porcine parvovirus, Porcine reproductive and respiratory syndrome virus, Porcine sapelovirus, Porcine teschovirus, Pestivirus, Rabies virus, Rhabdoviridae, Rotavirus, *Salmonella* sp., *Salmonella choleraesuis*, *Serpulina hyodysenteriae*, Spirochaetes, Staphylococci, *Staphylococcus hyicus*, Streptococci, *Streptococcus suis*, Swinepox virus, Swine influenzavirus, Togaviridae, Unclassified DNA virus, Vesiculovirus, *Yersinia pseudotuberculosis*, and others known in the art.

The immunomodulator compositions described herein may be particularly useful for treating or preventing conditions caused by an infectious agent or cancer. Such conditions include, without limitation, Actinobacillosis, African swine fever, anthrax, atrophic rhinitis, Aujeszky's disease, botulism, brucellosis, bullnose, classical swine fever, clostridial enterotoxaemia, colibacillosis, congenital CNS signs, contagious pyoderma in sucking pigs, encephalomyocarditis, enterovirus infection, exudative epidermitis, foot and mouth disease, foot rot, Glasser's disease, greasy pig disease, hog cholera, inclusion body rhinitis, intestinal adenomatosis, joint-ill, leptospirosis, listteriosis (septicaemic/visceral), liver lesions, mastitis-metritis-agalactia syndrome, malignant oedema, mycoplasmal pneumonia, mycoplasmal polyarthritis, mycoplasmal polyserositis, necrotic ear syndrome of pigs, necrotic rhinitis, necrotic stomatitis, oedema disease, osteomyelitis, otitis externa, parvovirus infection, pasteurellosis, *Pityriasis rosea*, pleuropneumonia, polyarthritis, porcine epidemic diarrhea, porcine reproductive and respiratory syndrome (PPRS), proliferative haemorrhagic enteropathy, *pseudotuberculosis*, pyelonephritis, rabies, ringworm, rotavirus infection, *salmonellosis*, streptococcal meningitis, streptococcal meningitis and arthritis, swine dysentery, swine erysipelas, swine fever, swine influenza, swine pox, swine vesicular disease, talfan, teschen, tetanus, transmissible gastroenteritis, vesicular diseases, vesicular exanthema of swine, vesicular stomatitis, vomiting and wasting disease, white-spotted kidney, and others known in the art.

E. Administration

A variety of administration routes are available. The particular mode selected will depend, of course, upon the particular biological agents selected, the age and general health status of the subject, the particular condition being treated and the dosage required for therapeutic efficacy. The methods of this invention may be practiced using any mode of administration that produces effective levels of activation of an immune response without causing clinically unacceptable adverse effects. The compositions may conveniently be presented in unit dosage form and may be prepared by any of the methods well known in the art.

The immunomodulator composition may be administered intravenously, intramuscularly, intradermally, intraperitoneally, intramammary, transdermally, intrarectally, mucosally, subcutaneously, by spray, orally, intraocularly, intratracheally, intranasally, topically, ocularly, or by other methods known in the art. In one aspect, the immunomodulator is administered subcutaneously. In another aspect, the immunomodulator may be administered intramuscularly. In another aspect, the immunomodulator is administered as a spray. In another aspect, the immunomodulator may be administered orally. In another aspect, the immunomodulator may be administered subcutaneously.

In one respect, the immunomodulator may be administered by itself to the subject prior to challenge (or infection). In another aspect, the immunomodulator may be administered by itself to the subject post challenge (or infection). In another aspect, the immunomodulator may be administered by itself to the subject at the same time as challenge (or infection).

In some aspects, the immunomodulator composition may be co-administered at the same time as the vaccination prior to challenge. In some aspects, the immunomodulator composition may be co-administered at the same time as the vaccination at the same time as challenge (or infection). In some aspects, the co-administration may include administering the vaccine and immunomodulator in the same general location on the subject at two different sites next to each other (i.e., injections next to each other at the neck of the subject), on opposing sides of the subject at the same general location (i.e., one on each side of the neck), or on different locations of the same subject. In some aspects, the immunomodulator composition can be administered prior to vaccination and challenge. In some aspects, the immunomodulator composition may be administered after vaccination but prior to challenge. The immunomodulator composition can be administered after challenge to a subject that has been vaccinated prior to challenge (or infection).

A skilled artisan will recognize that administration routes may vary depending upon the subject and the health or state of the subject. The administration routes provided for are for exemplary purposes and are provided without limitation.

Vaccination may be performed at any age. The vaccine may be administered subcutaneously, by spray, orally, intramuscularly, intramammary, intradermally, transdermally, intrarectally, mucosally, intraocularly, intratracheally, intranasally, topically, ocularly, or by other methods know in the art. Oral vaccines may be administered in feed or water. Further, it is contemplated that the methods of the invention may be used based on routine vaccination schedules.

The immunomodulator composition may also be administered subcutaneously, by spray, orally, intramuscularly, intramammary, intradermally, transdermally, intrarectally, mucosally, intraocularly, intratracheally, intranasally, topically, ocularly, or by other methods know in the art. For example, the immunomodulator composition can be administered intramuscularly. Alternatively, the immunomodulator composition can be administered subcutaneously.

The immunomodulator may be administered to a subject from about 1 to about 14 days prior to challenge or from about 1 to about 14 days post challenge. For example, the immunomodulator can be administered from about 1 to about 7 days prior to challenge or from about 1 to about 7 days post challenge. The immunomodulator is suitably administered 1, 2, 3, 4, 5, 6, 7 days prior to challenge or 1, 2, 3, 4, 5, 6, 7 days post challenge.

Other delivery systems may include time-release, delayed release, or sustained release delivery systems. Such systems can avoid repeated administrations of the compositions therefore increasing convenience. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109.

Delivery systems also include non-polymer systems that are lipids including sterols such as cholesterol, cholesterol esters, and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to, erosional systems in which an agent of the invention is contained in a form within a matrix such as those described in U.S. Pat. Nos. 4,452,775, 4,675,189, and 5,736,152, and diffusional systems in which an active component permeates at a controlled rate from a polymer such as described in U.S. Pat. Nos. 3,854,480, 5,133,974, and 5,407,686. In addition, pump-based hardware delivery systems can be used, some of which are adapted for implantation.

As various changes could be made in the above composition, products, and methods without departing from the scope of the invention, it is intended that all matter contained in the above description and in the examples given below shall be interpreted as illustrative and not in a limiting sense.

Definitions

The term "effective amount" refers to the amount necessary or sufficient to realize a desired biologic effect. For example, an effective amount of immunomodulator for treating or preventing an infectious disease is that amount necessary to cause the development of an immune response upon exposure to the microbe, thus causing a reduction in the amount of microbe within the subject and preferably the eradication of the microbe. The effective amount for any particular application can vary depending on such factors as the disease or condition being treated, the size of the subject, or the severity of the disease or condition. One of ordinary skill in the art can empirically determine the effective amount of immunomodulator without necessitating undue experimentation.

The term "cytokine" refers to an immune enhancing protein family. The cytokine family includes hematopoietic growth factor, interleukins, interferons, immunoglobulin superfamily molecules, tumor necrosis factor (TNF) family molecules and chemokines (i.e. proteins that regulate the migration and activation of cells, particularly phagocytic cells). Exemplary cytokines include, without limitation, interleukin-2 (IL-2), interleukin-12 (IL-12), interleukin-15 (IL-15), interleukin-18 (IL-18), interferon-$\alpha$ (IFN-$\alpha$), and interferon-$\gamma$ (IFN-$\gamma$).

The term "elicit" can be used interchangeably with the terms activate, stimulate, generate or upregulate.

The term "eliciting an immune response" in a subject refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a subject from one which is harmful or ineffective to one which is beneficial or protective).

The term "operatively linked" refers to linking a nucleic acid molecule to a transcription control sequence in a manner such that the molecule is able to be expressed when transfected (i.e., transformed, transduced or transfected) into a host cell. Transcriptional control sequences are sequences which control the initiation, elongation, and termination of transcription. Particularly important transcription control sequences are those which control transcription initiation, such as promoter, enhancer, operator and repressor sequences. A variety of such transcription control sequences are known to those skilled in the art. Preferred transcription control sequences include those which function in avian, fish, mammalian, bacteria, viral, plant, and insect cells. While any transcriptional control sequences may be used with the invention, the sequences may include naturally occurring transcription control sequences naturally associated with a sequence encoding an immunogen or immune stimulating protein.

The terms "nucleic acid molecule" and "nucleic acid sequence" can be used interchangeably and include DNA, RNA, or derivatives of either DNA or RNA. The terms also include oligonucleotides and larger sequences such as plasmids, such as the immunostimulatory plasmids described herein, and including both nucleic acid molecules that encode a protein or a fragment thereof, and nucleic acid molecules that comprise regulatory regions, introns, or other non-coding DNA or RNA. Typically, an oligonucleotide has a nucleic acid sequence from about 1 to about 500 nucleotides, and more typically, is at least about 5 nucleotides in length. The nucleic acid molecule can be derived from any source, including mammalian, fish, bacterial, insect, viral, plant, synthetic sources or combinations thereof. A nucleic acid molecule can be produced by methods commonly known in the art such as recombinant DNA technology (e.g., polymerase chain reaction (PCR), amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, or inverted in such a manner that such modifications do not substantially interfere with the nucleic acid molecule's ability to elicit an immune response useful in the methods of the present invention. A nucleic acid homologue may be produced using a number of methods known to those skilled in the art (see, for example, Sambrook et al., *Molecular Cloning: A Laboratory Manual*, Cold Spring Harbor Labs Press, 1989), which is incorporated herein by reference.

The terms "selectable marker" and "selectable marker gene" refer to a gene that encodes a product that protects the organism in which the gene is expressed from a selective agent (e.g., an antibiotic) or a condition that would normally kill the organism or inhibit its growth. Selectable marker genes are most commonly antibiotic resistance genes (e.g., kanamycin resistance genes, ampicillin resistance genes, chloramphenicol resistance genes, tetracycline resistance genes, etc.). Thus, for example, when *E. coli* cells are subjected to a transformation procedure to introduce a plasmid encoding a kanamycin resistance gene and then grown on or in media containing kanamycin, only the *E. coli* cells that have successfully taken up the plasmid and expressed the kanamycin resistance gene will survive. The terms "selectable marker" and "selectable marker gene" also include genes that code for enzymes involved in the synthesis of a compound that is essential for the growth of an organism. When introduced into an auxotrophic organism that is unable to synthesize the essential compound, such genes allow the organism to grow in a medium that has been supplemented with the essential compound. For example, bacterial cells that are auxotrophic for the amino acid lysine due to a mutation in or the absence of an enzyme involved in lysine biosynthesis normally are unable to grown on media that has not been supplemented with lysine. When such bacteria are subjected to a transformation procedure to introduce a plasmid encoding the enzyme involved in lysine biosynthesis, the bacteria that have successfully taken up the plasmid and expressed the enzyme will survive when grown on media that has not been supplemented with lysine. The terms "selectable marker" and "selectable marker gene" further include genes that allow for poison/antidote selection. For example, the ccdB gene encodes a protein that binds to DNA gyrase, an essential enzyme for cell division. Upon binding to DNA gyrase, the ccdB gene product impairs gene replication and induces cell death. Thus, bacterial expressing the ccdB gene product cannot survive. The ccdA gene encodes a protein (the "antidote") that acts as a natural inhibitor of the ccdB gene product. Thus, when bacteria having the ccdB gene in their bacterial genome are subjected to a transformation procedure to introduce a plasmid encoding the ccdA gene product, only the cells that successfully take up the plasmid and express the ccdA gene will survive.

The terms "screenable marker" and "screenable marker gene" refer to a gene that encodes a product that allows an observer to distinguish between cells expressing the screenable marker gene and cells that are not expressing the screenable marker gene. Screenable marker gene systems are well known in the art and include, for example, lacZ genes and genes encoding fluorescent proteins such as green fluorescent protein (GFP), yellow fluorescent protein (YFP), red fluorescent protein (RFP), blue fluorescent protein (BFP), or cyan fluorescent protein (CFP).

As used herein, the term "subject" refers to a member of the Suidae or porcine species, whether domestic or wild. In particular, the term "subject" refers to those that are commercially reared for breeding or meat production. Suitable porcine subjects include, without limitation, swine, hogs, pigs, gilts, suckling pigs, weaned pigs, feeder pigs, boar, and other porcine species members known in the art. In some aspects, subjects may be diagnosed with an infectious disease, may be at risk for an infectious disease, or may be experiencing an infectious disease. Subjects may be of any age including in utero, new born, adolescent, adult, middle age, or elderly.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

EXAMPLES

The following non-limiting examples are provided to further illustrate the present invention.

Example 1: The Immunomodulator Complex Enhances the Induction of Hemagglutination Inhibition Antibodies when Co-Administered with a Killed Commercial Swine Influenza Vaccine The purpose of this example was to evaluate the effects of the immunomodulator on induction of hemagglutination inhibition (HI) antibodies when co-administered with a killed commercial swine influenza vaccine.

Methods

Thirty-five pigs were received on site and placed into five pens (treatment groups T1, T2, T3, T4, and T5). The pigs were randomized to obtain similar weights in each treatment group. On Day 0 and Day 14, T2 through T4 received varying amounts of the immunomodulator with the recommended dose of a SIV commercial vaccine. The immunomodulator and the commercial vaccine were administered by subcutaneous inoculation in close proximity near the lymph node in the sub scapular region. T1 received the commercial vaccine only and T5 received the diluent only. Blood was collected for serum on days 0, 3, 7, 10, 14, 18, 21, 24, and 28 from each remaining pig except from pig ID 114 on day 18. The blood was processed for serum and transferred to a laboratory for final processing and hemagglutination inhibition (HAI) testing.

All laboratory procedures were performed according a standard method. Serum samples were pretreated with receptor destroying enzyme and adsorbed to chicken red blood cells prior to initiating the HAI assay to decrease non-specific binding to cRBC. Non-specific interactions may lead to false positive suggesting the presence of hemagglutination inhibition. Pre-treatment resulted in an initial 1:5 dilution so that the first dilution tested in the HAI assay was 1:10. The pre-treated serum was serially diluted two-fold. A constant amount of virus (4-8 hemagglutinating units) was then incubated with each dilution. After an incubation period of approximately 45 minutes, a 1% cultured red blood cell (cRBC) solution was added. The plates were observed for the inhibition of hemagglutination. The titer was calculated as the last dilution of serum that completely inhibited 4 to 8 viral hemagglutination units in all replicates.

Serum samples from Days 0, 3, 7, 10, 14, 18, 21, 24, and 28 were tested for anti-hemagglutination antibodies against swine influenza virus (SIV) H1N1. In addition, serum samples from Days 0, 3, 7, and 21 were also tested for anti-hemagglutination antibodies for SIV H3N2. These specific days were tested because of the results obtained during initial testing with H1N1.

Immunomodulator

An immunomodulator composition as described herein was used in this study. In particular, an immunomodulator composition described herein, including SEQ ID NO: 2, DOTIM, and a pharmaceutical carrier was used ("IC-Ex.1").

TABLE 1

Dilution of the immunomodulator

| Targeted dose ($\mu g^1$ per 2 mL) | Calculated dose ($\mu g$ per 2 mL) | Stock volume (mL) | Diluent (D5W) (mL) | Total volume$^2$ (mL) | Volume post dilution$^3$ (mL) | Dose Volume Per Animal (mL) |
|---|---|---|---|---|---|---|
| 200 | 200 | 10 | 24 | 34 | 29 | 2.0 |
| Remove 5 ml from the above 34 mL | | | | | | |
| 50 | 50 | 5 | 15 | 20 | 16 | 2.0 |
| Remove 4 ml from the above 20 mL | | | | | | |
| 10 | 10 | 4 | 16 | 20 | 20 | 2.0 |

$^1$micrograms $^2$Total volume of stock volume and diluent prior to removing volume for dilution $^3$Volume remaining for administration, (200 ug/2 mL dose to be used for treatment groups 2 and 5, total of 14 animals; 50 ug/2 mL dose to be used for treatment group 3, total of 7 animals; 10 ug/2 mL dose to be used for treatment group 4, total of 7 animals)

Animals

The swine were pure or cross breed and colostrum deprived until transport to the testing site. A total of 35 animals of mixed genders were purchased from a swine influenza negative farm and 35 animals were included into the study. The initial age of the pigs was approximately eight weeks at arrival and nine to ten weeks at inoculation. The initial body weight was appropriate for the pigs' age at the time of inoculation.

Piglets were not vaccinated after birth and were not treated with any treatments known to interfere with vaccination. Upon arrival to the clinical site, all piglets were observed for general health. Animals were acclimated for seven days prior to start of the study. Animals were observed once a day for clinical signs. Body temperature was taken once a day.

Piglets were selected from a herd without a current history of swine influenza and parent sows/gilts not vaccinated for SIV. Each individual was evaluated and determined to be in good health. Piglets were negative by serology (hemagglutination inhibition (HAI)) for swine influenza virus. On day −1 or 0, all piglets were clinically observed and either placed into a treatment group or excluded with a maximum of seven piglets per treatment group. Animals were excluded from the study if they had received treatment that would interfere with vaccination within 21 days prior to administration of treatment.

Study Design

TABLE 2

Study design.

| Treatment Group | Description | Vaccination (Day)[6] | Blood Collection (Day) | Number of Animals |
|---|---|---|---|---|
| T1 | Commercial SIV[1] vaccine (IM)[2] | 0, 14 | 0, 3, 7, 10, 14, 18, 21, 24, 28 | 7 |
| T2 | Commercial SIV vaccine (IM)+[3] immunomodulator[4] 200 microgram (SC)[5] | 0, 14 | 0, 3, 7, 10, 14, 18, 21, 24, 28 | 7 |
| T3 | Commercial SIV vaccine (IM)+[3] Immunomodulator 50 microgram (SC) | 0, 14 | 0, 3, 7, 10, 14, 18, 21, 24, 28 | 7 |
| T4 | Commercial SIV vaccine (IM)+[3] Immunomodulator 10 microgram (SC) | 0, 14 | 0, 3, 7, 10, 14, 18, 21, 24, 28 | 7 |
| T5 | Diluent (5% Dextrose and water) (SC) | 0, 14 | 0, 3, 7, 10, 14, 18, 21, 24, 28 | 5-7 |

[1]SIV = Swine Influenza Virus Commercial USDA licensed vaccine-for example, FLU-SURE Pfizer Animal Health, a 2 mL dose is given IM in the Sub Scapular region
[2]IM = Intramuscular route of injection
[3]Each component administered separately in the Sub Scapular region
[4]Immunomodulator
[5]SC = Subcutaneous route of injection-in the Sub Scapular region
[6]Day 0 is day of administration Animals were observed for clinical signs for the entire study period and during acclimation. Beginning on the day of challenge administration and continuing through necropsy day each study animal was assessed for clinical signs of abnormal respiration, abnormal attitude and pyrexia each morning.

The following table was used as a guide to the assignment of clinical score classification for the clinical signs of abnormal respiration and attitude. The clinical score was defined relative to similar, normal, healthy animals on the site.

TABLE 3

Clinical Scoring Guide.

| Clinical Score | Respiration |
|---|---|
| 0 | Normal rate and character. |
| 1 | Slightly increased rate and/or slightly abnormal character. |
| 2 | Moderately increased rate and/or abnormal character. |
| 3 | Severely increased rate and markedly abnormal character (may exhibit open-mouth breathing). |

| Clinical Score | Attitude |
|---|---|
| 0 | Normal-bright, alert, responsive. Normal appetite/rumen fill. |
| 1 | Mild Depression-reduced responsiveness and/or decreased appetite. |
| 7 | Moderate to Marked Depression-may be reluctant to stand. |
| 3 | Moribund-unable to stand without assistance. |

Animals observed for abnormal clinical signs, including anorexia, coughing, fever, serous discharge from eyes and nose, ataxia, coma, convulsions, erythema, hyper-excitability, hyper-salivation, lameness, recumbence, tenesmus and tremors.

Study Day 0 was the same for all animals and was the day of administration of immunomodulator treatment to animals in groups T2, T3 and T4. All animals receiving immunomodulator were injected subcutaneously. All animals receiving vaccine were administered according to the label instruction. All animals receiving immunomodulator were injected near a lymph node in the sub scapular region. Vaccine and immunomodulator were administered separately in close proximity to each other.

Animals were bled for serum while on the farm of origin prior to weaning and shipment, for the purpose of determining suitability for inclusion in the study. A minimum of three pigs per litter were sampled.

Blood samples (approximately 5-7 mLs per animal/collection) for SIV serology were collected on study days 0 (prior to vaccination), and on day 3, day 7, day 10, day 14, day 18, day 21, day 24, and day 28.

Blood samples were processed for serum using BBL standard operating procedures (SOPs) and each sample was aliquoted into two separate volumes. Serum samples were tested by HAI assay using BBL SOPs with 8 units of hemagglutinating (HA) virus. Serum samples were tested with homologous and heterologous viruses.

Animals were weighed on study days −7, 0, 7, 14 and 21, and 28 or prior to necropsy. Only animals that died or were euthanized for humane reasons were necropsied to determine the cause of illness by a veterinarian. Pigs were euthanized by barbiturate overdose administered by the attending veterinarian. Necropsies were handled according to SOPs in place at the test facility. On study Day 28 all remaining animals were euthanized by humane methods by barbiturate overdose administered by the attending veterinarian according to facility SOPs.

Results

There were no apparent clinical manifestations resulting from the immunomodulator test article. Two pigs died during the study. The cause of death was a prolapsed rectum in both cases. Two additional pigs were removed from the study due to lameness and the onset of stress. On Day 28, all remaining pigs were weighed and euthanized after blood collection.

Table 4 provides data from Days 0, 3, 7, 10, 14, 18, 21, 24, and 28 serum samples tested for anti-hemagglutination antibodies against a SIV H1N1 isolate. See Table 5 for data from Days 0, 3, 7, and 21 serum samples tested for anti-hemagglutination antibodies to a Sly H3N2 isolate. Test serum samples with a HI titer of 20 against H1N1 and 10 against H3N2 were reported as positive. This was due to non-specific background of the serum to each virus type.

TABLE 4

Hemagglutination Inhibition Titer Against SIV H1N1

| Animal ID | Pen No. | Txt Grp | Day 0 | Day 3 | Day 7 | Day 10 | Day 14 | Day 18 | Day 21 | Day 24 | Day 28 |
|---|---|---|---|---|---|---|---|---|---|---|---|
| 110 | 4 | 1 | 10 | 10 | 80 | 40 | 80 | 40 | 160 | 160 | 80 |
| 124 | 4 | 1 | 10 | 10 | 160 | 80 | 160 | 80 | 80 | 80 | 80 |
| 127 | 4 | 1 | 5 | 5 | 5 | 5 | 5 | 5 | 5 | 5 | 5 |
| 129 | 4 | 1 | 5 | 5 | 5 | 5 | 5 | 5 | 5 | 5 | 5 |
| 135 | 4 | 1 | 5 | 5 | 5 | 5 | 5 | 5 | 5 | 5 | 5 |
| 146 | 4 | 1 | 5 | 5 | 5 | 5 | 5 | 5 | 5 | NS | NS |
| 150 | 4 | 1 | 5 | 5 | 5 | 5 | 5 | 5 | 5 | 5 | 5 |
| Ave | | | 6 | 6 | 38 | 21 | 38 | 21 | 38 | 43 | 30 |
| Geometric Mean Ave | | | 6 | 6 | 12 | 10 | 12 | 10 | 12 | 14 | 13 |
| 103 | 2 | 2 | 10 | 10 | 160 | 160 | 160 | 40 | 80 | 80 | 80 |
| 117 | 2 | 2 | 5 | 5 | 160 | 160 | 160 | 80 | 80 | 80 | 80 |
| 119 | 2 | 2 | 10 | 20 | 640 | 640 | 320 | 640 | 320 | 320 | 320 |
| 123 | 2 | 2 | 5 | 5 | 320 | 640 | 320 | 320 | 640 | 320 | 320 |
| 128 | 2 | 2 | 5 | 5 | 5 | 5 | 5 | 5 | 5 | 5 | 5 |
| 144 | 2 | 2 | 5 | 5 | 5 | 5 | 5 | NS | NS | NS | NS |
| 145 | 2 | 2 | 5 | 5 | 5 | 5 | 5 | 5 | 5 | 5 | 5 |
| Ave | | | 6 | 8 | 185 | 231 | 139 | 182 | 188 | 135 | 135 |
| Geometric Mean Ave | | | 6 | 7 | 49 | 54 | 44 | 50 | 57 | 50 | 50 |
| 109 | 3 | 3 | 5 | NS | NS | NS | NS | NS | NS | NS | NS |
| 111 | 3 | 3 | 5 | 10 | 640 | 640 | 640 | 320 | 1280 | 1280 | 640 |
| 116 | 3 | 3 | 10 | 10 | 160 | 80 | 80 | 80 | 80 | 80 | 40 |
| 126 | 3 | 3 | 5 | 5 | 5 | 5 | 5 | 5 | 5 | 5 | 5 |
| 130 | 3 | 3 | 5 | 5 | 5 | 5 | 5 | 5 | 5 | 5 | 5 |
| 136 | 3 | 3 | 5 | 5 | 5 | 5 | 5 | 5 | 5 | 5 | 5 |
| 137 | 3 | 3 | 5 | 5 | 5 | 5 | 5 | 5 | 5 | 5 | 5 |
| Ave | | | 6 | 7 | 137 | 123 | 123 | 70 | 230 | 230 | 117 |
| Geometric Mean Ave | | | 6 | 6 | 20 | 18 | 18 | 16 | 20 | 20 | 16 |
| 108 | 5 | 4 | 5 | 5 | 160 | 160 | 160 | 40 | 160 | 160 | 80 |
| 113 | 5 | 4 | 5 | 10 | 320 | 640 | 320 | 320 | 320 | 320 | 160 |
| 118 | 5 | 4 | 10 | 10 | 160 | 160 | 160 | 160 | 160 | 160 | 80 |
| 120 | 5 | 4 | 10 | 10 | 320 | 160 | 320 | 320 | 160 | 160 | NS |
| 125 | 5 | 4 | 5 | 5 | 5 | 5 | 5 | 5 | 5 | 5 | 5 |
| 133 | 5 | 4 | 5 | 5 | 5 | 5 | 5 | 5 | 5 | 5 | 5 |
| 143 | 5 | 4 | 5 | 5 | 5 | 5 | 5 | 5 | 5 | 5 | 5 |
| Ave | | | 6 | 7 | 139 | 162 | 139 | 122 | 116 | 116 | 56 |
| Geometric Mean Ave | | | 6 | 7 | 44 | 44 | 44 | 36 | 40 | 40 | 22 |
| 102 | 1 | 5 | 5 | 5 | 10 | 10 | 5 | 5 | 5 | 5 | 10 |
| 114 | 1 | 5 | 10 | 10 | 10 | 10 | 5 | NS | 5 | 5 | 5 |
| 115 | 1 | 5 | 5 | 10 | 10 | 5 | 5 | 5 | 5 | 20 | 40 |
| 121 | 1 | 5 | 5 | 10 | 10 | 10 | 10 | 10 | 10 | 10 | 10 |
| 122 | 1 | 5 | 5 | 5 | 10 | 10 | 10 | 10 | 10 | 10 | 10 |
| 134 | 1 | 5 | 5 | 5 | 5 | 5 | 5 | 5 | 5 | 5 | 5 |
| 149 | 1 | 5 | 5 | 5 | 5 | 5 | 5 | 5 | 5 | 5 | 5 |
| Ave | | | 6 | 7 | 9 | 8 | 6 | 7 | 6 | 9 | 12 |
| Geometric Mean Ave | | | 6 | 7 | 8 | 7 | 6 | 6 | 6 | 7 | 9 |

NS—no sample
5—represents a titer of <10
10—non-specific background
Challenge virus—H1N1 SIV Lot VS24Nov09Iowa73-SIVp1
Vaccination Days = Day 0 and Day 14

TABLE 5

Hemagglutination Inhibition Titer Against SIV H3N2.

| Animal ID | Pen No. | Txt Grp | Day 0 | Day 3 | Day 7 | Day 21 |
|---|---|---|---|---|---|---|
| 110 | 4 | 1 | 5 | 5 | 5 | 20 |
| 124 | 4 | 1 | 5 | 5 | 5 | 40 |

TABLE 5-continued

Hemagglutination Inhibition Titer Against SIV H3N2.

| Animal ID | Pen No. | Txt Grp | Day 0 | Day 3 | Day 7 | Day 21 |
|---|---|---|---|---|---|---|
| 127 | 4 | 1 | 5 | 5 | 5 | 20 |
| 129 | 4 | 1 | 5 | 5 | 5 | 5 |
| 135 | 4 | 1 | 5 | 5 | 5 | 5 |
| 146 | 4 | 1 | 5 | 5 | 5 | 5 |
| 150 | 4 | 1 | 5 | 5 | 5 | 5 |
| Ave | | | 5 | 5 | 5 | 14 |
| Geometric Mean Ave | | | 5 | 5 | 5 | 10 |
| 103 | 2 | 2 | 5 | 5 | 80 | 20 |
| 117 | 2 | 2 | 5 | 5 | 5 | 5 |
| 119 | 2 | 2 | 5 | 5 | 5 | 10 |
| 123 | 2 | 2 | 5 | 5 | 5 | 40 |
| 128 | 2 | 2 | 5 | 5 | 5 | 5 |
| 144 | 2 | 2 | 5 | 5 | 5 | NS |
| 145 | 2 | 2 | 5 | 5 | 5 | 5 |
| Ave | | | 5 | 5 | 16 | 14 |
| Geometric Mean Ave | | | 5 | 5 | 7 | 10 |
| 109 | 3 | 3 | 5 | NS | NS | NS |
| 111 | 3 | 3 | 5 | 5 | 10 | 20 |
| 116 | 3 | 3 | 5 | 5 | 20 | 80 |
| 126 | 3 | 3 | 5 | 5 | 5 | 5 |
| 130 | 3 | 3 | 5 | 5 | 5 | 10 |
| 136 | 3 | 3 | 5 | 5 | 5 | 10 |
| 137 | 3 | 3 | 5 | 5 | 5 | 10 |
| Ave | | | 5 | 5 | 8 | 23 |
| Geometric Mean Ave | | | 5 | 5 | 7 | 14 |
| 108 | 5 | 4 | 5 | 5 | 5 | 5 |
| 113 | 5 | 4 | 5 | 5 | 10 | 20 |
| 118 | 5 | 4 | 5 | 5 | 5 | 10 |
| 120 | 5 | 4 | 5 | 5 | 5 | 5 |
| 125 | 5 | 4 | 5 | 5 | 5 | 5 |
| 133 | 5 | 4 | 5 | 5 | 5 | 10 |
| 143 | 5 | 4 | 5 | 5 | 5 | 10 |
| Ave | | | 5 | 5 | 6 | 9 |
| Geometric Mean Ave | | | 5 | 5 | 6 | 8 |
| 102 | 1 | 5 | 5 | 5 | 5 | 5 |
| 114 | 1 | 5 | 5 | 5 | 5 | 5 |
| 115 | 1 | 5 | 5 | 5 | 5 | 5 |
| 121 | 1 | 5 | 5 | 5 | 5 | 5 |
| 122 | 1 | 5 | 5 | 5 | 5 | 5 |
| 134 | 1 | 5 | 5 | 5 | 5 | 5 |
| 149 | 1 | 5 | 5 | 5 | 5 | 5 |
| Ave | | | 5 | 5 | 5 | 5 |
| Geometric Mean Ave | | | 5 | 5 | 5 | 5 |
| HA challenge | | | 4 | 4 | 4 | 4 |

NS—no sample
5—represents a titer of <10
10—non-specific background
Challenge virus—H1N1 SIV Lot VS24Nov09Iowa73-SIVp1
Vaccination Days = Day 0 and Day 14

Discussion

The purpose of this study was to evaluate the effects of the immunomodulator composition on induction of hemagglutination inhibition (HI) antibodies when co-administered with a killed commercial swine influenza vaccine. To this end, a total of thirty-five colostrum-deprived pigs were separated into five treatment groups and each treatment group received an initial inoculation and a boost fourteen days later of various amounts of immunomodulator with a commercial SIV vaccine. There were no apparent clinical manifestations resulting from the immunomodulator test article during the twenty-eight day study. However, there were a total of four pigs removed from the study due to death or euthanized for humane reasons.

All serum samples collected were assayed for hemagglutination inhibition to H1N1. A select number of study days were also assayed for hemagglutination inhibition to H3N2. FIGS. 4 and 5 present the geometric mean calculated for each treatment group for each day assayed. There was a marked increase in the geometric mean with treatment groups that received 200 ug and 10 ug of immunomodulator in combination with the commercial vaccine compared to the vaccine only inoculated group to the H1N1 isolate. There was also an increase in geometric mean with the treatment group that received 50 ug of immunomodulator with the commercial vaccine compared to the vaccine only inoculated group, especially at Day 21. Seroconversion to H3N2 also appeared earlier when the immunomodulator was inoculated.

The actual mean of the HAI titers are also presented in FIGS. 6 and 7. These graphs represent more of an individual titer within each treatment group. This is most apparent with treatment group 3 after the Day 14 boost. Although only two pigs seroconverted to the H1N1, one pig had a high HAI titer (see Table 5).

There was seroconversion to both SIV isolates. See Tables 6A and 6B and FIG. 8 (Day 21 results) presenting the number of pigs where seroconversion was detected using this method compared to the total number of pigs in each treatment group.

TABLE 6A

| Summary of Seroconversion No. Pigs seroconverted* to H1/N1/Total | | | | | |
|---|---|---|---|---|---|
| | Txt 1 Vacc Only | Txt 2 Vacc + 200 ug | Txt 3 Vacc + 50 ug | Txt 4 Vacc + 10 ug | Txt 5 D5W Only |
| Day 0 | 0/7 | 0/7 | 0/7 | 0/7 | 0/7 |
| Day 3 | 0/7 | 1/7 | 0/6 | 0/7 | 0/7 |
| Day 7 | 2/7 | 4/7 | 2/6 | 4/7 | 0/7 |
| Day 10 | 2/7 | 4/7 | 2/6 | 4/7 | 0/7 |
| Day 14 | 2/7 | 4/7 | 2/6 | 4/7 | 0/7 |
| Day 18 | 2/7 | 4/6 | 2/6 | 4/7 | 0/6 |
| Day 21 | 2/7 | 4/6 | 2/6 | 4/7 | 0/7 |
| Day 24 | 2/6 | 4/6 | 2/6 | 4/7 | 0/7 |
| Day 28 | 2/6 | 4/6 | 2/6 | 3/6 | 1/7** |

*Animals with a titer of > 10 = seroconversion
**High background in one sample

TABLE 6B

| Summary of Seroconversion No. Pigs seroconverted* to H3N2/Total | | | | | |
|---|---|---|---|---|---|
| | Txt 1 Vacc Only | Txt 2 Vacc + 200 ug | Txt 3 Vacc + 50 ug | Txt 4 Vacc + 10 ug | Txt 5 D5W Only |
| Day 0 | 0/7 | 0/7 | 0/7 | 0/7 | 0/7 |
| Day 3 | 0/7 | 0/7 | 0/6 | 0/7 | 0/7 |
| Day 7 | 0/7 | 1/7 | 2/6 | 1/7 | 0/7 |
| Day 21 | 3/7 | 3/6 | 5/6 | 4/7 | 0/7 |

In conclusion, the immunomodulator complex enhanced the induction of hemagglutination inhibition antibodies when co-administered with a killed commercial swine influenza vaccine.

Example 2: The Immunomodulator with Porcine Reproductive and Respiratory Syndrome (PRRS) Vaccine Aids in Early Virus Clearing in the Lungs of Pigs A study was conducted to evaluate the intensity and quality of the immune response, as well as the level of protective immunity, elicited in swine by a PRRS modified live vaccine (MLV) vaccine given concurrently with 50 μg (RxII) or 10 μg (RxI) doses of the immunomodulator. The parameters were compared to the same host response to immunization with the same MLV vaccine but administered without the immunomodulator. The level of protective immunity was determined by measuring the reduction of clinical syndrome observed in vaccinated and virulent PRRS virus challenged animals as compared to unvaccinated and challenged controls.

In a controlled PRRS challenge the RxII (PRRS vaccine+ 50 microgram of immunomodulator) group had higher body weight gain, lower virus load in the lung and had detectable interferon in all the animals as compared to animals in group (RxIII) receiving PRRS vaccine alone. The study suggests that the immunomodulator with PRRS vaccine aids in early virus clearance in the lungs which was not observed in PRRS vaccinated (RxIII) animals.

Study Design

The group Rx I (T5) received PRRS MLV PrimePac vaccine+10 μg of immunomodulator. The group Rx II (T4) received PRRS MLV PrimePac vaccine+50 μg of immunomodulator. The group Rx III (T5) received PRRS MLV PrimePac vaccine alone.

TABLE 7

Study design.

| Group | Treatment | Suite | Pen | Number of Animals |
|---|---|---|---|---|
| T1 | No vaccine/No challenge | A | 1 | 6 |
| T2 | No vaccine/challenged | A | 5 | 6 |
| T3 (Rx III) | Commercial PRRS vaccine/ challenged | A | 3 and 6 | 9 |
| T4 (Rx II) | Commercial PRRS vaccine + 50 microgram of immunomodulator by SC route + challenged | A | 2 and 8 | 9 |
| T5 (Rx I) | Commercial PRRS vaccine + 10 microgram of immunomodulator by SC route + challenged | A | 4 and 7 | 9 |

SC = Subcutaneous route of injection

Immunomodulator

The immunomodulator used in this study is the immunomodulator described above in Example 1.

Animals

The immunomodulator cationic liposome-plasmid complex was supplied as a lyophilized powder contained in 5 mL (1.25 mL fill) vials. The test article was shipped and stored at 2-8° C. and was not frozen. The immunomodulator was formulated in a Tris-HCl lactose buffer, pH 6.8. The immunomodulator was reconstituted immediately before use by the addition of sterile water for injection (SWFI) USP. The containers and reconstitution volumes were the following:

5 mL Vial contains 425 μg (refer to CoA): Reconstitute with 1.25 mL of SWFI 10 mL Water, Sterile, Preservative-free (For Injections/USP), Abbott No.: 488710100 (Fisher Scientific AB4887-10-1)

The immunomodulator was reconstituted with sterile water for injection under a laminar flow hood using aseptic techniques. The lyophilized immunomodulator was removed from the refrigerated storage (2-8° C.) and the vial was allowed to reach room temperature for approximately 5 minutes prior to reconstitution. A syringe and 18-gauge needle were used to measure 0.5 mL (2 mL vial) or 1.25 mL (5 mL vial) of sterile water for injection and gradually inject into one 2 mL or 5 mL vial of lyophilized immunomodulator, respectively. The time of reconstitution was recorded on the label and study drug preparation worksheet. The vial was gently swirled (not vortexed) for at least 30 seconds and allowed to sit for at least 5 minutes. The vial was again gently swirled (not vortexed) for at least 30 seconds. The reconstituted immunomodulator material had a white translucent appearance. The reconstituted vial was stored with ice pack until used. The reconstituted immunomodulator material was stable when used within 4-6 hours. The reconstituted immunomodulator was diluted in dextrose 5% in sterile water as indicated in Table 8.

TABLE 8

Immunomodulator dilution.

| Doses | Targeted dose (2 ml) | Calculated dose (2 ml) | Stock volume (mL) | Diluent (D5W) | Total volume | Dose Volume Per Animal |
|---|---|---|---|---|---|---|
| 17 | 50 | 50 | 2.5 ml (1.25 ml/vial) | 31.5 | 34 | 2.0 |
| Remove 6 ml from above 34 ml | | | | | | |
| 15 | 10 | 10 | 6 ml | 24 | 30 | 2.0 |

Note:
The diluted immunomodulator was kept in an ice bath. The diluted immunomodulator was used within 4 hours after dilution. Time of dilution and time of injection of the last calf were recorded.

A total of 39 SPF pigs of similar body weight (Tables 9 to 13), free of all major swine pathogens including PRRS virus, *mycoplasma* and circovirus, were used in this study. The animals were negative for PRRS antibodies by serology. The initial age of the pigs was approximately 7 to 9 weeks at acclimation. All piglets were not vaccinated after birth and not treated with any treatments known to interfere with PRRS vaccination. Animals were acclimated for 7 days prior to start of the study. Animals were observed once a day for clinical signs. Body temperature was taken once a day.

Animals were observed for clinical signs for the entire study period and during acclimation. Beginning on the day of challenge administration and continuing through necropsy day each study animal were assessed for clinical signs of abnormal respiration, abnormal attitude and pyrexia each morning. For welfare reasons some animals were observed more than once daily. No animals had respiratory or attitude score of 3 and thus needed no medication and were not euthanized by the investigator for humane reasons.

The following were used as a guide to the assignment of clinical score classification for the clinical signs of abnormal respiration and attitude. The clinical scores were defined relative to similar, normal, healthy animals on the site. Care was taken to account for normal differences between animals and to distinguish normal physiological responses from pathological responses.

Respiratory Scoring:
  0=Normal. Thoracic breathing with some abdominal movement
  1=Mild respiratory distress. Some abdominal breathing
  2=Moderate respiratory distress. Exaggerated abdominal and labored breathing
  3=Severe respiratory distress. Very labored breathing, abdominal breathing. Mouth open, cyanosis of nose and ear Activity/Depression Scoring:
0=Normal. Pigs react briskly/grunt upon opening the door. The pigs are active, playful and curious. Look towards the door, approach the gate and sniff. Show interest in food and water. If excited, they might urinate and defecate.
1=Mild. Get up upon stimulation but slow or show no much interest or curiosity. Will go back to lying down quickly. Some interest in food 2=Moderate. Pronounced inactivity and reluctance to get up/move. Prostration, staggering, in coordination.
3=Severe. Non-responsive, will not get up.
Treatment Methods After a seven day acclimation period, those animals in groups T3 to T5 (Rx III to Rx I) were vaccinated. All animals receiving immunomodulator (T4 & T5) were injected subcutaneously. All animals receiving PRRS vaccine T3 to T5 were administered intramuscularly with approximately 5×10$^4$ tissue culture infectious dose 50 (TCID50) dose in a 2 ml volume of the PRRS MLV strain PrimePac. As used herein, "TCID50" refers to the amount of a pathogenic agent required to produce a pathological change in 50% of the cells inoculated. All animals receiving immunomodulator were injected near a lymph node in the sub scapular region. Vaccine and immunomodulator were administered separately in close proximity to each other. Animals in groups T1 and T2 were injected with 2 ml of spent culture supernatant from uninfected cells used to grow the virus (MARC-145 cells).

Four weeks after vaccination, animals in groups T2 to T5 were challenged with approximately 2×10$^4$ TCID50 of PRRS virus strain NADC-20 in a 2 ml volume given half of the dose intramuscularly and the other half intranasally. The unvaccinated and challenged animals assigned to group T2 served to establish the severity of clinical syndrome resulting from the infection by the virulent NADC-20 PRRS virus, while the animals allocated to group Ti was used to provide the normal parameters of growth and health.

The degree of protective immunity elicited by the vaccination was determined based on viral load in serum and lung as well as by a comparison of body weight (BW) changes and the manifestation of depression and respiratory signs. Clinical parameters were monitored daily for ten days after the challenge. The level of viremia (blood) was determined at 0, 4, 7 and 10 days after challenge by measuring infectious virus titer in serum in ZMAC cells. Viral load in lung tissue were determined by virological methods.

Ten days after the challenge, all the study animals were euthanized and lung samples for viral load were collected. An experienced pathologist assessed pathological changes in the lung at the macro and microscopic levels.

To measure the development of virus-specific immunity, peripheral blood samples were collected from each animal at days –7, 0, 4, 7, 14 and 28 (prior to challenge) and after immunization and on day 38 (prior to euthanasia). From these samples, serum and PBMC were obtained and the intensity of the humoral and cell-mediated immunities of each animal was measured. The antibody titer was determined using serum virus-neutralization test and the frequency of PRRS virus-specific interferon (IFN)-secreting cells (IFN-SC) separately against the vaccine virus (PrimePac) as well as the challenge virus (NADC-20) were performed.

Animals were weighed on study days –7, 0, 7, 14 and 21, and 28 and prior to euthanasia (day 38). No animals died during the study or were euthanized for humane reasons and thus no interim necropsy was performed.
Statistical Analysis Data received and analyzed consisted of serum (measured on days 4, 7 and 10) and lung and IFN titers, body weights (measured on Day 0, 6 and 10), clinical scores and temperatures (measured daily for 10 days post-treatment), and three types of scoring at necropsy. Scores for Alveolar Septal Thickening, Distribution of Thickening, and Inflammatory Cells in Airways were recorded, ranging from 0 to 3.

All lung titers were transformed by adding one (+1) to each titer, converted using natural log, prior to analyses. Least square means were calculated and back-transformed to represent each group's central tendency (i.e., geometric mean) for any time period and tabularized). IFN titers were not transformed.

Where multiple measurements were recorded, a repeated measures analysis of variance was used (if a baseline—nearest study day 0—was available, a covariate analysis was used). If a parameter was measured only once, then an analysis of variance was used. In all models, the fixed effect of TRT was tested for differences between the 5 treatment groups. A Bonferroni adjustment to the p-value was used due to the multiple treatment groups.

Figure 9:
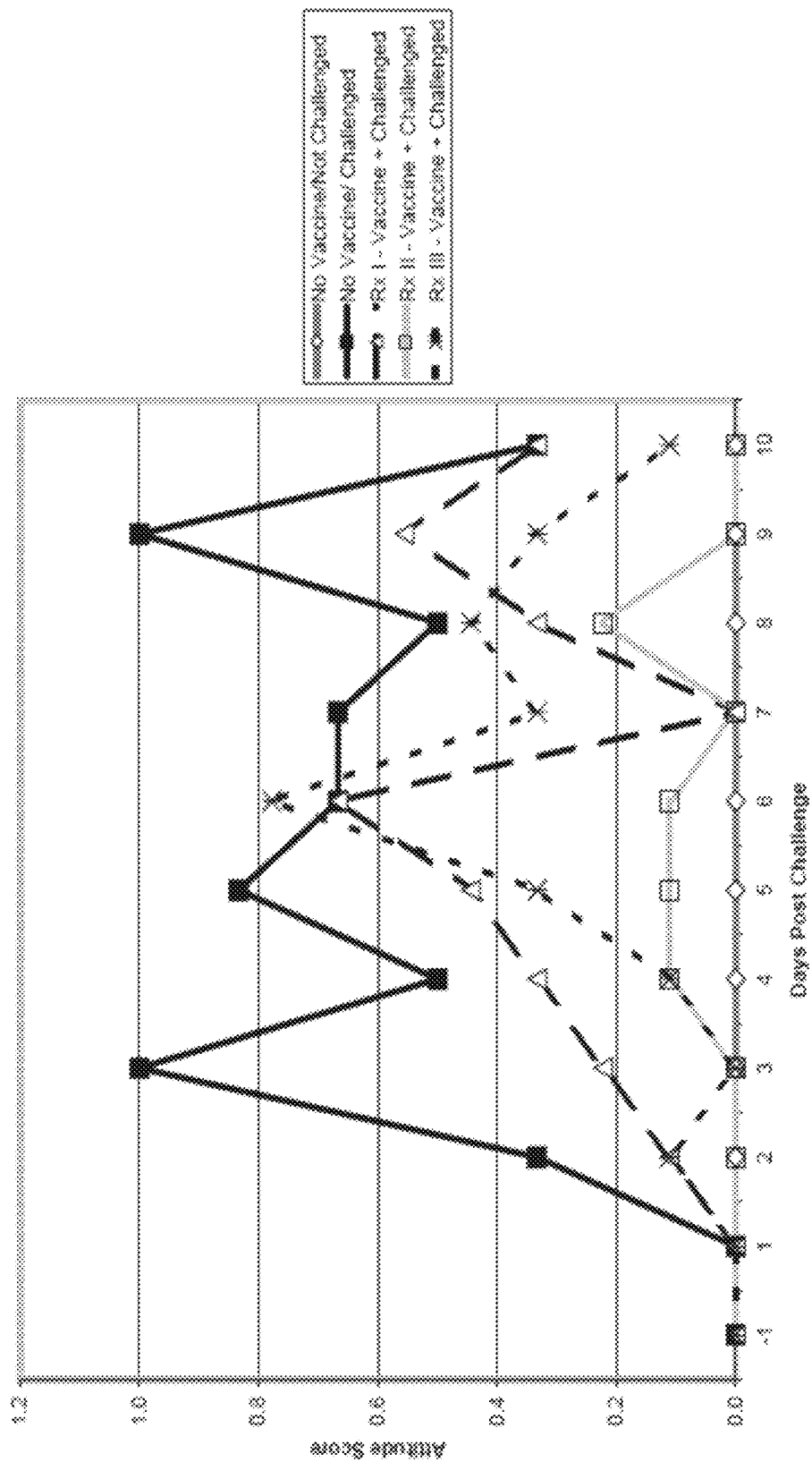
FIG. 9 graphically illustrates the daily average attitude scores of pigs following challenge for each treatment group, including, no vaccine/not challenged (open diamond), no vaccine/challenged (filled square), Rx I vaccine plus 10 µg immunomodulator plus challenge (open triangle), Rx II vaccine plus 50 µg immunomodulator plus challenge (open square), Rx III vaccine plus challenge (star)

For the necropsy scores and clinical scores, chi-square analyses were used. An alpha level of 0.05 was deemed statistically significant. All analyses were performed using SAS 9.2 software.
Results and Discussion No treatment related adverse events were noted. The daily average attitude scores following challenge by group are included in FIG. 9 (Average Daily Attitude Score). Individual animal attitude score by group following challenge are included in Tables 9 to 13. Non vaccinated and not-challenged group had an attitude score of 0 throughout the study (Table 9: Daily Attitude Score—Rx). Non vaccinated and challenged group had mean attitude score ranged from 0.3 to 1 for study days 2 to 10 (Table 10: Daily Attitude Score Not Vaccinated/Challenged). The PPRS vaccinated+immunomodulator 10 µg and challenged group (RxI) had mean attitude score ranged from 0.1 to 0.7 for study days 2 to 10 (Table 11: Daily Attitude Score—RxI). The PPRS vaccinated+immunomodulator 50 µg and challenged group (RxII) had mean attitude score ranged from 0.1 to 0.2 for study days 4 to 8 and no attitude scores on study days 7, 9 and 10 (Table 12: Daily Attitude Score—RxII). The PPRS vaccinated and challenged group (RxIII) had mean attitude score ranged from 0.1 to 0.8 for study days 2, and 4 to 10 (Table 13: Daily Attitude Score—III).

TABLE 9

Daily Attitude Score - Rx.

| | Pig ID | –1 | 1 | 2 | 3 | 4 | 5 | 6 | 7 | 8 | 9 | 10 |
|---|---|---|---|---|---|---|---|---|---|---|---|---|
| Rx | 51 | 0 | 0 | 0 | 0 | 0 | 0 | 0 | 0 | 0 | 0 | 0 |
| No Vaccine/ | 52 | 0 | 0 | 0 | 0 | 0 | 0 | 0 | 0 | 0 | 0 | 0 |
| Not Challenged | 53 | 0 | 0 | 0 | 0 | 0 | 0 | 0 | 0 | 0 | 0 | 0 |
| | 54 | 0 | 0 | 0 | 0 | 0 | 0 | 0 | 0 | 0 | 0 | 0 |
| | 55 | 0 | 0 | 0 | 0 | 0 | 0 | 0 | 0 | 0 | 0 | 0 |
| Pen 1 | 56 | 0 | 0 | 0 | 0 | 0 | 0 | 0 | 0 | 0 | 0 | 0 |
| Average | | 0 | 0 | 0 | 0 | 0 | 0 | 0 | 0 | 0 | 0 | 0 |

TABLE 10

Daily Attitude Score Not Vaccinated/Challenged

| | Pig ID | –1 | 1 | 2 | 3 | 4 | 5 | 6 | 7 | 8 | 9 | 10 |
|---|---|---|---|---|---|---|---|---|---|---|---|---|
| Not Vaccinated/ | 75 | 0 | 0 | 0 | 1 | 0 | 0 | 1 | 1 | 1 | 1 | 0 |
| Challenged | 76 | 0 | 0 | 1 | 1 | 1 | 1 | 0 | 1 | 1 | 2 | 0 |
| | 77 | 0 | 0 | 1 | 1 | 2 | 2 | 1 | 1 | 1 | 1 | 1 |
| Pen 5 | 78 | 0 | 0 | 0 | 1 | 0 | 1 | 1 | 1 | 0 | 2 | 1 |
| | 79 | 0 | 0 | 0 | 1 | 0 | 0 | 0 | 0 | 0 | 0 | 0 |
| | 81 | 0 | 0 | 0 | 1 | 0 | 1 | 1 | 0 | 0 | 0 | 0 |
| Average | | 0.0 | 0.0 | 0.3 | 1.0 | 0.5 | 0.8 | 0.7 | 0.7 | 0.5 | 1.0 | 0.3 |

TABLE 11

Daily Attitude Score - RxI.

| | Pig ID | -1 | 1 | 2 | 3 | 4 | 5 | 6 | 7 | 8 | 9 | 10 |
|---|---|---|---|---|---|---|---|---|---|---|---|---|
| Average | | 0.0 | 0.0 | 0.1 | 0.2 | 0.3 | 0.4 | 0.7 | 0.0 | 0.3 | 0.6 | 0.3 |
| Rx I | 66 | 0 | 0 | 0 | 0 | 0 | 0 | 1 | 0 | 1 | 1 | 0 |
| Vaccinated | 67 | 0 | 0 | 0 | 0 | 0 | 0 | 1 | 0 | 0 | 0 | 0 |
| and | 68 | 0 | 0 | 0 | 1 | 0 | 1 | 1 | 0 | 0 | 1 | 0 |
| Challenged | 69 | 0 | 0 | 0 | 0 | 1 | 0 | 0 | 0 | 0 | 0 | 0 |
| | 70 | 0 | 0 | 0 | 0 | 0 | 0 | 0 | 0 | 0 | 0 | 0 |
| Pens 3 and 6 | 71 | 0 | 0 | 0 | 0 | 0 | 1 | 1 | 0 | 0 | 0 | 0 |
| | 72 | 0 | 0 | 0 | 0 | 0 | 0 | 0 | 0 | 0 | 0 | 1 |
| | 73 | 0 | 0 | 1 | 1 | 2 | 2 | 1 | 0 | 1 | 2 | 1 |
| | 74 | 0 | 0 | 0 | 0 | 0 | 0 | 1 | 0 | 1 | 1 | 1 |

TABLE 12

Daily Attitude Score - RxII.

| | Pig ID | -1 | 1 | 2 | 3 | 4 | 5 | 6 | 7 | 8 | 9 | 10 |
|---|---|---|---|---|---|---|---|---|---|---|---|---|
| Average | | 0.0 | 0.0 | 0.0 | 0.0 | 0.1 | 0.1 | 0.1 | 0.0 | 0.2 | 0.0 | 0.0 |
| Rx II | 57 | 0 | 0 | 0 | 0 | 0 | 0 | 0 | 0 | 0 | 0 | 0 |
| Vaccinated | 58 | 0 | 0 | 0 | 0 | 1 | 0 | 0 | 0 | 0 | 0 | 0 |
| and | 59 | 0 | 0 | 0 | 0 | 0 | 0 | 0 | 0 | 1 | 0 | 0 |
| Challenged | 60 | 0 | 0 | 0 | 0 | 0 | 0 | 0 | 0 | 0 | 0 | 0 |
| | 61 | 0 | 0 | 0 | 0 | 0 | 0 | 0 | 0 | 1 | 0 | 0 |
| Pens 2 and 8 | 62 | 0 | 0 | 0 | 0 | 0 | 1 | 1 | 0 | 0 | 0 | 0 |
| | 63 | 0 | 0 | 0 | 0 | 0 | 0 | 0 | 0 | 0 | 0 | 0 |

TABLE 12-continued

Daily Attitude Score - RxII.

| Pig ID | -1 | 1 | 2 | 3 | 4 | 5 | 6 | 7 | 8 | 9 | 10 |
|---|---|---|---|---|---|---|---|---|---|---|---|
| 64 | 0 | 0 | 0 | 0 | 0 | 0 | 0 | 0 | 0 | 0 | 0 |
| 65 | 0 | 0 | 0 | 0 | 0 | 0 | 0 | 0 | 0 | 0 | 0 |

TABLE 13

Daily Attitude Score - RxIII.

| | Pig ID | -1 | 1 | 2 | 3 | 4 | 5 | 6 | 7 | 8 | 9 | 10 |
|---|---|---|---|---|---|---|---|---|---|---|---|---|
| Average | | 0.0 | 0.0 | 0.1 | 0.0 | 0.1 | 0.3 | 0.8 | 0.3 | 0.4 | 0.3 | 0.1 |
| Rx III | 80 | 0 | 0 | 0 | 0 | 0 | 0 | 0 | 0 | 0 | 0 | 0 |
| Vaccinated | 82 | 0 | 0 | 0 | 0 | 1 | 2 | 2 | 1 | 1 | 0 | 0 |
| and | 83 | 0 | 0 | 0 | 0 | 0 | 0 | 0 | 0 | 0 | 0 | 0 |
| Challenged | 84 | 0 | 0 | 1 | 0 | 0 | 0 | 0 | 0 | 0 | 0 | 0 |
| | 85 | 0 | 0 | 0 | 0 | 0 | 0 | 0 | 0 | 0 | 0 | 0 |
| | 86 | 0 | 0 | 0 | 0 | 0 | 0 | 1 | 0 | 1 | 1 | 0 |
| Pens 4 and 7 | 87 | 0 | 0 | 0 | 0 | 0 | 0 | 2 | 1 | 0 | 0 | 0 |
| | 88 | 0 | 0 | 0 | 0 | 0 | 0 | 1 | 0 | 0 | 0 | 0 |
| | 89 | 0 | 0 | 0 | 0 | 0 | 1 | 1 | 1 | 2 | 2 | 1 |

Figure 10:
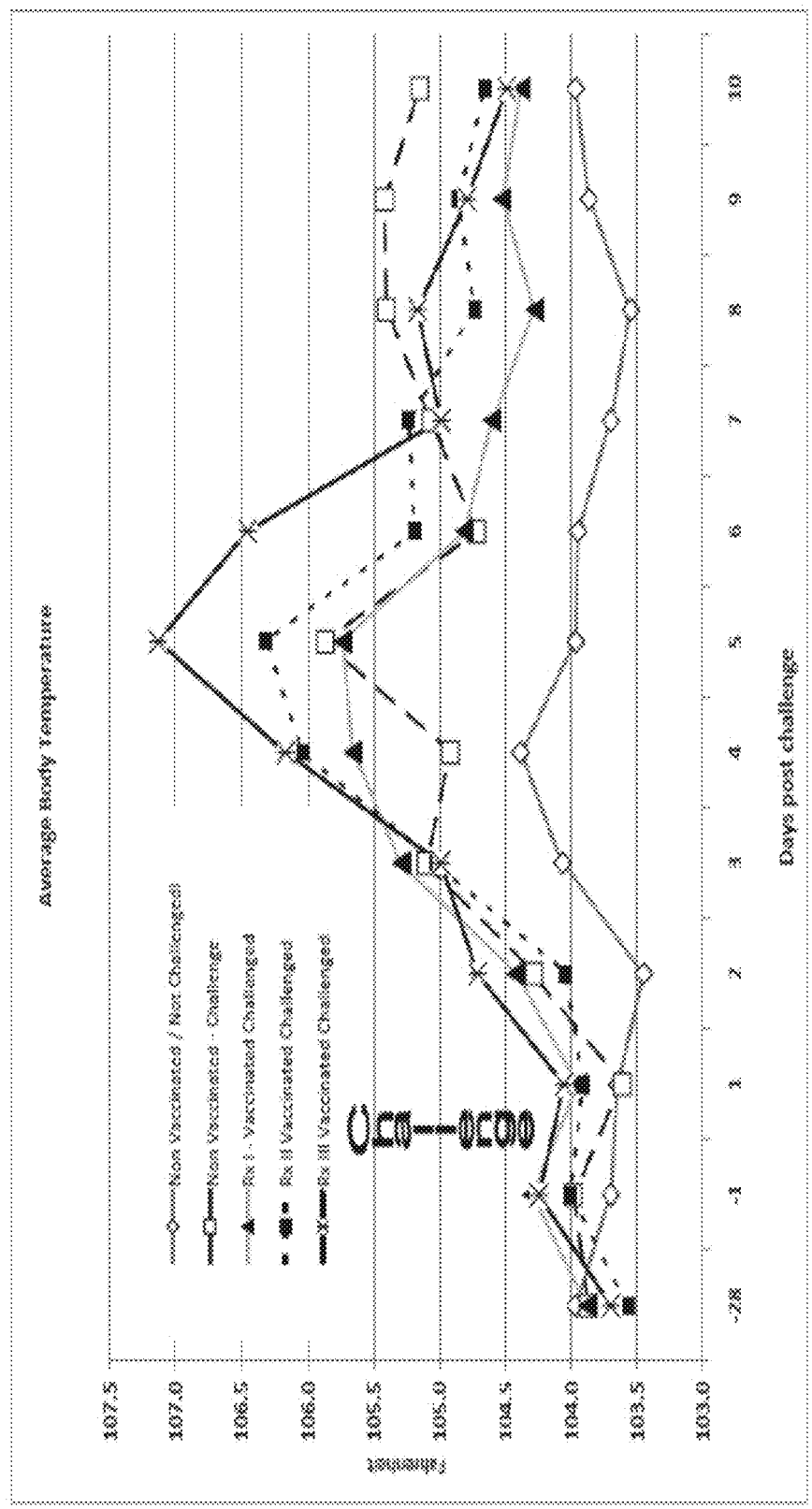
FIG. 10 graphically illustrates the average body temperature of pigs from before the challenge to day 10 post challenge for each treatment group, including, no vaccine/not challenged (open diamond), no vaccine/challenged (open square), Rx I vaccine plus 10 µg immunomodulator plus challenge (filled triangle), Rx II vaccine plus 50 µg immunomodulator plus challenge (filled square), Rx III vaccine plus challenge (star)

The average body temperature on study day −1 by group ranged from 103.7° F. to 104.3° F. The challenged animals had a peak body temperature on study day 5 and by group it ranged from 104.0° F. to 107.1° F. as shown in FIG. 10. Individual animal body temperatures by day are included in Tables 14 to 18.

TABLE 14

Body Temperature - Rx.

| | | Study Day | | | | | | | | | | | |
|---|---|---|---|---|---|---|---|---|---|---|---|---|---|
| | Pig ID | -29 | -28 | -1 | 1 | 2 | 3 | 4 | 5 | 6 | 7 | 8 | 9 | 10 |
| Rx | 51 | 105.5 | 104.6 | 104.5 | 104.0 | 103.5 | 103.8 | 104.8 | 104.8 | 104.4 | 104.6 | 103.3 | 103.9 | 104.3 |
| not | 52 | 104.3 | 103.7 | 103.5 | 103.6 | 104.0 | 104.3 | 104.1 | 103.6 | 103.4 | 103.0 | 103.2 | 103.5 | 103.8 |
| Vaccinated | 53 | 104.3 | 104.0 | 103.8 | 103.4 | 103.3 | 104.0 | 104.4 | 103.5 | 103.9 | 104.0 | 103.7 | 104.0 | 103.6 |
| not | 54 | 104.0 | 103.7 | 103.5 | 103.5 | 102.6 | 104.1 | 105.0 | 104.2 | 103.8 | 103.7 | 103.4 | 104.3 | 104.3 |
| challenged. | 55 | 104.9 | 104.1 | 103.2 | 103.7 | 103.3 | 103.9 | 104.0 | 103.8 | 103.6 | 103.2 | 103.9 | 103.1 | 103.6 |
| Pen 1 | 56 | 104.4 | 103.7 | 103.7 | 103.7 | 104.0 | 104.3 | 104.0 | 103.9 | 104.6 | 103.7 | 103.8 | 104.4 | 104.2 |
| Average | | 104.6 | 104.0 | 103.7 | 103.7 | 103.5 | 104.1 | 104.4 | 104.0 | 104.0 | 103.7 | 103.6 | 103.9 | 104.0 |

TABLE 15

Body Temperature - Not Vaccinated challenged.

| | | Study Day | | | | | | | | | | | |
|---|---|---|---|---|---|---|---|---|---|---|---|---|---|
| | Pig ID | -29 | -28 | -1 | 1 | 2 | 3 | 4 | 5 | 6 | 7 | 8 | 9 | 10 |
| Not | 75 | 104.5 | 103.4 | 104.3 | 103.2 | 104.5 | 104.5 | 103.6 | 105.2 | 106.5 | 104.8 | 105.4 | 105.9 | 105.5 |
| Vaccinated | 76 | 104.6 | 104.4 | 103.4 | 103.8 | 104.2 | 104.7 | 103.9 | 104.8 | 105.0 | 103.0 | 104.2 | 106.1 | 105.3 |
| challenged | 77 | 104.8 | 104.3 | 105.3 | 104.1 | 105.0 | 106.5 | 107.2 | 106.7 | 104.3 | 105.4 | 106.0 | 104.6 | 104.5 |
| Pen 5 | 78 | 104.9 | 103.6 | 103.7 | 103.2 | 103.2 | 105.4 | 104.1 | 105.3 | 104.7 | 107.3 | 106.2 | 105.9 | 105.9 |
| | 79 | 105.7 | 104.4 | 103.9 | 104.7 | 104.2 | 103.9 | 104.3 | 107.0 | 104.3 | 105.2 | 105.1 | 105.5 | 105.2 |
| | 81 | 104.1 | 103.1 | 103.3 | 102.7 | 104.6 | 105.6 | 106.4 | 106.2 | 103.5 | 104.7 | 105.5 | 104.5 | 104.5 |
| Average | | 104.8 | 103.9 | 104.0 | 103.6 | 104.3 | 105.1 | 104.9 | 105.9 | 104.7 | 105.1 | 105.4 | 105.4 | 105.2 |

TABLE 16

Body Temperature - RxI.

| | | Study Day | | | | | | | | | | | | |
|---|---|---|---|---|---|---|---|---|---|---|---|---|---|---|
| | Pig ID | -29 | -28 | -1 | 1 | 2 | 3 | 4 | 5 | 6 | 7 | 8 | 9 | 10 |
| Rx I | 66 | 104.5 | 103.9 | 104.5 | 104.2 | 104.0 | 106.1 | 104.7 | 106.0 | 105.3 | 104.6 | 104.6 | 104.4 | 104.2 |
| Pens 3 & 6 | 67 | 105.5 | 104.1 | 104.5 | 103.8 | 104.7 | 104.9 | 105.4 | 105.8 | 106.0 | 106.6 | 105.3 | 105.6 | 105.2 |
| Vaccinated | 68 | 105.3 | 104.6 | 105.1 | 103.8 | 103.7 | 105.4 | 105.6 | 106.8 | 104.3 | 103.5 | 103.7 | 104.8 | 104.6 |
| Challenged | 69 | 104.1 | 103.2 | 103.9 | 104.2 | 104.1 | 104.3 | 104.5 | 104.4 | 104.9 | 104.7 | 104.4 | 103.3 | 104.3 |
| | 70 | 103.7 | 104.1 | 104.1 | 103.4 | 104.3 | 106.0 | 104.5 | 106.4 | 103.9 | 104.8 | 103.8 | 104.3 | 103.5 |
| | 71 | 105.1 | 103.7 | 103.9 | 103.8 | 104.9 | 106.1 | 107.4 | 106.7 | 105.5 | 104.2 | 103.6 | 104.2 | 103.7 |
| | 72 | 104.4 | 104.3 | 104.0 | 104.5 | 104.6 | 105.2 | 105.3 | 105.4 | 104.8 | 104.5 | 104.7 | 105.4 | 104.9 |
| | 73 | 103.5 | 103.5 | 104.8 | 103.9 | 105.4 | 105.9 | 107.6 | 105.5 | 103.8 | 104.0 | 103.9 | 104.2 | 104.8 |
| | 74 | 105.0 | 104.5 | 103.9 | 103.9 | 104.1 | 103.7 | 105.9 | 104.6 | 104.8 | 104.5 | 104.5 | 104.5 | 104.2 |
| Average | | 104.6 | 103.9 | 104.3 | 103.9 | 104.4 | 105.3 | 105.7 | 105.7 | 104.8 | 104.6 | 104.3 | 104.5 | 104.4 |

TABLE 17

Body Temperature - RxII.

| | | Study Day | | | | | | | | | | | | |
|---|---|---|---|---|---|---|---|---|---|---|---|---|---|---|
| | Pig ID | -29 | -28 | -1 | 1 | 2 | 3 | 4 | 5 | 6 | 7 | 8 | 9 | 10 |
| Rx II Pens 2 | 57 | 104.6 | 103.3 | 103.7 | 104.1 | 103.8 | 105.3 | 107.6 | 106.3 | 104.2 | 104.7 | 104.9 | 105.9 | 105.3 |
| and 8 | 58 | 104.2 | 103.0 | 104.5 | 104.0 | 105.0 | 107.0 | 107.5 | 107.0 | 104.8 | 104.4 | 104.3 | 104.6 | 104.9 |
| Vaccinated | 59 | 104.5 | 104.5 | 103.7 | 104.1 | 104.0 | 104.0 | 106.0 | 106.6 | 106.1 | 105.4 | 104.6 | 104.6 | 104.9 |
| Challenged | 60 | 104.3 | 103.4 | 103.1 | 104.0 | 103.5 | 105.5 | 106.8 | 106.6 | 105.4 | 105.4 | 104.8 | 104.8 | 104.6 |
| | 61 | 104.4 | 103.4 | 104.5 | 104.2 | 103.3 | 104.2 | 104.5 | 105.5 | 105.1 | 105.4 | 104.5 | 104.0 | 103.7 |
| | 62 | 104.2 | 103.6 | 104.6 | 103.0 | 104.3 | 105.0 | 106.0 | 106.9 | 104.5 | 104.5 | 103.8 | 103.7 | 103.9 |
| | 63 | 105.5 | 103.7 | 103.4 | 103.8 | 104.4 | 104.1 | 105.6 | 107.5 | 106.9 | 106.8 | 105.6 | 106.3 | 106.7 |
| | 64 | 104.4 | 103.0 | 104.3 | 103.5 | 103.5 | 105.1 | 105.0 | 105.1 | 104.3 | 104.6 | 104.4 | 104.6 | 104.2 |
| | 65 | 104.0 | 104.2 | 104.3 | 104.5 | 104.6 | 105.0 | 105.3 | 105.4 | 105.4 | 105.9 | 105.7 | 105.2 | 103.7 |
| Average | | 104.5 | 103.6 | 104.0 | 103.9 | 104.0 | 105.0 | 106.0 | 106.3 | 105.2 | 105.2 | 104.7 | 104.9 | 104.7 |

TABLE 18

Body Temperature - RxIII.

| | | Study Day | | | | | | | | | | | | |
|---|---|---|---|---|---|---|---|---|---|---|---|---|---|---|
| | Pig ID | -29 | -28 | -1 | 1 | 2 | 3 | 4 | 5 | 6 | 7 | 8 | 9 | 10 |
| Rx III | 80 | 104.5 | 103.7 | 104.1 | 103.5 | 103.7 | 104.2 | 106.1 | 106.6 | 106.5 | 105.2 | 105.8 | 105.5 | 105.3 |
| Pens 4 and 7 | 82 | 104.5 | 103.7 | 104.0 | 104.0 | 106.2 | 106.2 | 106.8 | 108.2 | 106.8 | 105.4 | 106.0 | 104.3 | 104.3 |
| Vacc + Chall | 83 | 104.8 | 103.4 | 104.2 | 104.5 | 104.0 | 105.5 | 107.0 | 107.0 | 106.4 | 104.8 | 105.0 | 104.7 | 104.5 |
| | 84 | 104.8 | 103.0 | 103.5 | 103.9 | 106.6 | 106.1 | 106.1 | 106.3 | 105.5 | 104.5 | 104.6 | 104.4 | 104.1 |
| | 85 | 104.8 | 104.5 | 104.1 | 103.9 | 103.9 | 103.4 | 104.8 | 107.4 | 105.3 | 103.9 | 104.5 | 104.7 | 103.5 |
| | 86 | 104.7 | 103.3 | 104.7 | 104.6 | 103.9 | 105.5 | 106.9 | 107.0 | 107.2 | 106.5 | 106.2 | 105.2 | 104.5 |
| | 87 | 104.3 | 103.9 | 103.6 | 104.7 | 105.0 | 104.8 | 107.9 | 107.9 | 107.9 | 106.1 | 105.9 | 105.7 | 105.3 |
| | 88 | 104.8 | 104.0 | 105.2 | 103.8 | 104.1 | 104.4 | 103.9 | 106.5 | 106.3 | 103.6 | 103.8 | 104.8 | 105.2 |
| | 89 | 104.6 | 103.8 | 104.7 | 103.6 | 105.0 | 104.8 | 106.0 | 107.3 | 106.2 | 104.9 | 104.7 | 103.8 | 103.7 |
| Average | | 104.6 | 103.7 | 104.2 | 104.1 | 104.7 | 105.0 | 106.2 | 107.1 | 106.5 | 105.0 | 105.2 | 104.8 | 104.5 |

Figure 11:
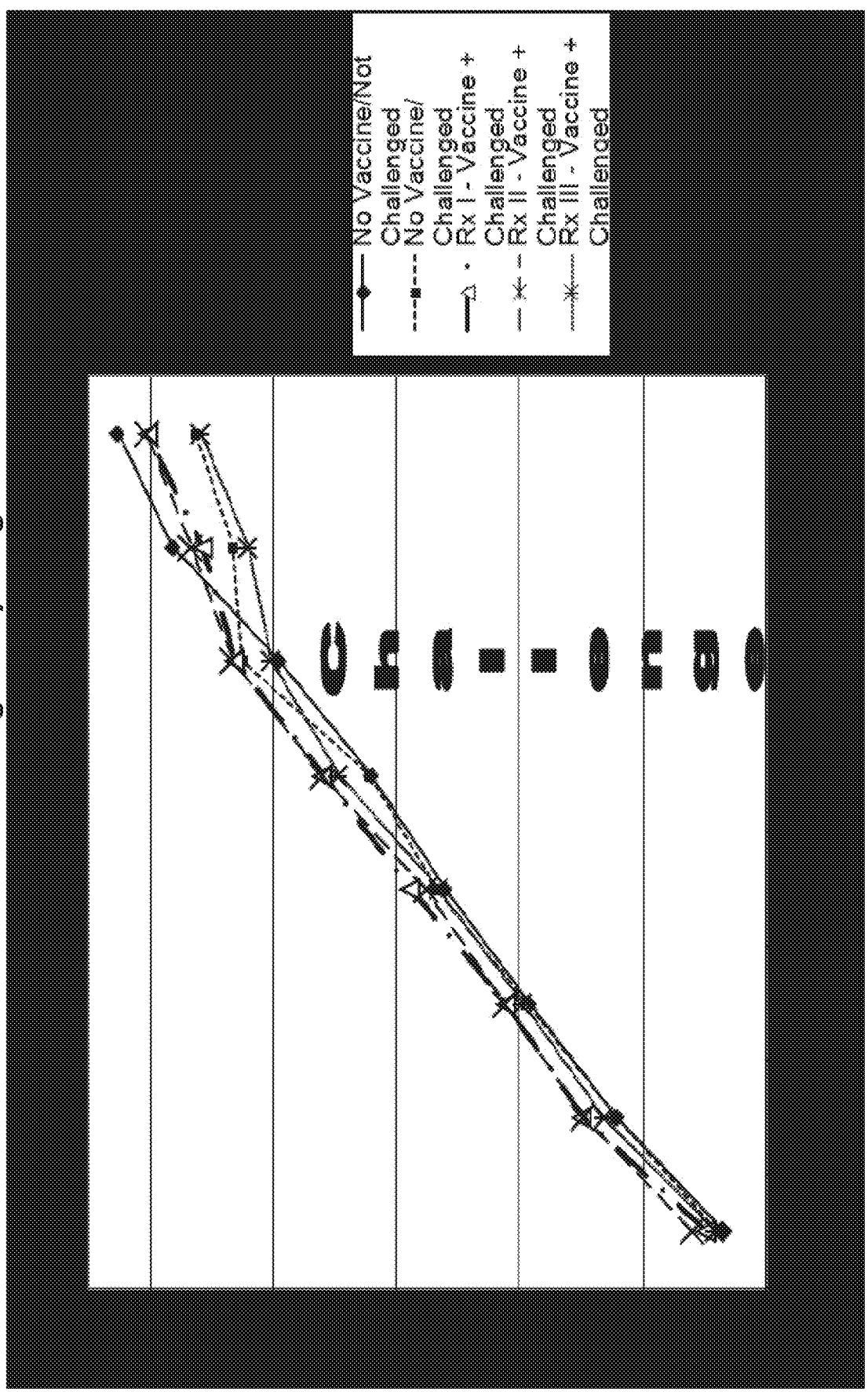
FIG. 11 graphically illustrates the average body weight by group prior to and after challenge with virulent PRRS virus for treatment groups including no vaccine/not challenged (filled diamond), no vaccine/challenged (filled square), Rx I vaccine plus 10 µg immunomodulator plus challenge (open triangle), Rx II vaccine plus 50 µg immunomodulator plus challenge (cross), Rx III vaccine plus challenge (star)
Figure 12:
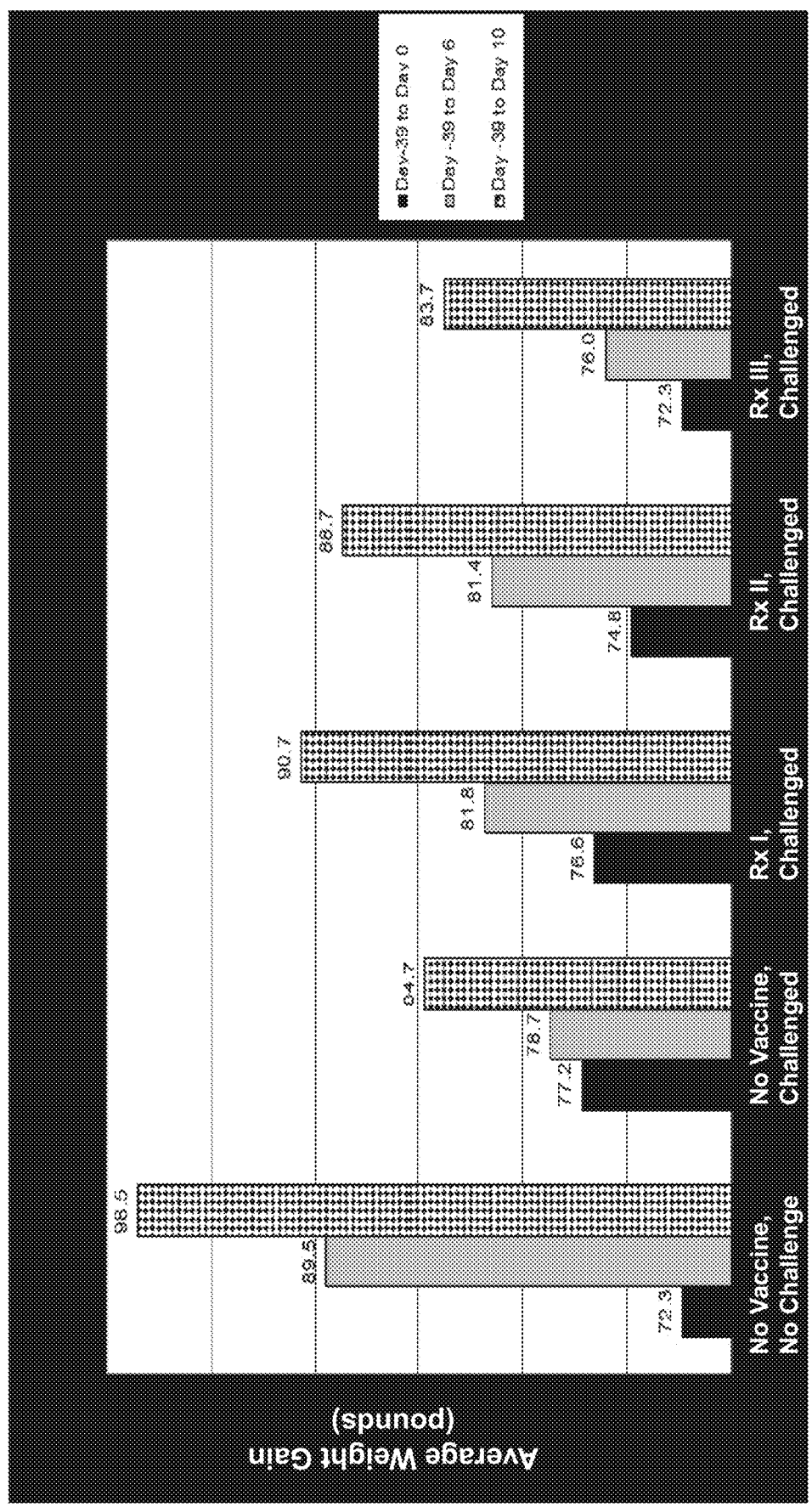
FIG. 12 graphically illustrates the average body weight gain by groups from day −39 to day 10, including gains from day −39 to day 0 (black), day −39 to day 6 (gray), and day −39 to day 10 (dotted)
Figure 13:
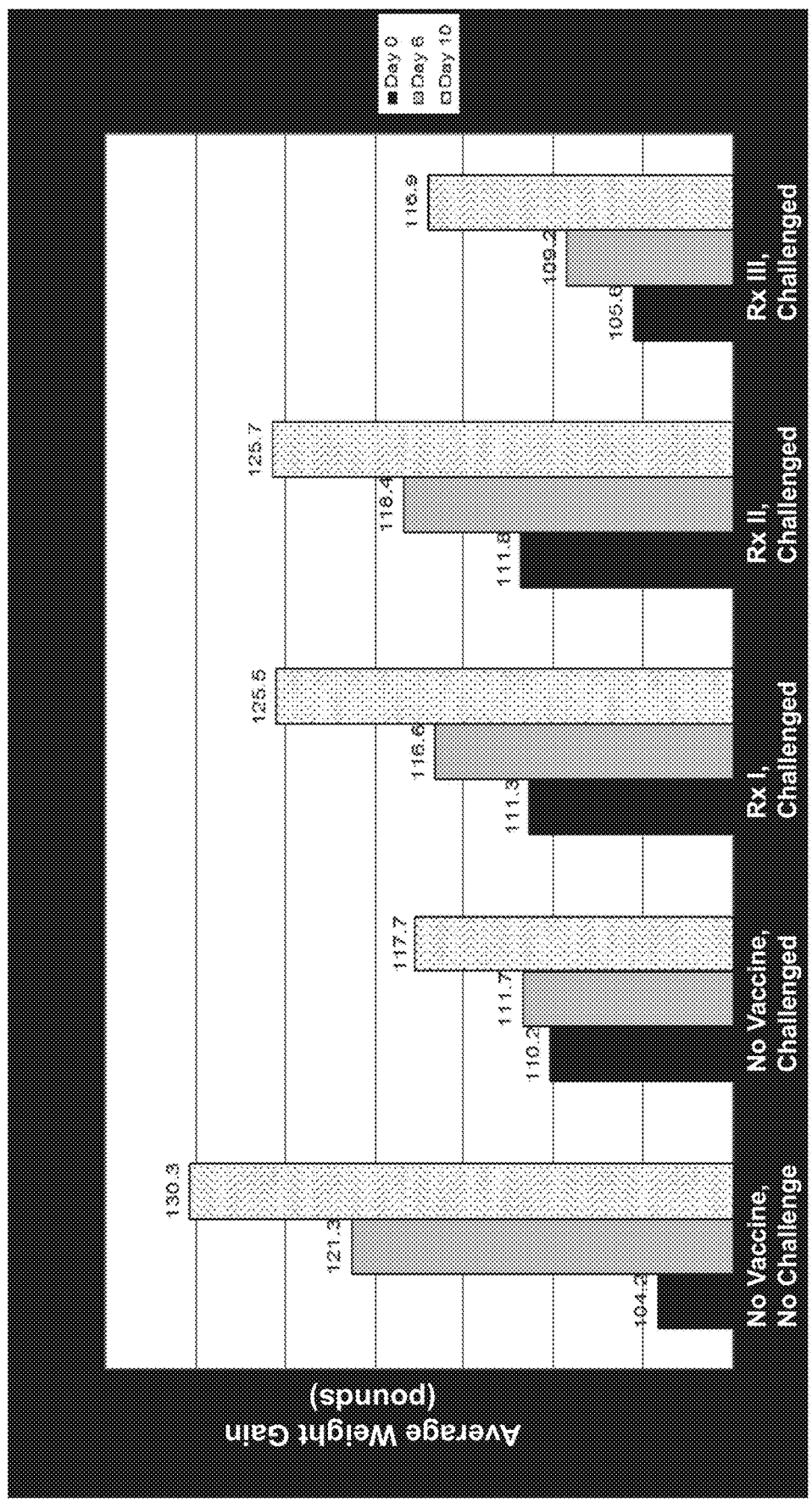
FIG. 13 graphically illustrates the average post challenge body weight by groups on day 0 (black), day 6 (gray), and day 10 (dotted)
Figure 14:
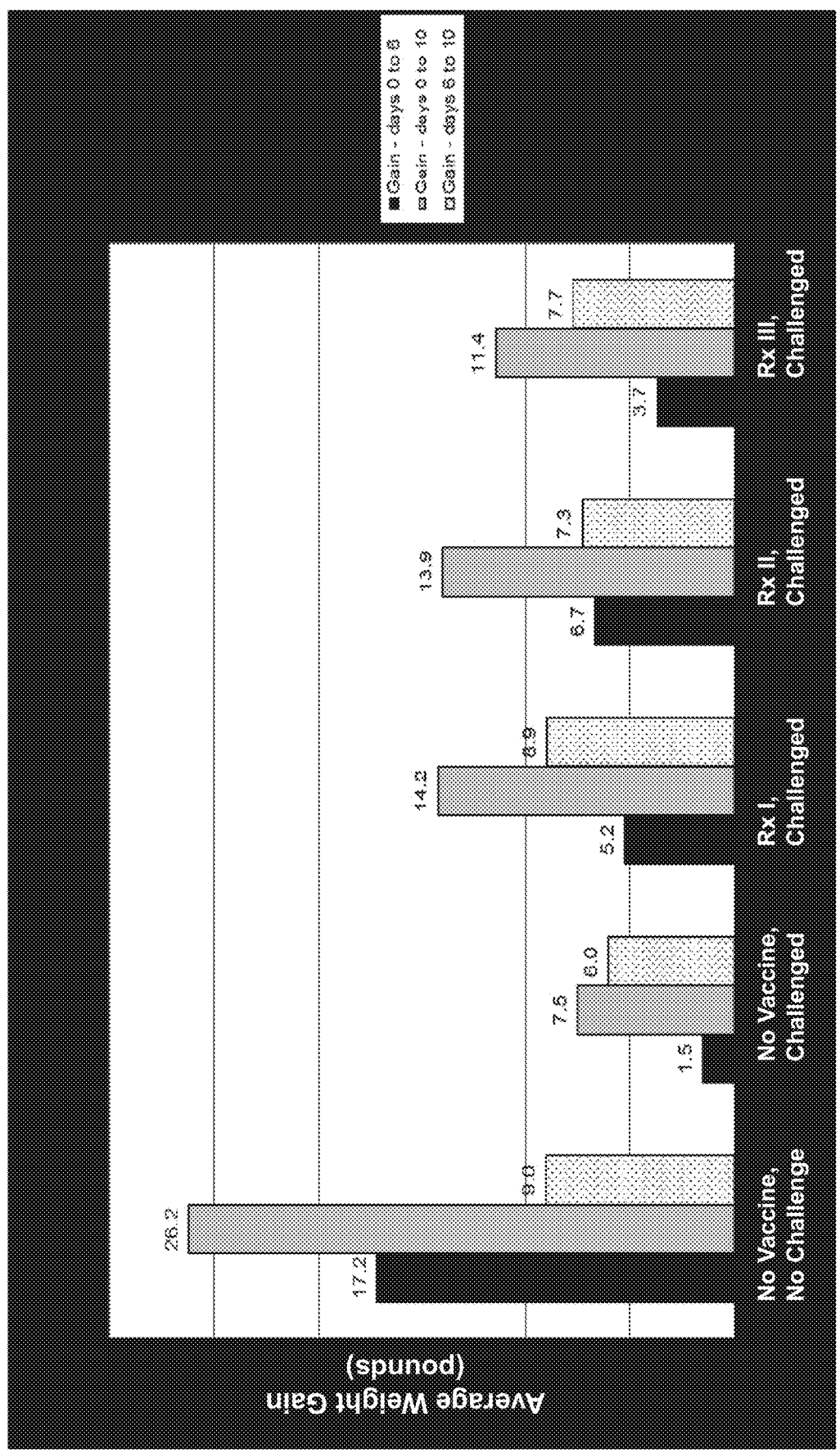
FIG. 14 graphically illustrates the post challenge body weight gain for days 0 to 6 (black), days 0 to 10 (gray), and days 6 to 10 (dotted)
Figure 15:
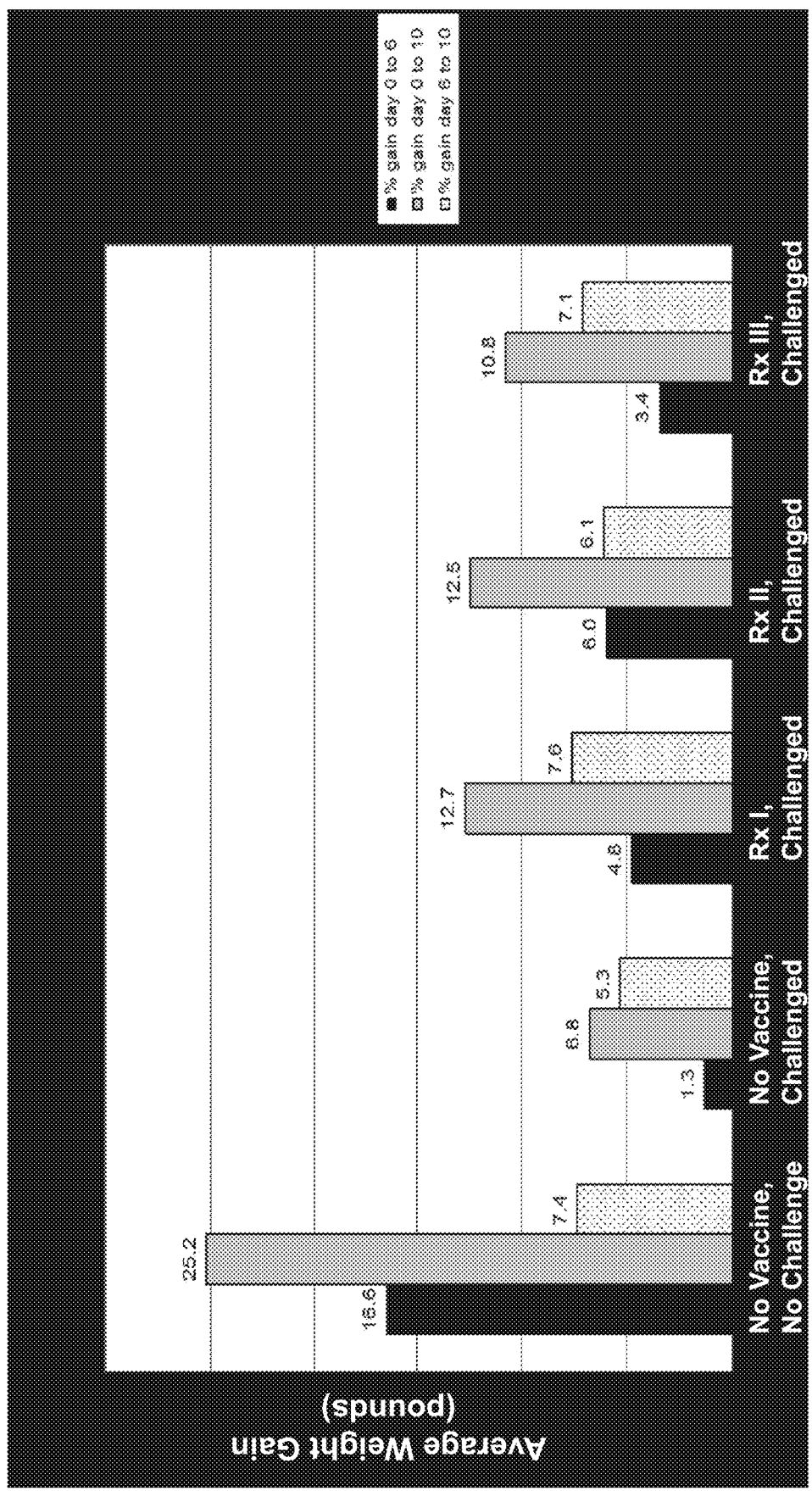
FIG. 15 graphically illustrates the post challenge body weight gain percent for days 0 to 6 (black), days 0 to 10 (gray), and days 6 to 10 (dotted)

Average body weights by group prior to and after challenge with virulent PPRS virus are included in FIG. 11. Average body weight gain (Day 10 weight-Day -39 weight) by groups from Day -39 to Day 10 are included in FIG. 12 from Day -39. Among the PRRS virus challenged groups, IC-Ex.1 immunomodulator administered groups (RxI and RxII) had higher body weight gain on Day 10 when compared to unvaccinated or PRRS vaccinated (RxIII) groups. Individual animal body weights are included in Tables 19 to 23. At the end of the study (Day 10), among the PRRS virus challenged groups, IC-Ex.1 immunomodulator groups (RxI and RxII) had higher body weight, 125.5 and 125.7 pounds, respectively; as compared to unvaccinated or PRRS vaccinated (RxIII) groups with 116.9 and 117.7 pounds, respectively (FIG. 13). After challenge among the PRRS virus challenged groups, IC-Ex.1 immunomodulator+PRRS vaccinated groups (RxI and RxII) had higher body weight gain, 14.2 (12.7%) and 13.9 (12.5%) pounds, respectively (FIGS. 14 and 15); as compared to unvaccinated or PRRS vaccinated (RxIII) groups with 7.5 (6.8%) and 11.4 (10.8%) pounds, respectively and. Individual animal body weights after challenge are included in Tables 19 to 23.

TABLE 19

Body Weight (Pounds) Rx Not Vaccinated and Not Challenged.

| | Pig | Study Day | | | | | | | |
|---|---|---|---|---|---|---|---|---|---|
| Rx | ID | -39 | -29 | -21 | -14 | -7 | 0 | 6 | 10 |
| Not Vaccinated | 51 | 30.0 | 44.0 | 60.0 | 74.0 | 85.0 | 103.0 | 120.0 | 130.0 |

TABLE 19-continued

Body Weight (Pounds) Rx Not Vaccinated and Not Challenged.

| Rx | Pig ID | Study Day -39 | -29 | -21 | -14 | -7 | 0 | 6 | 10 |
|---|---|---|---|---|---|---|---|---|---|
| Not challenged | 52 | 34.0 | 51.0 | 64.0 | 74.0 | 87.0 | 97.0 | 117.0 | 124.0 |
| | 53 | 33.0 | 51.0 | 65.0 | 79.0 | 92.0 | 100.0 | 119.0 | 128.0 |
| | 54 | 27.0 | 49.0 | 64.0 | 79.0 | 91.0 | 108.0 | 124.0 | 133.0 |
| | 55 | 34.0 | 50.0 | 64.0 | 75.0 | 87.0 | 104.0 | 118.0 | 126.0 |
| | 56 | 33.0 | 51.0 | 64.0 | 82.0 | 93.0 | 113.0 | 130.0 | 141.0 |
| Average | | 31.8 | 49.3 | 63.5 | 77.2 | 89.2 | 104.2 | 121.3 | 130.3 |

TABLE 20

Body Weight (Pounds) Not vaccinated challenged.

| | Pig ID | Study Day -39 | -29 | -21 | -14 | -7 | 0 | 6 | 10 |
|---|---|---|---|---|---|---|---|---|---|
| Vaccinated Challenged | 75 | 31.0 | 47.0 | 60.0 | 73.0 | 88.0 | 102.0 | 101.0 | 107.5 |
| | 76 | 34.0 | 51.0 | 66.0 | 82.0 | 94.0 | 115.0 | 115.0 | 115.5 |
| | 77 | 36.0 | 55.0 | 73.0 | 87.0 | 97.0 | 118.0 | 126.0 | 136.0 |
| | 78 | 33.0 | 47.0 | 62.0 | 75.0 | 87.0 | 107.0 | 106.0 | 110.0 |
| | 79 | 30.0 | 45.0 | 59.0 | 76.0 | 84.0 | 105.0 | 110.0 | 117.5 |
| | 81 | 34.0 | 51.0 | 63.0 | 79.0 | 86.0 | 114.0 | 112.0 | 119.5 |
| Average | | 33.0 | 49.3 | 63.8 | 78.72 | 89.3 | 110.2 | 111.7 | 117.7 |

TABLE 21

Body Weight (Pounds) Rx I Vaccinated Challenged.

| | Pig ID | Study Day -39 | -29 | -21 | -14 | -7 | 0 | 6 | 10 |
|---|---|---|---|---|---|---|---|---|---|
| Rx I Vaccinated + Challenged | 66 | 32.0 | 50.0 | 63.0 | 79.0 | 94.0 | 108.0 | 116.0 | 125.0 |
| | 67 | 37.0 | 58.0 | 73.0 | 86.0 | 101.0 | 118.0 | 123.0 | 129.5 |
| | 68 | 31.0 | 56.0 | 71.0 | 90.0 | 105.0 | 121.0 | 131.0 | 143.5 |
| | 69 | 32.0 | 53.0 | 66.0 | 79.0 | 90.0 | 96.0 | 107.0 | 111.0 |
| | 70 | 30.0 | 58.0 | 70.0 | 88.0 | 102.0 | 121.0 | 120.0 | 130.0 |
| | 71 | 35.0 | 48.0 | 62.0 | 76.0 | 92.0 | 107.0 | 105.0 | 114.5 |
| | 72 | 38.0 | 57.0 | 62.0 | 79.0 | 87.0 | 101.0 | 105.0 | 111.5 |
| | 73 | 37.0 | 57.0 | 71.0 | 88.0 | 104.0 | 115.0 | 122.0 | 130.0 |
| | 74 | 41.0 | 57.0 | 68.0 | 80.0 | 98.0 | 115.0 | 120.0 | 134.5 |
| Average | | 34.8 | 54.9 | 67.3 | 82.8 | 97.0 | 111.3 | 116.6 | 125.5 |

TABLE 22

Body Weight (Pounds) Rx II vaccinated challenged.

| | Pig ID | Study Day -39 | -29 | -21 | -14 | -7 | 0 | 6 | 10 |
|---|---|---|---|---|---|---|---|---|---|
| Rx II Vaccinated + Challenged | 57 | 42.0 | 62.0 | 73.0 | 82.0 | 102.0 | 120.0 | 127.0 | 138.0 |
| | 58 | 38.0 | 58.0 | 70.0 | 83.0 | 97.0 | 113.0 | 118.0 | 126.5 |
| | 59 | 37.0 | 50.0 | 63.0 | 76.0 | 92.0 | 107.0 | 113.0 | 115.5 |
| | 60 | 38.0 | 58.0 | 72.0 | 81.0 | 105.0 | 119.0 | 124.0 | 133.0 |
| | 61 | 34.0 | 50.0 | 63.0 | 80.0 | 92.0 | 107.0 | 110.0 | 116.5 |
| | 62 | 37.0 | 56.0 | 69.0 | 85.0 | 100.0 | 117.0 | 127.0 | 132.5 |
| | 63 | 38.0 | 55.0 | 70.0 | 83.0 | 95.0 | 111.0 | 114.0 | 122.0 |
| | 64 | 36.0 | 54.0 | 66.0 | 80.0 | 93.0 | 107.0 | 118.0 | 125.0 |
| | 65 | 33.0 | 49.0 | 62.0 | 73.0 | 98.0 | 105.0 | 115.0 | 122.5 |
| Average | | 37.0 | 54.7 | 67.6 | 80.3 | 97.1 | 111.8 | 118.4 | 125.7 |

TABLE 23

Body Weight (Pounds) Rx III vaccinated challenged.

| | Pig ID | Study Day -39 | -29 | -21 | -14 | -7 | 0 | 6 | 10 |
|---|---|---|---|---|---|---|---|---|---|
| Rx III Vaccinated + Challenged | 80 | 33.0 | 51.0 | 62.0 | 77.0 | 91.0 | 104.0 | 111.0 | 118.0 |
| | 82 | 35.0 | 54.0 | 69.0 | 83.0 | 99.0 | 114.0 | 120.0 | 125.5 |
| | 83 | 30.0 | 46.0 | 60.0 | 73.0 | 87.0 | 95.0 | 98.0 | 107.5 |
| | 84 | 38.0 | 56.0 | 63.0 | 80.0 | 93.0 | 105.0 | 113.0 | 120.5 |
| | 85 | 30.0 | 50.0 | 67.0 | 74.0 | 95.0 | 102.0 | 103.0 | 113.5 |
| | 86 | 34.0 | 52.0 | 67.0 | 82.0 | 102.0 | 111.0 | 118.0 | 127.0 |
| | 87 | 34.0 | 52.0 | 66.0 | 80.0 | 95.0 | 105.0 | 103.0 | 106.0 |
| | 88 | 32.0 | 52.0 | 65.0 | 79.0 | 96.0 | 110.0 | 112.0 | 122.5 |
| | 89 | 33.0 | 49.0 | 63.0 | 76.0 | 92.0 | 104.0 | 105.0 | 112.0 |
| Average | | 33.2 | 51.3 | 64.7 | 78.2 | 94.4 | 105.6 | 109.2 | 116.9 |

TABLE 24

Post Challenge Body Weight - Not vaccinated Not challenged Rx.

| | Pig ID | Day 0 | Day 6 | Gain days 0 to 6 | Average daily gain 0 to 6 days | % gain day 0 to 6 | Day 10 | Gain days 0 to 10 | Average daily gain 0 to 10 days | % gain day 0 to 10 | Gain days 6 to 10 | Average daily gain 6 to 10 days | % gain day 6 to 10 |
|---|---|---|---|---|---|---|---|---|---|---|---|---|---|
| Rx Not Vaccinated Not challenged | 51 | 103 | 120 | 17.0 | 2.83 | 116.5 | 130 | 27.0 | 2.7 | 126.2 | 10 | 2.5 | 108.3 |
| | 52 | 97 | 117 | 20.0 | 3.33 | 120.6 | 124 | 27.0 | 2.7 | 127.8 | 7 | 1.8 | 106.0 |
| | 53 | 100 | 119 | 19.0 | 3.17 | 119.0 | 128 | 28.0 | 2.8 | 128.0 | 9 | 2.3 | 107.6 |
| | 54 | 108 | 124 | 16.0 | 2.67 | 114.8 | 133 | 25.0 | 2.5 | 123.1 | 9 | 2.3 | 107.3 |
| | 55 | 104 | 118 | 14.0 | 2.33 | 113.5 | 126 | 22.0 | 2.2 | 121.2 | 8 | 2.0 | 106.8 |
| | 56 | 113 | 130 | 17.0 | 2.83 | 115.0 | 141 | 28.0 | 2.8 | 124.8 | 11 | 2.8 | 108.5 |
| Average | | 104.2 | 121.3 | 17.2 | 2.9 | 116.6 | 130.3 | 26.2 | 2.6 | 125.2 | 9.0 | 2.3 | 107.4 |

TABLE 25

Post Challenge Body Weight - (Pounds) Not vaccinated challenged.

| | Pig ID | Day 0 | Day 6 | Gain days 0 to 6 | Average daily gain 0 to 6 days | % gain days 0 to 6 | Day 10 | Gain days 0 to 10 | Average daily gain 0 to 10 days | % gain 0 to 10 | Gain days 6 to 10 | Average daily gain 6 to 10 days | % gain day 6 to 10 |
|---|---|---|---|---|---|---|---|---|---|---|---|---|---|
| Rx | 75 | 102 | 101 | −1.0 | −0.17 | 99.0 | 107.5 | 5.5 | 0.6 | 105.4 | 6.5 | 1.6 | 106.4 |
| Not | 76 | 115 | 115 | 1.0 | 0.00 | 100.0 | 115.5 | 0.5 | 0.1 | 1..04 | 0.5 | 0.1 | 100.4 |
| Vaccinated | 77 | 118 | 126 | 8.0 | 1.33 | 106.8 | 136 | 18.0 | 1.8 | 115.3 | 10 | 2.5 | 107.9 |
| Challenged | 78 | 107 | 106 | −1.0 | −0.17 | 99.1 | 110 | 3.0 | 0.3 | 102.8 | 4 | 1.0 | 103.8 |
| | 79 | 105 | 110 | 5.0 | 0.83 | 104.8 | 117.5 | 12.5 | 1.3 | 111.9 | 7.5 | 1.9 | 106.8 |
| | 81 | 114 | 112 | −2.0 | −0.33 | 98.2 | 119.5 | 5.5 | 0.6 | 104.8 | 7.5 | 1.9 | 106.7 |
| Average | | 110.2 | 111.7 | 1.5 | 0.3 | 101.3 | 117.7 | 7.5 | 0.8 | 106.8 | 6.0 | 1.5 | 105.3 |

TABLE 26

Post Challenge Body Weight - (Pounds) vaccinated challenged Rx I.

| | Pig ID | Day 0 | Day 6 | Gain days 0 to 6 | Average daily gain 0 to 6 | % gain day 0 to 6 | Day 10 | Gain days 0 to 10 | Average daily gain 0 to 10 | % gain day 0 to 10 | Gain days 6 to 10 | Average daily gain 6 to 10 | % gain day 6 to 10 |
|---|---|---|---|---|---|---|---|---|---|---|---|---|---|
| Rx I | 66 | 108 | 116 | 8.0 | 1.33 | 107.4 | 125 | 17.0 | 1.7 | 115.7 | 9 | 2.3 | 107.8 |
| Vaccinated + | 67 | 118 | 123 | 5.0 | 0.83 | 104.2 | 129. | 11.5 | 1.2 | 109.7 | 6.5 | 1.6 | 105.3 |
| Challenged | 68 | 121 | 131 | 10.0 | 1.67 | 108.3 | 143. | 22.5 | 2.3 | 118.6 | 12.5 | 3.1 | 109.5 |
| | 69 | 96 | 107 | 11.0 | 1.83 | 111.5 | 111 | 15.0 | 1.5 | 115.6 | 4 | 1.0 | 103.7 |
| | 70 | 121 | 120 | −1.0 | −0.17 | 99.2 | 130 | 9.0 | 0.9 | 107.4 | 10 | 2.5 | 108.3 |
| | 71 | 107 | 105 | −2.0 | −0.33 | 98.1 | 114. | 7.5 | 0.8 | 107.0 | 9.5 | 2.4 | 109.0 |
| | 72 | 101 | 105 | 4.0 | 0.67 | 104.0 | 111. | 10.5 | 1.1 | 110.4 | 6.5 | 1.6 | 106.2 |
| | 73 | 115 | 122 | 7.0 | 1.17 | 106.1 | 130 | 15.0 | 1.5 | 113.0 | 8 | 2.0 | 106.6 |
| | 74 | 115 | 120 | 5.0 | 0.83 | 104.3 | 134. | 19.5 | 2.0 | 117.0 | 14.5 | 3.6 | 112.1 |
| Average | | 111.3 | 116.6 | 5.2 | 0.9 | 104.8 | 125. | 14.2 | 1.4 | 112.7 | 8.9 | 2.2 | 107.6 |

TABLE 27

Post Challenge Body Weight - (Pounds) vaccinated challenged Rx II.

| | Pig ID | Day 0 | Day 6 | Gain days 0 to 6 | Average daily gain 0 to 6 | % gain day 0 to 6 | Day 10 | Gain days 0 to 10 | Average daily gain 0 to 10 | % gain day 0 to 10 | Gain days 6 to 10 | Average daily gain 6 to 10 | % gain day 6 to 10 |
|---|---|---|---|---|---|---|---|---|---|---|---|---|---|
| Rx II | 57 | 120 | 127 | 7.0 | 1.17 | 105.8 | 138 | 18.0 | 1.8 | 115.0 | 11 | 2.8 | 108.7 |
| Vaccinated + | 58 | 113 | 118 | 5.0 | 0.83 | 104.4 | 126.5 | 13.5 | 1.4 | 111.9 | 8.5 | 2.1 | 107.2 |
| Challenged | 59 | 107 | 113 | 6.0 | 1.00 | 105.6 | 115.5 | 8.5 | 0.9 | 107.9 | 2.5 | 0.6 | 102.2 |
| | 60 | 119 | 124 | 5.0 | 0.83 | 104.2 | 133 | 14.0 | 1.4 | 111.8 | 9 | 2.3 | 107.3 |
| | 61 | 107 | 110 | 3.0 | 0.50 | 102.8 | 116.5 | 9.5 | 1.0 | 108.9 | 6.5 | 1.6 | 105.9 |
| | 62 | 117 | 127 | 10.0 | 1.67 | 108.5 | 132.5 | 15.5 | 1.6 | 113.2 | 5.5 | 1.4 | 104.3 |
| | 63 | 111 | 114 | 3.0 | 0.50 | 102.7 | 122 | 11.0 | 1.1 | 109.9 | 8 | 2.0 | 107.0 |
| | 64 | 107 | 118 | 11.0 | 1.83 | 110.3 | 125 | 18.0 | 1.8 | 116.8 | 7 | 1.8 | 105.9 |
| | 65 | 105 | 115 | 10.0 | 1.67 | 109.5 | 122.5 | 17.5 | 1.8 | 116.7 | 7.5 | 1.9 | 106.5 |
| Average | | 111.8 | 118.4 | 6.7 | 1.1 | 106.0 | 125.7 | 13.9 | 1.4 | 112.5 | 7.3 | 1.8 | 106.1 |

TABLE 28

Post Challenge Body Weight - (Pounds) vaccinated challenged Rx II.

| | Pig ID | Day 0 | Day 6 | Gain days 0 to 6 | Average daily gain 0 to 6 days | % gain day 0 to 6 | Day 10 | Gain days 0 to 10 | Average daily gain 0 to 10 days | % gain day 0 to 10 | Gain days 6 to 10 | Average daily gain 6 to 10 days | % gain day 6 to 10 |
|---|---|---|---|---|---|---|---|---|---|---|---|---|---|
| Rx III | 80 | 104 | 111 | 7.0 | 1.17 | 106.7 | 118 | 14.0 | 1.4 | 113.5 | 7 | 1.8 | 106.3 |
| Vaccinated + | 82 | 114 | 120 | 6.0 | 1.00 | 105.3 | 125.5 | 11.5 | 1.2 | 110.1 | 5.5 | 1.4 | 104.6 |
| Challenged | 83 | 95 | 98 | 3.0 | 0.50 | 103.2 | 107.5 | 12.5 | 1.3 | 113.2 | 9.5 | 2.4 | 109.7 |
| | 84 | 105 | 113 | 8.0 | 1.33 | 107.6 | 120.5 | 15.5 | 1.6 | 114.8 | 7.5 | 1.9 | 106.6 |
| | 85 | 102 | 103 | 1.0 | 0.17 | 101.0 | 113.5 | 11.5 | 1.2 | 111.3 | 10.5 | 2.6 | 110.2 |
| | 86 | 111 | 118 | 7.0 | 1.17 | 106.3 | 127 | 16.0 | 1.6 | 114.4 | 9 | 2.3 | 107.6 |
| | 87 | 105 | 103 | −2.0 | −0.33 | 98.1 | 106 | 1.0 | 0.1 | 101.0 | 3 | 0.8 | 102.9 |
| | 88 | 110 | 112 | 2.0 | 0.33 | 101.8 | 122.5 | 12.5 | 1.3 | 111.4 | 10.5 | 2.6 | 109.4 |
| | 89 | 104 | 105 | 1.0 | 0.17 | 101.0 | 112 | 8.0 | 0.8 | 107.7 | 7 | 1.8 | 106.7 |
| Average | | 1055.6 | 109.2 | 3.7 | 0.6 | 103.4 | 116.9 | 11.4 | 1.1 | 110.8 | 7.7 | 1.9 | 107.1 |

Figure 16:
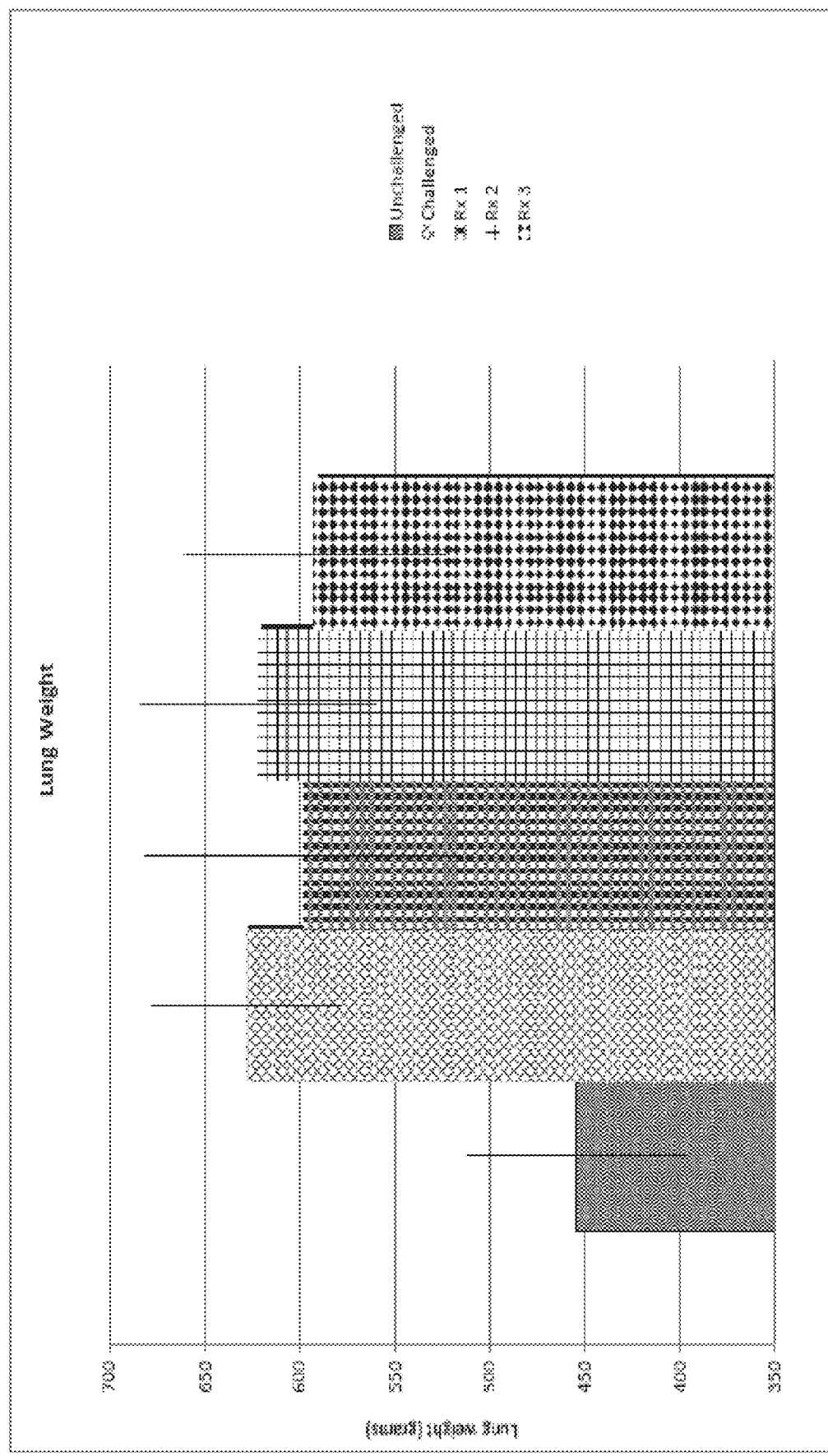
FIG. 16 graphically illustrates lung weight by groups, including unchallenged (filled squares), challenged (open diamonds), Rx 1 vaccine plus 10 µg immunomodulator plus challenge (filled and open squares), Rx 2 vaccine plus 50 µg immunomodulator plus challenge (open squares), and Rx 3 (filled and open diamonds)
Figure 17:
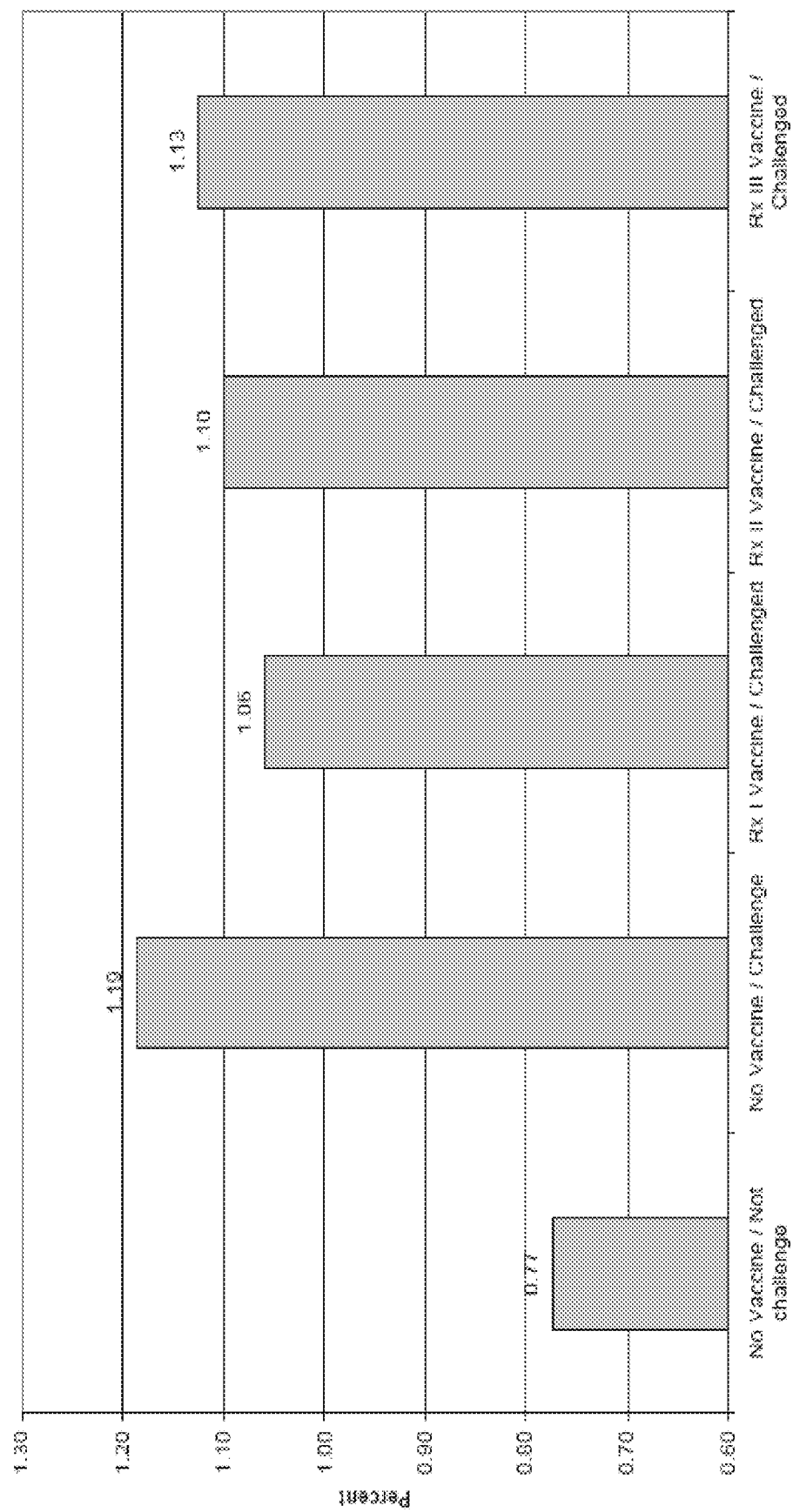
FIG. 17 graphically illustrates lung weight by groups as percent of body weight including no vaccine/not challenged, no vaccine/challenged, Rx I vaccine plus 10 µg immunomodulator/challenged, Rx II vaccine plus 50 µg immunomodulator/challenged, and Rx III vaccine/challenged.

Average lung weights by groups are included in FIG. 16. Average lung weights as percent of body weights by groups are included in FIG. 17. All the animals in the challenged groups had higher lung to body weight ratio and ranged from 1.06 (RxI) to 1.19 (non-vaccinated control) as compared to 0.77 for non-challenged control.

PRRS virus was isolated from serum samples on days 4, 7 and 10 following challenge. The non-challenged control animals remained negative for virus isolation supporting the integrity of the biosecurity implemented in the study. On study day 10 all the animals in non-vaccinated challenged animals were positive for virus isolation and ranged from $0.06\times10^4$ to $3.16\times10^4$ TCID50 per ml. Animals vaccinated with PRRS vaccine had low virus titer in the serum on Day 10. In RxI group, 7 of 9 animals were negative for virus isolation on Day 10. In RxII group, 5 of 9 animals were negative for virus isolation on Day 10. In RxIII group, 7 of 9 animals were negative for virus isolation on Day 10, as shown in Table 29.

TABLE 29

PRRSV titration in serum after challenge.

| Rx | Pig | Day post challenge |  |  |
|---|---|---|---|---|
|  |  | 4 | 7 | 10 |
|  |  | # × $10^4$ TCID50/ml |  |  |
| Not Vaccine/not chall. | 51 | Neg | neg | neg |
|  | 52 | Neg | neg | neg |
|  | 53 | Neg | neg | neg |
|  | 54 | Neg | neg | neg |
|  | 55 | Neg | neg | neg |
|  | 56 | Neg | neg | neg |
|  |  | Neg | neg | neg |
| Not Vaccine/challenged | 75 | 5.62 | 5.62 | 0.32 |
|  | 76 | 1.78 | 17.80 | 3.16 |
|  | 77 | 0.56 | 0.32 | 0.06 |
|  | 78 | 5.62 | 3.16 | 0.32 |
|  | 79 | 0.56 | 1.00 | 0.56 |
|  | 81 | 0.56 | 0.56 | 3.16 |
| mean |  | 2.45 | 4.74 | 1.26 |
| Rx I | 66 | 0.32 | 0.03 | 0 |
|  | 67 | 5.62 | 10.00 | 0.06 |
|  | 68 | 0.18 | 0.02 | 0.10 |
|  | 69 | 1.78 | 0.06 | 0 |
|  | 70 | 0.56 | 0.56 | 0 |
|  | 71 | 0.32 | 0.03 | 0 |
|  | 72 | 17.80 | 1.78 | 0 |
|  | 63 | 0.18 | 0.00 | 0 |
|  | 74 | 0.32 | 0.03 | 0 |
| mean |  | 3.01 | 1.39 | 0.02 |
| RxII | 57 | 3.16 | 0.06 | 0 |
|  | 58 | 5.62 | 0.0 | 0 |
|  | 59 | 1.00 | 3.16 | 0.32 |
|  | 60 | 1.00 | 0.03 |  |
|  | 61 | 5.62 | 0.06 | 0 |
|  | 62 | 3.16 | 0.18 |  |
|  | 63 | 0.56 | 0.06 | 0.10 |
|  | 64 | 1.78 | 0.03 | 0.02 |
|  | 65 | 0.56 | 0.56 | 0.01 |
| mean |  | 2.50 | 0.46 | 0.06 |
| Rx III | 80 | 3.16 | 0.32 | 0 |
|  | 82 | 1.78 | 0.56 | 0 |
|  | 83 | 0.56 | 0.06 | 0 |
|  | 84 | 0.56 | 0.06 | 0 |
|  | 85 | 1.78 | 0.32 | 0 |
|  | 86 | 0.56 | 0.18 | 0.06 |
|  | 87 | 5.62 | 0.32 | 0 |
|  | 88 | 0.32 | 0.18 | 0.56 |
|  | 89 | 1.78 | 0.03 | 0 |
| mean |  | 1.79 | 0.22 | 0.07 |

Figure 18:
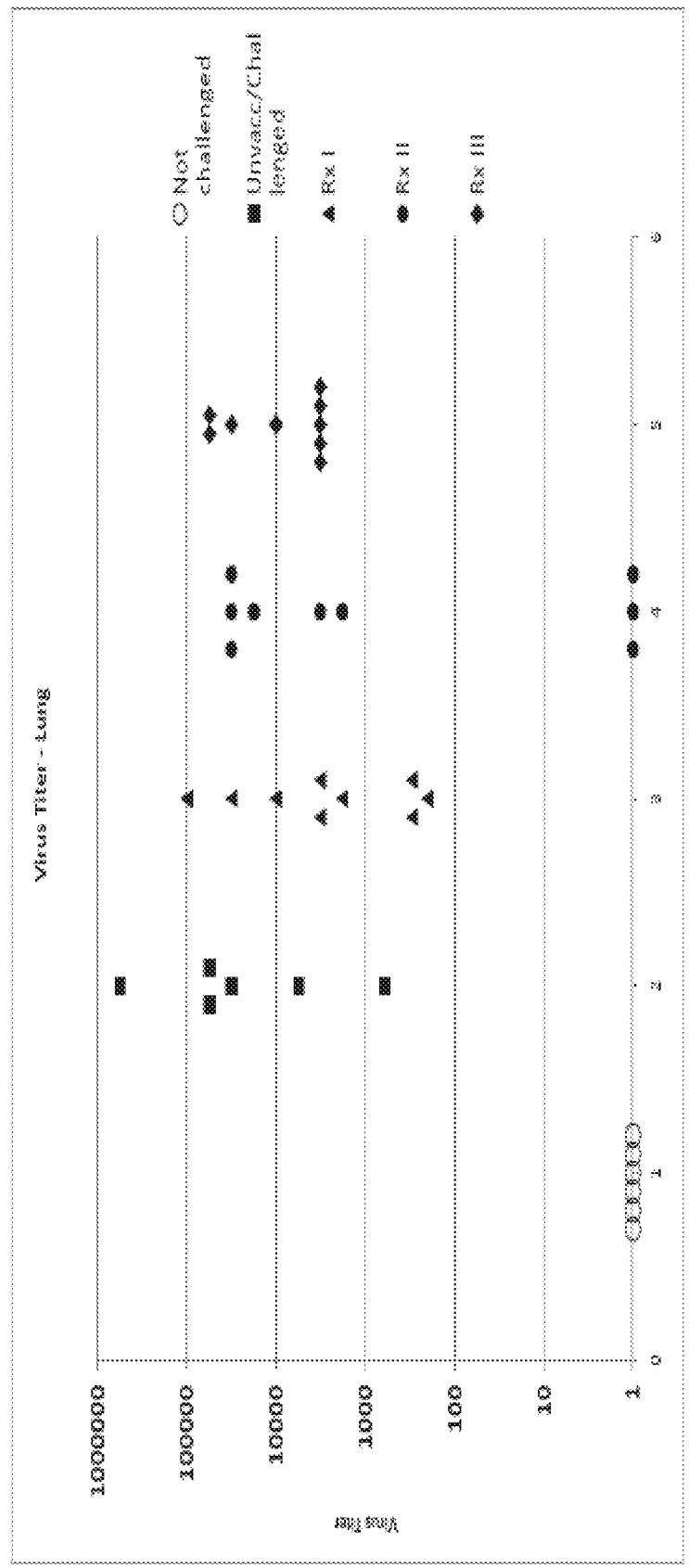
FIG. 18 graphically illustrates the PRRS virus isolated from the treatment groups including not challenged (open circle), no vaccine/challenged (filled square), Rx I vaccine plus 10 µg immunomodulator/challenged (filled triangle), Rx II vaccine plus 50 µg immunomodulator/challenged (filled circle), and Rx III vaccine/challenged (filled diamond)
Figure 19:
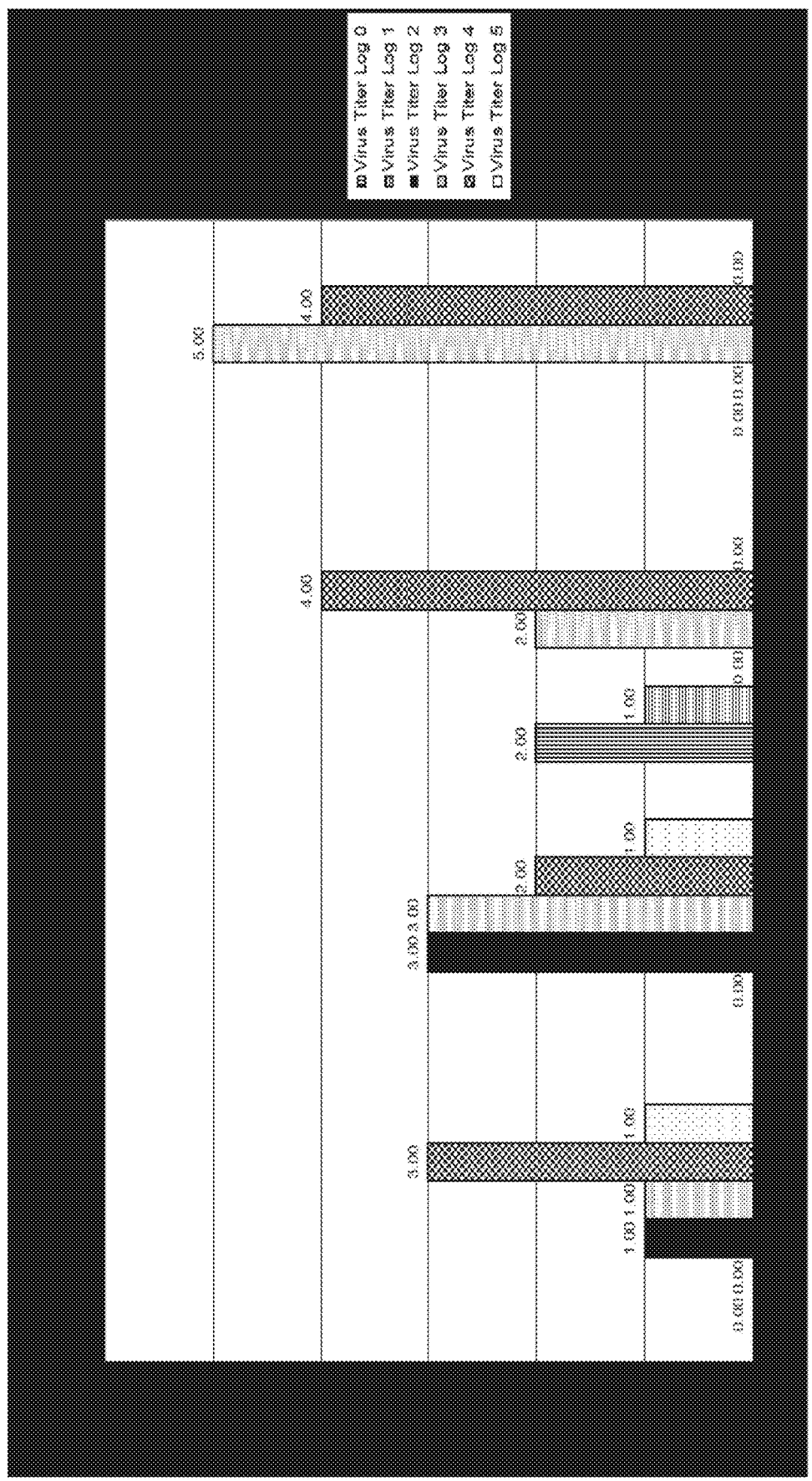
FIG. 19 graphically illustrates the lung virus titer isolated for by group.
Figure 20:
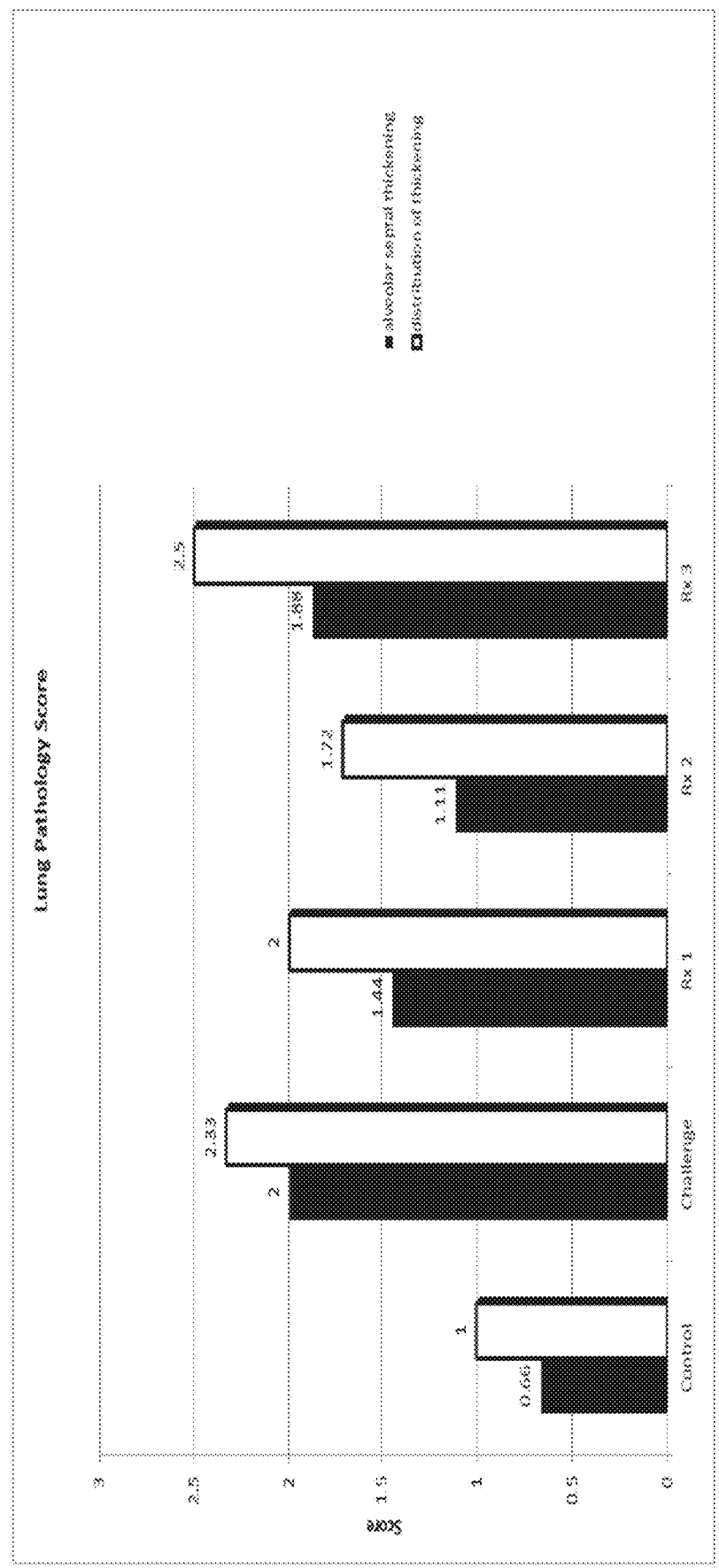
FIG. 20 graphically illustrates lung pathology scores for treatment groups including control, challenge, Rx I vaccine plus 10 µg immunomodulator/challenged, Rx II vaccine plus 50 µg immunomodulator/challenged, and Rx III vaccine/challenged based on alveolar septal thickening and distribution of thickening.

PRRS virus was isolated from individual animal lung samples. The non-challenged control animals' lung samples were negative for virus isolation supporting the integrity of the biosecurity implemented in the study. In group RxII two of nine animals were negative for virus isolation and one animal had less than $10^2$ virus in their lung samples. In all other animals in challenged groups the lung samples had titer ranged from $1.78\times10^2$ to $1.0\times10^5$ (FIGS. 18 and 19). Microscopic lung lesions for each animal were described in Tables 30 to 34. Among the challenged animals the lungs from animals in group RxII had the lowest average alveolar septal thickening and distribution of thickening corresponding to the lower virus recovery in this group (FIG. 20).

TABLE 30

Lung Pathology - Not vaccinated and Not challenged (Rx).

| Rx | Pig No. | Lung sample | Alveolar septal thickening | Distribution of thickening | Inflammatory cells in airways | comments |
|---|---|---|---|---|---|---|
| Not Vaccinated | 51 | Left | 1 | 0 | 0 |  |
|  |  | Right | 1 | 1 | 0 |  |
|  | 52 | Left | 0 | 0 | 0 |  |
| Pen 1 |  | Right | 0 | 0 | 0 |  |
|  | 53 | Left | 0 | 0 | 0 |  |
|  |  | Right | 0 | 0 | 0 |  |
|  | 54 | Left | 1 | 2 | 0 |  |
|  |  | Right | 1 | 2 | 0 |  |
|  | 55 | Left | 1 | 2 | 0 |  |
|  |  | Right | 1 | 2 | 0 |  |
|  | 56 | Left | 1 | 1 | 1 | Lymphocytes, plasma cells and neutrophils in bronchioles |

TABLE 30-continued

Lung Pathology - Not vaccinated and Not challenged (Rx).

| Rx | Pig No. | Lung sample | Alveolar septal thickening | Distribution of thickening | Inflammatory cells in airways | comments |
|---|---|---|---|---|---|---|
| | | Right | 1 | 1 | 1 | Lymphocytes, plasma cells and neutrophils in bronchioles |
| | Average | | 0.7 | 1.0 | 0.2 | |

Pathology score criteria

Alveolar septal thickening

0 - no thickening (normal)

1 - mild (relative)

2 - moderate (relative)

3 - severe (relative)

Distribution of alveolar septal thickening

0 - no lesion (normal)

1 - focal thickening of septa

2 - multifocal thickening of septa

3 - diffuse thickening of septa.

TABLE 31

Lung Pathology - Not vaccinated and challenged.

| | Pig No. | Lung sample | Alveolar septal thickening | Distribution of Thickening | Inflammatory cells in airways | comments |
|---|---|---|---|---|---|---|
| Not Vaccinated/ challenged | 75 | Left | 1 | 2 | 1 | Neutrophils bronchi, bronchioles, alveoli |
| | | Right | 3 | 3 | 2 | Neutrophils, macrophages bronchi, |
| | 76 | Left | 2 | 2 | 1 | Macrophages, lymphocytes, plasma cells |
| | | Right | 2 | 2 | 1 | Macrophages, lymphocytes, plasma cells |
| Pen 5 | 77 | Left | 2 | 3 | 1 | Neutrophils bronchi |
| | | Right | 3 | 2 | 1 | Neutrophils bronchi |
| | 78 | Left | 3 | 3 | 3 | Neutrophils, macrophages, |
| | | Right | 3 | 3 | 3 | Neutrophils, macrophages, |
| | 79 | Left | 1 | 2 | 0 | |
| | | Right | 2 | 2 | 2 | Neutrophils, lymphocytes, plasma |
| | 81 | Left | 1 | 2 | 0 | |
| | | Right | 1 | 2 | 0 | |
| | Averag | | 2.0 | 2.3 | 1.3 | |

Pathology score criteria

Alveolar septal thickening

0 - no thickening (normal)

1 - mild (relative)

2 - moderate (relative)

3 - severe (relative)

Distribution of alveolar septal thickening

0 - no lesion (normal)

1 - focal thickening of septa

2 - multifocal thickening of septa

3 - diffuse thickening of septa

TABLE 32

Lung Pathology - Vaccinated and Challenged Rx I.

| | Pig No. | Lung sample | Alveolar septal thickening | Distribution of thickening | Inflammatory cells in airways | comments |
|---|---|---|---|---|---|---|
| Rx I | 66 | Left | 1 | 2 | 1 | Macrophages, neutrophils |
| Vaccinated + | | Right | 1 | 2 | 1 | Macrophages, neutrophils |
| Challenged | 67 | Left | 1 | 2 | 0 | |
| Pens 3 and 6 | | Right | 2 | 3 | 2 | Lymphocytes, plasma cells, macrophages alveoli |
| | 68 | Left | 1 | 2 | 1 | Macrophages, lymphocytes, plasma cells alveoli |
| | | Right | 0 | 0 | 0 | |
| | 69 | Left | 1 | 2 | 0 | |
| | | Right | 0 | 0 | 1 | Macrophages alveoli |
| | 70 | Left | 1 | 2 | 3 | Macrophages, lymphocytes, plasma cells neutrophils alveoli |
| | | Right | 1 | 2 | 3 | Macrophages, lymphocytes, plasma cells neutrophils alveoli bronchi |
| | 71 | Left | 2 | 3 | 1 | Macrophages, lymphocytes, plasma cells alveoli |
| | | Right | 2 | 3 | 1 | Macrophages, lymphocytes, plasma cells alveoli |
| | 72 | Left | 3 | 2 | 3 | Neutrophils, macrophages bronchioles, bronchi, alveoli |
| | | Right | 3 | 3 | 3 | Neutrophils, macrophages bronchioles, bronchi, alveoli |
| | 73 | Left | 1 | 2 | 1 | Macrophages alveoli, bronchi |
| | | Right | 2 | 1 | 0 | |
| | 74 | Left | 2 | 3 | 1 | Neutrophils, macrophages bronchi, bronchioles |
| | | Right | 2 | 2 | 1 | Neutrophils, macrophages bronchi, bronchioles |
| | | Average | 1.4 | 2.0 | 1.3 | |

Pathology score criteria
Alveolar septal thickening
0 - no thickening (normal)
1 - mild (relative)
2 - moderate (relative)
3 - severe (relative)
Distribution of alveolar septal thickening
0 - no lesion (normal)
1 - focal thickening of septa
2 - multifocal thickening of septa
3 - diffuse thickening of septa

TABLE 33

Lung Pathology - Vaccinated and Challenged Rx II.

| | Pig No. | Lung sample | Alveolar septal thickening | Distribution of Thickening | Inflammatory cells in airways | comments |
|---|---|---|---|---|---|---|
| Rx II | 57 | Left | 1 | 3 | 0 | |
| Vaccinated + | | Right | 0 | 0 | 0 | |
| Challenged | 58 | Left | 2 | 3 | 2 | Lymphocytes, plasma cells, eosinophils, neutrophils bronchioles and bronchi |
| | | Right | 2 | 3 | 2 | Lymphocytes, plasma cells, eosinophils, neutrophils |
| Pens 2 and 8 | 59 | Left | 2 | 2 | 2 | Neutrophils in bronchi, lymphocytes, plasma cells, |
| | | Right | 2 | 2 | 2 | Neutrophils in bronchi, lymphocytes, plasma cells, |
| | 60 | Left | 2 | 3 | 1 | Lymphocytes, plasma cells, neutrophils alveoli |
| | | Right | 2 | 3 | 1 | Lymphocytes, plasma cells, neutrophils alveoli |
| | 61 | Left | 0 | 0 | 0 | |
| | | Right | 0 | 0 | 0 | |
| | 62 | Left | 2 | 3 | 3 | Neutrophils, lymphocytes, plasma cells alveoli |
| | | Right | 1 | 1 | 1 | Macrophages alveoli |

TABLE 33-continued

Lung Pathology - Vaccinated and Challenged Rx II.

| Pig No. | Lung sample | Alveolar septal thickening | Distribution of Thickening | Inflammatory cells in airways | comments |
|---|---|---|---|---|---|
| 63 | Left | 1 | 2 | 3 | Lymphocytes, plasma cells, neutrophils, macrophages alveoli |
|  | Right | 1 | 2 | 3 | Lymphocytes, plasma cells, neutrophils, macrophages alveoli |
| 64 | Left | 1 | 2 | 0 |  |
|  | Right | 1 | 2 | 0 |  |
| 65 | Left | 0 | 0 | 0 |  |
|  | Right | 0 | 0 | 0 |  |
| Average |  | 1.1 | 1.7 | 1.1 |  |

Pathology score criteria
Alveolar septal thickening
0 - no thickening (normal)
1 - mild (relative)
2 - moderate (relative)
3 - severe (relative)
Distribution of alveolar septal thickening
0 - no lesion (normal)
1 - focal thickening of septa
2 - multifocal thickening of septa
3 - diffuse thickening of septa

TABLE 34

Lung Pathology - Vaccinated and Challenged Rx III.

|  | Pig No. | Lung sample | Alveolar septal thickening | Distribution of thickening | Inflammatory cells in airways | comments |
|---|---|---|---|---|---|---|
| Vaccinated + |  | Right | 2 | 3 | 1 | Neutrophils bronchi |
| Challenge | 82 | Left | 2 | 3 | 0 |  |
|  |  | Right | 2 | 3 | 0 |  |
| Pens 4 and 7 | 83 | Left | 2 | 3 | 0 |  |
|  |  | Right | 2 | 3 | 0 |  |
|  | 84 | Left | 2 | 2 | 0 |  |
|  |  | Right | 2 | 2 | 0 |  |
|  | 85 | Left | 1 | 2 | 0 |  |
|  |  | Right | 1 | 2 | 0 |  |
|  | 86 | Left | 1 | 2 | 0 |  |
|  |  | Right | 3 | 3 | 1 | Neutrophils, macrophages bronchi |
|  | 87 | Left | 2 | 3 | 2 | Neutrophils bronchioles, alveoli |
|  |  | Right | 2 | 3 | 2 | Neutrophils bronchioles, alveoli |
|  | 88 | Left | 2 | 2 | 1 | Neutrophils bronchi, bronchioles |
|  |  | Right | 1 | 3 | 0 |  |
|  | 89 | Left | 2 | 2 | 1 | Neutrophils bronchi |
|  |  | Right | 2 | 1 | 0 |  |
|  | Avg. |  | 1.9 | 2.5 | 0.5 |  |

Figure 21:
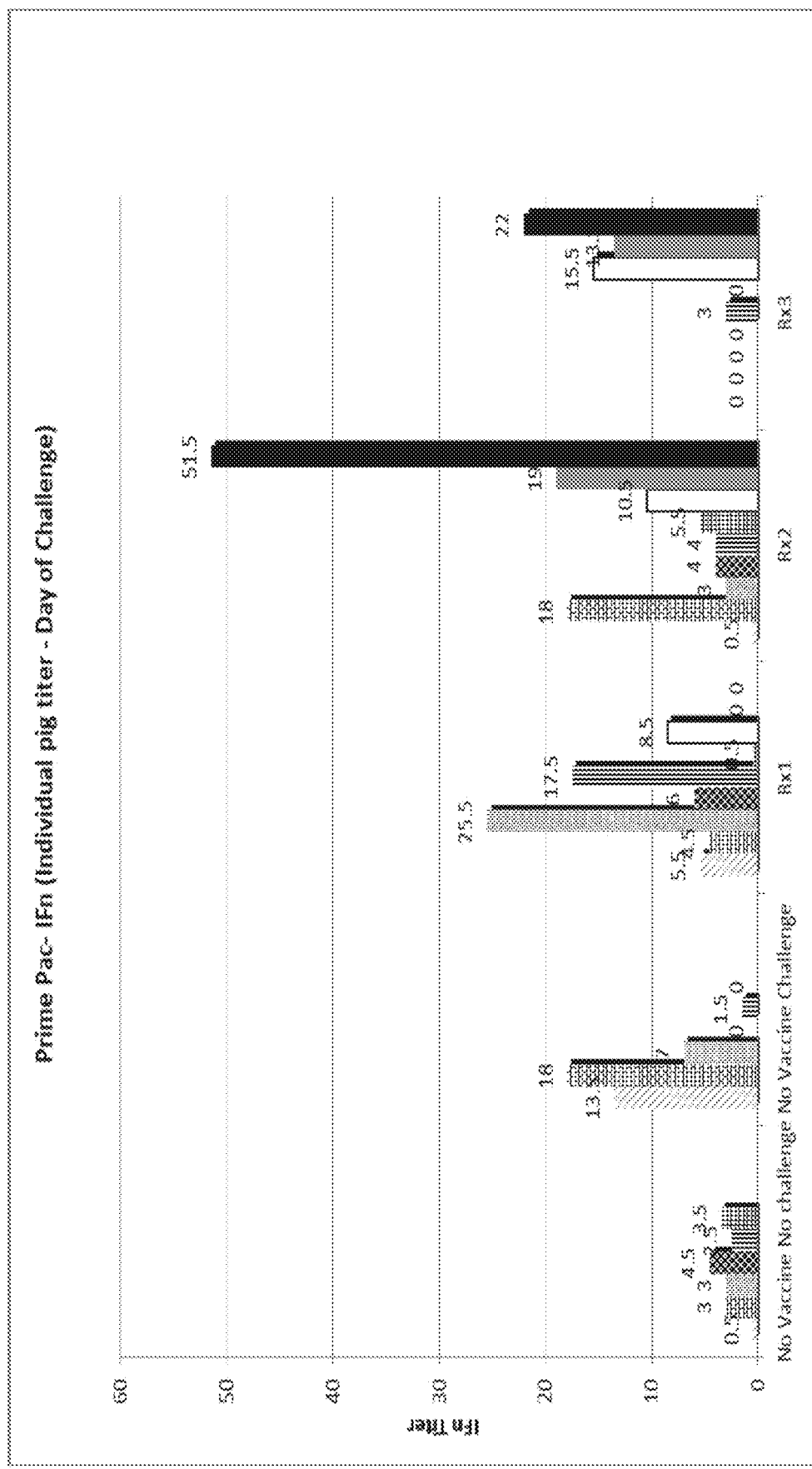
FIG. 21 graphically illustrates interferon titers of individual animals in each treatment group including no vaccine/no challenge, no vaccine/challenge, Rx I vaccine plus 10 µg immunomodulator/challenged, Rx II vaccine plus 50 µg immunomodulator/challenged, and Rx III vaccine/challenged.

Pathology score criteria
Alveolar septal thickening
0 - no thickening (normal)
1 - mild (relative)
2 - moderate (relative)
3 - severe (relative)
Distribution of alveolar septal thickening
0 - no lesion (normal)
1 - focal thickening of septa
2 - multifocal thickening of septa
3 - diffuse thickening of septa Interferon titers of individual animals are included in FIG. 21 and Table 35. All the nine animals in RxII (PRRS vaccine+50 µg of immunomodulator) group and 7 of 9 in RxI (PRRS vaccine+10 µg of immunomodulator) had detectable interferon titers as compared to 4 of nine animals in RxIII (PRRS vaccine) group.

TABLE 35

Prime Pac - IFN Titer - Day of Challenge.

| | 1 | 2 | 3 | 4 | 5 | 6 | 7 | 8 | 9 |
|---|---|---|---|---|---|---|---|---|---|
| Not | 0.5 | 3 | 3 | 4.5 | 2.5 | 3.5 | | | |
| No Vaccine | 13.5 | 18 | 7 | 0 | 1.5 | 0 | | | |
| Rx1 - Challenged | 5.5 | 4.5 | 25.5 | 6 | 17.5 | 0.5 | 8.5 | 0 | 0 |
| Rx2 - Challenged | 0.5 | 18 | 3 | 4 | 4 | 5.5 | 10.5 | 19 | 51.5 |
| Rx3 - Challenged | 0 | 0 | 0 | 0 | 3 | 0 | 15.5 | 13.5 | 22 |

In conclusion, in a controlled PRRS challenge the RxII (PRRS vaccine+50 µg of immunomodulator) group had higher body weight gain, lower virus load in the lung and had detectable interferon in all the animals as compared to animals in group (RxIII) receiving PRRS vaccine alone. The study suggests that the immunomodulator with PRRS vaccine aids in early virus clearance in the lungs which was not observed in PRRS vaccinated (RxIII) animals.

Example 3: A Single Intramuscular Injection of the Immunomodulator Administered to Pigs Before or after Laboratory Challenge with PRRS Virus Reduces Lung Lesions A study was conducted to determine the effectiveness of the immunomodulator to reduce lung lesions in PRRS challenged and recently weaned pigs. The pigs were artificially challenged with PRRS virus on Study Day 0. The study evaluated 5 treatment groups, 4 challenged (Groups B [administered Immunomodulator on Study Day 2], C [administered Immunomodulator on Study Day −1], D [administered Immunomodulator on Study Day 0] and E [administered 5% dextrose as placebo control]) with a one-time intranasal inoculum of $4 \times 10^6$ PRRSV (strain NADC-20) and 1 sham challenged (Group A) group on Study Day 0. Pigs were approximately nine to ten weeks of age on Study Day 0. Each of the four PRRSV challenged Groups were represented in each pen. Clinical scores were recorded daily from Study Day −2 to Study Day 16. Pigs were posted for necropsy over a two day period (Study Day 15 and 16) for evaluation of lung lesions and recovery of PRRSV by lung lavage and virus isolation. Immunomodulator treated pigs in Groups C and D had statistically lower (p-values 0.0095 and 0.0247 respectively) lung lesions scores (9.7% and 13.9%, respectively) compared to the average of 32.9% of total lung lobe involvement in Group E placebo control pigs. One adverse event was reported during the time course of the study but was identified as unrelated to the investigational veterinary product.

Study Design

TABLE 36

Treatment Groups.

| *Study Groups | Group Description | Study D 0 PRRS (NADC-20 strain) Challenge | Study Day of Immunomodulator (50 µg/hd) administration (Study Day) | Vehicle Control (volume equivalent to Immunomodulator) [Study Day] | Sample Size (n) |
|---|---|---|---|---|---|
| A | Strict Control | — | — | −1, 0, 2 | 6 |
| B | Vehicle and PRRSV control | ✓ | — | −1, 0, 2 | 10 |
| C | Immunomodulator pre PRRSV- challenge group | ✓ | −1 | 0, 1 | 10 |
| D | Immunomoduiator Day concurrent with PRRSV- challenge group | ✓ | 0 | −1, 2 | 10 |
| E | Immunomodulator Day 2 post PRRSV-challenge group | ✓ | 2 | −1, 0 | 10 |

TABLE 37

Test System Summary Table

| | |
|---|---|
| Breed | Yorkshire × Landrace × Hampshire |
| Animal Attributes | Weaned pigs/SPF for PRRSV |
| Facility Attributes | BL2 shower-out facility - each pen was an enclosed room with cinder block construction and a sliding steal retaining door with a viewing window |
| Range of date of birth of study animals | 2 Mar. 2011 to 7 Mar. 2011 |
| Age range at Study-Day 0 (Day of PRRSV Challenge) | 9 to 10 weeks of age |
| Weight range at treatment allocation | 12 lbs to 51 lbs [5.4 kg to 23.12 kg] |
| Weight range at necropsy | 48.2 lbs to 112.2 lbs [21.8 kg to 50.8 kg] |
| PRRSV Strain | NADC-20 |
| PRRSV Titer | $2 \times 10^6$ TCID50/ml of suspension |

TABLE 37-continued

Test System Summary Table

| | |
|---|---|
| Inoculum Route | Intranasal |
| Inoculum Dose | 2 ml (1 ml per nare) of the $2 \times 10^6$ TCID50/ml suspension |
| Strict Control pigs | Sham inoculated/5% dextrose water on Study Day −1, 0 and 2 not PRRSV challenged |
| Treatment group housing | Each group was represented in each pen except for Group A (strict control pigs) in pens 9 and 11 |
| Number of pens | 12 pens total (10 pens of 4 pigs representing groups B, C, D and E in each pen and 2 pens of 3 pigs representing Group A) |
| Treatment Code Key | |

| | Enrolled | | Analyzed | |
|---|---|---|---|---|
| Group A - Strict control pigs; | 3♂ | 3♀ | 3♂ | 3♀ |
| Group B - Immunomodulator on Study Day 2; | 3♂ | 7♀ | 3♂ | 6♀ |
| Group C - Immunomodulator on Study Day -1 | 8♂ | 2♀ | 7♂ | 2♀ |
| Group D - Immunomodulator on Study Day 0 | 5♂ | 5♀ | 5♂ | 5♀ |
| Group E - No Immunomodulator (5% dextrose water) | 4♂ | 4♀ | 4♂ | 6♀ |
| Total | 23♂ | 23♀ | 22♂ | 22♀ |

| | |
|---|---|
| Immunomodulator Lot Number | 1-FIN-0958, 5 mL glass vial containing 600 µg pDNA in lyophilized form |
| Immunomodulator Reconstitution media | 3 mL Sterile water for injection packaged in 100 mL glass vials |
| Immunomodulator dilution media | 5% dextrose water packaged in a 250 mL plastic bag |
| Immunomodulator dose | Dosed on a per head basis (2 mL per pig i.m. to achieve a dose of 50 µg/pig) |
| Necropsy dates | Study Days 15 and 16 (15 and 16 days post-challenge with PRRSV) |
| Efficacy endpoints | Respiratory and depression clinical scores, gross and microscopic lung lesion scores, serum viremia, viral lung load and IFN-α. Body temperature and body weights were collected as secondary variables |

Masking was accomplished through separation of function. Any study personnel involved in daily observations, clinical scoring, assessment of gross and microscopic lung pathology, processing of samples or interpretation of laboratory results remained masked to the association between Treatment Group number and administered Test Material. The allocation list and treatment code key was removed from the study site and retained by the sponsor for the duration of the in-life phase of the study.

Animals

Pigs were Yorkshire X Landrace X Hampshire cross. Pigs were between nine and ten weeks of age at the time of Test Material administration. Demographics of the study population is provided in Table 38 below.

TABLE 38

Study population demographics.

| | Treatment Code | Planned | Enrolled | Analyzed |
|---|---|---|---|---|
| Animals | | No. ♂male, 23 ♀female: 23 Barrows; Gilts | Number of animals (23♂; 23♀) Barrows; Gilts | Number of animals (.22♂, 22♀) Barrows; Gilts |
| Groups | E | Placebo (Vehicle) Controls: (NA♂; NA♀) Balanced gender across groups was not a protocol criteria, ideal population would be balanced | Placebo Controls: (4♂; 6♀) | Placebo Controls: (4♂; 6♀) |
| | | Test product: (NA♂; NA♀) Balanced gender across groups was not a protocol criteria | Test product (♂16♀14) | Test product (15♂ 13♀) |
| | C | Day-1 Test Product Administration | (♂8♀2) | (♂7♀2) Excluded pig # 25 |
| | D | Day 0 Test Product Administration | (♂5♀5) | (♂5♀5) |
| | B | Day 2 Test Product Administration | (♂3♀7) | (♂3♀6) Excluded pig #40 |
| | — | Positive control: (NA♂; NA♀) | Positive control: (NA♂, NA♀) | Positive control: (NA♂; NA♀) |

TABLE 38-continued

Study population demographics.

| Treatment Code | Planned | Enrolled | Analyzed |
|---|---|---|---|
| A | Negative control (Strict Control Group): (3♂; 3♀) | Negative control: (3♂; 3♀) | Negative control: (3♂; 3♀) |

Serum collected from all n=46 candidate pigs on Study Day −14 (27 Apr. 2011) were analyzed for PRRSV antibodies using an IDEXX Laboratories Herdchek PRRS virus antibody test kit Serial No: 09418-LF113 Expiration Date: 1 Nov. 2011. All candidate pigs were determined negative for PRRSV.

For inclusion in the study, a pig must not have received, at any time, PRRS vaccination; have traceable records verifying birth date, place of origin and certification of SPF status for PRRS and *mycoplasma*; rectal temperature of 104° F. on Study Day −1; respiratory score and depression score of 0 on Study Days −1 and 0; have no complicating injuries or illnesses not associated with PRRS challenge on the respective day of Test Material administration; and be physically healthy as determined by general health observation on Study Day −1.

Pigs were excluded from eligibility for Test Material administration and challenge infection if on the respective day of Test Material administration or challenge infection pigs had the following attributes: affected by a complicating injury or a non-target systemic disease that would confound study results or prevent completion of the study; or a respiratory score not equal to 0 on Study Day −1 and 0.

Immunomodulator

The immunomodulator used in this study is described above in Example 1.

Pigs allocated to immunomodulator treatment groups received a single one-time intramuscular injection of a 2 mL suspension of immunomodulator and 5% dextrose water to deliver 50 µg of immunomodulator plasmid DNA. Pigs were observed twice daily for general health observations.

Study Procedures

Rectal body temperatures were recorded on all pigs on Study Days −2, −1, 0, 2, 4, 7, 10, 14 and the day of necropsy. Rectal body temperatures were collected using a Welch Allyn SureTemp-plus® digital thermometer.

Body weights were obtained on all pigs on Study Days −14 (for allocation to treatment group), −7, 0, 7, 10 and 14. Weights recorded on Study Day 10 were disqualified for analysis due to missing data forms resulting in an incomplete dataset for Study Day 10.

The inocula for this study was prepared from a pool of two separate stocks (Stock #31411 and #41911) of NADC-20 PRRSV recovered from a single passage in ZMAC cells (swine alveolar macrophages). Stock #31411 had a titer of $5 \times 10^6$ and was subsequently diluted at 1:25 to obtain a $2 \times 10^6$ TCID50/ml. The diluted stock was subsequently combined with Stock 41911 that had an original titer of $2 \times 10^6$ TCID50/ml. The pooled inoculum was titrated and determined to have a titer of $1.8 \times 10^6$ TCID50/ml. To determine the titration, tenfold serial dilutions of the inoculum were prepared and 100 µl/well of each dilution were plated in quadruplicates. The presence of virus was scored based on apoptosis and/or cell death of ZMAC cells observed in respective wells. The titer was calculated by using the Reed and Muench method.

Each pig was subsequently administered 2 mL of the $1.8 \times 10^6$ TCID50/mL PRRS virus intranasally (1 mL per nare) for a final inoculum of approximately $4 \times 10^6$ TCID50/mL of PRRSV. To facilitate the conduct of procedures and minimize stress on the pigs, each pig was placed in a Panepinto sling purchased from Lomir Biomedical Inc. (Malone, N.Y.).

To increase the success of infection, the PRRSV suspension was administered with the use of a pediatric mucosal atomization device (Wolfe Tory Medical, Inc. Salt Lake City, Utah) attached to the end of a disposable 3 mL syringe. The inoculum was administered incrementally during inspiration.

The level of serum viremia was determined on Study Days −2, 4, 7, 10 and 14 relative to PRRSV challenge on Study Day 0. The presence of infectious PRRS virus in the peripheral blood of pigs was determined from sera obtained from clotted venous blood samples. Venous blood (5-10 cc) was collected in red top Vacutainer tubes and allowed to clot. Serum (1-2 cc) was harvested from these tubes within two hours after collection and stored in aliquots at −80° C. until further analysis. Determination of viremia was accomplished by preparing ten-fold serial dilutions of serum in RPMI-1640. A 0.1 ml volume of the diluted serum samples was transferred in triplicate to 96-well tissue culture plates containing a suspension of approximately $3 \times 10^4$ of ZMAC cells (pig alveolar macrophages) in a 0.1 ml volume. After 3 days of culture at 37° C. in a 5% $CO_2$ atmosphere, the presence of virus-induced cytopathic effect was scored. The number of tissue culture infectious dose 50 (TCID50) was determined using the method of Reed and Muench.

Viral load in lung tissue was determined in lung tissue samples collected at necropsy. Virus load in the lung was determined from bronchoalveolar lavage (BAL) fluid collected from the right middle lobe. The BAL sample was obtained by infusing 10 ml of sterile saline into the right middle lobe, using a 20 mL syringe connected to a catheter placed into the bronchi leading to this lobe. Following a gentle massage of the lobe the infused fluid was removed by suction of the fluid with the same syringe used for the infusion. Approximately 5 ml of lavage fluid was recovered. Determination of virus load in lung tissue was accomplished by preparing ten-fold serial dilutions of BAL fluid in RPMI-1640. A 0.1 ml volume of the diluted serum samples was transferred in triplicate to 96-well tissue culture plates containing a suspension of $3 \times 10^4$ of the pig alveolar macrophages in a 0.1 ml volume. After 3 days of culture at 37° C. in a 5% $CO_2$ atmosphere, the presence of virus-induced cytopathic effect was scored. TCID50 was determined using the method of Reed and Muench.

At necropsy the lungs were removed from the thoracic cavity, photographed (dorsal and ventral aspects with the pig ear tag captured in each photo) and gross lesions scored by the veterinary pathology resident, based on the scoring system described by Halbur et al (1995). Briefly, five (5.0) potential points were assigned to each of the dorsal and ventral aspects of the anterior lobe, middle lobe and accessory lobe. Fifteen points (15.0) were assigned to the dorsal caudal lobe and twelve and a half (12.5) points assigned to the ventral aspect of the caudal lobe. Each lung lobe (dorsal and ventral aspects of the lung) was observed and the estimated percentage of the lung affected with gross lesions was documented on the sponsor supplied data capture form. A final lesion score was assigned to each lobe by multiplying the maximum score for the lobe by the percent of the lobe affected. For example, if 20% of the dorsal caudal lobe had observed lesions, the lesion score for that lobe was calculated as (20*15)/100=a lesion score of 3.

Figure 22:
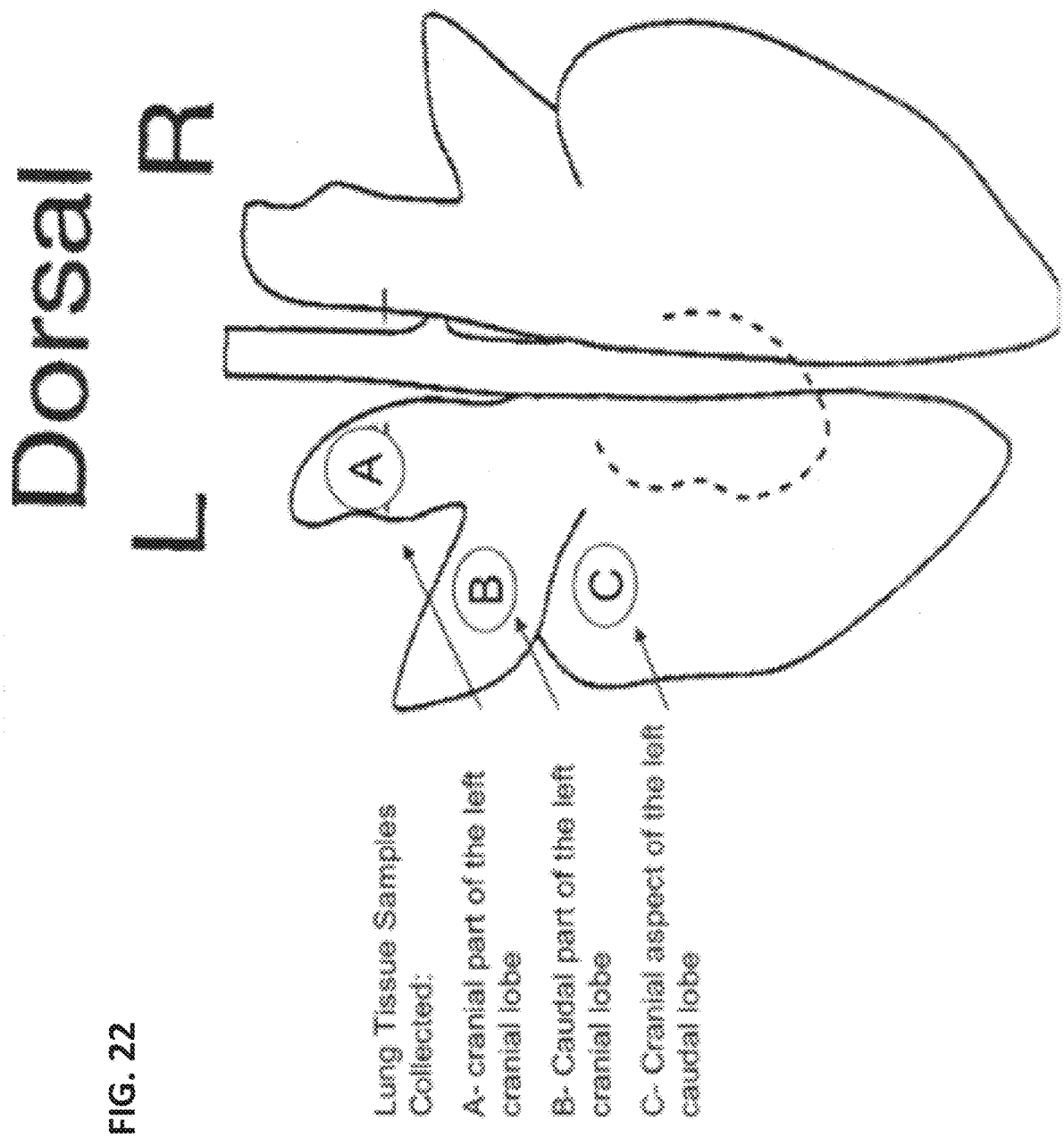
FIG. 22 depicts areas of the lungs from which tissue samples were taken to assess microscopic lesions.

To assess microscopic lesions in lung tissue sections, approximately 1 cm thick x 5 cm long×5 cm wide samples were taken from each lung (see FIG. 22):
  a) the cranial part of the left cranial lobe,
  b) the caudal part of the left cranial lobe and
  c) the cranial part of the left caudal lobe.

The samples were fixed for at least 48 hours in 10% neutral buffered formalin and then processed and embedded in paraffin in an automated tissue processor. 3-5 μm thick sections were cut and stained with hematoxylin and eosin. Tissue processing (paraffin embedding, sectioning and staining), was conducted at the Histology laboratory of the University of Illinois Veterinary Diagnostic Laboratory.

Lung sections were examined and given an estimated score of severity of interstitial pneumonia based on the following four criteria:
  A. Alveolar septal thickening: 0—no thickening (normal); 1—mild (relative); 2—moderate (relative); 3—severe (relative)
  B. Distribution of Alveolar septal thickening: 0—no lesion (normal); 1—focal thickening of septa; 2—multifocal thickening of septa; 3—diffuse thickening of septa
  C. Bronchus-associated lymphoid tissue (BALT) development: 0—minimal cells to normal BALT; 1—mildly increased in numbers; 2—moderately increased in numbers; 3—severely increased in numbers.
  D. Evidence of inflammation in the airway: 0—None; 1—mild; 2—moderate; 3—severe.

Venous blood (8-10 mL) was obtained from study animals on Study Days −2, 4, 7 and 14 by venipuncture using green top Vacutainer tubes (sodium heparin). Peripheral blood mononuclear cells were isolated from these samples within four hours after collecting the blood by density centrifugation using Ficoll-Hypaqe1077. The isolated cells were suspended in RPMI-1640 medium supplemented with 10% fetal bovine serum. The cells were incubated without any exogenous stimulator (to measure spontaneous production of cytokines) or in the presence of 2 μg/mL of the toll-like receptor 9 (TLR9) agonist ODN D19 (Qiagen, Valencia, Calif.), which is a CpG-containing, type A oligodeoxynucleotide (ODN). Cell culture supernatants were subsequently collected after 16 hours of culture and frozen until further use. The amount of IFN-α in the resulting culture supernatants was determined using a specific ELISA as described before (Calzada-Nova et al., 2010).

Statistical Methods

The evaluation of the disease model consisted of analyzing the gross lung and micro lung data between the two control groups. A statistically significant difference was required to show the challenged control group exhibited adequate disease as compared to the non-challenged strict control group. Gross lung scores (sum total of the each of the lobes) were compared using an analysis of variance testing for group effects. Each of the three (3) micro lung scores (alveolar septal thickening, airway inflammation and BALT development) were compared using a non-parametric Wilcoxon Ranked Sum test. The remaining analyses included on groups 2 through 5 (challenged control and immunomodulator groups), provided the above disease model validation was met.

Data with repeated measurements (i.e., IFN-α) were analyzed using a repeated measures analysis of variance and included a baseline covariate where applicable. The covariance structure with the smallest AIC result was used. Arc sine transformations were applied as needed, to closer approximate normal data distributions.

Data with a single endpoint (gross lung scores) were analyzed with an analysis of variance. All models above incorporated pen as a factor in the model. Micro lung (septal, airway and BALT) scores were analyzed using a non-parametric Wilcoxin Ranked Sum test. All analyses were performed using SAS 9.2 and an alpha of 0.1 was used to distinguish significant effects.

Results

Both the gross and micro lung scores exhibited a significant treatment effect when comparing the strict control versus the challenged control groups (p-values of 0.0015, 0.0037, 0.0249 and 0.0010, for gross, septal, airway and BALT, respectively). Hence, disease model validation was met.

Figure 24:
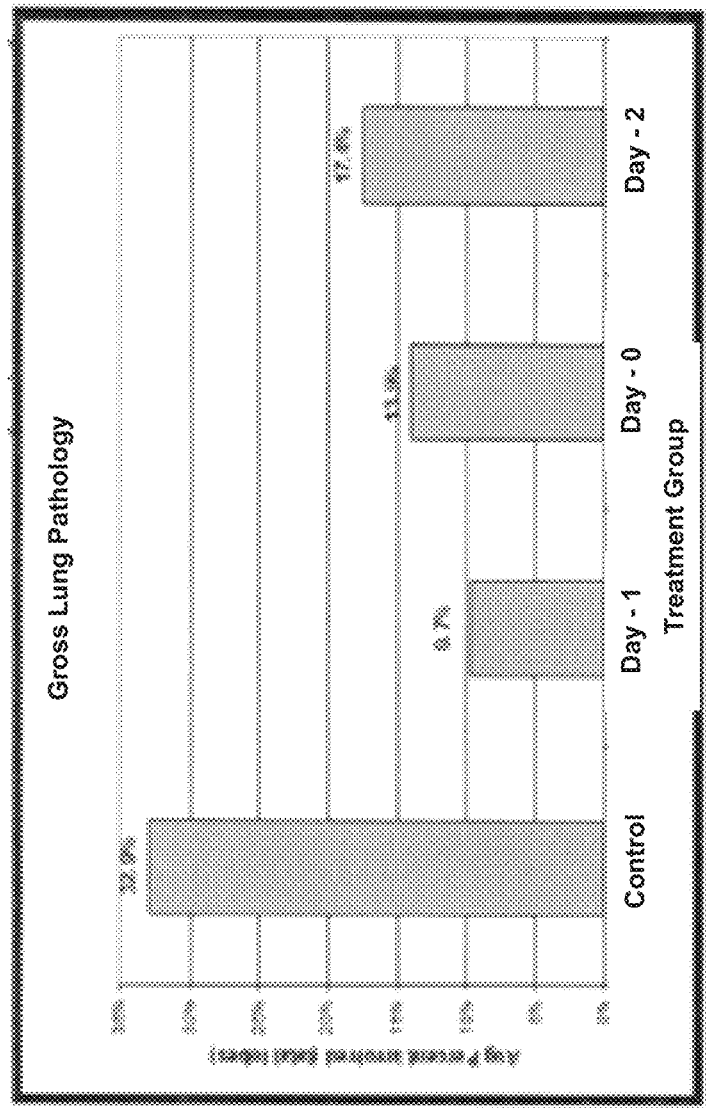
FIG. 24 shows the gross lung pathology, represented by the sum total lobe scores for each animal, between the control group and each of the immunomodulator treatment groups (day −1, day 0, and day 2)
Figure 25:
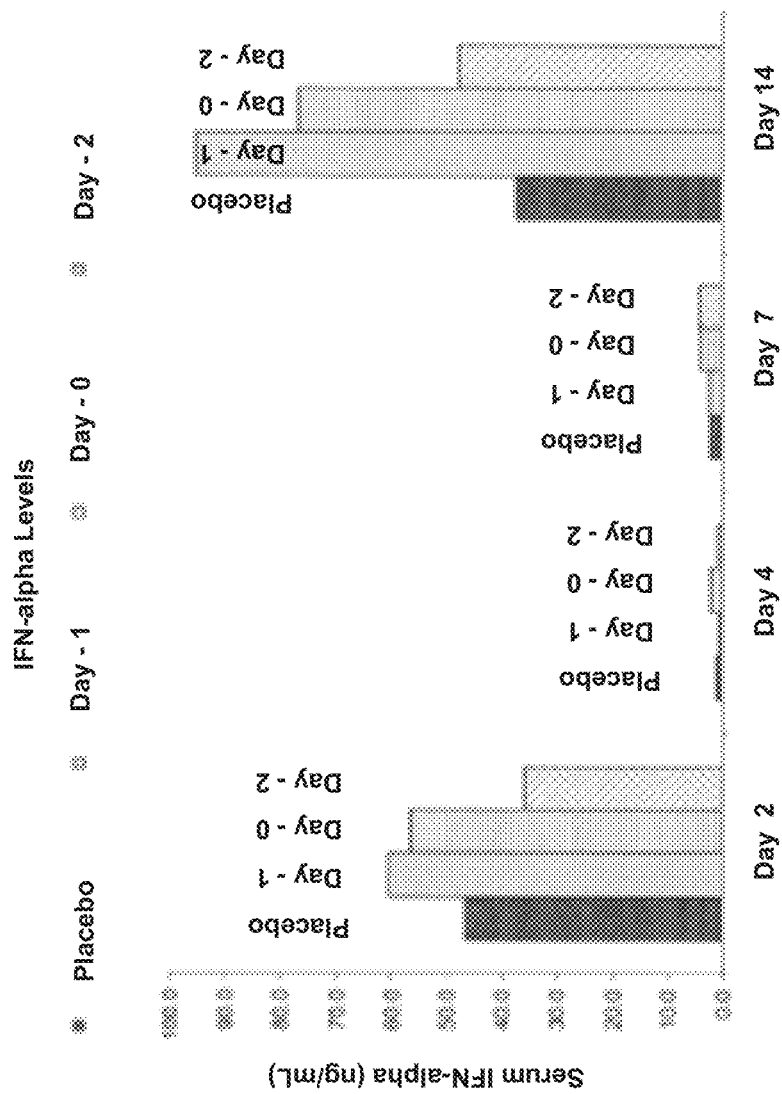
FIG. 25 shows the IFN-α serum levels for the control group and each of the immunomodulator treatment groups (day −1, day 0, and day 2)

Gross lung pathology, represented by the sum total lobe scores for each animal, exhibited a statistically significant difference between the control group and each of the immunomodulator groups (p-values of 0.0095, 0.0247 and 0.0736 for immunomodulator day −1, immunomodulator day 0 and immunomodulator day 2, respectively), as shown in FIG. 24. Micro lung total pathology scores did not exhibit any statistically significant differences between the treatment groups (0.8786, 0.5788 and 0.5865 for septal, airway and BALT tissues). IFN-α results, shown in FIG. 25, did not result in any statistically significant differences for any day on the study (overall treatment effect was 0.1653).

Discussions and Conclusions

Gross lung lesions scores were significantly reduced in each of the treatment groups relative to placebo control animals in this study. Based on these data, the immunomodulator can reduce lung lesion scores in healthy recently weaned pigs with limited exposure to other viral or bacterial respiratory pathogens: in other words, a PRRSV-only respiratory challenge.

Interferon levels oscillated as predicted in the face of a PRRSV challenge. Suppression of IFN-α levels is hallmark sequelae of PRRSV infection and was evident in this study where IFN-α levels were greatly reduced in samples collected on Study Day 4 and 7 relative to Study Day −2. The immunomodulator did not result in a significant difference in IFN-α levels in any of the collection periods. Intriguing, however, is the near 2 fold increase in IFN-α production of macrophages collected on Study Day 14 from pigs treated with the immunomodulator on Study Days −1 (Group C) and those treated on Study Day 0 (Group D). These data suggest that the immunomodulator may provide a priming effect in the lungs by perhaps enhancing the capability of resident macrophages to produce higher levels of IFN-α following subsequent activation of a TLR9 signaling event. This observation may warrant further exploration perhaps in a two treatment PRRSV model, such that pigs are treated with the immunomodulator at Day −14 and again at Day −1 prior to challenge.

Figure 23:
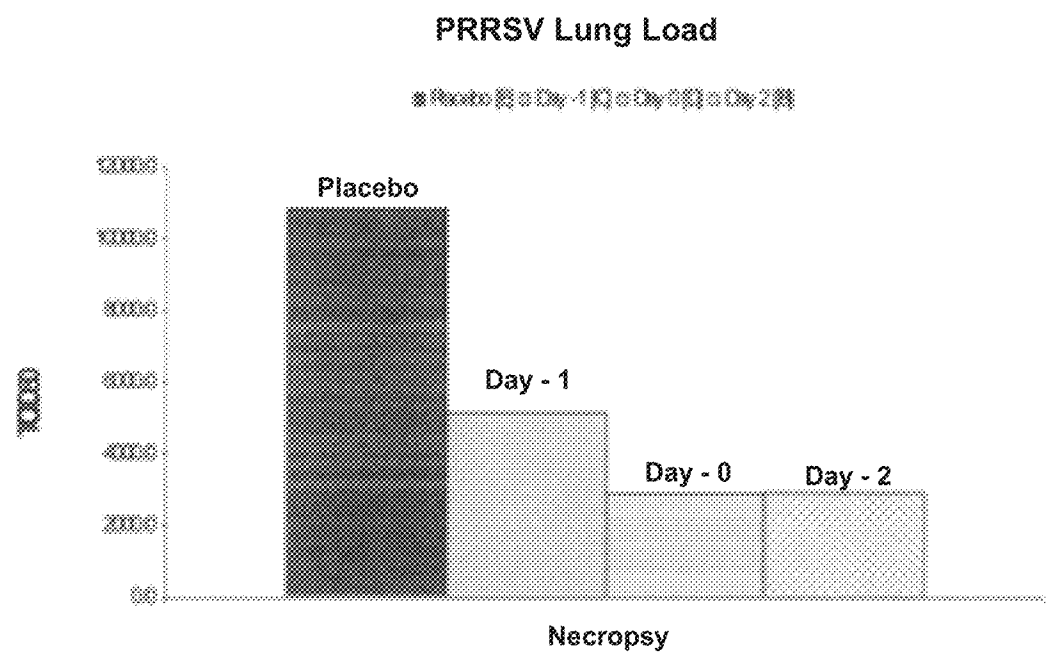

A statistically significant decrease in PRRS viremia was not observed in immunomodulator treated groups. However on Day 7, in the Day-1 treated group, there was a pronounced, albeit not significant, reduction in serum viremia. Viral lung load, shown in FIG. 23, was arithmetically reduced in all but one immunomodulator treatment group in both studies relative to placebo treated pigs; however, these reductions were not statistically significant. There is no evidence or indication that immunomodulator administration is enhancing viral lung load or viremia. This latter statement counters prior observations reported in the literature that suggest in vitro incubation of swine peripheral blood mononuclear cells in high concentrations of IFN-α enhances PRRSV uptake. There is no indication in this study that the immunomodulator enhanced PRRSV serum viremia or lung load.

Example 4: Positive Effect of Immunomodulator Administered as a Single Intramuscular Injection to Pigs One Day Prior to Laboratory Challenge with a NADC.2-Strain of PRRS Virus A study was carried out to titrate the dose of immunomodulator in growing pigs. The test system evaluated five treatment groups, four PRRS virus-challenged groups (Groups A [administered 50 µg immunomodulator on Study Day −1], B [administered 5% dextrose water on Study Day −1], C [administered 75 µg of immunomodulator on Study Day −1] and D [administered 25 µg of immunomodulator on Study Day −1]) with a one-time intranasal administration of 2 mL of a 5.38×10$^5$ TCID50 PRRSV (strain NADC-20) suspension), and one sham challenged group (Group E—strict controls) on Study Day 0. Pigs were approximately 7.5 to 8.5 weeks of age on Study Day 0. Each immunomodulator treated group was represented by two pigs in each pen such that pigs were housed in six pens of eight pigs (three pens in one suite and three pens in an adjacent suite) and one pen of eight strict control pigs in a third suite.

Results were considered statistically significant at a p-value of 0.10. A significant treatment affect was observed for respiratory scores on Study Day 12 (p-value of 0.0719). For the pair wise comparison between the control group (Group B) versus each of the immunomodulator groups on Study Days 3, 4, 6, 7, and 12, significantly greater (more lethargic) attitude scores were observed for the immunomodulator 50 pg treated group compared to the control group on Study Day 7 (p-value of 0.0902). Conversely, significantly lower (approaching normal) attitude scores were observed in the immunomodulator 75 µg treated group compared to the control group on Study Day 12 (p-value of 0.0932). Pair-wise control group comparisons with each of the immunomodulator groups on each day resulted in significantly lower serum viremia for immunomodulator administered at a dose of 25 µg (Days 4 and 7) and 75 µg (Day 7 only) and significantly higher serum viremia on Study Day 14 administered the 50 µg dose. However, only the reductions observed on Study Day 7 for the 25 µg group and the 75 µg group are considered clinically relevant as the difference between a transformed viremia count observed on Day 4 in the 25 µg Group was only 28 versus 18. No significant differences were observed in gross or microscopic lung lesions, clinical scores, viral lung load, body weight, body temperatures or body weight to lung weight ratio. There was one adverse event reported in this study and was determined to not be related to the investigational veterinary product.

The objective of this study was to titrate the dose of immunomodulator by administering a single i.m. injection of 25 µg, 50 µg or 75 µg of immunomodulator to recently weaned pigs one day (Study Day −1) before laboratory challenge with a NADC-20 strain of PRRSV on Study Day 0. The effectiveness of immunomodulator was compared to placebo treated PRRSV challenged pigs.

Primary response variables for efficacy were daily clinical scores for attitude and respiration (Study Days −2 until Study Day 14), serum viremia (Study Days −2, 4, 7, 10 and the day of necropsy), gross and microscopic lung pathology and lung viremia on the day of necropsy (14 or 15 [±1 d] days post-PRRSV challenge). Body temperature (Study Days −2, −1, 0, 4, 7, 10 and the day of necropsy) and Body weight (Study Days 0, 7, 10 and 14) were recorded as secondary and indirect measures of efficacy. A body weight was also collected on Study Day 7 (7 Jun. 2011) for allocation of pigs to treatment groups and pens.

Study Design

This was an experimental challenge study that utilized commercially sourced recently weaned pigs confirmed seronegative for PRRSV and *Mycoplasma hyopneumoniae*. A listing of treatment groups is provided in Table 40 and Table 41 below.

TABLE 40

Treatment Groups.

| *Study Groups | Group Description | Study Day −1 Administer Immunomodulator | Study Day −1 administer 5% Dextrose Control (volume equivalent to Immunomodulator) | Study Day 0 PRRSV (NADC-20 strain) Challenge | Sample Size (n) |
|---|---|---|---|---|---|
| I | Strict Control | — | ✓ | — | 8 |
| II | Placebo and PRRSV control | | ✓ | ✓ | 12 |
| III | Immunomodulator 25 µg group | ✓ | — | ✓ | 12 |
| IV | Immunomodulator 50 µg group | ✓ | — | ✓ | 12 |
| V | Immunomodul ator 75 µg group | ✓ | — | ✓ | 12 |

*For count purposes only, do not represent treatment group Identifiers

TABLE 41

Schedule of Events.

| Study Day | Study Event |
|---|---|
| −7 | Pigs onsite |
| | Bleed for PRRSV serology |
| | Begin 1x daily observations continuing to the last day of the in-life phase of the study |
| | Body weight obtained for randomization |
| | Pigs allocated to treatment groups and housed in respective pens |
| −2 | Body Temperatures |
| | Begin 1x clinical observations until Study Day 14 (clinical observations and daily general observations should be at least 6 hrs apart to provide a 2x per day observation of the animals |
| | Bleed for Serum Viremia |
| −1 | Body temperature |
| | Administer Test Material |
| 0 | Body weight |
| | Body temperature |
| | Administer PRRSV Challenge |
| 4 | Body Temperature |
| | Serum Viremia |
| 7 | Body Temperature |
| | Serum Viremia |
| | Body Weight |
| 10 | Body Temperature |
| | Serum Viremia |
| | Body Weight |
| 14 | Body Weight |
| | Necropsy |
| | Body Temperature |
| | Serum Viremia |
| | Gross pathology |
| | Lung tissue collection for microscopic lung pathology |
| 15 | Necropsy |
| | Body Temperature |
| | Serum Viremia and BAL |
| | Gross pathology |
| | Lung tissue collection for microscopic lung pathology |

TABLE 42

Test System Summary Table

| | |
|---|---|
| Breed | Yorkshire × Landrace × Hampshire |
| Animal Attributes | Weaned pigs/SPF for PRRSV and mycoplasma |
| Facility Attributes | BL2 shower-out facility: each suite contained three pens. Each suite was cinder block construction and a sliding steal retaining door with a viewing window. Each suite had separate air handling units. |
| Range of date of birth of study animals | 23 Apr. 2011 to 28 Apr. 2011 |
| Age range at Study Day 0 | 7.5 to 8.5 weeks of age |
| Weight range at treatment allocation | 28.9 lbs to 44.8 lbs [13.1 kg to 20.3 kg] |
| Weight range at necropsy | 29.3 lbs to 85.8 lbs [13.2 kg to 38.9 kg] |
| PRRSV Strain | NADC-20 |
| PRRSV Titer | $5.38 \times 10^5$ TCID50/ml of suspension |
| Inoculum Route | Intranasal |
| Inoculum Dose | 2 ml (1 ml per nare) of the $5.38 \times 10^5$ TCID50/ml suspension |
| Strict Control pigs | Sham inoculated/5% dextrose water on Study Day −1 and not PRRSV challenged |
| Treatment group housing | Each group was represented in each pen except for Group E (strict control pigs) |
| Number of pens | 12 pens total (6 pens of 12 pigs representing groups A, B, C and D in each pen and 1 pen of 8 strict control pigs representing Group E) |

| Treatment Code Key | | Enrolled | Analyzed |
|---|---|---|---|
| AH IVP and CP administrations occurred on Study day −1 | Group A: Immunomodulator 50 ug | 12 | 11 |
| | Group B: No Immunomodulator, 5% dextrose water | 12 | 11 |
| | Group C: Immunomodulator 75 ug | 12 | 12 |
| | Group D: Immunomodulator 25 ug | 12 | 11 |
| | Group E: Strict Controls | 8 | 8 |
| | Total | 56 | 53 |
| Immunomodulator Lot Number | 1-FIN-0958, 5 mL glass vial containing 600 μg pDNA in lyophilized form | | |
| Immunomodulator Reconstitution media | 3 mL Sterile water for injection packaged in 100 mL glass vials | | |
| Immunomodulator dilution media | 5% dextrose water packaged in a 250 mL plastic bag | | |
| Immunomodulator dose | Dosed on a per head basis (2 mL per pig i.m. to achieve a dose of 25, 50 or 75 mcg /pig) | | |
| Necropsy dates | Study Days 14 and 15 (14 and 15 days post-challenge with PRRSV) | | |

TABLE 42-continued

Test System Summary Table

| | |
|---|---|
| Efficacy endpoints | Respiratory and attitude clinical scores, gross and microscopic lung lesion scores, serum viremia, viral lung load and body weight to lung weight ratio. Body temperature and body weights were collected as secondary variables |

Masking was accomplished through separation of function. Any study personnel involved in daily observations, clinical scoring, assessment of gross and microscopic lung pathology, processing of samples or interpretation of laboratory results remained masked to the association between Treatment Group number and administered Test Material. The allocation list and treatment code key was removed from the study site and retained by the sponsor for the duration of the in-life phase of the study.

Pigs were sorted by descending body weight and blocked, without regard to gender, consecutively from highest body weight to lowest body using the RAND( ) function in Excel.

Animals

Pigs utilized in this study originated from a single commercial swine farm that had not received any PRRSV vaccinations, were PRV stage free and brucellosis class free status herd. The pigs were confirmed PRRSV and *Mycoplasma hyopneumoniae* sero-negative. ELISA results are retained in the study file.

For inclusion in the study, a pig must not have received, at any time, PRRSV vaccination; have traceable records verifying approximate age, farm of origin, and verification of PRRSV status; have a rectal temperature of 105° F. on Study Day −1; have a respiratory score and depression score of 0 on Study Day −1 and 0; and be physically healthy as determined by general health observation on Study Days −1 and 0.

Immunomodulator

The immunomodulator used in this study is the same immunomodulator described above in Example 1.

Study Procedures

Body temperatures were determined rectally for each enrolled pig beginning on Study Days −2 and −1 (prior to dosing), 0 (prior to challenge), 2, 4, 7, 10 (prior to necropsy), and day of necropsy. Body weight of pigs was obtained on Study Days −7 (for treatment and pen allocation only), 0, 7, 10 and 14.

The NADC (National Animal Disease Center)—20 PRRS virus was originally isolated in MARC-145 cells inoculated with liver tissue from a sow (NO 35358) that aborted in an atypical PRRS abortion storm and was euthanized as part of a diagnostic investigation in 1996. The isolate is maintained at the NADC in Ames, Iowa Each pig was subsequently administered 2 mL of the of the $5.38 \times 10^5$ TCID50/ml suspension intranasally (1 mL per nare). To increase the success of infection, the PRRSV suspension was administered with the use of a pediatric mucosal atomization device (Wolfe Tory Medical, Inc. Salt Lake City, Utah) attached to the end of a disposable 3.0 mL syringe. The inoculum was administered incrementally during inspiration.

Quantitative assessment of infectious PRRS viral load was determined on all pigs on Study Days −2, 4, 7, 10 and the day of necropsy by virus isolation (VI) according to the following procedures.

Determination of viremia was accomplished by preparing tenfold serial dilutions of serum in MEM media containing 2% horse serum, 1× antibiotic/antimycotic, and 1× L-glutamine. A 0.2 ml volume of the diluted serum samples was transferred in triplicate to 96-well tissue culture plates containing pre-seeded Marc-145 cells. After 4 days of cul-

TABLE 43

Dilution Steps for Test Material Preparation.

| Treatment Group (Group -μg of IVP or control group description) | mL of 200 μg/mL immunemodulator suspended in sterile water to add to 50 mL conical tube | mL of 5% Dextrose to add to reconstituted immune-modulator | Final of Volume Test Material | Final Concentration (μg/mL) of Diluted immunemodulator | Volume (mL) of Diluted immunemodulator to administer to each pig |
|---|---|---|---|---|---|
| D - 25 μg | 1.5 | 22.5 | 24 | 12.5 | 2 |
| A - 50 μg | 3.0 | 21.0 | 24 | 25 | 9 |
| C - 75 μg | 4.5 | 19.5 | 24 | 37.5 | 2 |
| B - Placebo and E - Strict Control Pigs | 3.0 mL sterile water | 21.0 | 24 | 0 | 2 |

Pigs allocated to immunomodulator treatment groups received a single one-time intramuscular injection of a 2 mL suspension of immunomodulator and 5% dextrose water to deliver 25, 50 or 75 μg of immunomodulator plasmid DNA. Pigs were observed twice daily for general health observations and once per day specifically for the assessment and recording of clinical scores associated with respiration and attitude.

ture at 37° C. in a 5% $CO_2$ atmosphere, the presence of virus was determined in an immunofluorescence assay (IFA) using PRRSV monoclonal antibody SDOW-17-F. The TCID50 was calculated using the Spearman-Karber method.

Viral load in lung tissue was determined in lung tissue samples collected at necropsy. Virus load in the lung was determined from bronchoalveolar lavage (BAL) fluid collected from the right middle lobe. Quantification of virus from the sample was achieved.

At necropsy the lungs were removed from the thoracic cavity, photographed (dorsal and ventral aspects with the pig ear tag captured in each photo) and gross lesions scored by the pathologist, based on the scoring system described by Halbur et al (1995). Briefly, five (5.0) potential points were assigned to each of the dorsal and ventral aspects of the anterior lobe, middle lobe and accessory lobe. Fifteen points (15.0) were assigned to the dorsal caudal lobe and twelve and a half (12.5) points assigned to the ventral aspect of the caudal lobe.

Each lung lobe (dorsal and ventral aspects of the lung) was observed and the estimated percentage of the lung affected with gross lesions was documented on the sponsor supplied data capture form. The sponsor assigned a final lesion score to each lobe by multiplying the maximum score for the lobe by the percent of the lobe affected. For example, if 20% of the dorsal caudal lobe had observed lesions, the lesion score for that lobe was calculated as (20×15)/100=a lesion score of 3.

To assess microscopic lesions in lung tissue sections, approximately 1 cm thick x 5 cm long×5 cm wide samples were taken from each lung (FIG. 22):
a) the cranial part of the left cranial lobe,
b) the caudal part of the left cranial lobe and
c) the cranial part of the left caudal lobe.

The samples were fixed for at least 48 hours in 10% neutral buffered formalin and then processed and embedded in paraffin in an automated tissue processor.

Lung sections were examined and given an estimated score of severity of interstitial pneumonia based on the following four criteria:
A. Alveolar septal thickening: 0—no thickening (normal); 1—mild (relative); 2—moderate (relative); 3—severe (relative)
B. Distribution of Alveolar septal thickening: 0—no lesion (normal); 1—focal thickening of septa; 2—multifocal thickening of septa; 3—diffuse thickening of septa
C. BALT development: 0—minimal cells to normal BALT; 1—mildly increased in numbers; 2—moderately increased in numbers; 3—severely increased in numbers.
D. Evidence of inflammation in the airway: 0—None; 1—mild; 2—moderate; 3—severe.

All pigs were observed and scored once daily, beginning on Study Day −2 until Study Day 14, for respiration and attitude according to the following scoring criteria.

TABLE 44

Scoring Criteria.

| Clinical Observation | Clinical Signs |
| --- | --- |
| Respiration | 0 = Normal. Thoracic breathing with some abdominal movement |
| | 1 = Mild respiratory distress. Some abdominal breathing |
| | 2 = Moderate respiratory distress. Exaggerated abdominal and labored breathing |
| | 3 = Severe respiratory distress. Very labored breathing, abdominal breathing. Mouth open, cyanosis of nose and ear |
| Depression/Activity | 0 = Normal. Pigs react briskly/grunt upon opening the door. The pigs are active, playful and curious. Look towards the door, approach the gate and sniff. Show interest in food and water. If excited, they might urinate and defecate |
| | 1 = Mild. Get up upon stimulation but slow or show little interest or curiosity. |

TABLE 44-continued

Scoring Criteria.

| Clinical Observation | Clinical Signs |
| --- | --- |
| | Will go back to lying down quickly. Some interest in food |
| | 2 = Moderate. Pronounced inactivity and reluctance to get up/move. Prostration, staggering, ataxia |
| | 3 = Severe. Non-responsive, will not get up |

Statistical Methods

The evaluation of the disease model consisted of analyzing the gross lung and micro lung data between the two control groups. A statistically significant difference is required to show the challenged control group exhibited adequate disease as compared to the non-challenged strict control group. Gross lung scores (sum total of the each of the lobes) were compared using an analysis of variance testing for group effects. Each of the four (4) micro lung scores (alveolar septal thickening, distribution of septa) thickening, airway inflammation and BALT development) were compared using a non-parametric Wilcoxon Ranked Sum test.

The remaining analyses included on Groups 2 through 5 (challenged control and immunomodulator treated groups), provided the above disease model validation was met.

Clinical scores (respiratory and attitude scores) were analyzed for each day by Fisher's Exact test. If the overall treatment group effect was significant on any one day, then pair-wise comparisons were performed between the control group versus each of the immunomodulator groups (3 comparisons) for this day.

Data with repeated measurements (serum viremia, body weights, body temperature) were analyzed using a repeated measures analysis of variance and included a baseline covariate where applicable. The covariance structure with the smallest AIC result was used. Arc sine transformations were applied as needed, to closer approximate normal data distributions.

Data with a single endpoint (gross lung scores, lung viremia (BAL) and body weight to lung weight ratio) were analyzed with an analysis of variance. All models above incorporated pen as a factor in the model and transformation of dependent variables where appropriate.

Micro lung (septal, Dseptal, airway and BALT) scores were analyzed using a non-parametric Wilcoxon Ranked Sum test.

All analyses were performed using SAS 9.2 and an alpha of 0.1 was used to distinguish significant effects.

Results

Both the gross and micro lung scores exhibited a significant treatment effect when comparing the strict control versus the challenged control groups (p-values of 0.0021, 0.0038, 0.0631, 0.0001 and 0.0016, for gross, septal, septal distribution, airway and BALT, respectively). Hence, disease model validation was met.

Respiratory scores demonstrated significant treatment group difference only on Study Day 12 (p-value of 0.0719). For the other Study Days, respiratory scores resulted in no significant treatment group differences (p-values of 0.1202 or greater). The pair wise comparison between the control groups versus each of the immunomodulator groups (three comparisons) on Study Day 12 showed no significant pair-wise treatment differences (p-values of 0.2174 or greater).

Attitude scores demonstrated significant treatment group difference on day 3, 4, 6, 7, and 12 (p-values of 0.0349, 0.0831, 0.0349, 0.0073, 0.0699 respectively). For the other study days, respiratory scores resulted in no significant treatment group differences (p-values of 0.1960 or greater). For the pair wise comparison between the control group versus each of the immunomodulator treated groups on Study Days 3, 4, 6, 7, and 12. Significantly greater attitude scores were observed for the immunomodulator 50 μg treatment group versus the control group on Study Day 7 (p-value of 0.0902). Conversely, significantly lower attitude scores were observed in the immunomodulator 75 μg treated group versus the control group on Study Day 12 (p-value of 0.0932).

Figure 26:
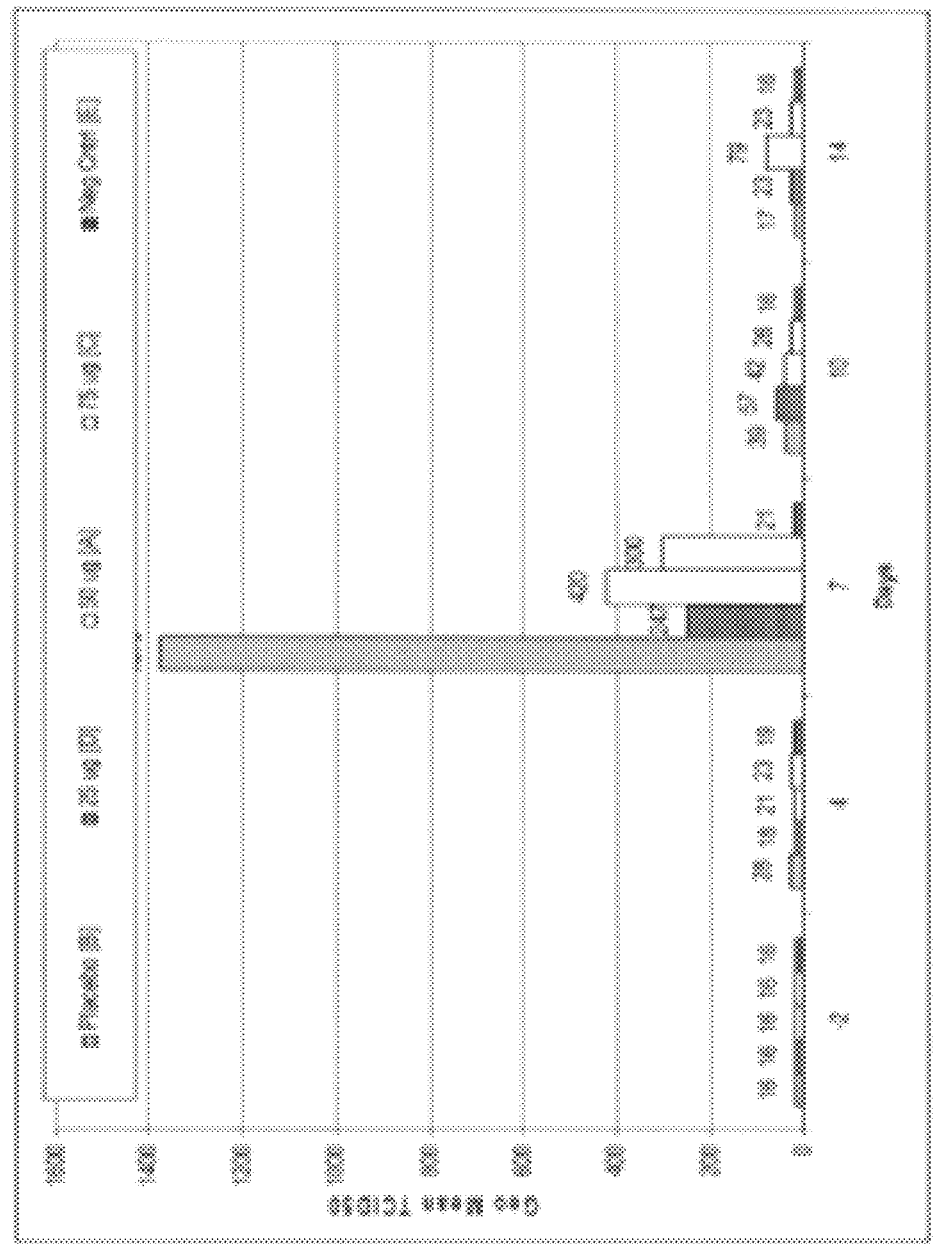
FIG. 26 graphically illustrates the serum viremia mean on days −2, 4, 7, 10 and 14 for treatment groups including placebo, 25 µg immunomodulator, 50 µg immunomodulator, 75 µg immunomodulator, and negative control.

Serum viremia data resulted in a statistically significant treatment x day interaction (p=0.0797), as shown in FIG. 26. Pair-wise control group comparisons with each of the immunomodulator groups on each day resulted in significantly lower serum viremia for immunomodulator 25 μg (Days 4 and 7) and immunomodulator 75 μg (Day 7 only) and significantly higher serum viremia for immunomodulator 50 μg on Study Day 14.

Gross lung pathology, (represented by the sum total lobe scores for each animal), exhibited no statistically significant treatment group difference (overall treatment effect was 0.8685).

Figure 28:
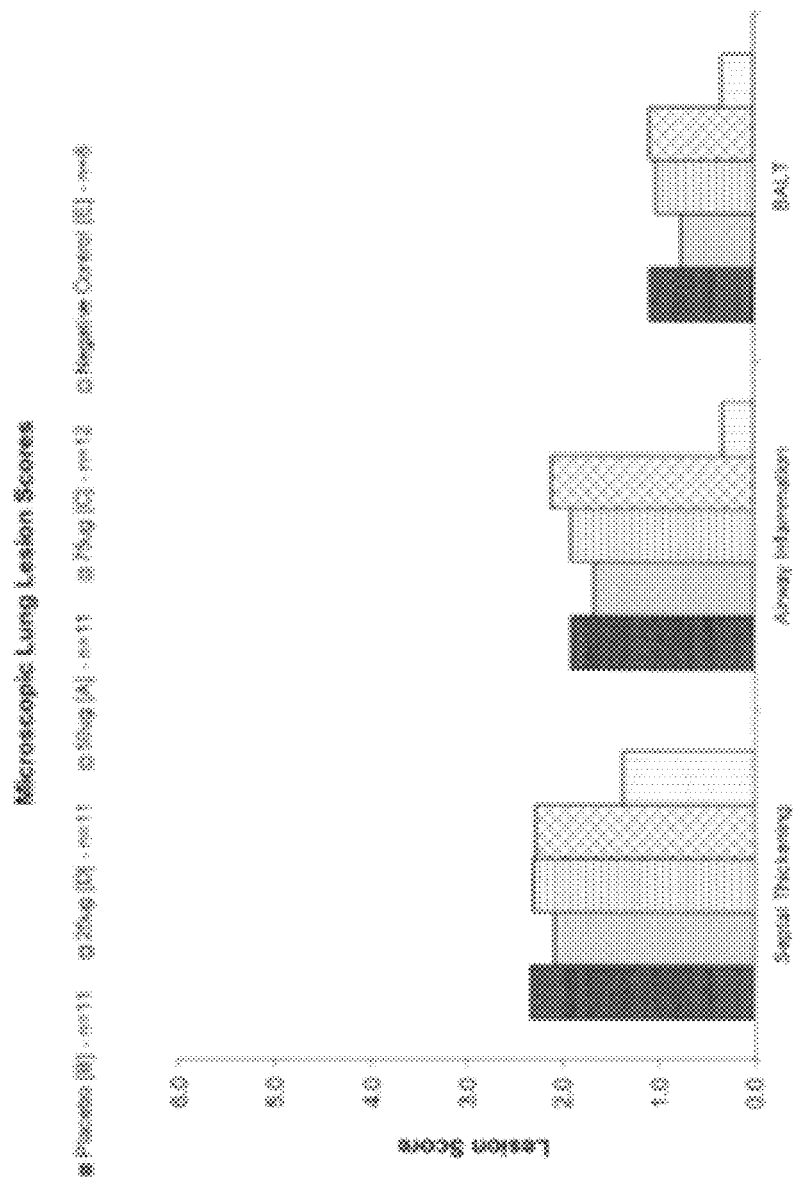
FIG. 28 shows the microscopic lung lesion scores between the treatment groups including placebo, 25 µg immunomodulator, 50 µg immunomodulator, 75 µg immunomodulator, and negative control; and, FIG. 29 shows the prevalence of diarrhea associated with enterotoxigenic *E. coli* (F18 pili, the EAST1, STa, and STb toxins, and AIDA adhesin genes) in weaned pigs across treatment groups.

Micro lung total pathology scores, shown in FIG. 28, did not exhibit any statistically significant differences between the treatment groups (p-values of 0.6726, 0.2801 and 0.2901 for septal, airway and BALT tissues). Total distribution septal thickening score showed significant treatment difference (p-value of 0.0075). For the pair wise comparison between the control group versus each of the immunomodulator groups, significant differences could only be observed between the control group and immunomodulator 75 μg group (p-value=0.0043).

Discussions and Conclusions

Figure 27:
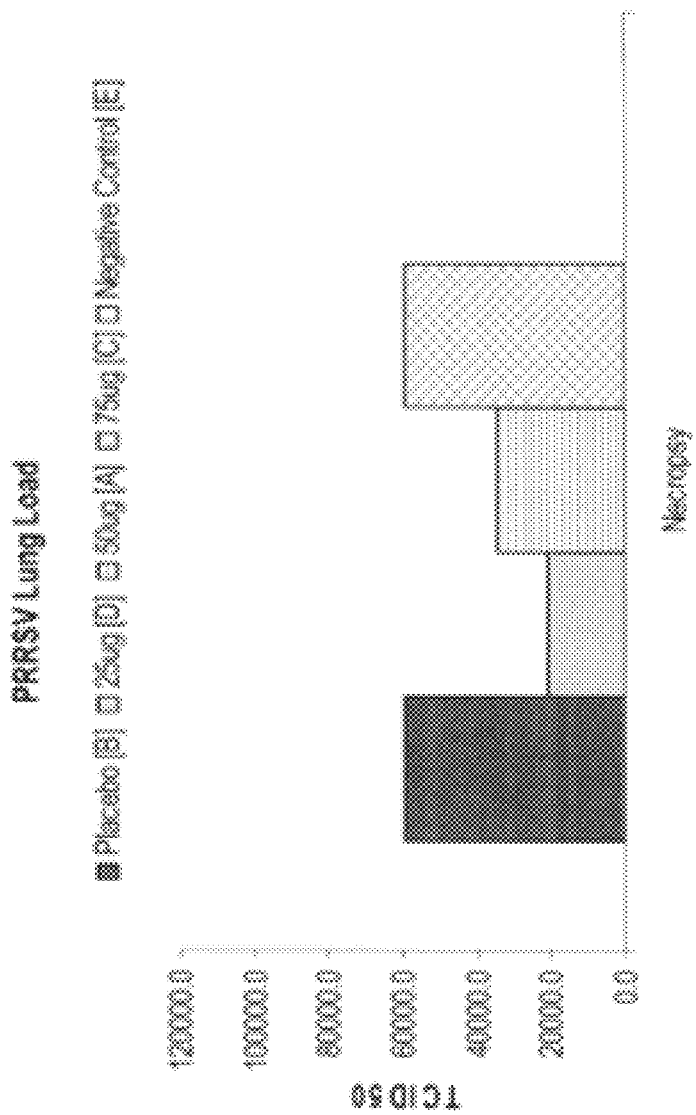
FIG. 27 shows the mean PRRSV viral lung load between the treatment groups including placebo, 25 µg immunomodulator, 50 µg immunomodulator, 75 µg immunomodulator, and negative control.

The geometric mean serum viremia was greatly reduced in the all of the immunomodulator treated groups on Study Day 7 relative to the placebo challenged group. Also, the mean viral lung load was markedly lower in the 25 μg and 50 μg treated pigs relative to the placebo treated challenged pigs, as shown in FIG. 27. Similar results were observed in another study whereby mean viral lung load showed a marked reduction in immunomodulator treated pigs. It is apparent that the immunomodulator is providing a measurable level of efficacy in reducing PRRSV lung load.

Example 5. Efficacy of Immunomodulator Composition in an *E. coli* Challenge Model in Neonatal Piglets The study was conducted to evaluate the efficacy of an immunomodulator composition in susceptible newborn piglets by virulent *Escherichia coli* K88 challenge. All sows in the study were negative for *E. coli* K88 in their fecal samples. No treatment related adverse events were reported. All piglets in the study were challenged a few hours after farrowing. The piglets from sows 4009, 2694, 10040, 4001, and 2088 were challenged with *E. coli* culture batch 1. The piglets from sows 2082, 217, and 215 were challenged with *E. coli* culture batch 2.

32 piglets were necropsied during the study. The cause of death or early termination for 31 piglets was due to colibacillosis. One piglet (305 T2) was laid on by the sow and was found dead. All piglets died or euthanized (31 pigs) due to colibacillosis lost body weight except for one pig (331 T1). All piglets that survived (37 pigs) the duration of the study gained body weight. The body weight gain ranged from 240 to 1,540 grams. Piglets born to sow 2088 did not have clinical signs as compared to piglets born to other sows. Only two piglets (342 T1 and 336 T3) had a fecal score of 2 at one observation. The analyses were performed with or without inclusion of piglets from this sow. 13 of 23 (57%) pigs treated with saline died due to colibacillosis. 9 of 22 (41%) pigs treated with immunomodulator composition 1× died due to colibacillosis. 9 of 23 (39%) pigs treated with immunomodulator composition 5× died due to colibacillosis. Excluding the piglets from one sow (2088) the analysis were as follows: 13 of 20 (65%) pigs treated with saline died due to colibacillosis. 9 of 19 (53%) pigs treated with Immunomodulator composition 1× died due to colibacillosis.

9 of 20 (45%) pigs treated with IC-Ex.1 5× died due to colibacillosis. *E. coli* strain MVS #2 was able to induce mortality, clinical signs and diarrhea in susceptible neonatal piglets challenged on the day of birth. Treating piglets with immunomodulator composition numerically reduced the mortality in both the treated groups (1× and 5×) as compared to control, but was not statistically different.

Materials and Methods

Test animals.

Nine Hermitage maternal lines—classic Hybrid™ pregnant sows owned by Klitz farm of rural West Point, Nebr., were tested and confirmed to be negative for *E. coli* K88 in their feces. Eight pregnant sows were purchased and moved to Farrowing Unit 4 within Klitz farm facility. Sows received no *E. coli* K88 vaccine and antimicrobial agents for at least 30 days prior to farrowing. Eight litters of neonatal piglets entered the study. The sows and piglets were free of concurrent disease that could confound the interpretation of clinical data.

Animal Feed and Water.

Sows were fed ad libitum lactation ration via feeders and ad libitum water via automatic waterers. Waterers and feeders were checked daily and cleaned as needed. The sole source of food for the piglets was milk (nursing) from the sow.

Concomitant Medication.

Sodium monensin mixed feed was administered to sows.

Housing.

Sows were housed in the Farrowing Unit 4. During the study, the animals were exposed to approximately 12 hours of light per day and high and low temperature ranged from 70° F. to 73° F., and humidity ranged from 49 to 69%.73° F., and humidity ranged from 49 to 69%.

Study Design Summary.

The details of the treatment groups are listed in Table 52. The study had three groups of piglets. Piglets in group T1, T2 and T3 received saline, IC-Ex.1 1× and 5×, respectively. All piglets in the study were injected with 2 mL of appropriate test material by intramuscular route.

Testing for K88 Pili Antigen.

Fecal samples from pregnant sows were collected and transported to the lab. The samples were diluted and streaked on to MacConkey agar plates and incubated overnight at ~37° C. *E. coli* like colonies were selected from the plates and tested in an agglutination test using antisera specific for *E. coli* K88 pili (Abcam Scientifics). The pregnant sows selected and purchased for the study were negative for *E. coli* with K88 pili.

Randomization.

Each sow farrowed 7 to 12 piglets. Piglets were identified with duplicate unique ear tags. Within litter, piglets were ranked by descending order of body weight and first 6 (one sow farrowed 7 piglets) or 9 (7 sows farrowed 10 to 12 piglets) ranked piglets were included in to the study. The piglets in the study from each litter were randomly assigned to one of three treatment groups (Tables 52). 69 piglets were included into the study.

Challenge Culture Preparation.

Two batches of challenge cultures were prepared. For each batch, one vial of E. coli K-88 isolate (MVS #2, 4th passage) was removed from the ultra-low freezer and thawed at room temperature. A loopful of E. coli K-88 culture was removed from the vial, and streaked on to a 5% sheep blood agar (BA) plate. The BA plate was incubated overnight at 37° C. in a 5% $CO_2$ incubator. The colonies on the BA plates were observed for purity and beta hemolytic zones. Five beta hemolytic colonies from the BA plate were picked and transferred to a tube containing 10 mL of pre-warmed Tryptic Soy broth (TSB) and dispersed it by pipetting several times to form an uniform suspension. The suspension was transferred to a flask containing 200 mL of pre-warmed TSB. The flask was incubated at 37° C. for approximately six hours. After incubation, the culture was tested for optical density (OD) at 600 nm. The OD for batch 1 and 2 cultures was 1.16 and 1.12, respectively. The cultures were diluted to 0.85 OD, and transported 500 mL and 450 mL of batch 1 and 2, respectively to the farrowing unit 4 for challenge.

Challenge Procedure.

Piglets were withheld from the sow for approximately one hour prior and one hour after challenge (total two hours). All piglets in the study were challenged orally with 5 mL of prepared challenge culture.

Test Material.

Saline:

Saline lot number A110901-3 with an expiration date of September 2013 was purchased from Vedco. Each 100 mL of saline contained 0.9 gram of sodium chloride and water for injection. Saline was used as control material.

Sterile Water:

Sterile water for injection, lot number 6000844 with an expiration date of September 2013 was purchased in 100 mL vials from APP Pharmaceuticals, LLC. Sterile water was used to rehydrate immunomodulator composition.

5% Dextrose:

Five % dextrose USP, lot number 19-112-JT with an expiration date of January 2014 was purchased in 250 mL bags from Hospira Inc. Five % dextrose was used to dilute rehydrated immunomodulator composition.

Immunomodulator Composition Preparation:

Immunomodulator vials were removed from the refrigerator and allowed to warm to room temperature. Each vial was rehydrated immediately before use by the addition of 2 mL of sterile water. The vial was swirled for 30 seconds, and allowed to sit at room temperature for 5 minutes. The rehydrated immunomodulator composition was diluted using 5% dextrose according to the dilution scheme in Table 45. The diluted immunomodulator composition was stored with cold pack until use (approximately for 2 hours).

TABLE 45

Immunomodulator composition dilution scheme.

| Treatment | Stock IC-Ex. 1 Volume (mL)[2] | Diluent -D5W (mL)[3] | Total Volume (mL) | Total doses |
|---|---|---|---|---|
| IC-Ex.1 1X (T2) | 1 | 59 | 60 | 30 |
| IC-Ex.1 5X (T3) | 1 | 11 | 12 | 6 |

Treatment.

Approximately two hours after challenge, the piglets were treated. Each piglet was given 2 mL of appropriate treatment (see Tables 48 to 51) by intramuscular route, in the right side of neck. The piglets in group T1, T2 and T3 received saline, immunomodulator composition 1x, and 5x, respectively.

Clinical Assessment.

Prior to enrollment Sows and piglets were observed by the study veterinarian and were found to be healthy. Following challenge, the piglets were observed twice daily until Day 5.

Scoring Details.

Piglets were individually examined and a cotton swab was gently inserted into the rectum to help assess fecal consistency. The animals were scored (see Tables 46 and 47) twice a day after challenge:

TABLE 46

Fecal Scores.

0: Normal, solid faces.
1: Semi-solid feces.
2: Watery feces with some solid material.
3: Profuse watery feces with no solid material.
4: Animals that died or removed and euthanized for humane reasons received a score of 4

TABLE 47

General physical condition scores.

0: Appears normal.
1: Slight dehydration and/or slightly gaunt and/or rough hair-coat.
2: Dehydrated. gaunt irrespective of hair-coat.
3: Pig is unable to stand without help (feeble).
4: Animals that died or removed and euthanized for humane reasons received a score of 4

Body Weight.

Piglets were weighed prior to challenge (Tables 48 to 51), prior to termination or on the day of death or euthanasia.

Statistical Analysis.

Animals were considered clinically ill if they had a general physical score of 2 or higher for at least one day during the five day observation period. Animals were considered positive for fecal score if they had a fecal sore of 2 or higher for at least two observations during the five day observation period.

Results

All sows in the study were negative for E. coli K88 in their fecal samples. The piglets had no treatment related adverse events. All piglets in the study were challenged few hours after farrowing. The piglets from sows 4009, 2694, 10040, 4001, and 2088 were challenged with E. coli culture batch 1, and pre and post titers were $1.04 \times 10^9$ CFU/mL and $9.6 \times 10^8$ CFU/mL, respectively. The piglets from sows 2082, 217, and 215 were challenged with E. coli culture batch 2, and pre and post titers were $9.9 \times 10^8$ CFU/mL and $9.0 \times 10^8$ CFU/mL, respectively.

Thirty two piglets were necropsied during the study. The cause of death or early termination for 31 piglets was due to colibacillosis. One piglet (305 T2) was laid on by the sow and was found dead.

All piglets died or euthanized (31 pigs) due to colibacillosis lost body weight except for one pig (331 T1). All pigs that survived (37 pigs) the duration of the study gained body weight.

The body weight gain ranged from 240 to 1,540 grams. Piglets born to sow 2088 did not have clinical signs as compared to piglets born to other sows. Only two piglets (342 T1 and 336 T3) had a fecal score of 2 at one observation. The analyses were performed with or without inclusion of piglets from this sow. 13 of 23 (57%) pigs treated with saline died due to colibacillosis. 9 of 22 (41%) pigs treated with immunomodulator composition 1× died due to colibacillosis. 9 of 23 (39%) pigs treated with immunomodulator composition 5× died due to colibacillosis. Excluding the piglets from one sow (2088) the analysis were as follows: 13 of 20 (65%) pigs treated with saline died due to colibacillosis. 9 of 19 (53%) pigs treated with immunomodulator composition 1× died due to colibacillosis. 9 of 20 (45%) pigs treated with immunomodulator composition 5× died due to colibacillosis.

*Escherichia coli* strain MVS #2 was able to induce mortality, clinical signs and diarrhea in susceptible neonatal piglets challenged on the day of birth. Treating piglets with immunomodulator composition numerically reduced the mortality in both the treatment groups (1× and 5×) as compared to controls, but was not statistically different. The study may be repeated in a larger sample providing adequate power for statistical analysis.

TABLE 48

Randomization and allocation of piglets to treatment group (Sows ID 4009 and 2694)

|  | Body weight Kg | Treatment |
|---|---|---|
| Sow ID 40095 Pig ID | | |
| 304 | 1.66 | T1 |
| 302 | 1.54 | T3 |
| 301 | 1.50 | T2 |
| 303 | 1.10 | T3 |
| 305 | 1.10 | T2 |
| 306 | 0.86 | T1 |
| Sow ID 2694 Pig ID | | |
| 311 | 2.00 | T3 |
| 314 | 1.92 | T1 |
| 307 | 1.90 | T2 |
| 315 | 1.86 | T1 |
| 310 | 1.80 | T3 |
| 309 | 1.76 | T2 |
| 312 | 1.68 | T3 |
| 313 | 1.66 | T1 |
| 308 | 1.56 | T2 |

T1 = Saline
T2 = IC-Ex. 1 1X
T3 = IC-Ex. 1 5X

TABLE 49

Randomization and allocation of piglets to treatment group (Sows ID 10040 and 4001).

|  | Body weight Kg | Treatment |
|---|---|---|
| Sow ID 10040 Pig ID | | |
| 319 | 1.56 | T2 |
| 320 | 1.46 | T1 |
| 324 | 1.44 | T3 |
| 316 | 1.34 | T3 |
| 321 | 1.20 | T1 |
| 318 | 1.18 | T2 |
| 323 | 1.18 | T2 |
| 317 | 0.94 | T3 |
| 322 | 0.94 | T1 |
| Sow ID 4001 Pig ID | | |
| 325 | 1.70 | T3 |
| 332 | 1.68 | T1 |

TABLE 49-continued

Randomization and allocation of piglets to treatment group (Sows ID 10040 and 4001).

|  | Body weight Kg | Treatment |
|---|---|---|
| 326 | 1.62 | T2 |
| 329 | 1.60 | T2 |
| 327 | 1.50 | T3 |
| 331 | 1.46 | T1 |
| 328 | 1.38 | T1 |
| 333 | 1.38 | T2 |
| 330 | 1.26 | T3 |

T1 = Saline
T2 = IC-Ex. 1 1X
T3 = IC-Ex. 1 5X

TABLE 50

Randomization and allocation of piglets to treatment group.

| Sow ID 2088 Pig ID | Body weight Kg | Treatment | Sow ID 2082 Pig ID | Body weight Kg | Treatment |
|---|---|---|---|---|---|
| 336 | 1.68 | T3 | 345 | 2.02 | T2 |
| 337 | 1.66 | T2 | 344 | 1.90 | T1 |
| 338 | 1.66 | T1 | 349 | 1.78 | T3 |
| 334 | 1.44 | T2 | 351 | 1.74 | T3 |
| 341 | 1.28 | T3 | 346 | 1.50 | T2 |
| 342 | 1.16 | T1 | 350 | 1.26 | T1 |
| 335 | 1.14 | T2 | 347 | 1.16 | T2 |
| 339 | 1.12 | T1 | 348 | 1.00 | T1 |
| 340 | 1.00 | T3 | 343 | 0.98 | T3 |

T1 = Saline
T2 = IC-Ex. 1 1X
T3 = IC-Ex. 1 5X

TABLE 51

Randomization and allocation of piglets to treatment group (Sows ID 217 and 215)

| Sow ID 217 Pig ID | Body weight Kg | Treatment | Sow ID 215 Pig ID | Body weight Kg | Treatment |
|---|---|---|---|---|---|
| 352 | 1.98 | T2 | 363 | 2.06 | T2 |
| 357 | 1.76 | T1 | 361 | 2.00 | T1 |
| 360 | 1.76 | T3 | 365 | 1.86 | T3 |
| 353 | 1.72 | T2 | 362 | 1.76 | T2 |
| 359 | 1.70 | T1 | 367 | 1.74 | T3 |
| 354 | 1.58 | T3 | 366 | 1.66 | T1 |
| 356 | 1.50 | T3 | 364 | 1.62 | T3 |
| 358 | 1.40 | T2 | 369 | 1.50 | T2 |
| 355 | 1.30 | T1 | 368 | 1.46 | T1 |

T1 = Saline
T2 = IC-Ex. 1 1X
T3 = IC-Ex. 1 5X

TABLE 52

Treatment groups.

| Treatment Group | Treatment | Dose | Challenge |
|---|---|---|---|
| T1 | Saline | 2 mL/pig IM | *Escherichia coli* strain MVS #2 |
| T2 | IC-Ex. 1 1X | 2 mL/pig IM | *Escherichia coli* strain MVS #2 |
| T3 | IC-Ex. 1 5X | 2 mL/pig IM | *Escherichia coli* strain MVS #2 |

The treatments were administered ~2 hours after challenge in order to evaluate treatment effect.

TABLE 53

Body weight of pigs died or euthanized - (Sow ID 4009 and 2694)

| Sow ID 4009 Pig ID | Body weight Kg | Treatment | Sow ID 2694 Pig ID | Body weight Kg | Treatment |
|---|---|---|---|---|---|
| 301# | 2.68 | T2 | 307# | 3.02 | T2 |
| 302# | 2.34 | T3 | 308** | 1.24 | T2 |
| 303# | 2.02 | T3 | 309# | 2.96 | T2 |
| 304** | 1.18 | T1 | 310# | 3.22 | T3 |
| 305* | 1.12 | T2 | 311# | 3.54 | T3 |
| 306# | 1.42 | T1 | 312# | 3.04 | T3 |
|  |  |  | 313# | 2.82 | T1 |
|  |  |  | 314** | 1.54 | T1 |
|  |  |  | 315# | 3.32 | T1 |

T1 = Saline
T2 = IC-Ex. 1 1X
T3 = IC-Ex. 1 5X
*Laid on by Sow
**Died or euthanized due to colibacillosis
Euthanized at the end of the study

TABLE 54

Body weight of pigs died or euthanized (Sows ID 10040 and 4001).

| Sow ID 10040 Pig ID | Body weight Kg | Treatment | Sow ID 4001 Pig ID | Body weight Kg | Treatment |
|---|---|---|---|---|---|
| 316** | 1.00 | T3 | 325** | 1.26 | T3 |
| 317** | 0.72 | T3 | 326# | 2.66 | T2 |
| 318** | 0.90 | T2 | 327# | 2.78 | T3 |
| 319# | 2.42 | T2 | 328** | 1.18 | T1 |
| 320** | 1.12 | T1 | 329# | 2.42 | T2 |
| 321** | 0.86 | T1 | 330** | 0.92 | T3 |
| 322** | 0.92 | T1 | 331** | 1.50 | T1 |
| 323# | 1.88 | T2 | 332** | 1.26 | T1 |
| 324** | 1.10 | T3 | 333** | 1.04 | T2 |

T1 = Saline
T2 = IC-Ex. 1 1X
T3 = IC-Ex. 1 5X
*Laid on by Sow
**Died or euthanized due to colibacillosis
Euthanized at the end of the study

TABLE 55

Body weight of pigs died or euthanized (Sows ID 2088 and 2082)

| Sow ID 2088 Pig ID | Body weight Kg | Treatment | Sow ID 2082 Pig ID | Body weight Kg | Treatment |
|---|---|---|---|---|---|
| 334# | 2.66 | T2 | 343** | 0.82 | T3 |
| 335# | 2.02 | T2 | 344# | 2.72 | T1 |
| 336# | 2.34 | T3 | 345** | 1.52 | T2 |
| 337# | 2.76 | T2 | 346# | 2.50 | T2 |
| 338# | 2.64 | T1 | 347# | 1.96 | T2 |
| 339# | 1.96 | T1 | 348** | 0.66 | T1 |
| 340# | 1.68 | T3 | 349# | 2.02 | T3 |
| 341# | 2.10 | T3 | 350** | 1.00 | T1 |
| 342# | 1.80 | T1 | 351# | 2.86 | T3 |

T1 = Saline
T2 = IC-Ex. 1 1X
T3 = IC-Ex. 1 5X
*Laid on by Sow
**Died or euthanized due to colibacillosis
Euthanized at the end of the study

TABLE 56

Body weight of pigs died or euthanized (Sows ID 217 and 215)

| Sow ID 217 Pig ID | Body weight Kg | Treatment | Sow ID 215 Pig ID | Body weight Kg | Treatment |
|---|---|---|---|---|---|
| 352** | 1.48 | T2 | 361** | 1.54 | T1 |
| 353** | 1.30 | T2 | 362** | 1.20 | T2 |
| 354# | 2.78 | T3 | 363# | 3.50 | T2 |
| 355# | 2.52 | T1 | 364** | 1.14 | T3 |
| 356# | 2.44 | T3 | 365# | 2.88 | T3 |
| 357# | 2.80 | T1 | 366# | 1.16 | T1 |
| 358** | 1.06 | T2 | 367** | 1.28 | T3 |
| 359** | 1.38 | T1 | 368# | 2.30 | T1 |
| 360** | 1.28 | T3 | 369# | 1.18 | T2 |

T1 = Saline
T2 = IC-Ex. 1 1X
T3 = IC-Ex. 1 5X
*Laid on by Sow
**Died or euthanized due to colibacillosis
Euthanized at the end of the study

TABLE 57

Pigs post challenge body weight gain or loss (Sows ID 4009 and 2694)

| Sow ID 4009 Pig ID | Body weight Kg (gain or loss) | Treatment | Sow ID 2694 Pig ID | Body weight Kg (gain or loss) | Treatment |
|---|---|---|---|---|---|
| 301# | 1.18 | T2 | 307# | 1.12 | T2 |
| 302# | 0.80 | T3 | 308** | -0.32 | T2 |
| 303# | 0.92 | T3 | 309# | 1.2 | T2 |
| 304** | -0.48 | T1 | 310# | 1.42 | T3 |
| 305* | 0.02 | T2 | 311# | 1.54 | T3 |
| 306# | 0.56 | T1 | 312# | 1.36 | T3 |
|  |  |  | 313# | 1.16 | T1 |
|  |  |  | 314** | -0.38 | T1 |
|  |  |  | 315# | 1.46 | T1 |

T1 = Saline
T2 = IC-Ex. 1 1X
T3 = IC-Ex. 1 5X
*Laid on by Sow
**Died or euthanized due to colibacillosis
Euthanized at the end of the study

TABLE 58

Pigs post challenge body weight gain or loss (Sows ID 10040 and 4001).

| Sow ID 10040 Pig ID | Body weight Kg (gain or loss) | Treatment | Sow ID 4001 Pig ID | Body weight Kg (gain or loss) | Treatment |
|---|---|---|---|---|---|
| 316** | -0.34 | T3 | 325** | -0.44 | T3 |
| 317** | -0.22 | T3 | 326# | 1.04 | T2 |
| 318** | -0.28 | T2 | 327# | 1.28 | T3 |
| 319# | 0.86 | T2 | 328** | -0.2 | T1 |
| 320** | -0.34 | T1 | 329# | 0.82 | T2 |
| 321** | -0.34 | T1 | 330** | -0.34 | T3 |
| 322** | -0.02 | T1 | 331** | 0.04 | T1 |
| 323# | 0.70 | T2 | 332** | -0.42 | T1 |
| 324** | -0.34 | T3 | 333** | -0.34 | T2 |

T1 = Saline
T2 = IC-Ex. 1 1X
T3 = IC-Ex. 1 5X
*Laid on by Sow
**Died or euthanized due to colibacillosis
Euthanized at the end of the study

TABLE 59

Pigs post challenge body weight gain or loss (Sows ID 2088 and 2082)

| Sow ID 2088 Pig ID | Body weight Kg (gain or loss) | Treatment | Sow ID 2082 Pig ID | Body weight Kg (gain or loss) | Treatment |
|---|---|---|---|---|---|
| 334# | 1.22 | T2 | 343** | −0.16 | T3 |
| 335# | 0.88 | T2 | 344# | 0.82 | T1 |
| 336# | 0.66 | T3 | 345** | −0.50 | T2 |
| 337# | 1.10 | T2 | 346# | 1.00 | T2 |
| 338# | 0.98 | T1 | 347# | 0.80 | T2 |
| 339# | 0.84 | T1 | 348** | −0.34 | T1 |
| 340# | 0.68 | T3 | 349# | 0.24 | T3 |
| 341# | 0.82 | T3 | 350** | −0.26 | T1 |
| 342# | 0.64 | T1 | 351# | 1.12 | T3 |

T1 = Saline
T2 = IC-Ex. 1 1X
T3 = IC-Ex. 1 5X
*Laid on by Sow
**Died or euthanized due to colibacillosis
Euthanized at the end of the study

TABLE 60

Pigs post challenge body weight gain or loss (Sows ID 217 and 215)

| Sow ID 217 Pig ID | Body weight Kg (gain or loss) | Treatment | Sow ID 215 Pig ID | Body weight Kg (gain or loss) | Treatment |
|---|---|---|---|---|---|
| 352** | −0.50 | T2 | 361** | −0.46 | T1 |
| 353** | −0.42 | T2 | 362** | −0.56 | T2 |
| 354# | 1.20 | T3 | 363# | 1.44 | T2 |
| 355# | 1.22 | T1 | 364** | −0.48 | T3 |
| 356# | 0.94 | T3 | 365# | 1.02 | T3 |
| 357# | 1.04 | T1 | 366** | −0.50 | T1 |
| 358** | −0.34 | T2 | 367** | −0.46 | T3 |
| 359** | −0.32 | T1 | 368# | 0.84 | T1 |
| 360** | −0.48 | T3 | 369** | −0.32 | T2 |

T1 = Saline
T2 = IC-Ex. 1 1X
T3 = IC-Ex. 1 5X
*Laid on by Sow
**Died or euthanized due to colibacillosis
Euthanized at the end of the study

TABLE 61

Clinical scores of piglets born to sow 4009.

| Group | Piglet ID | Pre Challenge FS | Pre Challenge PS | Post challenge Day 0 AM FS | Post challenge Day 0 AM PS | Post challenge Day 0 PM FS | Post challenge Day 0 PM PS | Post challenge Day 1 AM FS | Post challenge Day 1 AM PS | Post challenge Day 1 PM FS | Post challenge Day 1 PM PS | Post challenge Day 2 AM FS | Post challenge Day 2 AM PS | Post challenge Day 2 PM FS | Post challenge Day 2 PM PS | Post challenge Day 3 AM FS | Post challenge Day 3 AM PS | Post challenge Day 3 PM FS | Post challenge Day 3 PM PS | Post challenge Day 4 AM FS | Post challenge Day 4 AM PS | Post challenge Day 4 PM FS | Post challenge Day 4 PM PS | Post challenge Day 5 AM FS | Post challenge Day 5 AM PS | Post challenge Day 5 PM FS | Post challenge Day 5 PM PS |
|---|---|---|---|---|---|---|---|---|---|---|---|---|---|---|---|---|---|---|---|---|---|---|---|---|---|---|---|
| T2 | 301 | 0 | 0 | 0 | 0 | 3 | 2 | 2 | 0 | 1 | 0 | 0 | 0 | 0 | 0 | 0 | 0 | 1 | 1 | 0 | 0 | 0 | 0 | 0 | 0 | 0 | 0 |
| T3 | 302 | 0 | 0 | 0 | 0 | 3 | 1 | 2 | 0 | 2 | 1 | 0 | 0 | 0 | 1 | 0 | 0 | 0 | 1 | 1 | 1 | 0 | 0 | 0 | 0 | 0 | 0 |
| T3 | 303 | 0 | 0 | 0 | 0 | 3 | 1 | 2 | 0 | 0 | 1 | 0 | 1 | 0 | 0 | 0 | 0 | 1 | 1 | 0 | 0 | 0 | 0 | 0 | 0 | 0 | 0 |
| T1 | 304 | 0 | 0 | 0 | 0 | 3 | 2 | D | D | D | D | D | D | D | D | D | D | D | D | D | D | D | D | D | D | D | D |
| T2 | 305 | 0 | 0 | 0 | 0 | D | D | D | D | D | D | D | D | D | D | D | D | D | D | D | D | D | D | D | D | D | D |
| T1 | 306 | 0 | 0 | 0 | 0 | 3 | 1 | 3 | 2 | 3 | 2 | 0 | 1 | 0 | 0 | 0 | 1 | 1 | 1 | 1 | 1 | 0 | 1 | 1 | 0 | 1 | 0 |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 62

Clinical scores of piglets born to sow 2694.

| Group | Piglet ID | Pre Challenge FS | Pre Challenge PS | Post challenge Day 0 AM FS | Post challenge Day 0 AM PS | Post challenge Day 0 PM FS | Post challenge Day 0 PM PS | Post challenge Day 1 AM FS | Post challenge Day 1 AM PS | Post challenge Day 1 PM FS | Post challenge Day 1 PM PS | Post challenge Day 2 AM FS | Post challenge Day 2 AM PS | Post challenge Day 2 PM FS | Post challenge Day 2 PM PS | Post challenge Day 3 AM FS | Post challenge Day 3 AM PS | Post challenge Day 3 PM FS | Post challenge Day 3 PM PS | Post challenge Day 4 AM FS | Post challenge Day 4 AM PS | Post challenge Day 4 PM FS | Post challenge Day 4 PM PS | Post challenge Day 5 AM FS | Post challenge Day 5 AM PS | Post challenge Day 5 PM FS | Post challenge Day 5 PM PS |
|---|---|---|---|---|---|---|---|---|---|---|---|---|---|---|---|---|---|---|---|---|---|---|---|---|---|---|---|
| T2 | 307 | 0 | 0 | 0 | 0 | 2 | 0 | 1 | 0 | 0 | 0 | 0 | 0 | 0 | 0 | 0 | 0 | 0 | 0 | 0 | 0 | 0 | 0 | 0 | 0 | 0 | 0 |
| T2 | 308 | 0 | 0 | 0 | 0 | 3 | 2 | D | D | D | D | D | D | D | D | D | D | D | D | D | D | D | D | D | D | D | D |
| T2 | 309 | 0 | 0 | 0 | 0 | 3 | 0 | 2 | 0 | 0 | 0 | 0 | 0 | 0 | 0 | 0 | 0 | 0 | 0 | 0 | 0 | 0 | 0 | 0 | 0 | 0 | 0 |
| T3 | 310 | 0 | 0 | 0 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 |
| T3 | 311 | 0 | 0 | 0 | 0 | 1 | 0 | 1 | 0 | 0 | 1 | 0 | 0 | 0 | 0 | 0 | 0 | 0 | 0 | 0 | 0 | 0 | 0 | 0 | 0 | 0 | 0 |
| T3 | 312 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| T1 | 313 | 0 | 0 | 0 | 0 | 3 | 1 | 2 | 1 | 1 | 1 | 0 | 0 | 0 | 0 | 0 | 0 | 0 | 0 | 0 | 0 | 0 | 0 | 0 | 0 | 0 | 0 |

TABLE 62-continued

Clinical scores of piglets born to sow 2694.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T1 | 314 | 0 | 0 | 0 | 0 | 3 | 1 | D | D | D | D | D | D | D | D | D | D | D | D | D | D | D | D | D | D | D | D |
| T1 | 315 | 0 | 0 | 0 | 0 | 3 | 0 | 2 | 0 | 0 | 1 | 0 | 0 | 0 | 0 | 0 | 0 | 0 | 0 | 0 | 0 | 0 | 0 | 0 | 0 | 0 | 0 |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 63

Clinical scores of piglets born to sow 10040.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T3 | 316 | 0 | 0 | 0 | 0 | 2 | 1 | 3 | 1 | D | D | D | D | D | D | D | D | D | D | D | D | D | D | D | D | D | D |
| T3 | 317 | 0 | 0 | 0 | 0 | 3 | 1 | D | D | D | D | D | D | D | D | D | D | D | D | D | D | D | D | D | D | D | D |
| T2 | 318 | 0 | 0 | 0 | 0 | 3 | 1 | 3 | 2 | D | D | D | D | D | D | D | D | D | D | D | D | D | D | D | D | D | D |
| T2 | 319 | 0 | 0 | 0 | 0 | 1 | 1 | 2 | 1 | 2 | 2 | 0 | 1 | 0 | 1 | 0 | 1 | 0 | 0 | 0 | 0 | 0 | 0 | 0 | 0 | 0 | 0 |
| T1 | 320 | 0 | 0 | 0 | 0 | 3 | 1 | 3 | 2 | 3 | 2 | D | D | D | D | D | D | D | D | D | D | D | D | D | D | D | D |
| T1 | 321 | 0 | 0 | 0 | 0 | 3 | 2 | D | D | D | D | D | D | D | D | D | D | D | D | D | D | D | D | D | D | D | D |
| T1 | 322 | 0 | 0 | 0 | 0 | 2 | 1 | 3 | 2 | D | D | D | D | D | D | D | D | D | D | D | D | D | D | D | D | D | D |
| T2 | 323 | 0 | 0 | 0 | 0 | 1 | 1 | 3 | 2 | 3 | 2 | 2 | 2 | 0 | 1 | 0 | 1 | 0 | 1 | 0 | 1 | 0 | 1 | 0 | 0 | 0 | 0 |
| T3 | 324 | 0 | 0 | 0 | 0 | 1 | 1 | 2 | 1 | D | D | D | D | D | D | D | D | D | D | D | D | D | D | D | D | D | D |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 64

Clinical scores of piglets born to sow 4001.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T3 | 325 | 0 | 0 | 0 | 0 | 3 | 2 | D | D | D | D | D | D | D | D | D | D | D | D | D | D | D | D | D | D | D | D |
| T2 | 326 | 0 | 0 | 0 | 0 | 3 | 1 | 3 | 1 | 1 | 1 | 0 | 0 | 0 | 0 | 0 | 0 | 1 | 0 | 1 | 0 | 0 | 0 | 1 | 0 |
| T3 | 327 | 0 | 0 | 0 | 0 | 3 | 1 | 2 | 0 | 1 | 0 | 0 | 0 | 0 | 0 | 0 | 0 | 0 | 0 | 0 | 0 | 0 | 0 | 0 | 0 |
| T1 | 328 | 0 | 0 | 0 | 0 | 3 | 2 | 3 | 3 | D | D | D | D | D | D | D | D | D | D | D | D | D | D | D | D | D | D |
| T2 | 329 | 0 | 0 | 0 | 0 | 3 | 1 | 3 | 1 | 0 | 1 | 0 | 1 | 0 | 1 | 0 | 0 | 1 | 1 | 0 | 0 | 0 | 0 | 0 | 0 |
| T3 | 330 | 0 | 0 | 0 | 0 | 2 | 1 | 3 | 3 | D | D | D | D | D | D | D | D | D | D | D | D | D | D | D | D | D | D |
| T1 | 331 | 0 | 0 | 0 | 0 | 3 | 1 | 3 | 3 | D | D | D | D | D | D | D | D | D | D | D | D | D | D | D | D | D | D |

TABLE 64-continued

Clinical scores of piglets born to sow 4001.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T1 | 332 | 0 | 0 | 0 | 0 | 3 | 2 | D | D | D | D | D | D | D | D | D | D | D | D | D | D | D | D | D | D |
| T2 | 333 | 0 | 0 | 0 | 0 | 3 | 2 | 3 | 3 | D | D | D | D | D | D | D | D | D | D | D | D | D | D | D | D |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 65

Clinical scores of piglets born to sow 2088.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T2 | 334 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| T2 | 335 | 0 | 0 | 0 | 0 | 0 | 0 | 1 | 0 | 1 | 1 | 0 | 0 | 0 | 0 | 0 | 0 | 0 | 0 | 0 | 0 | 0 | 0 | 0 | 0 |
| T3 | 336 | 0 | 0 | 0 | 0 | 0 | 0 | 0 | 0 | 2 | 1 | 0 | 0 | 0 | 0 | 0 | 1 | 0 | 0 | 0 | 0 | 0 | 0 | 0 | 0 |
| T2 | 337 | 0 | 0 | 0 | 0 | 0 | 0 | 1 | 0 | 0 | 0 | 0 | 0 | 0 | 0 | 1 | 0 | 0 | 0 | 0 | 0 | 0 | 0 | 0 | 0 |
| T1 | 338 | 0 | 0 | 0 | 0 | 1 | 0 | 1 | 0 | 0 | 0 | 1 | 0 | 0 | 0 | 0 | 0 | 0 | 0 | 0 | 0 | 0 | 0 | 0 | 0 |
| T1 | 339 | 0 | 0 | 0 | 0 | 0 | 0 | 1 | 0 | 0 | 0 | 0 | 0 | 0 | 0 | 0 | 0 | 0 | 1 | 0 | 1 | 0 | 0 | 0 | 0 |
| T3 | 340 | 0 | 0 | 0 | 0 | 0 | 0 | 0 | 0 | 0 | 1 | 0 | 1 | 0 | 1 | 0 | 1 | 0 | 0 | 0 | 1 | 0 | 1 | 0 | 1 |
| T3 | 341 | 0 | 0 | 0 | 0 | 1 | 0 | 1 | 0 | 0 | 1 | 0 | 1 | 0 | 1 | 0 | 1 | 0 | 0 | 0 | 1 | 0 | 1 | 0 | 0 |
| T1 | 342 | 0 | 0 | 0 | 0 | 1 | 0 | 2 | 1 | 1 | 1 | 0 | 1 | 0 | 1 | 0 | 1 | 0 | 1 | 0 | 1 | 0 | 1 | 0 | 0 |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 66

Clinical scores of piglets born to sow 2082.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T3 | 343 | 0 | 0 | 0 | 0 | 2 | 0 | 3 | 1 | 2 | 1 | 2 | 2 | 3 | 3 | D | D | D | D | D | D | D | D | D | D |
| T1 | 344 | 0 | 0 | 0 | 0 | 1 | 1 | 3 | 1 | 2 | 1 | 2 | 1 | 2 | 1 | 1 | 0 | 0 | 0 | 1 | 0 | 2 | 1 | 2 | 0 |
| T2 | 345 | 0 | 0 | 0 | 0 | 1 | 0 | 2 | 0 | 2 | 1 | 2 | 2 | 2 | 2 | 3 | 2 | 2 | 2 | 3 | 2 | 3 | 2 | D | D |
| T3 | 346 | 0 | 0 | 0 | 0 | 2 | 0 | 1 | 1 | 0 | 0 | 1 | 1 | 1 | 0 | 1 | 0 | 1 | 1 | 0 | 1 | 0 | 1 | 0 | 0 |
| T2 | 347 | 0 | 0 | 0 | 0 | 0 | 0 | 3 | 1 | 0 | 0 | 0 | 1 | 0 | 1 | 1 | 1 | 0 | 1 | 0 | 1 | 0 | 0 | 0 | 0 |
| T1 | 348 | 0 | 0 | 0 | 0 | 2 | 3 | 3 | 2 | 3 | 2 | D | D | D | D | D | D | D | D | D | D | D | D | D | D |
| T3 | 349 | 0 | 0 | 0 | 0 | 0 | 0 | 2 | 1 | 2 | 2 | 2 | 2 | 1 | 2 | 3 | 2 | 2 | 1 | 3 | 2 | 2 | 2 | 1 | 1 |

TABLE 66-continued

Clinical scores of piglets born to sow 2082.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS |
| T1 | 350 | 0 | 0 | 0 | 0 | 2 | 1 | 3 | 2 | D | D | D | D | D | D | D | D | D | D | D | D | D | D | D | D |
| T3 | 351 | 0 | 0 | 0 | 0 | 0 | 0 | 1 | 0 | 0 | 0 | 0 | 0 | 0 | 0 | 0 | 0 | 1 | 0 | 0 | 0 | 0 | 0 | 0 | 0 |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = Bay 98-7089 1X
T3 = Bay 98-7089 5X

TABLE 67

Clinical scores of piglets born to Sow 217.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS |
| T2 | 352 | 0 | 0 | 0 | 0 | 3 | 0 | 3 | 2 | D | D | D | D | D | D | D | D | D | D | D | D | D | D | D | D |
| T2 | 353 | 0 | 0 | 0 | 0 | 3 | 1 | 3 | 3 | D | D | D | D | D | D | D | D | D | D | D | D | D | D | D | D |
| T3 | 354 | 0 | 0 | 0 | 0 | 1 | 0 | 3 | 2 | 1 | 1 | 0 | 1 | 0 | 0 | 0 | 0 | 1 | 0 | 0 | 0 | 0 | 0 | 0 | 0 |
| T1 | 355 | 0 | 0 | 0 | 0 | 2 | 1 | 3 | 2 | 0 | 0 | 0 | 1 | 0 | 0 | 0 | 0 | 0 | 1 | 0 | 0 | 0 | 0 | 0 | 0 |
| T3 | 356 | 0 | 0 | 0 | 0 | 3 | 1 | 3 | 1 | 0 | 0 | 0 | 0 | 0 | 0 | 0 | 1 | 1 | 1 | 0 | 1 | 0 | 1 | 0 | 0 |
| T1 | 357 | 0 | 0 | 0 | 0 | 3 | 1 | 3 | 2 | 0 | 0 | 0 | 0 | 0 | 0 | 0 | 0 | 0 | 0 | 0 | 0 | 0 | 0 | 0 | 0 |
| T2 | 358 | 0 | 0 | 0 | 0 | 2 | 1 | 3 | 2 | 3 | 2 | D | D | D | D | D | D | D | D | D | D | D | D | D | D |
| T1 | 359 | 0 | 0 | 0 | 0 | 3 | 1 | D | D | D | D | D | D | D | D | D | D | D | D | D | D | D | D | D | D |
| T3 | 360 | 0 | 0 | 0 | 0 | 3 | 1 | 3 | 2 | 3 | 2 | D | D | D | D | D | D | D | D | D | D | D | D | D | D |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = Bay 98-7089 1X
T3 = Bay 98-7089 5X

TABLE 68

Clinical scores of piglets born to sow 215.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS |
| T1 | 361 | 0 | 0 | 0 | 0 | 2 | 0 | 3 | 2 | 3 | 2 | D | D | D | D | D | D | D | D | D | D | D | D | D | D |
| T2 | 362 | 0 | 0 | 0 | 0 | 2 | 1 | 3 | 1 | D | D | D | D | D | D | D | D | D | D | D | D | D | D | D | D |
| T2 | 363 | 0 | 0 | 0 | 0 | 2 | 1 | 3 | 1 | 1 | 0 | 0 | 1 | 0 | 1 | 0 | 0 | 0 | 0 | 0 | 0 | 0 | 0 | 0 | 0 |
| T3 | 364 | 0 | 0 | 0 | 0 | 2 | 1 | 3 | 2 | D | D | D | D | D | D | D | D | D | D | D | D | D | D | D | D |
| T3 | 365 | 0 | 0 | 0 | 0 | 1 | 0 | 3 | 1 | 1 | 1 | 0 | 1 | 0 | 0 | 1 | 0 | 1 | 1 | 0 | 1 | 0 | 0 | 0 | 0 |
| T1 | 366 | 0 | 0 | 0 | 0 | 3 | 1 | 3 | 2 | D | D | D | D | D | D | D | D | D | D | D | D | D | D | D | D |
| T3 | 367 | 0 | 0 | 0 | 0 | 1 | 1 | 3 | 2 | D | D | D | D | D | D | D | D | D | D | D | D | D | D | D | D |

TABLE 68-continued

Clinical scores of piglets born to sow 215.

| Group | Piglet ID | Pre Challenge | | Post challenge Day 0 AM | | Post challenge Day 0 PM | | Post challenge Day 1 AM | | Post challenge Day 1 PM | | Post challenge Day 2 AM | | Post challenge Day 2 PM | | Post challenge Day 3 AM | | Post challenge Day 3 PM | | Post challenge Day 4 AM | | Post challenge Day 4 PM | | Post challenge Day 5 AM | | Post challenge Day 5 PM | |
|---|---|---|---|---|---|---|---|---|---|---|---|---|---|---|---|---|---|---|---|---|---|---|---|---|---|---|---|
| | | FS | PS | FS | PS | FS | PS | FS | PS | FS | PS | FS | PS | FS | PS | FS | PS | FS | PS | FS | PS | FS | PS | FS | PS | FS | PS |
| T1 | 368 | 0 | 0 | 0 | 0 | 3 | 1 | 3 | 2 | 0 | 0 | 1 | 0 | 0 | 0 | 0 | 0 | 0 | 0 | 0 | 0 | 0 | 0 | 0 | 0 | 0 | 0 |
| T2 | 369 | 0 | 0 | 0 | 0 | 2 | 1 | 3 | 3 | D | D | D | D | D | D | D | D | D | D | D | D | D | D | D | D | D | D |

D = Died or Euthanized due to severe clinical signs
FS = Fecal Score
0 Normal solid feces, 1 Semisolid feces, 2 Watery feces with some solid material, 3 Profuse watery feces with no solid material
PS = Physical Score
0 Appears normal, 1 Slight dehydration and/or slightly gaunt and/or rough hair-coat, 2 Dehydrated, gaunt irrespective of hair-coat, 3 Pig unable to stand without help (feeble)
T1 = Saline
T2 = IC-Ex. 1 1X
T3 = IC-Ex. 1 5X

TABLE 69

Post challenge mortality of pigs treated by sow and group.

| Sow ID | Total piglets | Treatment 1 Treated | Treatment 1 Mortality | Treatment 2 Treated | Treatment 2 Mortality | Treatment 3 Treated | Treatment 3 Mortality |
|---|---|---|---|---|---|---|---|
| 215 | 9 | 3 | 2 | 3 | 2 | 3 | 2 |
| 217 | 9 | 3 | 1 | 3 | 3 | 3 | 1 |
| 2082 | 9 | 3 | 2 | 3 | 1 | 3 | 1 |
| 2088 | 9 | 3 | 0 | 3 | 0 | 3 | 0 |
| 2694 | 9 | 3 | 1 | 3 | 1 | 3 | 0 |
| 4001 | 9 | 3 | 3 | 3 | 1 | 3 | 2 |
| 4009* | 5 | 2 | 1 | 1* | 0* | 2 | 0 |
| 10040 | 9 | 3 | 3 | 3 | 1 | 3 | 3 |
| Total | 69 | 23 | 13 | 22 | 9 | 23 | 9 |
| Percent | | | 57% | | 41% | | 39% |
| Protective Index | | | | | 28% | | 32% |

T1 = Saline
T2 = IC-Ex. 1 1X
T3 = IC-Ex. 1 5X
*One pig was laid on by Sow and was excluded

Example 6. Efficacy of Immunomodulator (IC-Ex.1) Composition in Preventing or Mitigating Diarrhea Associated with *E. coli* in a Natural Challenge Weaned Pig Model The objective of this study was to determine the clinical effectiveness of administering IC-Ex.1 to prevent or mitigate diarrhea associated with colibacillosis in weaned pigs housed within commercial confinement conditions.

The test system utilized two populations of commercial weaned pigs from two, separate source farms: a seeder pig (N=50) and candidate pig (N=454) population. The seeder pigs arrived at the site on Study Day −8. On Study Day −4, 50% of the seeder pigs were recorded as clinically affected with colibacillosis and confirmed positive for beta-hemolytic *E. coli* (bHEC). Pigs were determined clinically affected based on fecal scores (0=normal, 1=diarrhea). The fecal scoring method was used as the efficacy endpoint of the study when applied to enrolled pigs. All candidate pigs (candidates for enrollment) were weighed on Study Day −1. The average arrival body weight of the candidates was 13.6 lbs. Candidate pigs were 21 days old and were weaned the same day of arrival. To establish an outbreak of colibacillosis within the candidate population, upon arrival all candidate pigs were commingled with seeder pigs in a single pen. The following calendar day, 8% (36/454) of the candidate pigs were recorded as clinically affected with colibacillosis, which met the 5% threshold required to initiate Study Day 0.

On Study Day 0, all seeder pigs were removed from the study, individual fecal scores were recorded for each candidate pig, clinically affected candidate pigs were removed, and ten pens of 41 clinically normal candidate pigs were enrolled in the study and administered test material. Fecal scores were recorded on all enrolled pigs for 5 consecutive days (Study Days 1 through 5). The test system consisted of five treatment groups: a 2 mL volume of 5% dextrose water (D5W) administered per os (PO), a 20 µg dose of IC-Ex.1 administered PO in a 2 mL volume (PO_2), a 20 µg dose of IC-Ex.1 administered PO in a 10 mL volume (PO_10), a 20 µg dose of IC-Ex.1 administered intramuscularly (IM) in a 2 mL volume and a 20 µg dose of IC-Ex.1 administered intrarectally (IR) in a 1 mL volume. All doses of IC-Ex.1 were prepared as suspensions in D5W. Statistical analysis of the body weight, on Day 0, resulted in no statistical differences between treatment groups (p=0.1725). In this study, the 20 µg IM dose of IC-Ex.1 administered at weaning prevented the occurrence of diarrhea associated with enterotoxigenic *E. coli* (F18) by 33.3% (confidence interval [CI]; 21.9%, 43.1%) relative to the control group. In addition, the PO_2, PO_10, IM, and IR treatment groups mitigated the frequency of diarrhea relative to the control by 22.4% (CI; 17.8%, 27.1%), 18.5% (CI; 8.6%, 28.4%), 65.1%, (CI; 58.7%, 71.5%), and 20.4% (CI; 12.8%, 28%), respectively. No statistically significant (p>0.05) differences in mortality were observed between the five treatment groups. Of the 50 (seeder pig) fecal samples collected and submitted for culture, the E. coli F18 pilus antigen was detected in 92.0% (n=46) of the submitted samples. No other pili antigens were detected in this sample population. Additionally, the E. coli toxin gene EAST1 (100.0%, n=50), STa (92.0%, n=46), and STb (100.0%, n=50) along with the AIDA adhesion gene (12.0%, n=6) were recovered in this sample population.

In this study, the 2 mL intramuscular 20 μg dose of IC-Ex.1 administered at weaning prevented occurrence of diarrhea associated with enterotoxigenic E. coli (F18 pili antigen, the EAST1, STa, and STb toxin genes, and the AIDA adhesin gene). In addition, all treatment groups mitigated the frequency of diarrhea relative to the control.

TABLE 70

Study groups.

| Study Groups | Group Description | Treatment administration (Study Day) | Bay 98-7089 Per Animal Dose (μg) | Dose Volume (mL) | Dosing Route* | Number of pens of 41 pigs | Number of pigs enrolled per group |
|---|---|---|---|---|---|---|---|
| T01 | 5% Dextrose Control | 0 | 0 | 2 | PO | 2 | 82 |
| T02 | IC-Ex. 1 | 0 | 20 | 2 | PO | 2 | 82 |
| T03 | IC-Ex. 1 | 0 | 20 | 10 | PO | 2 | 82 |
| T04 | IC-Ex. 1 | 0 | 20 | 2 | IM | 2 | 82 |
| T05 | IC-Ex. 1 | 0 | 20 | 1 | IR | 2 | 82 |

*PO (Per os), IM (Intramuscular), IR (Intra-rectal)

Establishment of the Test System

TABLE 71

Clinical scoring method and criteria for classifying pigs as "clinically affected" with colibacillosis.

| Clinical observation | Fecal Score | Clinically Affected |
|---|---|---|
| Normal feces; no diarrhea present | 0 | No |
| Watery/liquid faces with little or no solid material | 1 | Yes |

Laboratory Diagnosis of E. coli in bHEC+ Pigs

Rectal Swab Collection from Potential bHEC+ Pigs.

A rectal swab was collected from seeder pigs the day of arrival and sent to MRI for isolation and semi-quantitative assessment of beta-hemolytic (bHEC) E. coli. A rectal sample was again collected from seeder/bHEC+ pigs at the study site when approximately 50% or more them exhibited clinical signs of colibacillosis. After approximately 50% of the seeder/bHEC+ pigs were clinically affected and confirmed bHEC+, a candidate pool of 454 pigs were purchased and commingled in a single pen with the seeder/bHEC+ pigs upon arrival to the study site.

Swab Collection, Handling and Laboratory Procedures.

Rectal swabs were collected and placed into tubes with Amies transport medium. The tubes were labeled with pig ID, study number, sample type and date of collection. The samples placed with cold packs and shipped within 24 hours after collection. All rectal swabs were processed according to the following procedure:

The rectal swab was direct streaked onto 5% sheep blood agar (BA) and MacConkey agar (MAC). The BA plate was streaked into the first quadrant and cross-streaked for isolation to allow for semi-quantitation of bHEC. Up to four swab samples were streaked onto a MAC plate. The BA and MAC plates were incubated aerobically overnight at 36° C.±2° C. The primary isolation BA plates were scored according to the following scheme for bHEC. The MAC was used to aid in determining if typical E. coli colonies were present.

A presumptive bHEC colony from the primary BA was sub-cultured onto a fresh BA and MAC. One (or more) isolate(s) was selected at the discretion of the evaluating technician. The same inoculum was used to inoculate triple sugar iron agar (TSI) and Simmon's Citrate agar (SC) slants. The BA, MAC and TSI slants were incubated overnight at 36±2° C. and the SC slants for 2 days at 36±2° C.

Isolates were confirmed as bHEC if the following criteria were met:

Isolates had typical colony morphology on MAC and showed beta hemolysis on BA

Typical TSI reaction of Acid/Acid/H2S-/gas

Typical negative SC reaction

E. coli isolates were further confirmed using the MALDI Biotyper Classification system.

Genotype testing was performed on all confirmed isolates at Iowa State University to evaluate the presence of the following genes: EAST 1 toxin, LT toxin, STa toxin, STb toxin, Stx1 toxin, Stx2 toxin, Stx2e toxin, F18 pilus, F41 pilus, K88 pilus, K99 pilus, 987P pilus, AIDA adhesin, EAEA adhesin, and PAA adhesin.

TABLE 72

Summary of genotypic characteristics of E. coli isolated from seeder pigs.
Summary of genotypic characteristics of E. coli isolated from the 50 seeder pigs:

| | EAST1 toxin | STa toxin | STb toxin | F18 pilus | AIDA adhesin |
|---|---|---|---|---|---|
| Number of isolates* | 50 | 46 | 50 | 46 | 6 |

*Multiple isolates were tested from each seeder pig
Note:
No additional toxin, pili, or adhesion genes were identified in this sample population.

Animal Inclusion Criteria

Seeder pigs were confirmed to harbor bHEC prior to purchase and/or be a contemporary of a cohort pigs that were confirmed bHEC+ prior to delivery to the study site did not receive any antibiotic administrations within 14 days prior to delivery to the study site. Seeder pigs were recently weaned and free of apparent injury or physical abnormalities by visual appraisal but may exhibit clinical signs of colibacillosis. And, seeder pigs were laboratory-confirmed to harbor bHEC (approximately 50%), classified as a "clinically affected" pig (as defined in Section 14 item 9 of the protocol) and had an alkaline fecal pH before commingled with candidate pigs.

Candidate pigs did not receive any antibiotic treatment within 14 days of arrival to the study site were weaned within 2 days or less prior to arrival to the study site were 19 days of age or older on the day of weaning were considered generally healthy based on visual appraisal prior to commingling with seeder pigs; pigs with weight-bearing lameness upon arrival remained eligible for enrollment in the study unless the condition was considered severe based on Veterinary observation. Mild lameness was expected in some animals following transport. Candidate pigs were classified as clinically normal, as defined in Section 15 item 8 of the protocol, on Study Day 0 but approximately 5% or more of its pen mates were clinically affected with colibacillosis based on scores recorded.

Animal Exclusion Criteria

Candidate pigs were excluded from enrollment if they possessed one or more of the following attributes on Study Day 0 at the time of pen placement/treatment allocation or treatment administration: Inguinal and/or umbilical hernias, rectal prolapses or other noticeable physical abnormalities or injuries that may confound normal growth performance of the animal as determined by Veterinary assessment of the condition, classified as "clinically affected" as defined in Section 15 item 9 of the protocol, non-weight bearing lameness as identified by a veterinarian, signs of neurological disease, moribund or end-stage illness pigs, extra pigs. Excluded pigs were recorded on the Animal Exclusion form.

Post-Treatment Removal Criteria

Enrolled pigs considered to be moribund due to colibacillosis were removed from the study and euthanized at the discretion of the attending veterinarian. These pigs were considered treatment failures. Enrolled pigs that became moribund or died for reasons other than colibacillosis were removed. These pigs were not considered treatment failures in the final analysis. Enrolled pigs affected by any other disease or condition that could confound study objectives or prevent completion of the study were removed from the study and euthanized. These animals were not considered treatment failures and were removed from the final analysis.

Seeder pigs were scored daily for clinical signs of colibacillosis using the clinical scoring criteria described in the protocol. Only clinically affected seeder pigs were recorded during this observation period. The pH of individual rectal swabs was recorded on at least one of the days with a diarrhea score of 1. When approximately 50% of the cohort of seeder pigs were classified as clinically affected and confirmed to harbor bHEC, a candidate pool of pigs was purchased and commingled with the seeder pigs.

Natural Challenge Phase Candidate: Seeder Commingling and Enrollment

Start of the natural challenge phase was the date the candidate pigs were commingled with seeder pigs: Study Day −1. The end of natural challenge phase was the date approximately 5% or more of the candidate pool of pigs was confirmed clinically affected with colibacillosis. On Study Day 0, 36 pigs (7.9%; 36 of 454) were considered clinically affected, had a diarrhea score of "1" and were removed from the study (not treated). Eight additional pigs meeting the inclusion criteria were removed (excess pigs). All remaining pigs met the inclusion criteria as listed above and were enrolled in the study. All seeder pigs were removed on Study Day 0 and recorded.

The study utilized pigs that were sourced from a commercial confinement swine facility and no antibiotics were administered prior to or at weaning. Candidate pigs were healthy and did not have ongoing colibacillosis at the time of purchase. All pigs were 21 days old the day they arrived at the study site. A body weight was recorded on all candidate pigs on Study Day −1 and recorded on the body weight form. Daily general health observations were conducted on all candidate and seeder pigs and recorded starting one day after arrival, until the end of the natural infection phase (Study Day 0). During this phase, only clinically affected or abnormal findings were scored. All candidate pigs were observed daily for clinical signs of colibacillosis.

Clinical Effectiveness Phase: Clinical Scoring and Adverse Event Reporting

When the Investigator was confident approximately 5% or more of the candidate pool was clinically affected with colibacillosis in a single day, a fecal score was determined for all pigs in the candidate pool. When the threshold of

TABLE 73

Study groups.

| Study Groups | Group Description | Treatment administration (Study Day) | Bay 98-7089 Per Animal Dose (μg) | Dose Volume (mL) | Dosing Route* | Number of pens of 41 pigs | Number of pigs enrolled per group |
|---|---|---|---|---|---|---|---|
| T01 | 5% Dextrose Control | 0 | 0 | 2 | PO | 2 | 82 |
| T02 | IC-Ex. 1 | 0 | 20 | 2 | PO | 2 | 82 |
| T03 | IC-Ex. 1 | 0 | 20 | 10 | PO | 2 | 82 |
| T04 | IC-Ex. 1 | 0 | 20 | 2 | IM | 2 | 82 |
| T05 | IC-Ex. 1 | 0 | 20 | 1 | IR | 2 | 82 |

*PO (Per os), IM (Intramuscular), IR (Intra-rectal)

Pigs allocated to the negative control group were administered a single PO administration of D5W delivered as described for pigs allocated to the PO IC-Ex.1 treatment group.

Study

Fifty seeder pigs were procured and delivered to the study site after a proportion of the pigs have been confirmed to harbor bHEC. A rectal swab was collected on all seeder pig after arrival to the study site. Swabs were sent to MRI Laboratories for isolation and identification of bHEC.

colibacillosis outbreak was confirmed by clinical diarrhea scores, the candidate pool of pigs was considered eligible for administration of test material. All study pens were filled sequentially as numbered (example: Pen 1, 2, 3 . . . ) with eligible candidate pigs. Efforts were made to maintain a balanced number of pigs across all pens. Starting on Study Day 0, all enrolled pigs (410) were observed daily for adverse events and fecal scores through Study Day 5. Daily general health observations were conducted on all enrolled pigs at the time of clinical observations.

Statistical Methods Used.

Prevented and mitigated fraction calculations with confidence intervals, (PF and MF packages in R, version 3.1.3), generalized linear mixed model (GLMM) and an analysis of variance (ANOVA) (SAS® Version 9.3; SAS Institute, Cary, N.C.) were used to evaluate the primary parameter of diarrhea, mortalities and average daily gains, respectively using an alpha of 0.05 as statistically significant. The pig was considered the experimental unit in this study. However, prevented fraction analyses considered the pen (n=2 per group) as the experimental unit of analyses.

TABLE 74

Summary of enrolled pigs body weight and ADG (study days 0 & 5).

| Treatment Code | Treatment Group | N | Day 0 Average Body Wgt (lb) | N | Day 5 Average Body Wgt (lb) | N | Average Daily Gain (ADG)* |
|---|---|---|---|---|---|---|---|
| T01 | 5% Dextrose Control | 82 | 14.22 | 82 | 13.88 | 82 | −0.070 |
| T02 | IC-Ex. 1 20 μg PO 2 mL | 81** | 13.64 | 79 | 13.02 | 79 | −0.140 |
| T03 | IC-Ex. 1 20 μg PO 10 mL | 82 | 13.68 | 81 | 13.30 | 61 | −0.076 |
| T04 | IC-Ex. 1 20 μg IM 2 mL | 82 | 14.49 | 81 | 14.27 | 61 | −0.045 |
| T05 | IC-Ex. 1 20 μg IR 2 mL | 82 | 13.52 | 82 | 13.10 | 82 | −0.085 |

*Adjusted least squares means ADG analyses resulted in no statistical differences between treatment groups (p = 0.1725, using ANOVA)
**The data for one animal in group T02 was removed from the analysis leaving only 61 animals to be evaluated for this treatment group. See protocol deviation #4 (see Section 11)

Model Validation.

Figure 29:
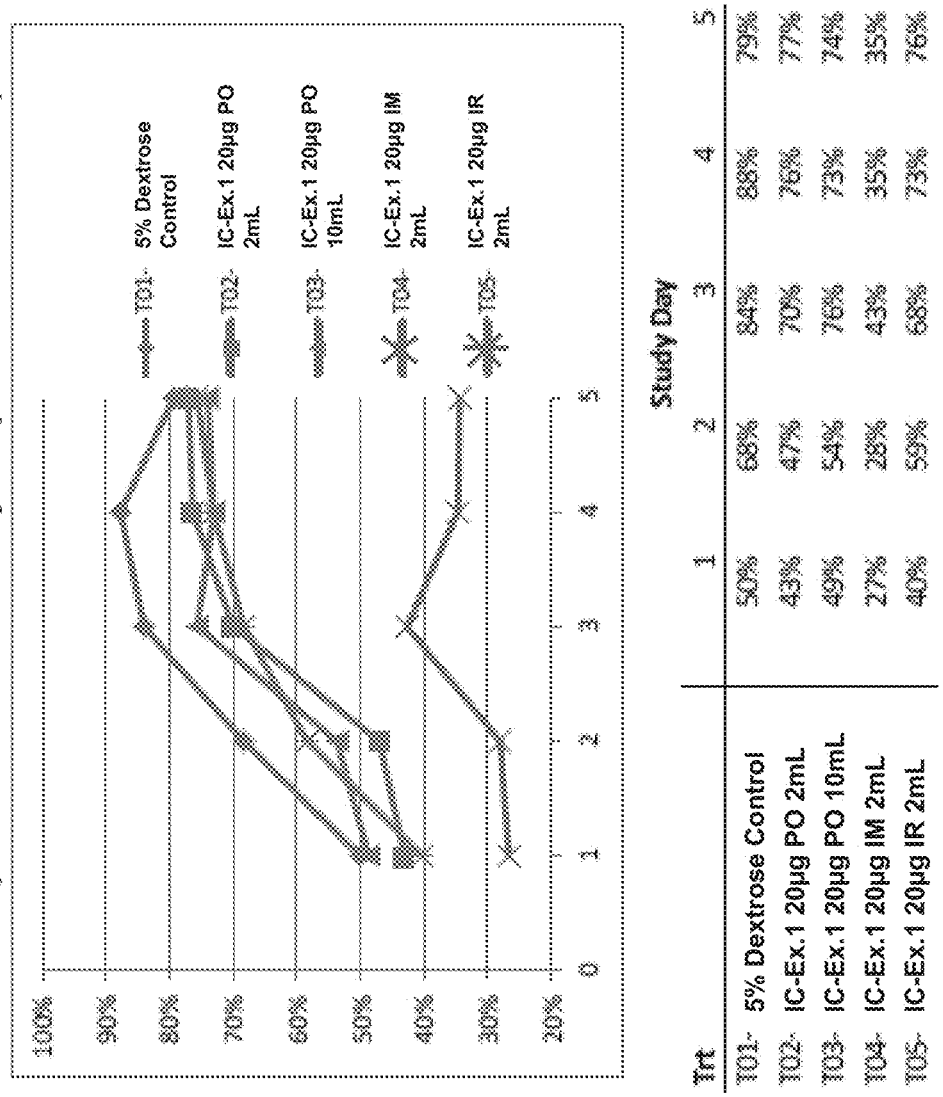

The number of Control group pigs (Study Group T01) exhibiting diarrhea during the course of the 5 day study period demonstrates this disease model was sufficient to test whether the treatment groups would have a positive effect in preventing the occurrence of diarrhea and/or mitigating the frequency of diarrhea associated with bHEC. This is illustrated in the FIG. 29 and Table 75.

TABLE 75

Cumulative incidence of diarrhea during Study days 1 to 5 and prevented fraction.

| Treatment Code | Treatment Group | SD1 | SD2 | SD3 | SD4 | SD5 | Prevented Fraction | Confidence Interval† Lower | Upper |
|---|---|---|---|---|---|---|---|---|---|
| T01 | Control | *50% | 77% | 95% | 99% | 99% | | | |
| T02 | IC-Ex. 1 20 μg PO 2 mL | 43% | 54% | 78% | 93% | 95% | 3.8% | −1.7% | 8.9% |
| T03 | IC-Ex. 1 20 μg PO 10 mL | 49% | 65% | 89% | 98% | 98% | 1.2% | −3.0% | 5.3% |
| T04 | IC-Ex. 1 20 μg IM 2 mL | 27% | 44% | 55% | 81% | 86% | 33.3% | 21.9% | 43.1% |
| T05 | IC-Ex. 1 20 μg IR 2 mL | 40% | 66% | 85% | 95% | 96% | 2.5% | −2.4% | 7.1% |

*% pigs having diarrhea at least once (cumulative for each Study Day)
†Prevented fractions calculated using RRmh function.

TABLE 76

Average percent diarrhea days (Study Days 1 to 5) and Mitigated Fraction.

| Treatment Code | Treatment Group | Average % Diarrhea Days | Median Mitigated Fraction | Confidence Interval† Lower | Upper |
|---|---|---|---|---|---|
| T01 | Control | 74% | | | |
| T02 | IC-Ex. 1 20 μg PO 2 mL | 63% | 22.4% | 17.8% | 27.1% |
| T03 | IC-Ex. 1 20 μg PO 10 mL | 85% | 18.5% | 8.6% | 28.4% |
| T04 | IC-Ex. 1 20 μg IM 2 mL | 33% | 85.1% | 58.7% | 71.9% |
| T05 | IC-Ex. 1 20 μg IR 2 mL | 63% | 20.4% | 12.8% | 28.0% |

†Mitigated fractions calculated using MF ClubBoot function.

The STa and STb toxins, the EAST1 toxin, the F18 pilus and the AIDA adhesin genes were found to be present in the majority of the 50 bHEC+ seeder pigs. The high incidence (99% by SD4) of diarrhea in the D5W treated group demonstrates that the candidate pigs were adequately challenged with bHEC by commingling with the seeder pig population.

Effectiveness of IC-Ex.1 to Prevent or Mitigate Colibacillosis in Weaned Pigs.

In this study, the 2 mL intramuscular 20 μg dose of IC-Ex.1 administered at weaning prevented occurrence of diarrhea associated with enterotoxigenic E. coli (F18 pili, the EAST1, STa, and STb toxins, and AIDA adhesin genes). In addition, all treatment groups mitigated the frequency of diarrhea relative to the control.

Example 8. Immunological Pathways and Cytokines Produced after Treatment with IC-Ex.1

The purpose of the experimental procedure was to determine the immunological pathways that are stimulated by IC-Ex.1.

Figure 30:
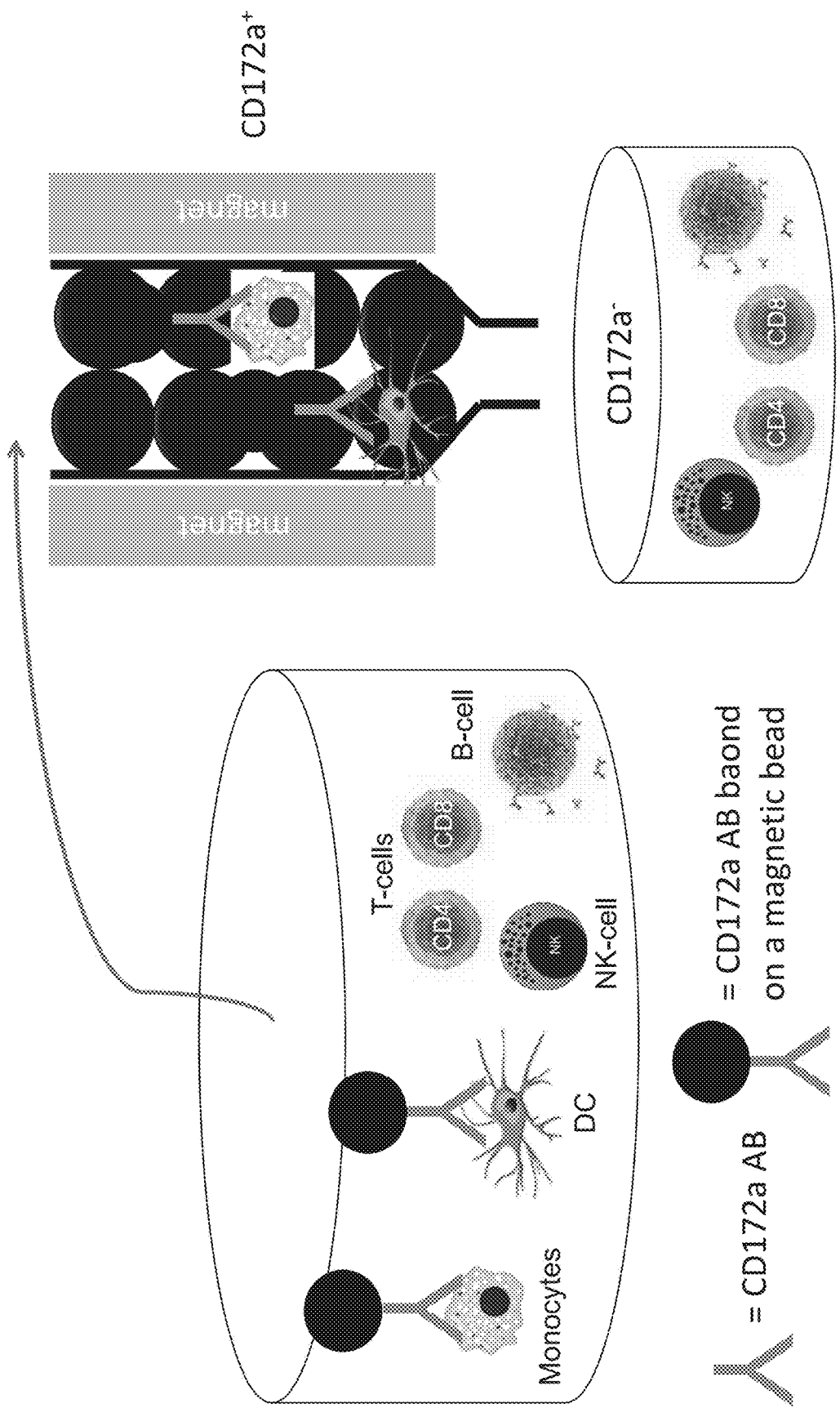
FIG. 30 illustrates isolated distinct blood cell types using magnetic cell separation.

Blood was drawn from PIGS and immune cells were isolated from the blood sample using magnetic cell separation (FIG. 30). 172a+ cell comprising dendritic cells and monocytes and 172a− cells comprising natural killer, T and B cells were cultured in vitro. Referring to Table 77, the cultures were stimulated with different concentrations of IC-Ex.1, well characterized immune stimulators CpG ODN, Gardiquimod, PAM3Cys and LPS, or empty control lipids and incubated for 18 hours. Supernatants were assayed using ELISA or Luminex Multiplexing for the presence of IFN-α, TNF-α, IL1 beta, IL10, IL12p40, Il4, IL6, IL8, IFN-γ.

Flow cytometry was used to determine the cell type responsible for cytokine production after IC-Ex.1 treatment. Cell cultures were treated with Brefeldin A. Brefeldin A acts to inhibit the Golgi complex so that cytokines produced in the cell remain within the cell. These retained cytokines can be detected with fluorophore-labeled antibodies.

TABLE 77

Immunostimulant Concentrations.

| Immunstimulant | (Potential) Receptor(s) | concentrations |
| --- | --- | --- |
| CpG ODN (D32) | TLR9 | 5 ug/ml, 1 ug/ml, 100 ng/ml, 10 ng/ml, 1 ng/ml |
| IC-EX. 1 | STING/TLR9,21/ other cytosolic DNA recongniztion mechanisms | 5 ug/ml, 1 ug/ml, 100 ng/ml, 10 ng/ml, 8 ng/ml, 5 ng/ml, 3 ng/ml, 1 ng/ml |
| Liposomes | — | 1 ug/ml, 100 ng/ml, 10 ng/ml, 1 ng/ml |
| Liposomes (other batch) | — | 1 ug/ml |
| Gardiquimod | TLR7 | 5 ug/ml |
| PAM3Cys | TLR2 | 10 ug/ml |
| LPS | TLR4 | 1 ug/ml |
| cGAMP | STING | 50 ug/ml, 10 ug/ml |

Results

A. Physiologically Relevant Doses of IC-Ex.1 Induce High Amounts of IFN-α.

Figure 31:
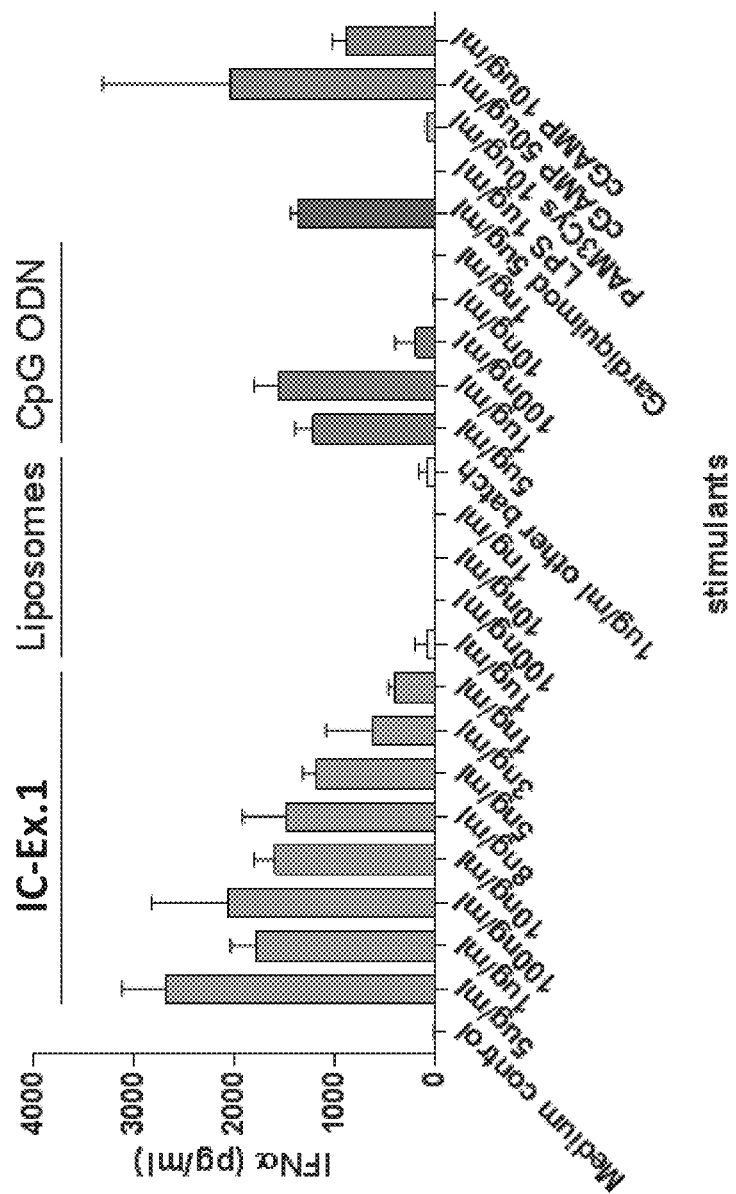
FIG. 31 shows that physiologically relevant concentrations of IC-Ex.1 stimulate the expression of IFN-α in the CD172a+ cells FIG. 32 graphically shows that CD172a− cells do not produce IFN-α after stimulation with IC-Ex.1 or with the known immune-stimulators.

FIG. 31 shows that physiologically relevant concentrations of IC-Ex.1 stimulate the expression of IFN-α in the CD172a+ cells. IFN-α is important in a host's defense against viruses and other intracellular pathogens.

Figure 32:
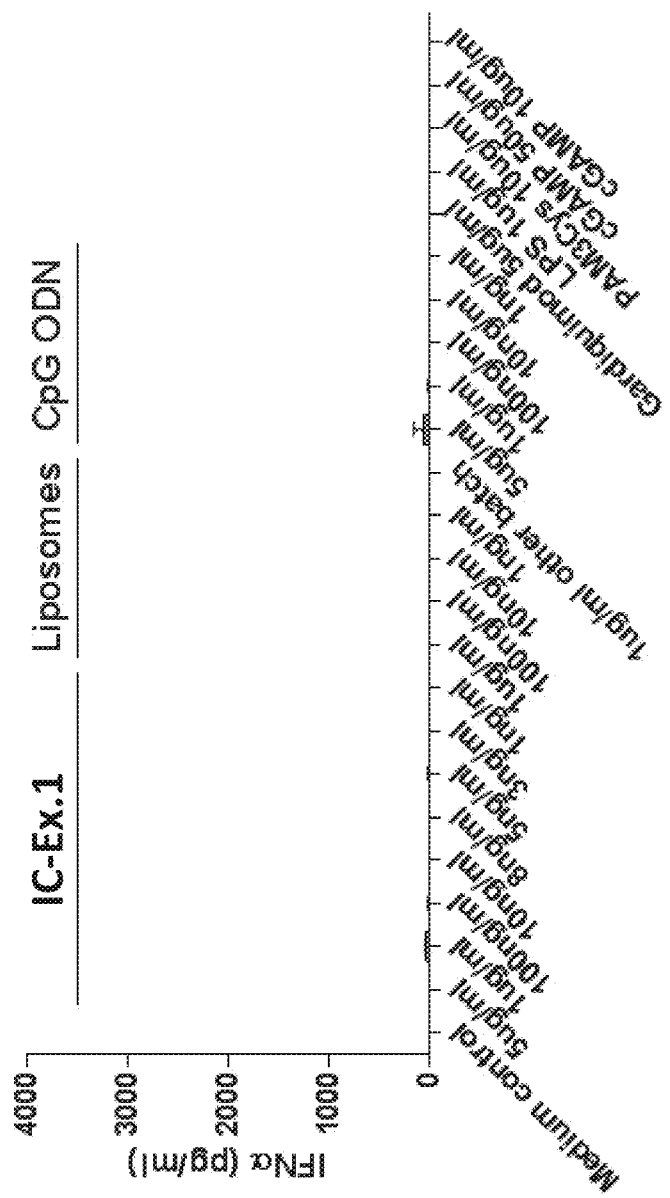
Figure 33:
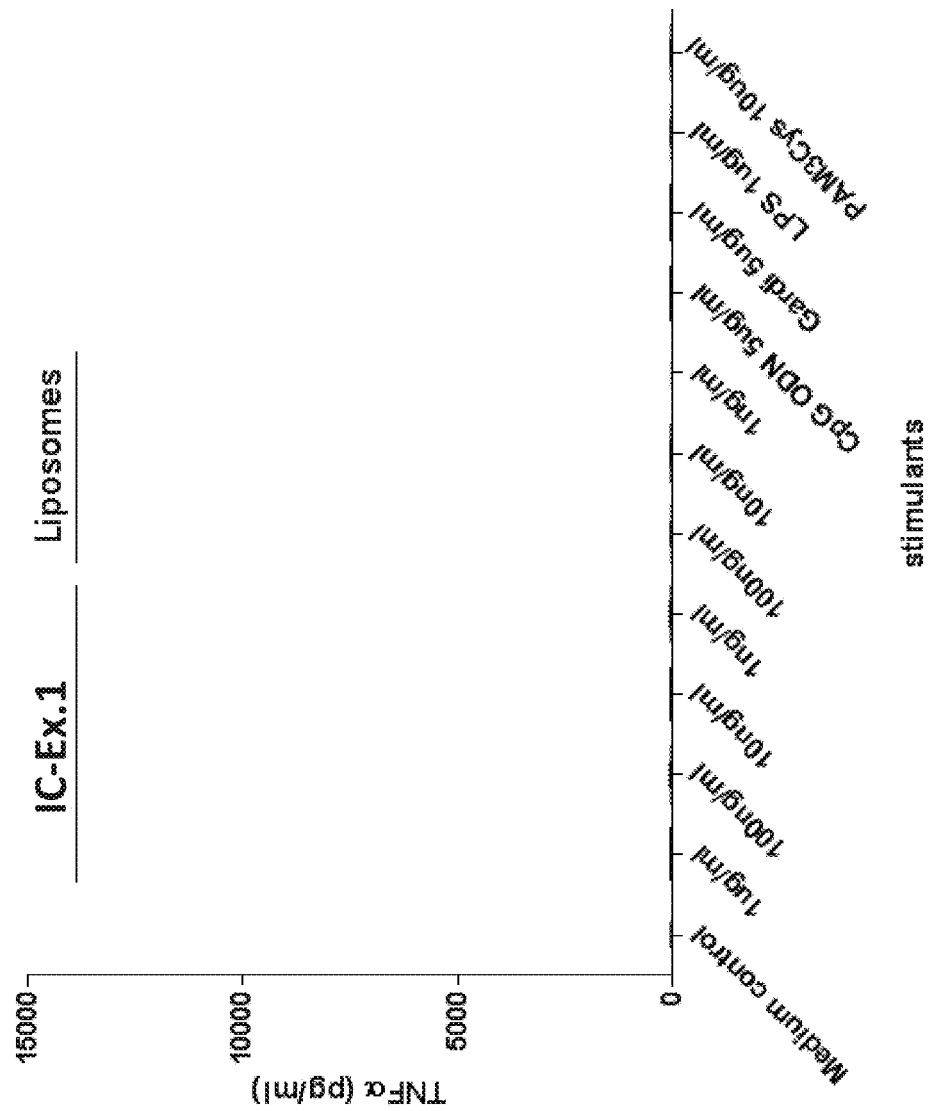
FIG. 33 graphically shows that TNF α is not produced in CD172a− cells.
Figures 37A, 37B, 37C, 37D:
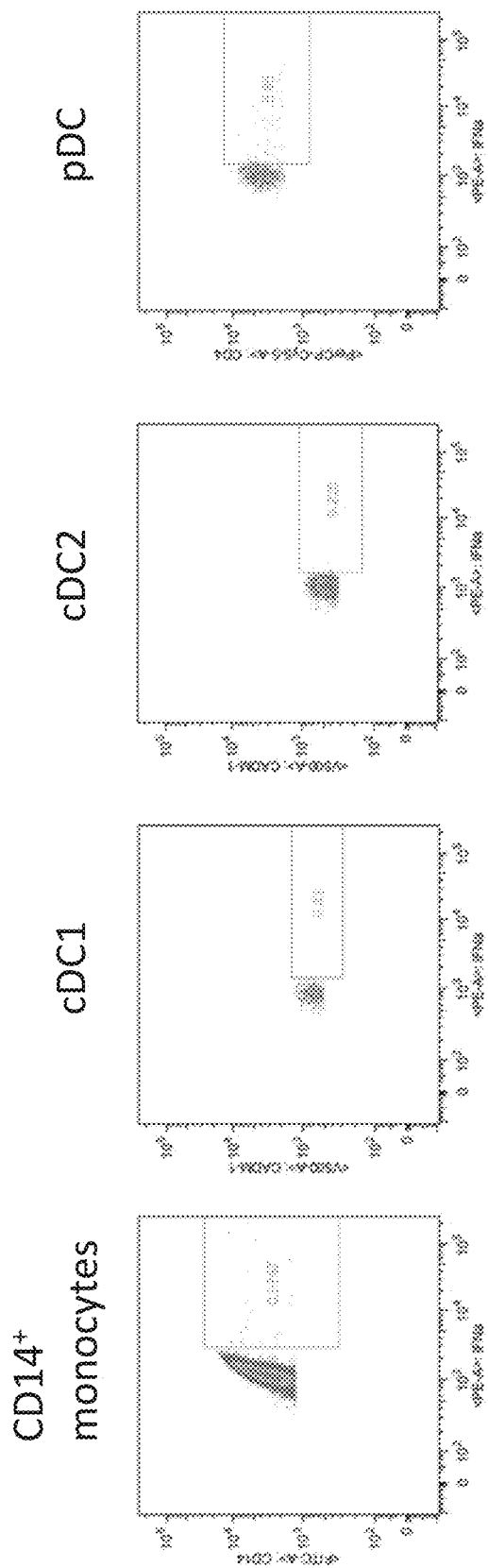
FIGS. 37A-D illustrate IFN-α production after stimulation with IC-Ex.1 (10 ng/mL) in CD14+, two types of conventional dendritic cells, and plasmacytoid dendritic cells, respectively.

In contrast, CD172a− cells did not produce cytokines after stimulation with IC-Ex.1, suggesting that IC-Ex.1 was not a potent activator cytokine expression in these cells. Because these cells require information from activated monocytes or dendritic cells to become activated, they are likely not the primary target of IC-Ex.1. However, these cells may be involved in a IC-Ex.1 response in vivo, but their involvement may not include direct interaction with IC-Ex. Referring to FIG. 32, CD172a− cells do not produce IFN-α after stimulation with IC-Ex.1 or with the known immune-stimulators. For the same reason that INF a is not produced by CD172a−, TNF α is also not produced in CD172a− cells after stimulation with IC-Ex.1 or the known stimulators (FIG. 33).

B. Plasmacytoid Dendritic Cells are Activated by IC-Ex.1 to Produce IFN-α.

Flow cytometry was employed to identify the cell type or types that are activated by IC-Ex.1 and produce cytokines as a result of IC-Ex.1 stimulation. Referring to FIGS. 34A-D, CD14+ monocytes, conventional dendritic cells (cCDs), and plasmacytoid dendritic cells (pDCs) stimulated with a control lipid failed to produce a significant amount of IFN-α. Similarly, FIGS. 35 A-C, FIGS. 36A-C, and FIGS. 37A-C show that CpG ODN, IC-Ex.1 (100 ng/mL), and IC-Ex.1 (10 ng/mL), respectively, do not stimulate CD14+ monocytes or cDCs. However, CpG ODN, IC-Ex.1 (100 ng/mL), and IC-Ex.1 (10 ng/mL) did stimulate IFN-α production in pDCs (FIGS. 35 D, 36 D, and 37 D, respectively).

Figure 38:
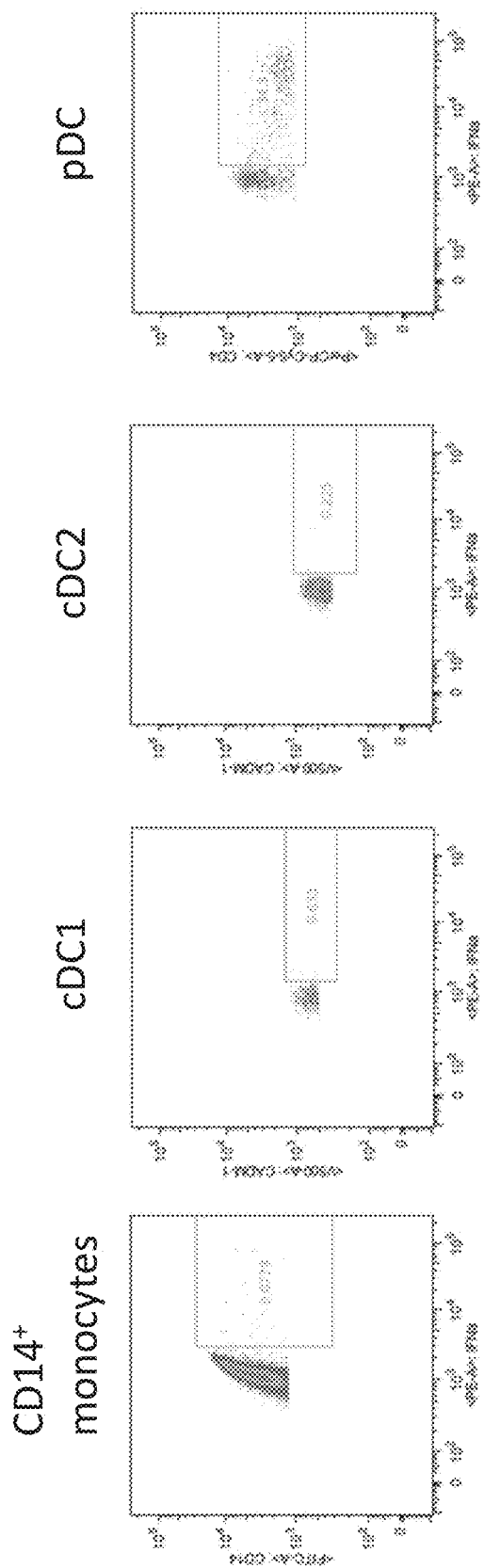
FIGS. 38A-D illustrate IFN-α production after stimulation with IC-Ex.1 (100 ng/mL0 in CD14+, two types of conventional dendritic cells, and plasmacytoid dendritic cells, respectively.
Figure 39:
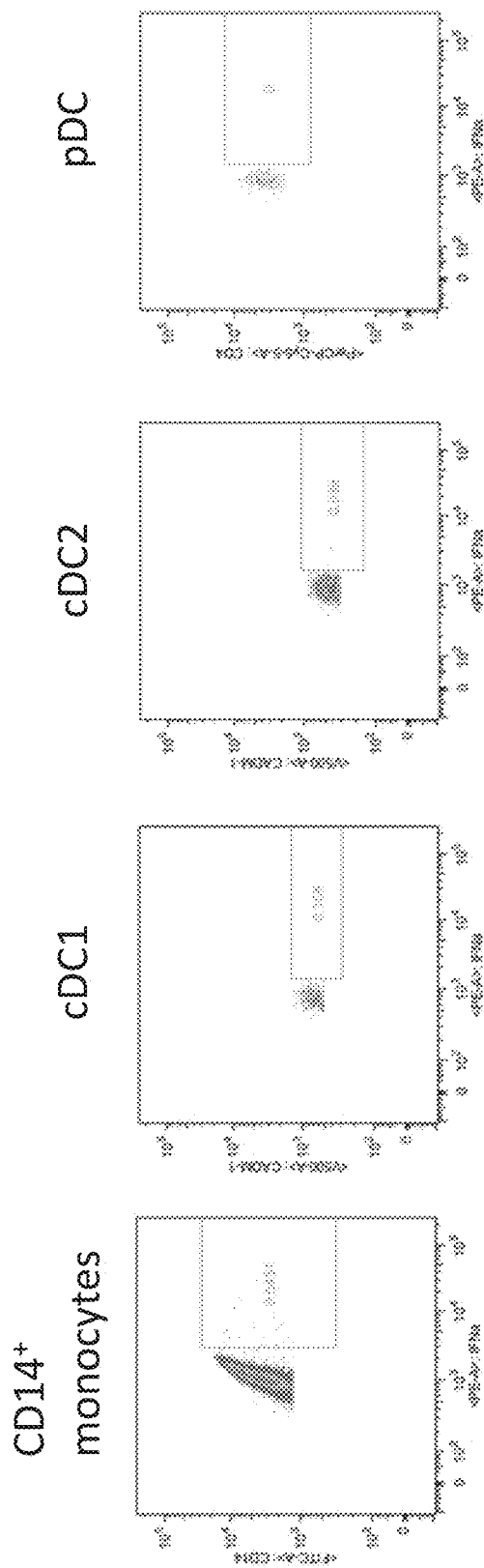
FIGS. 39A-D illustrate IFN-α production after stimulation with liposomes (100 ng/mL) in CD14+, two types of conventional dendritic cells, and plasmacytoid dendritic cells, respectively.

Direct comparison of IC-Ex.1 to liposomes show that the stimulatory effect in pDCs is most likely not due to the liposome alone but rather a combination of the liposome and the nucleic acid molecule as described above. FIGS. 38A-C and FIGS. 39A-C show that neither a 100 ng/mL concentration of IC-Ex.1 nor a 100 ng/mL concentration of liposomes elicited IFN-α production in CD14+ monocytes or cDCs. FIG. 38 D and FIG. 39 D illustrate the ability of IC-Ex.1 (100 ng/mL) to stimulate IFN-α production in pDCs while liposomes (100 ng/mL) failed to produce IFN-α in pDCs.

Figure 40:
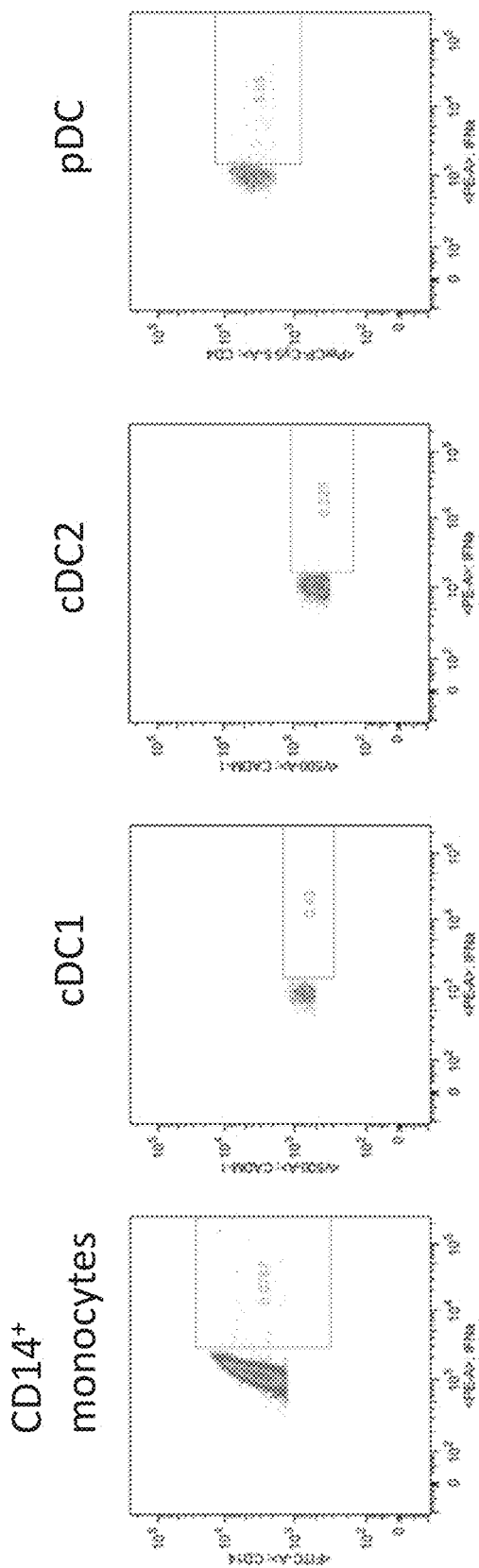
FIGS. 40A-D illustrate IFN-α production after stimulation with IC-Ex.1 (long/mL) in CD14+, two types of conventional dendritic cells, and plasmacytoid dendritic cells, respectively.
Figure 41:
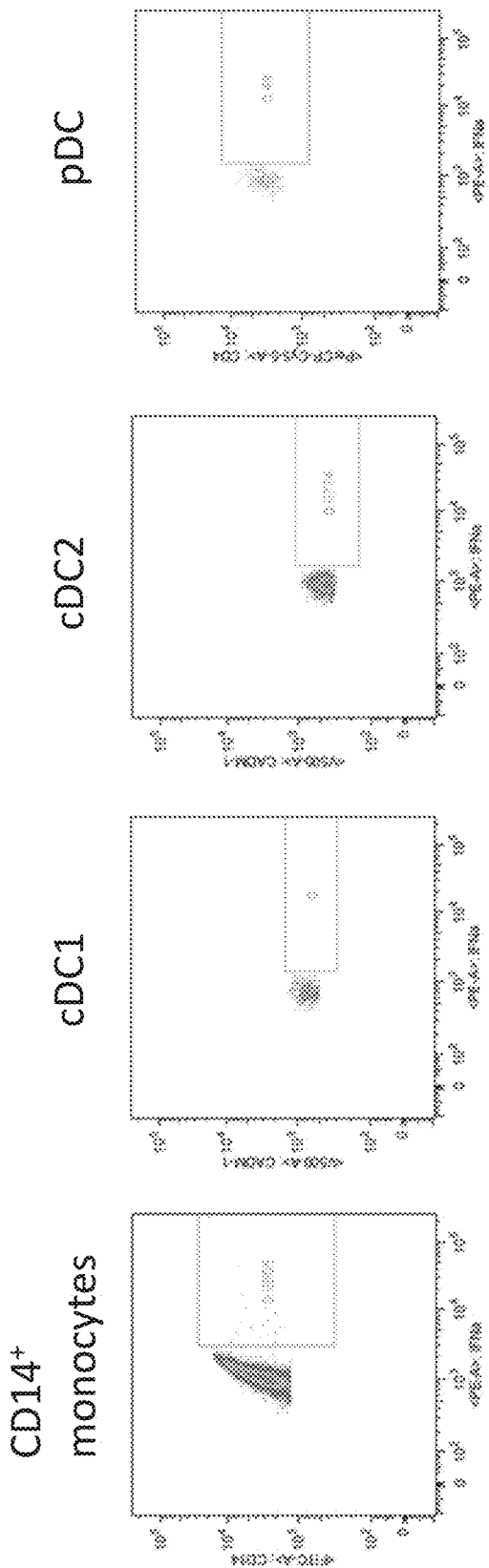
FIGS. 41A-D illustrate IFN-α production after stimulation with liposomes (10 ng/mL) in CD14+, two types of conventional dendritic cells, and plasmacytoid dendritic cells, respectively.

Even a 10 ng/mL of IC-Ex.1 is sufficient to generate cytokine production. While IC-Ex.1 (10 ng/mL) and liposomes (10 ng/mL) failed to produce IFN-α in CD14+ monocytes or cDCs (FIGS. 40A-C and FIGS. 41A-C), 10 ng/mL of IC-Ex.1 was sufficient to stimulate production of IFN-α in pDCs. 10 ng/mL of liposomes failed to produce results similar to 10 ng/mL of IC-Ex.1 (FIG. 40 D and FIG. 41 D).

Figure 42:
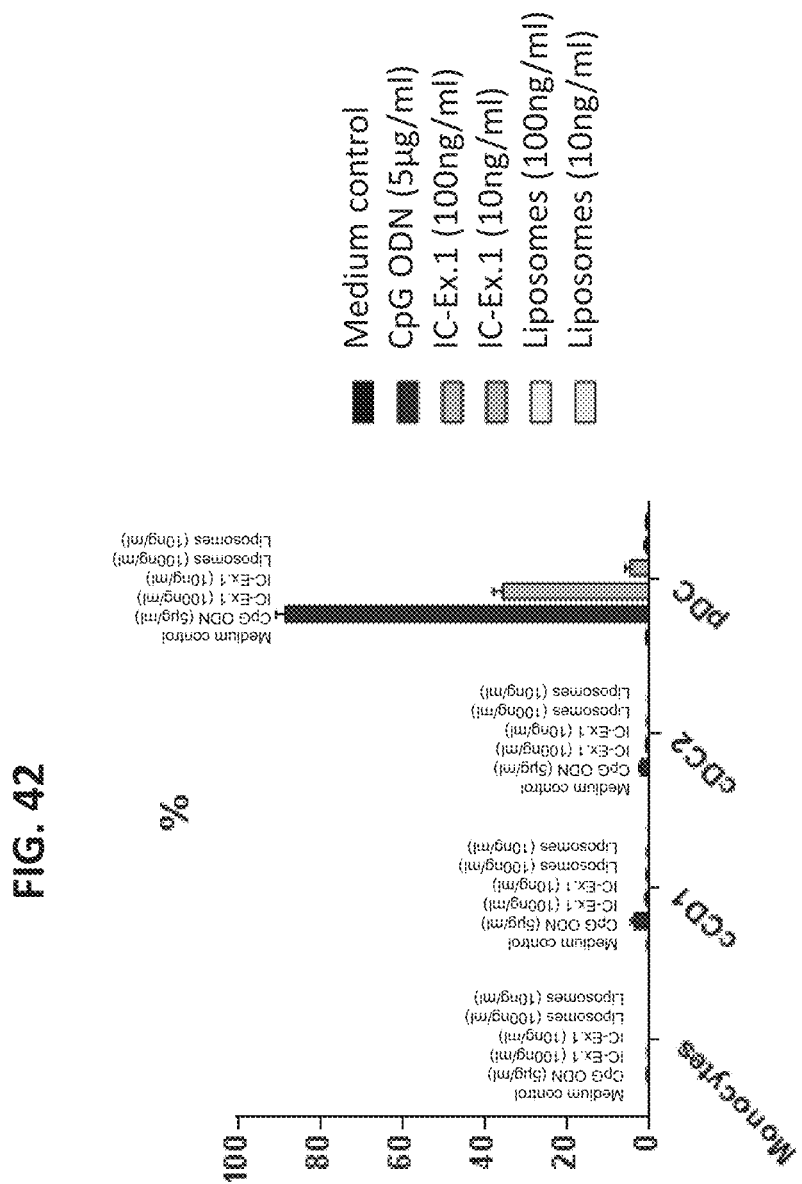
FIG. 42 graphically illustrates the percentage of cells that produce IFN-α.
Figure 43:
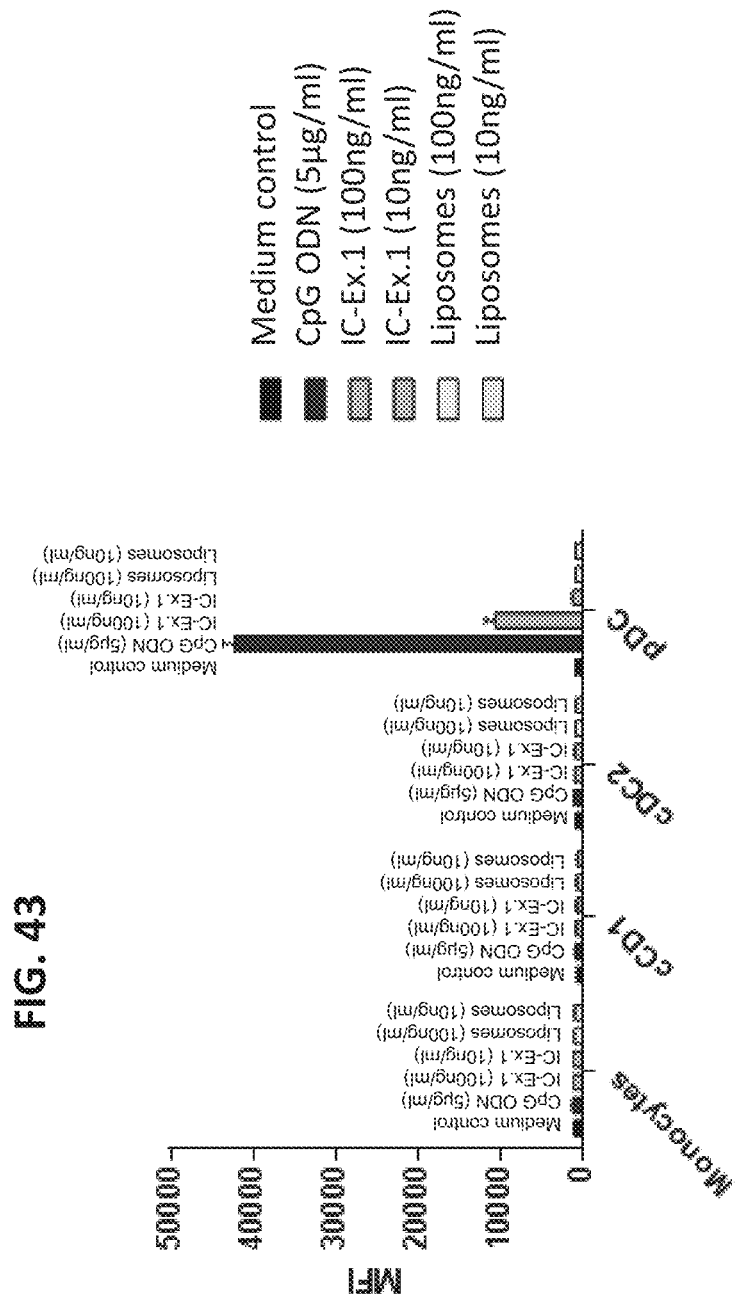
FIG. 43 graphically shows the mean fluorescence intensities generated by cells producing IFN-α.

Referring to FIG. 42, the percentage of cells identified as interferon producing cells is highest for CpG ODN and IC-Ex.1 (100 ng/mL and 10 ng/mL) in pDCs. Mean fluorescence intensity (MFI) is also highest for CpG ODN and IC-Ex.1 (100 ng/mL and 10 ng/mL) in pDCs (FIG. 43).

C. Physiologically Relevant Doses of IC-Ex.1 Induce IFN-γ and IL-4.

Figure 44:
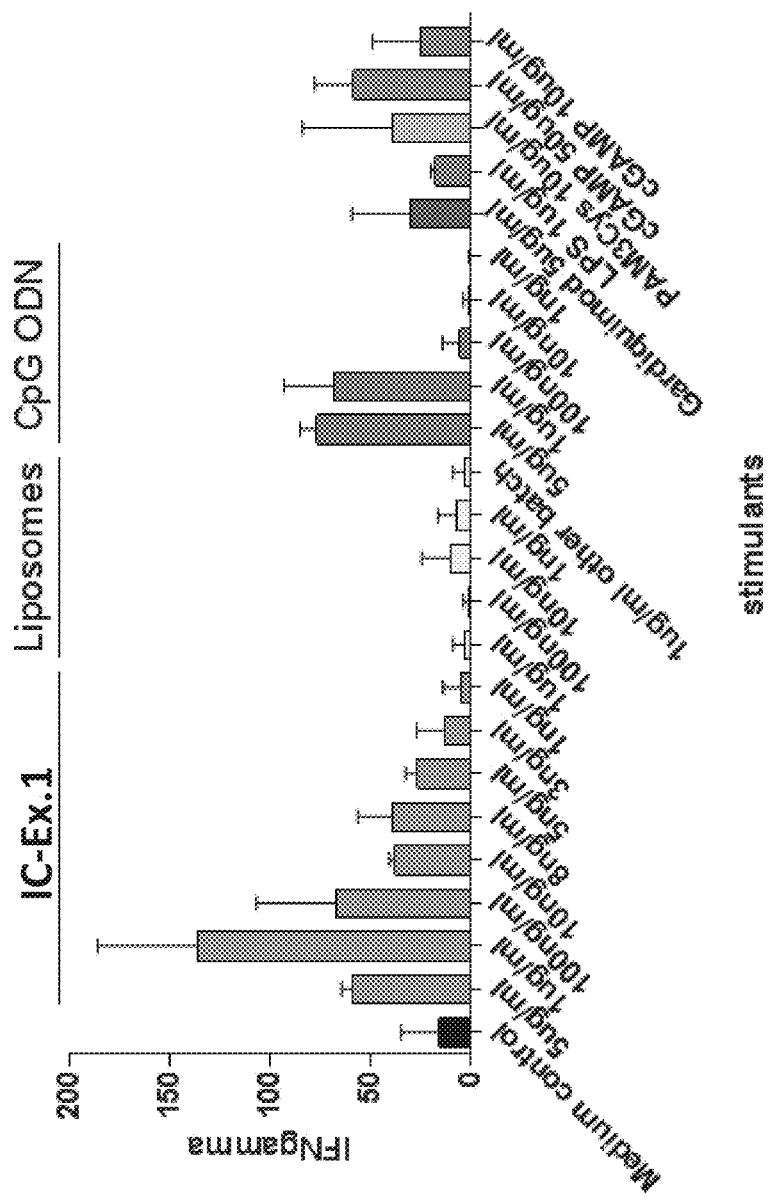
FIG. 44 graphically shows the comparative production of IFN-γ after stimulation with different immunostimulators or immunostimulator concentrations.

CD172+ enriched cells produced IFN-γ when stimulated with physiologically relevant doses of IC-Ex.1. This production may result from CD172− cells remaining in the CD172+ cell fraction because interplay between the cell types is necessary for IFN-γ production. Referring to FIG. 44, in comparison to the other known immunostimulants, IC-Ex.1 was surprisingly the most potent inducer of IFN-γ production, and even the least concentrated IC-Ex. 1 tested (1 ng/mL) induced the production of detectable amounts of IFN-γ. cGAMP was also tested for its ability to induce the production of IFN-γ. FIG. 44 also shows that cGAMP induces IFN-γ production, which indicates the STING pathway activation capability of producing IFN-γ.

Figure 45:
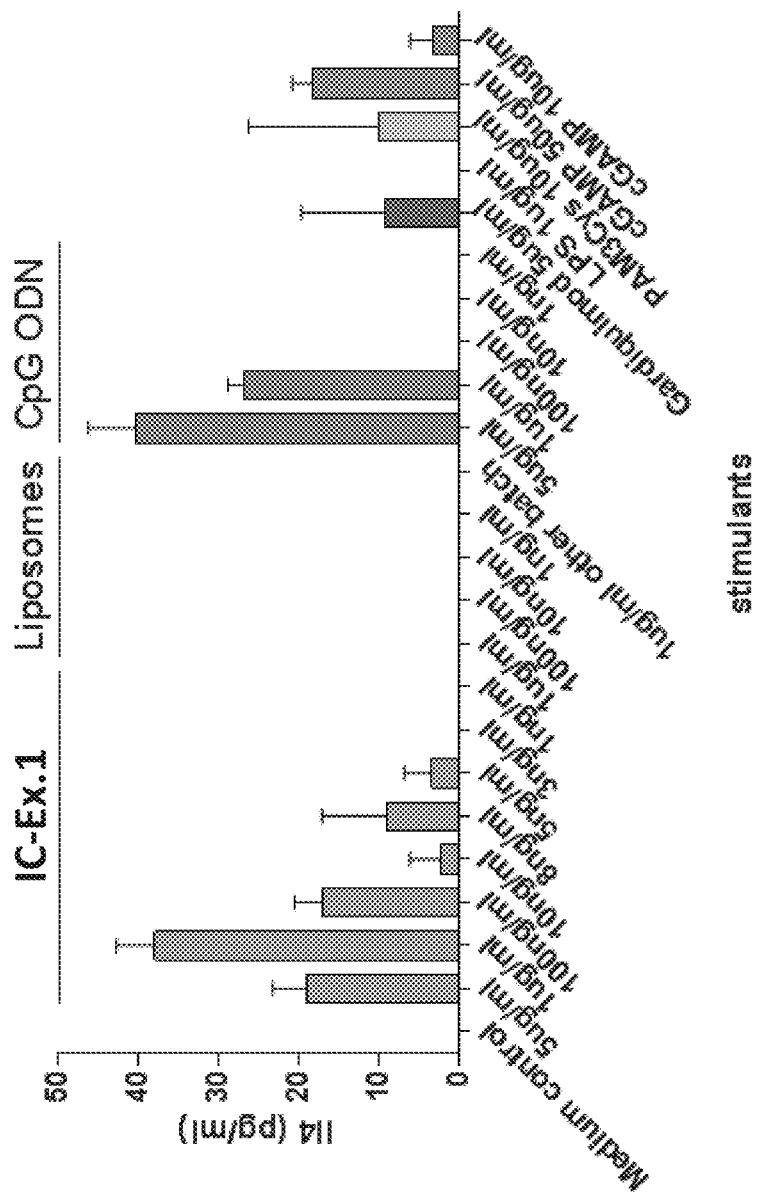
FIG. 45 illustrates IL-4 production in CD172a+ cells after stimulation with IC-Ex.1 and known immunostimulators.

CD172+ enriched cells also produced IL-4 when stimulated by physiologically relevant doses of IC-Ex.1. FIG. 45 shows that 1 μg/mL of IC-Ex.1 induces production of IL-4 at levels comparable to the highest dosage of CpG ODN (5 μg/mL).

Figure 46:
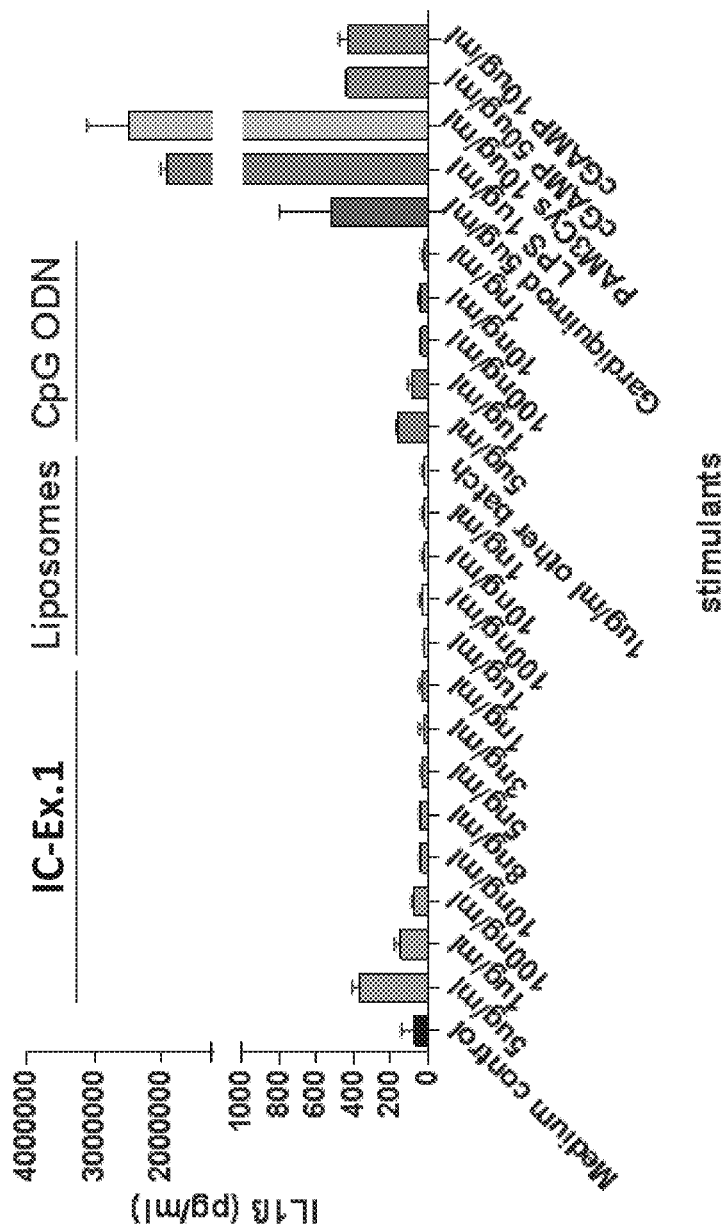
FIG. 46 illustrates IL-1β production in CD172a+ cells after stimulation with IC-Ex.1 and known immunostimulators.
Figure 47:
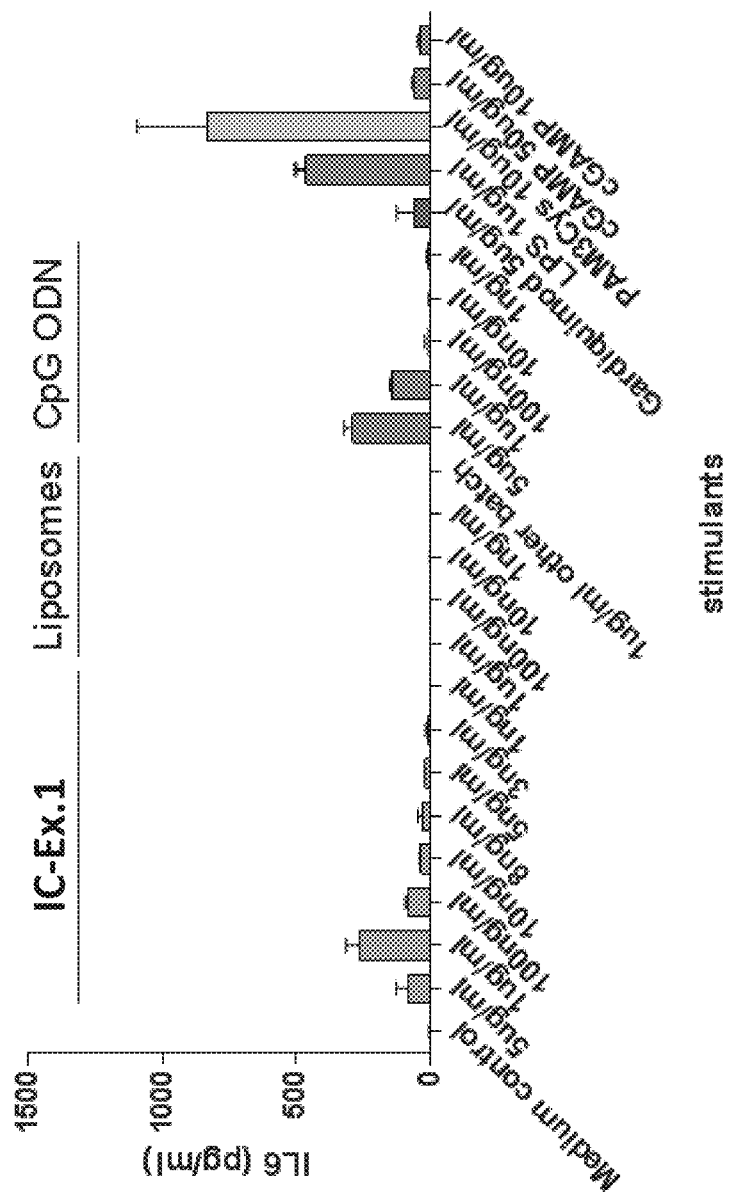
FIG. 47 illustrates IL-6 production in CD172a+ cells after stimulation with IC-Ex.1 and known immunostimulators.
Figure 48:
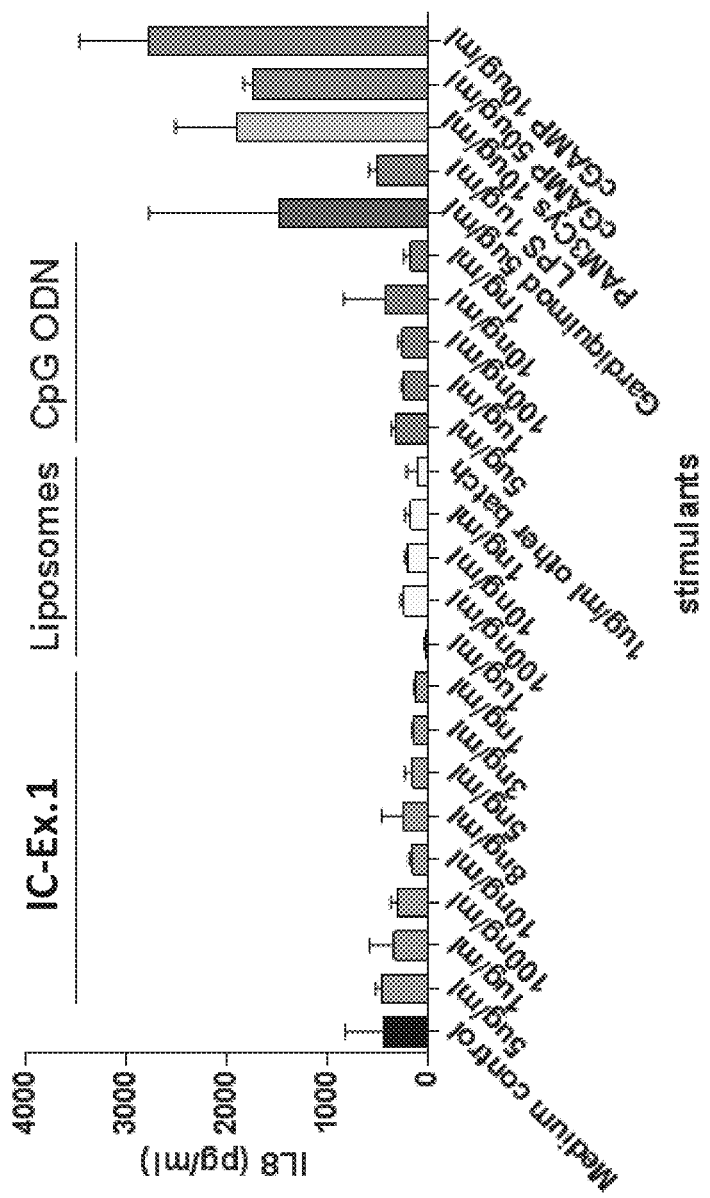
FIG. 48 illustrates IL-8 production in CD172a+ cells after stimulation with IC-Ex.1 and known immunostimulators.

Other cytokines are also produced after stimulation with IC-Ex.1, although at lower levels than stimulation with positive controls. For example, IC-Ex.1 was a weak inducer of IL-1l3, IL-6, IL-8, and IL-10. FIGS. 46-48 show that IC-Ex.1 induced expression of these cytokines at levels similar to that of CpG ODN, but below that of LPS (1 μg/mL) and PAM3Cys (10 μg/mL).

Example 9: IC-Ex.1 Protects Monocyte-Derived Macrophages Against PRRS Virus

The ability of IC-Ex.1 to confer resistance to viral infection was explored because IC-Ex.1 is an inducer of IFN-α and because IFN-α is a key component of host defense against viral infection. In vitro cultures of monocytes derived from pig's blood as described in Example 8 were treated with either IC-Ex.1 or IFN-γ, which is known to increase resistance to bacterial infection. Post-treatment, cells were inoculated with PRRS and evaluated for infection rate.

Results

Fewer cells treated with IC-Ex.1 prior to exposure to PRRS were infected compared to cells that were not treated. FIG. 49 shows that IC-Ex.1 pretreatment resulted in a percentage of cells infected with PRRS as cells pretreated with IFN-γ. The percentage of cells infected after IC-Ex.1 pretreatment is less than half the percentage of cells infected with PRRS with no pretreatment.

In view of the above, it will be seen that the several objects of the invention are achieved and other advantageous results attained.

As various changes could be made in the above products, compositions, and methods without departing from the scope of the invention, it is intended that all matter contained in the above description and shown in the accompanying drawings shall be interpreted as illustrative and not in a limiting sense.

What is claimed is:

1. A method of treating an infection in a recipient food production swine comprising administering an effective amount of an immunomodulator composition to the food production swine, wherein the immunomodulator composition comprises: (a) a nucleic acid sequence having at least 94% sequence identity with a sequence selected from the group consisting of SEQ ID NO: 1 and SEQ ID NO: 4, wherein the nucleic acid sequences comprises at least 280 CpG dinucleotides; and (b) a cationic liposome delivery vehicle, wherein the cationic liposome delivery vehicle comprises pairs of lipids selected from the group consisting of N-[1-(2,3-dioleyloxy)propyl]-N,N,N-trimethylammonium chloride (DOTMA) and cholesterol; N-[1-(2,3-dioleoyloxy)propyl]-N,N,N-trimethylammonium chloride (DOTAP) and cholesterol; 1-[2-(oleoyloxy)ethyl]-2-oleyl-3-

(2-hydroxyethyl) imidazolinium chloride (DOTIM) and cholesterol; and dimethyldioctadecylammonium bromide (DDAB) and cholesterol;

wherein the immunomodulator composition further comprises or is administered in combination with an immunogen derived from an infectious agent causing the infection, and wherein an immune response to the immunogen is increased in the food production swine with the combination as compared to the immune response in the food production swine elicited with the immunogen by itself.

2. The method of claim 1, wherein the administration is before exposure to the infectious agent comprising the immunogen.

3. The method of claim 1, wherein the administration is after exposure to the infectious agent comprising the immunogen.

4. The method of claim 1, wherein the immunogen is comprised in a vaccine.

5. The method of claim 1, wherein the immunomodulator composition further comprises a pharmaceutically acceptable carrier.

6. The method of claim 4, wherein the vaccine is a Porcine Reproductive and Respiratory Syndrome Virus (PRRSV) vaccine or *Escherichia coli* vaccine.

7. The method of claim 1, wherein the immunomodulator composition is administered intramuscularly in a single dose.

8. The method of claim 1, wherein the immunogen is derived from Porcine Reproductive and Respiratory Syndrome Virus (PRRSV) or *Escherichia coli*.

9. The method of claim 8, wherein the immunogen is derived from PRRSV.

* * * * *